(12) United States Patent
Boons et al.

(10) Patent No.: US 9,446,144 B2
(45) Date of Patent: *Sep. 20, 2016

(54) GLYCOPEPTIDE AND USES THEREOF

(71) Applicants: University of Georgia Research Foundation, Inc., Athens, GA (US); Alex Haley, Athens, GA (US)

(72) Inventors: Geert-Jan Boons, Athens, GA (US); Therese Buskas, Athens, GA (US); Sampat Ingale, San Diego, CA (US); Margaretha Wolfert, Athens, GA (US)

(73) Assignee: University of Georgia Research Foundation, Inc., Athens, GA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/145,745

(22) Filed: Dec. 31, 2013

(65) Prior Publication Data

US 2014/0212473 A1    Jul. 31, 2014

Related U.S. Application Data

(63) Continuation of application No. 13/002,180, filed as application No. PCT/US2009/003944 on Jul. 2, 2009, now abandoned, which is a continuation-in-part of application No. 12/217,376, filed on Jul. 3, 2008, now Pat. No. 7,820,797, which is a continuation-in-part of application No. PCT/US2007/000158, filed on Jan. 3, 2007.

(60) Provisional application No. 61/197,386, filed on Oct. 27, 2008, provisional application No. 61/127,710, filed on May 15, 2008, provisional application No. 60/755,881, filed on Jan. 3, 2006, provisional application No. 60/796,769, filed on May 2, 2006, provisional application No. 60/809,272, filed on May 30, 2006.

(51) Int. Cl.

| | |
|---|---|
| *A61K 47/48* | (2006.01) |
| *C07K 16/44* | (2006.01) |
| *A61K 9/127* | (2006.01) |
| *A61K 39/385* | (2006.01) |
| *A61K 39/00* | (2006.01) |
| *C07K 9/00* | (2006.01) |
| *C07K 14/22* | (2006.01) |
| *C07K 14/47* | (2006.01) |
| *C07K 16/30* | (2006.01) |
| *A61K 38/00* | (2006.01) |

(52) U.S. Cl.
CPC ........... *A61K 47/4833* (2013.01); *A61K 9/127* (2013.01); *A61K 39/0008* (2013.01); *A61K 39/0011* (2013.01); *A61K 39/385* (2013.01); *C07K 9/00* (2013.01); *C07K 14/22* (2013.01); *C07K 14/4727* (2013.01); *C07K 16/3076* (2013.01); *C07K 16/44* (2013.01); *A61K 38/00* (2013.01); *A61K 2039/545* (2013.01); *A61K 2039/55555* (2013.01); *A61K 2039/57* (2013.01); *A61K 2039/6018* (2013.01); *A61K 2039/6075* (2013.01); *C07K 2317/34* (2013.01); *C12N 2740/16011* (2013.01); *C12N 2740/16134* (2013.01); *G01N 2400/02* (2013.01); *G01N 2800/042* (2013.01); *G01N 2800/2821* (2013.01)

(58) Field of Classification Search
None
See application file for complete search history.

(56) References Cited

U.S. PATENT DOCUMENTS

| | | | |
|---|---|---|---|
| 5,108,934 | A | 4/1992 | Rokugawa et al. |
| 5,503,829 | A | 4/1996 | Ladant et al. |
| 5,679,784 | A | 10/1997 | Ladant et al. |
| 5,876,949 | A | 3/1999 | Dreyfuss et al. |
| 5,935,580 | A | 8/1999 | Ladant et al. |
| 6,168,804 | B1 | 1/2001 | Samuel et al. |
| 6,258,796 | B1 | 7/2001 | Richards |
| 6,413,935 | B1 | 7/2002 | Sette et al. |
| 6,544,952 | B1 | 4/2003 | Danishefsky et al. |
| 6,600,012 | B1 | 7/2003 | Agrawal et al. |
| 6,645,935 | B2 | 11/2003 | Danishefsky et al. |
| 6,676,946 | B2 | 1/2004 | Bay et al. |
| 7,659,240 | B2 * | 2/2010 | Kadiyala et al. ............. 514/1.1 |
| 7,820,797 | B2 | 10/2010 | Boons |
| 9,211,345 | B2 | 12/2015 | Boons et al. |
| 2002/0038017 | A1 | 3/2002 | Danishefsky et al. |
| 2002/0055121 | A1 | 5/2002 | Vielkind |
| 2003/0157115 | A1 | 8/2003 | Bay et al. |
| 2003/0157160 | A1 | 8/2003 | Budzynski et al. |
| 2004/0202673 | A1 | 10/2004 | Huang |
| 2006/0069238 | A1 | 3/2006 | Koganty et al. |

(Continued)

FOREIGN PATENT DOCUMENTS

| | | |
|---|---|---|
| WO | WO 95/07707 A1 | 3/1995 |
| WO | WO 98/43677 A1 | 10/1998 |

(Continued)

OTHER PUBLICATIONS

Muller et al. Lipopeptide adjuvants: monitoring and comparison of P3CSK4- and LPS-induced gene transcription. Int Immunopharmacol. Jul. 2002;2(8):1065-77.*
Lloyd et al. Comparison of O-linked carbohydrate chains in MUC-1 mucin from normal breast epithelial cell lines and breast carcinoma cell lines. Demonstration of simpler and fewer glycan chains in tumor cells. J Biol Chem. Dec. 27, 1996;271(52):33325-34.*
Kuduk et al., "Synthetic and immunological studies on clustered modes of mucin-related Tn and TF O-linked antigens: the preparation of a glycopeptide-based vaccine for clinical trials against prostate cancer," Dec. 9, 1998 *J. Am. Chem. Soc.* 120(48):12474-12485. Available online on Nov. 20, 1998.

(Continued)

*Primary Examiner* — Michelle S Horning
(74) *Attorney, Agent, or Firm* — Mueting, Raasch & Gebhardt, P.A.

(57) ABSTRACT

A glycolipopeptide comprising a carbohydrate component, a peptide component and a lipid component, for use as a therapeutic or prophylactic vaccine. Also provided are monoclonal and polyclonal antibodies that recognize the glycolipopeptide of the invention, as well as uses thereof.

10 Claims, 34 Drawing Sheets

(56) References Cited

U.S. PATENT DOCUMENTS

| | | |
|---|---|---|
| 2007/0160622 A1 | 7/2007 | Turnell et al. |
| 2008/0131495 A1 | 6/2008 | Longenecker |
| 2009/0041836 A1 | 2/2009 | Boons et al. |
| 2009/0196916 A1 | 8/2009 | Ingale et al. |
| 2009/0317414 A1 | 12/2009 | Pietersz et al. |
| 2010/0034825 A1 | 2/2010 | Clausen et al. |
| 2012/0039984 A1 | 2/2012 | Boons et al. |
| 2013/0236486 A1 | 9/2013 | Boons et al. |
| 2015/0087806 A1* | 3/2015 | Boons et al. ............... 530/322 |
| 2015/0299290 A1 | 10/2015 | Boons et al. |

FOREIGN PATENT DOCUMENTS

| | | |
|---|---|---|
| WO | WO 00/12536 A2 | 3/2000 |
| WO | WO 00/12536 A3 | 6/2000 |
| WO | WO 02/43699 A2 | 6/2002 |
| WO | WO 02/43699 A3 | 10/2002 |
| WO | WO 03/100060 A2 | 4/2003 |
| WO | WO 03/089574 A2 | 10/2003 |
| WO | WO 03/089574 A3 | 9/2005 |
| WO | WO 2007/067744 A2 | 6/2007 |
| WO | WO 2007/079448 A2 | 7/2007 |
| WO | WO 2007/146070 A2 | 12/2007 |
| WO | WO 2007/079448 A3 | 1/2008 |
| WO | WO 2007/146070 A3 | 4/2008 |
| WO | WO 2007/067744 A3 | 9/2009 |
| WO | WO 2010/002478 A2 | 1/2010 |
| WO | WO 2010/002478 A3 | 7/2010 |
| WO | WO 2010/002478 A4 | 8/2010 |
| WO | WO 2011/156751 A2 | 12/2011 |
| WO | WO 2011/156751 A3 | 7/2012 |

OTHER PUBLICATIONS

Xu et al. Direct and Indirect Role of Toll-Like Receptors in T Cell Mediated Immunity. 2004. *Cellular and Molecular Immunology.* 1(4):239-246.
U.S. Appl. No. 14/558,088; Office Action issued Mar. 2, 2015.
Abdel-Aal et al., "Immune and Anticancer Responses Elicited by Fully Synthetic Aberrantly Glycosylated MUC1 Tripartite Vaccines Modified by a TLR2 or TLR9 Agonist" *ChemBioChem,* 2014; 15:1508-1513.
Gavin et al., "Adjuvant-enhanced antibody responses occur without Toll-like receptor signaling" *Science,* Author Manuscript, available in PMC May 14, 2007; 7 pages; published in final edited form as *Science,* Dec. 22, 2006: 314(5807):1936-1938.
Ingale et al., "Increasing the Antigenicity of Synthetic Tumor-Associated Carbohydrate Antigens by Targeting Toll-Like Receptors", *Chembiochem.* Author Manuscript, available in PMC Feb. 13, 2009; 31 pages; published in final edited form as *Chembiochem.* Feb. 13, 2009; 10(3):455-463.
Ingale et al., "Increasing the Antigenicity of Synthetic Tumor-Associated Carbohydrate Antigens by Targeting Toll-Like Receptors" *Chembiochem,* Feb. 13, 2009; 10:455-463; epub Jan. 14, 2009.
Ingale et al., "Increasing the Antigenicity of Synthetic Tumor-Associated Carbohydrate Antigens by Targeting Toll-Like Receptors" Supporting Information (online); *Chembiochem,* Feb. 13, 2009; 10(3):455-463; epub Jan. 14, 2009.
Lakshminarayanan et al., "Immune recognition of tumor-associated mucin MUC1 is achieved by a fully synthetic aberrantly glycosylated MUC1 tripartite vaccine" *PNAS,* Jan. 3, 2012; 109(1):261-266; epub Dec. 14, 2011.
Lakshminarayanan et al., "Immune recognition of tumor-associated mucin MUC1 is achieved by a fully synthetic aberrantly glycosylated MUC1 tripartite vaccine" Supporting Information (online) *PNAS,* Jan. 3, 2012; 109(1):261-266; epub Dec. 14, 2011.
U.S. Appl. No. 14/558,088; Notice of Allowance issued Jun. 19, 2015; (10 pages).
U.S. Appl. No. 14/558,088; Notice of Allowance issued Nov. 4, 2015; (6 pages).
International Search Report mailed on Nov. 12, 2007, for PCT/US2007/000158.

Ada and Issacs, "Carbohydrate-protein conjugate vaccines," Feb. 2003 *Clin. Microbiol. Inf.* 9(2):79-85.
Adluri et al., "Immunogenicity of synthetic TF-KLH (keyhole limpet hemocyanin) and sTn-KLH conjugates in colorectal carcinoma patients," Sep. 1995 *Cancer Immunol. Immunother.* 41(3):185-192.
Akintonwa, "Theoretical mechanistic basis of the toxic effects and efficacy of dideoxycytidine in HIV:AIDS," Aug. 2001 *Medical Hypotheses* 57(2):249-251.
Akira et al., "Toll-like receptors: critical proteins linking innate and acquired immunity," Aug. 2001 *Nat. Immunol.* 2(8):675-680.
Akira and Takeda, "Toll-like receptor signalling," Jul. 2004 *Nat. Rev. Immunol.* 4(7):499-511.
Alexander et al., "Development of high potency universal DR-restricted helper epitopes by modification of high affinity DR-blocking peptides," Dec. 1994 *Immunity* 1(9):751-761.
Alexander et al., "Linear PADRE T helper epitope and carbohydrate B cell epitope conjugates induce specific high titer IgG antibody responses," Feb. 1, 2000 *J. Immunol.* 164(3):1625-1633.
Alexandrov et al., "Intein-mediated synthesis of geranylgeranylated Rab7 protein in vitro," May 22, 2002 *J. Am. Chem. Soc.* 124(20):5648-5649. Available online on Apr. 27, 2002.
Aliprantis et al., "Cell activation and apoptosis by bacterial lipoproteins through toll-like receptor-2," Jul. 30, 1999 *Science* 285(5428):736-739.
Anderson et al., "Effects of oligosaccharide chain length, exposed terminal group, and hapten loading on the antibody response of human adults and infants to vaccines consisting of *Haemophilus influenzae* type B capsular antigen unterminally coupled to the diphtheria protein CRM197," Apr. 1, 1989 *J. Immunol.* 142(7):2464-2468.
Apostolopoulos et al., "MUC1 and breast cancer," Feb. 1999 *Curr. Opin. Mol. Ther.* 1(1):98-103.
Ausubel et al. (eds.), *Current Protocols in Molecular Biology,* vols. 1-4, John Wiley & Sons, Inc., New York, NY, 1992-1996; title page, publisher's page and table of contents only (26 pages).
Baldus et al., "MUC1 and the MUCs: a family of human mucins with impact in cancer biology," 2004 *Crit. Rev. Clin. Lab. Sci.* 41(2):189-231.
Barber et al., "Possible mechanisms of mammalian immunocontraception," Mar. 2000 *J. Reprod. Immunol.* 46(2): 103-124.
Barchi, Jr., "Emerging roles of carbohydrates and glycomimetics in anticancer drug design," Mar. 2000 *Current Pharmaceutical Design* 6(4):485-501.
Berzofsky et al., "Strategies for designing and optimizing new generation vaccines," Dec. 2001 *Nat. Rev. Immunol.* 1(3):209-219.
Beutler, "Innate immunity: an overview," Feb. 2004 *Mol. Immunol.* 40(12):845-859.
Bevan, "Helping the CD8+T-cell response," Aug. 2004 *Nat. Rev. Immunol.* 4(8):595-602.
Blander and Medzhitov, "Toll-dependent selection of microbial antigens for presentation by dendritic cells," Apr. 6, 2006 *Nature* 440(7085):808-812. Available online on Feb. 19, 2006.
Boons, Geert-Jan, "Synthesis/Immunological Properties of Lewis Antigens," Grant Abstract, Grant No. 1RO1CA088986-01A2 [online]. National Cancer Institute, National Institutes of Health; project dates Jul. 15, 2002 to Jun. 30, 2006 [retrieved on Jan. 6, 2009]. Retrieved from the Internet: <http://crisp.cit.nih.gov/crisp/CRISP_LIB.getdoc?textkey=6546986&p_grant_num=1R01CA088986-01A2&p_query=&ticket=84444686&p_audit_session_id=393574951&p_keywords=>; 2 pgs.
Boons, Geert-Jan, "Synthesis/Immunological Properties of Lewis Antigens," Grant Abstract, Grant No. 5RO1CA088986-02 [online]. National Cancer Institute, National Institutes of Health; project dates Jul. 15, 2002 to Jun. 30, 2006 [retrieved on Jan. 6, 2009]. Retrieved from the Internet: <http://crisp.cit.nih.gov/crisp/CRISP_LIB.getdoc?textkey=6605801&p_grant_num=5R01CA088986-02&p_query=&ticket=84444686&p_audit_session_id=393574951&p_keywords=>; 2 pgs.
Boons, Geert-Jan, "Synthesis/Immunological Properties of Lewis Antigens," Grant Abstract, Grant No. 5RO1CA088986-03 [online]. National Cancer Institute, National Institutes of Health; project

(56) References Cited

OTHER PUBLICATIONS dates Jul. 15, 2002 to Jun. 30, 2006 [retrieved on Jan. 6, 2009]. Retrieved from the Internet: <http://crisp.cit.nih.gov/crisp/CRISP_LIB.getdoc?textkey=6752388&p_grant_num=5R01CA088986-03&p_query=&ticket=84444686&p_audit_session_id=393574951&p_keywords=>; 2 pgs.

Boons, Geert-Jan, "Synthesis/Immunological Properties of Lewis Antigens," Grant Abstract, Grant No. 5RO1CA088986-04 [online]. National Cancer Institute, National Institutes of Health; project dates Jul. 15, 2002 to Nov. 30, 2006 [retrieved on Jan. 6, 2009]. Retrieved from the Internet: <http://crisp.cit.nih.gov/crisp/CRISP_LIB.getdoc?textkey=6918562&p_grant_num=5R01CA088986-04&p_query=&ticket=84444686&p_audit_session_id=393574951&p_keywords=>; 2 pgs.

Boons, Geert-Jan, "A Fully Synthetic Carbohydrate-Based Cancer Vaccine," Grant Abstract, Grant No. 2RO1CA088986-05 [online]. National Cancer Institute, National Institutes of Health; project dates Jul. 15, 2002 to Nov. 30, 2006 [retrieved on Jan. 6, 2009]. Retrieved from the Internet: <http://crisp.cit.nih.gov/crisp/CRISP_LIB.getdoc?textkey=7212472&p_grant_num=2R01CA088986-05&p_query=&ticket=84444686&p_audit_session_id=393574951&p_keywords=>; 2 pgs.

Boons, Geert-Jan, "A Fully Synthetic Carbohydrate-Based Cancer Vaccine," Grant Abstract, Grant No. 5RO1CA088986-06 [online]. National Cancer Institute, National Institutes of Health; project dates Jul. 15, 2002 to Nov. 30, 2006 [retrieved on Jan. 6, 2009]. Retrieved from the Internet: <http://crisp.cit.nih.gov/crisp/CRISP_LIB.getdoc?textkey=7329834&p_grant_num=5R01CA088986-06&p_query=&ticket=84444686&p_audit_session_id=393574951&p_keywords=>; 1 pg.

Boons, Geert-Jan, "A Fully Synthetic Carbohydrate-Based Cancer Vaccine," Grant Abstract, Grant No. 5RO1CA088986-07 [online]. National Cancer Institute, National Institutes of Health; project dates Jul. 15, 2002 to Nov. 30, 2006 [retrieved on Jan. 6, 2009]. Retrieved from the Internet: <http://crisp.cit.nih.gov/crisp/CRISP_LIB.getdoc?textkey=7534051&p_grant_num=5R01CA088986-07&p_query=&ticket=84444686&p_audit_session_id=393574951&p_keywords=>; 1 pg.

Boons, Geert-Jan, "Site-Specific Glycosylation of Glycolylated Human IgG-Fc Antibodies," Grant Abstract, Grant No. 2P41RR005351-160092 [online]. National Center for Research Resources, National Institutes of Health; project dates Apr. 4, 2005 to Jan. 31, 2006 [retrieved on Mar. 31, 2009]. Retrieved from the Internet: <http://crisp.cit.nih.gov/crisp/CRISP_LIB.getdoc?textkey=7181439&p_grant_num=2P41RR005351-160092&p_query=&ticket=91024570&p_audit_session_id=412712484&p_keywords=>; 1 pg.

Boons, Geert-Jan, "New Synthetic Endotoxin Antagonists," Grant Abstract, Grant No. 2P41RR005351-160093 [online]. National Center for Research Resources, National Institutes of Health; project dates Apr. 4, 2005 to Jan. 31, 2006 [retrieved on Mar. 31, 2009]. Retrieved from the Internet: <http://crisp.cit.nih.gov/crisp/CRISP_LIB.getdoc?textkey=7181440&p_grant_num=2P41RR005351-160093&p_query=&ticket=91024570&p_audit_session_id=412712484&p_keywords=>; 1 pg.

Boons, Geert-Jan, "The Role of Multivalency in the Mode-of-Action," Grant Abstract, Grant No. 2P41RR005351-160096 [online]. National Center for Research Resources, National Institutes of Health; project dates Apr. 4, 2005 to Jan. 31, 2006 [retrieved on Mar. 31, 2009]. Retrieved from the Internet: <http://crisp.cit.nih.gov/crisp/CRISP_LIB.getdoc?textkey=7181449&p_grant_num=2P41RR005351-160096&p_query=&ticket=91024570&p_audit_session_id=412712484&p_keywords=>; 1 pg.

Boons et al., "Preparation of a well-defined sugar-peptide conjugate: a possible approach to a synthetic vaccine against *Neisseria meningitidis*," 1991 *Boorg. Med.. Chem. Lett.* 1(6):303-308.

Boons et al., "Stereoselective glycosylations using chiral auxiliaries," Abstract of oral presentation [online]. Abstract No. CARB 4, Division of Carbohydrate Chemistry. *229$^{th}$ American Chemical Society (ACS) National Meeting*. San Diego, CA; Mar. 13-17, 2005. Available online [retrieved on Mar. 31, 2009]. Retrieved from the Internet: <http://oasys2.confex.com/acs/229nm/techprogram/>; 1 pg.

Boons, "Novel approaches for the design and synthesis of selective glycosidase inhibitors," Abstract of oral presentation [online]. Abstract No. CARB 14, Division of Carbohydrate Chemistry. *229$^{th}$ American Chemical Society (ACS) National Meeting*. San Diego, CA; Mar. 13-17, 2005. Available online [retrieved on 2009-03-31]. Retrieved from the Internet: <http://oasys2.confex.com/acs/229nm/techprogram/>; 1 pg.

Borman, "Cancer vaccine is best in class: three part carbohydrate vaccine elicits strong anticancer response," Sep. 12, 2005 *Chemical & Engineering News* 83(37):10. Available online [retrieved on Mar. 31, 2009]. Retrieved from the Internet: <http://pubs.acs.org/cen/news/83/i37/8337notw3.html>; 2 pgs.

Borrabeck (ed.), *Antibody Engineering, 2nd Edition*. Oxford University Press, Inc.: New York, NY. Copyright 1995. Title page, publishers page, and table of contents only (4 pages).

Braun, "Covalent lipoprotein from the outer membrane of *Escherichia coli*," Oct. 31, 1975 *Biochim. Biophys. Acta* 415(3):335-377.

Bundle, "A carbohydrate vaccine exceeds the sum of its parts," Oct. 2007 *Nat. Chem. Biol.* 3(10):605-606.

Buskas et al., "The immunogenicity of the tumor-associated antigen Lewis$^y$ may be suppressed by a bifunctional cross-linker required for coupling to a carrier protein," Jul. 19, 2004 *Chem. Eur. J.* 10(14):3517-3523.

Buskas et al., "Towards a fully synthetic carbohydrate-based anti-cancer vaccine: synthesis and immunological evaluation of a lipidated glycopeptide containing the tumor-associated Tn antigen," Sep. 19, 2005 *Angew. Chem.* 117(37):6139-6142. Available online on Aug. 18, 2005. Also published concurrently in *Angew. Chem. Int. Ed.* 44(37):5985-5988.

Buskas et al., "Glycopeptides as versatile tool for glycobiology," 2006 *Glycobiology* 16(8):113R-136R. Available online on May 4, 2006.

Cappello et al., "Immunization of mice with fucosyl-GM1 conjugated with keyhole limpet hemocyanin results in antibodies against human small-cell lung cancer cells," Nov. 1999 *Cancer Immunol. Immunother.* 48(9):483-492.

Caroff et al., "Structural and functional analyses of bacterial lipopolysaccharides," Jul. 2002 *Microbes Infect.* 4(9):915-926.

Carpino, "1-Hydroxy-7-azabenzotriazole. An efficient peptide coupling additive," May 1993 *J. Am. Chem. Soc.* 115:4397-4398.

Cato et al., "Highly efficient stereospecific preparation of Tn and TF building blocks using thioglycosyl donors and the $Ph_2SO/Tf_2O$ promotor system," Aug. 2005 *J. Carbohydr. Chem.* 24(4-6):503-516.

Chow et al., "Toll-like receptor-4 mediates lipopolysaccharide-induced signal transduction," Apr. 16, 1999 *J. Biol. Chem.* 274(16):10689-10692.

Comer et al., "Characterization of a mouse monoclonal antibody specific for O-linked *N*-acetylglucosamine," Jun. 15, 2001 *Anal. Biochem.* 293(2):169-177. Available online on May 17, 2001.

Croce and Segal-Eiras, "The use of carbohydrate antigens for the preparation of vaccines for therapy in breast cancer," Nov. 2002 *Drugs Today (Barc.)* 38(11):759-768.

Dabbagh and Lewis, "Toll-like receptors and T-helper-1/T-helper-2 responses," Jun. 2003 *Curr. Opin. Infect. Dis.* 16(3):199-204.

Danishefsky et al., "From the laboratory to the clinic: A retrospective on fully synthetic carbohydrate-based anticancer vaccines," Mar. 2000 *Angew Chem. Int. Ed.* 39(5):836-863.

Dentin et al., "Hepatic glucose sensing via the CREB coactivator CRTC2," Mar. 7, 2008 *Science* 319(5868):1402-1405.

Dias and Hart, "*O*-GlcNAc modification in diabetes and Alzheimer's disease," Nov. 2007 *Mol. BioSyst.* 3(11):766-772. Available online on Aug. 29, 2007.

Diekman et al., "Evidence for a unique N-linked glycan associated with human infertility on sperm CD52: a candidate contraceptive vaccinogen," Oct. 1999 *Immunol. Rev.* 171:203-211.

Dillon et al., "A toll-like receptor 2 ligand stimulates Th2 responses in vivo, via induction of extracellular signal-regulated kinase

(56) References Cited

OTHER PUBLICATIONS mitogen-activated protein kinase and c-Fos in dendritic cells," Apr. 15, 2004 *J. Immunol.* 172(8):4733-4743.

Dixon and Darveau, "Lipopolysaccharide heterogeneity: innate host responses to bacterial modification of lipid A structure," Jul. 2005 *J. Dent. Res.* 84(7):584-595.

Dube and Bertozzi, "Glycans in cancer and inflammation—potential for therapeutics and diagnostics," Jun. 2005 *Nat. Rev. Drug Discov.* 4:(6)477-488.

Dudkin et al., "Toward a fully synthetic carbohydrate-based HIV antigen design," Aug. 11, 2004 *J. Am. Chem.Soc.* 126:9560-9562.

Dziadek et al., "Synthetic vaccines consisting of tumor-associated MUC1 glycopeptide antigens and bovine serum albumin," Nov. 25, 2005 *Angew. Chem. Int. Ed.* 44(46):7624-7630. Available online on Oct. 25, 2005.

Dziadek et al., "A fully synthetic vaccine consisting of a tumor-associated glycopeptide antigen and a T-cell epitope for the induction of a highly specific humoral immune response," Nov. 25, 2005 *Angew. Chem. Int. Ed.* 44(46):7630-7635. Available online on Oct. 25, 2005.

Eisen et al., "Alternatives to conventional vaccines—mediators of innate immunity," Jan. 2004 *Curr. Drug Targets* 5(1):89-105.

Feizi and Childs, "Carbohydrate structures of glycoproteins and glycolipids as differentiation antigens, tumour-associated antigens and components of receptor systems," Jan. 1985 *Trends in Biochem. Sci.* 10(1):24-29.

Finn, "Cancer vaccines: between the idea and the reality," Aug. 2003 *Nat. Rev. Immunol.* 3(8):630-641.

Fox et al., "Carbohydrates and glycoproteins of *Bacillus anthracis* and related bacilli: targets for biodetection," Aug. 2003 *J. Microbiol. Meth.* 54(2):143-152.

Gavin et al., "Adjuvant-enhanced antibody responses in the absence of toll-like receptor signaling," Dec. 22, 2006 *Science* 314(5807):1936-1938.

Ghiringhelli et al., "Links between innate and cognate tumor immunity," Apr. 2007 *Curr. Opin. Immunol.* 19(2):224-231. Available online on Feb. 15, 2007.

Gibbons et al., "Lipidic peptides. I. Synthesis, resolution, and structural elucidation of lipidic amino acids and their homo- and hetero-oligomers," 1990 *Liebigs Ann. Chem.* 1990:1175-1183.

Goffard et al., "Role of N-linked glycans in the functions of hepatitis C virus envelope glycoproteins," Jul. 2005 *J. of Virology* 79(13):8400-8409.

Goldblatt, "Recent developments in bacterial conjugate vaccines," Jul. 1998 *J. Med. Microbiol.* 47(7):563-567.

Grogan et al., "Synthesis of lipidated green fluorescent protein and its incorporation in supported lipid bilayers," Oct. 19, 2005 *J. Am. Chem. Soc.* 127(41):14383-14387. Available online on Sep. 22, 2005.

Hakomori and Zhang, "Glycosphingolipid antigens and cancer therapy," Feb. 1997 *Chem. Biol.* 4(2):97-104.

Hakomori, "Cancer-associated glycosphingolipid antigens: their structure, organization, and function," 1998 *Acta Anat. (Basel)* 161(1-4):79-90.

Haltiwanger et al., "Modulation of O-linked N-acetylglucosamine levels on nuclear and cytoplasmic proteins in vivo using the peptide O-GlcNAc-β-N-acetyleglucosaminidase inhibitor O-(2-acetamido-2-deoxy-D-glucopyranosylidene)amino-N-phenylcarbamate," Feb. 6, 1998 *J. Biol. Chem.* 273(6):3611-3617.

Hang and Bertozzi, "The chemistry and biology of mucin-type O-linked glycosylation," Sep. 1, 2005 *Bioorg. Med. Chem.* 13(17):5021-5034. Available online on Jul. 7, 2005.

Harlow et al., *Antibodies: A Laboratory Manual*, Cold Spring Harbor Laboratory Press, Cold Spring Harbor, NY; copyright 1988. Title page, publisher's page, and table of contents only (8 pages).

Hart et al., "Cycling of O-linked β-N-acetylglucosamine on nucleocytoplasmic proteins," Apr. 26, 2007 *Nature* 446(7139):1017-1022.

Hilyard et al., "Protein Engineering of Antibody Combining Sites," in *Protein Engineering: A practical approach* The Practical Approach Series. Rees et al. (Eds.), IRL Press at Oxford University Press: Oxford, England. Copyright 1992. Title page, publisher's page, and table of contents only. 12 pages.

Horwitz et al., "MCF-7: a human breast cancer cell line with estrogen, androgen, progesterone, and glucocorticoid receptors," Dec. 1975 *Steroids* 26(6):785-795.

Housley et al., "O-GlcNAc regulates FoxO activation in response to glucose," Jun. 13, 2008 *J. Biol. Chem.* 283(24):16283-16292. Available online on Apr. 17, 2008.

Huse et al. "Generation of a large combinatorial library of the immunoglobulin repertoire in phage lambda," Dec. 8, 1989 *Science* 246(4935):1275-1281.

Ingale et al., "Synthesis of glycolipopeptide as vaccine against cancer," Poster Abstract [online]. Abstract No. CARB 81, Division of Carbohydrate Chemistry. 229th *American Chemical Society (ACS) National Meeting.* San Diego, CA; Mar. 13-17, 2005. Available online [retrieved on Jan. 6, 2009]. Retrieved from the Internet: <http://oasys2.confex.com/acs/229nm/techprogram/P839449.HTM>; 1 pg.

Ingale et al., "Synthesis of glyco(lipo)peptides by liposome-mediated native chemical ligation," Dec. 7, 2006 *Org. Lett.* 8(25):5785-5788. Available online on Nov. 16, 2006.

Ingale et al., "Robust immune responses elicited by a fully synthetic three-component vaccine," Oct. 2007 *Nat. Chem. Biol.* 3(10):663-667. Available online on Sep. 2, 2007.

International Search Report issued on May 13, 2010, for PCT/US2009/003944.

Jackson et al., "A totally synthetic vaccine of generic structure that targets Toll-like receptor 2 on dendritic cells and promotes antibody or cytotoxic T cell responses," Oct. 26, 2004 *Proc. Nat. Acad. Sci. USA* 101(43):15440-15445. Available online on Oct. 15, 2004.

Jennings et al., "Synthetic glycoconjugates has human vaccines," in *Neoglycoconjugates, Preparation and Applications.* Lee et al. (Eds), Academic Press: San Diego, CA. Copyright 1994. Title page, publisher's page, and pp. 325-371.

Jiang and Koganty, "Synthetic vaccines: the role of adjuvants in immune targeting," Aug. 2003 *Curr. Med. Chem.* 10(15):1423-1439.

Jones et al., "Replacing the complementarity-determining regions in a human antibody with those from a mouse," May 29, 1986 *Nature* 321(6069):522-525.

Jones, "Vaccines based on the cell surface carbohydrates of pathogenic bacteria," Jun. 2005 *An. Acad. Bras. Cienc.* 77(2):293-324. Available online on May 9, 2005.

Kagan et al., "Comparison of antigen constructs and carrier molecules for augmenting the immunogenicity of the monosaccharide epithelial cancer antigen Tn," May 2005 *Cancer Immunol. Immunother.* 54(5):424-430. Available online on Dec. 30, 2004.

Kaiser et al., "Color test for detection of free terminal amino groups in the solid-phase synthesis of peptides," Apr. 1970 *Anal. Biochem.* 34(2):595-598.

Kawai and Akira, "TLR signaling," Feb. 2007 *Semin. Immunol.* 19(1):24-32. Available online on Feb. 1, 2007.

Keil et al., "Zür Entwicklung von antitumor-impfstoffen: ein synthetischse konkugat aus tumorassoziiertem MUC-lglycopeptidantigen und dem tetanustoxin-epitop," Jan. 2001 *Angew. Chem.* 113(2):379-382. Available online on Jan. 19, 2001.

Keil et al., "Towards the development of antitumor vaccines: a synthetic comjugate of a tumor-associated MUC1 glycopeptide antigen and a tetanus toxin epitope," Jan. 19, 2001 *Angew. Chem. Int. Ed.* 40(2):366-369.

Kensil et al., "Separation and characterization of saponins with adjuvant activity from *Quillaja saponaria* Molina cortex," Jan. 15, 1991 *J. Immunol.* 146(2):431-437.

Kersten and Crommelin, "Liposomes and ISCOMS as vaccine formulations," Jul. 17, 1995 *Biochim. Biophys. Acta* 1241(2):117-138.

Knorr et al., "New coupling reagents in peptide chemistry," 1989 *Tetrahedron Lett.* 30(15):1927-1930.

Koganty et al., "Glycopeptide- and carbohydrate-based synthetic vaccines for the immunotherapy of cancer," May 1996 *Drug Disc. Today* 1(5):190-198.

(56) References Cited

OTHER PUBLICATIONS

Kohler and Milstein, "Continuous cultures of fused cells secreting antibody of predefined specificity," Aug. 7, 1975 *Nature* 256(5517):495-497.

Koppel et al., "Distinct functions of DC-SIGN and its homologus L-SIGN (DC-SIGNR) and mSIGNR1 in pathogen recognition and immunue regulation," 2005 *Cellular Microbiology* 7(2):157-165.

Koppitz et al., "Syntheis of Unnatural Lipophilic N-(9H-Fluoren-9-ylmethoxy)carbonyl-substituted α-Amino Acids and Their Incorporation into Cyclic RGD-Peptides: A Structure-Activity Study," Jun. 30, 1997 *Helv. Chim. Acta* 80(4):1280-1300.

Kreppel and Hart, "Regulation of a cytosolic and nuclear O-GlcNAc transferase. Role of the tetratricopeptide repeats," Nov. 5, 1999 *J. Biol. Chem.* 274(45):32015-32022.

Krikorian et al., "A peptide carrier with a built-in vaccine adjuvant: construction of immunogenic conjugates," Jul.-Aug. 2005 *Bioconjug. Chem.* 16(4):812-819. Available online on Jun. 10, 2005.

Kuberan and Linhardt, "Carbohydrate based vaccines," 2000 *Curr. Org. Chem.* 4(6):653-677.

Kudryashov et al., "Toward optimized carbohydrate-based anticancer vaccines: epitope clustering, carrier structure, and adjuvant all influence antibody responses to Lewis$^y$ conjugates in mice," Mar. 13, 2001 *Proc. Natl. Acad. Sci. U.S.A.* 98(6):3264-3269.

Kuduk et al., Synthetic and immunological studies on clustered modes of mucin-related Tn and TF O-Linked Antigens: The Preparation of glycopeptide-based vaccine for Clinical Trials against Prostate Cancer. J. Am. Chem. Soc., 1998, 120 (48), pp. 12474-12485.

Leclerc et al., "Identification of a T-cell epitope adjacent to neutralization antigenic site 1 of poliovirus type 1," Feb. 1991 *J. Virol.* 65(2):711-718.

Lee and Iwasaki, "Innate control of adaptive immunity: dendritic cells and beyond," Feb. 2007 *Semin. Immunol.* 19(1):48-55. Available online on Feb. 5, 2007.

Lefebvre et al., "Does O-GlcNAc play a role in neurodegenerative diseases?" Apr. 2005 *Exp. Rev. Proteomics* 2(2):265-275.

Lin and Karin, "A cytokine-mediated link between innate immunity, inflammation, and cancer," May 2007 *J. Clin. Invest.* 117(5):1175-1183.

Livingston and Ragupathi, "Carbohydrate vaccines that induce antibodies against cancer. 2. Previous experience and future plans," Oct. 1997 *Cancer Immunol. Immunother.* 45(1):10-19.

Lloyd, "Philip Levine award lecture. Blood group antigens as markers for normal differentiation and malignant change in human tissues," Jan. 1987 *Am. J Clin. Pathol.* 87(1):129-139.

Lo-Man et al., "Anti-tumor immunity provided by a synthetic multiple antigenic glycopeptide displaying a tri-Tn glycotope," Feb. 15, 2001 *J. Immunol.* 166(4):2849-2854.

Lo-Man et al., "A fully synthetic therapeutic vaccine candidate targeting carcinoma-associated Tn carbohydrate antigen induces tumor-specific antibodies in nonhuman primates," Jul. 15, 2004 *Cancer Res.* 64(14):4987-4994.

Martinez et al., "Synthesis and biological activities of some pseudopeptide analogues of tetragastrin: the importance of the peptide backbone," Dec. 1985 *J. Med. Chem.* 28(12):1874-1879.

Martinez-Fleites et al., "Structure of an O-GlcNAc transferase homolog provides insight into intracellular glycosylation," Jul. 2008 *Nat. Struct. Mol. Bio.* 15(7):764-765. Available online on Jun. 8, 2008.

Martinez-Grau and Marco-Contelles, "Carbocycles from carbohydrates via free radical cyclizations: new synthetic approaches to glycomimetics," 1998 *Chemical Society Reviews* 27(2): 155-162.

McGeary et al., "Lipid and carbohydrate based adjuvant/carriers in immunology," Jul. 2003 *J. Peptide Sci.* 9(7):405-418.

Medzhitov and Janeway, Jr., "Decoding the patterns of self and nonself by the innate immune system," Apr. 12, 2002 *Science* 296(5566):298-300.

Mendonca-Previato et al., "Protozoan parasite-specific carbohydrate structures," Oct. 2005 *Curr. Opin. Struct. Biol.* 15(5):499-505. Available online on Sep. 8, 2005.

Metzger et al., "Synthesis of $N_\alpha$-Fmoc protected derivatives of S-(2,3-dihydroxypropyl)-cysteine and their application in peptide synthesis," Dec. 1991 *Int. J. Peptide Protein Res.* 38(6):545-554.

Meyer-Bahlburg et al., "B cell-intrinsic TLR signals amplify but are not required for humoral immunity," Dec. 24, 2007 *J. Exp. Med.* 204(13):3095-3101. Available online on Nov. 26, 2007.

Mitchell et al., "Solid-phase synthesis of O-linked glycopeptide analogues of enkephalin," Apr. 6, 2001 *J. Org. Chem.* 66(7):2327-2342. Available online on Mar. 14, 2001.

Moore et al., "The adjuvant combination monophosphoryl lipid A and QS21 switches T cell responses induced with a soluble recombinant HIV protein from Th2 to Th1," Jun. 4, 1999 *Vaccine* 17(20-21):2517-2527.

Musselli et al., "Keyhole limpet hemocyanin conjugate vaccines against cancer: the Memorial Sloan Kettering experience," Oct. 2001 *J. Cancer Res. Clin. Oncol.* 127(Supp 2):R20-R26.

Nakada et al., "Elucidation of an essential structure recognized by an anti-GalNAcα-Ser(Thr) monoclonal antibody (MLS 128)," Jul. 5, 1991 *J. Biol. Chem.* 266(19): 12402-12405.

Nakada et al., "Epitopic structure of Tn glycophorin A for an anti-Tn antibody (MLS 128)," Mar. 15, 1993 *Proc. Nati. Acad. Sci. USA* 90(6):2495-2499.

Ni et al., "Toward a carbohydrate-based HIV-1 vaccine: synthesis and immunological studies of oligomannose-containing glycoconjugates," Mar.-Apr. 2006 *Bioconjug. Chem.* 17(2):493-500. Available online on Feb. 21, 2006.

Nozawa et al., "HMMC-1: A humanized monoclonal antibody with therapeutic potential against mullerian duct-related carcinomas," Oct. 15, 2004 *Clin. Can. Res.* 10:7071-7078.

"Nuclear Pore-O-linked Glycoprotein" antibody datasheet [online]. Affinity BioReagents: Golden, CO. No copyright date available [retrieved on Jul. 6, 2009]. Catalog No. MAI-071. Retrieved from the Internet: <http://www.bioreagents.com/products/printProductDetail/printProductDetails.cfm?catnbr=MA1-071>; 2 pgs.

Nyame et al., "Antigenic glycans in parasitic infections: implications for vaccines and diagnostics," Jun. 15, 2004 *Arch. Biochem. Biophys.*, 426(2):182-200. Available online on May 6, 2004.

"O-GlcNAc Monoclonal Antibody" datasheet [online]. Covance: Emeryville, CA. Product Revision date: Mar. 28, 2007 [retrieved on Apr. 14, 2009]. Retrieved from the Internet: <https://store.crpinc.com/pdfdatasheet.aspx?catalogno=MMS-248R>; 2 pgs.

"O-GlcNAc Western Blot Detection Kit" datasheet [online]. Pierce: Rockford, IL. Copyright 2004 [retrieved on Jul. 6, 2009]. Retrieved from the Internet: <http://www.piercenet.com/files/1435as4.pdf>; 4 pgs.

Ohn et al., "A functional RNAi screen links O-GlcNAc modification of ribosomal proteins to stress granule and processing body assembly," Oct. 2008 *Nat. Cell Biol.* 10(10):1224-1231. Available online on Sep. 14, 2008.

"O-linked N-acetylglucosamine" antibody datasheet [online]. Affinity BioReagents: Golden, CO. No copyright date available [retrieved on Jul. 6, 2009]. Catalog No. MAI-076. Retrieved from the Internet: <http://www.bioreagents.com/products/printProductDetail/printProductDetails.cfm?catnbr =MAI-076>; 2 pgs.

"O-linked N-acetylglucosamine" antibody datasheet [online]. Affinity BioReagents: Golden, CO. No copyright date available [retrieved on Jul. 6, 2009]. Catalog No. MAI-072. Retrieved from the Internet: <http://www.bioreagents.com/products/printProductDetail/printProductDetails.cfm?catnbr =MAI-072; 2 pgs.

O'Neill, "How Toll-like receptors signal: what we know and what we don't know," Feb. 2006 *Curr Opin Immunol* 18(1):3-9. Available online on Dec. 15, 2005.

OpDeBeeck et al., "Biogenesis of hepatitis C virus envelope glycoproteins," 2001 *J. Gen. Virol.* 82(11):2589-2595. Available online on Jun. 20, 2001.

Orlandi et al., "Cloning immunoglobulin variable domains for expression by the polymerase chain reaction," May 1989 *Proc. Nat'l Acad. Sci. USA* 86(10):3833-3837.

(56) References Cited

OTHER PUBLICATIONS

Ouerfelli et al., "Synthetic carbohydrate-based antitumor vaccines: challenges and opportunities," Oct. 2005 *Expert Rev. Vaccines* 4(5):677-685.

Pan et al., "Synthesis and immunological properties of N-modified GM3 antigens as therapeutic cancer vaccines," Feb. 10, 2005 *J. Med. Chem.* 48(3):875-883. Available online on Jan. 13, 2005.

Pasare and Medzhitov, "Toll-like receptors and acquired immunity," Feb. 2004 *Semin. Immunol.* 16(1):23-26.

Pasare and Medzhitov, "Toll-dependent control mechanisms of DC4 T cell activation," Nov. 16, 2004 *Immunity* 21(5):733-741. Available online on Apr. 5, 2005.

Pashine et al., "Targeting the innate immune response with improved vaccine adjuvants," Apr. 2005 *Nat. Med. Supp.* 11(4):S63-S68.

Pier, "Application of vaccine technology to prevention of *Pseudomonas aeruginosa* infections," Oct. 2005 *Expert Rev. Vaccines* 4(5):645-656.

Pulendran, "Tolls and beyond—many roads to vaccine immunity," Apr. 26, 2007 *N. Engl. J. Med.* 356(17):1776-1778.

Raetz and Whitfield, "Lipopolysaccharide endotoxins," 2002 *Annu. Rev. Biochem.* 71:635-700. Available online on Nov. 9, 2001.

Ragupathi, "Carbohydrate antigens as targets for active specific immunotherapy," Nov. 1996 *Cancer Immunol. Immunother.* 43(3):152-157.

Reddish et al., "Specificities of anti-sialyl-Tn and anti-Tn monoclonal antibodies generated using novel clustered synthetic glycopeptide epitopes," Aug. 1997 *Glycoconj. J.* 14(5):549-560.

Reichel et al., "Synthetic carbohydrate-based vaccines: synthesis of an L-*glycero*-D-*manno*-heptose antigen-T-epitope-lipopeptide conjugate," 1997 *Chem. Commun.* 21:2087-2088.

Reichel et al., "Stereochemical dependence of the self-assembly of the immunoadjuvants Pam$_3$ Cys and Pam$_3$ Cys-Ser," 1999 *J. Am. Chem. Soc.* 121(35):7989-7997. Available online on Aug. 21, 1999.

Reis et al., "Development and characterization of an antibody directed to an α-N-acetyl-D-galactosamine glycosylated MUC2 peptide," Jan. 1998 *Glycoconj. J.* 15(1):51-62.

Rex-Mathes et al., "Immunological detection of O-GlcNAc," 2002 *Meth. Mol. Bio.* 194:73-87.

Riechmann et al., "Reshaping human antibodies for therapy," Mar. 24, 1988 *Nature* 332(6162):323-327.

Roach et al., "The evolution of vertebrate Toll-like receptors," Jul. 5, 2005 *Proc. Nat'l. Acad. Sci. USA* 102(27):9577-9582. Available online on Jun. 23, 2005.

Roth et al., "Synthesis of thiol-reactive lipopeptide adjuvants. Incorporation into liposomes and study of their mitogenic effect on mouse splenocytes," May-Jun. 2004 *Bioconj. Chem.* 15(3):541-553. Available online on May 1, 2004.

Sabbatini et al., "Immunization of ovarian cancer patients with a synthetic Lewis$^y$-protein conjugate vaccine: a phase 1 trial," Jul. 1, 2000 *Int. J. Cancer*, 87(1):79-85.

Sanders and Kerr, "Lewis blood group and CEA related antigens; coexpressed cell-cell adhesion molecules with roles in the biological progression and dissemination of tumours," Aug. 1999 *J. Clin. Path. Mol. Pathol.* 52(4): 174-178.

Schultheiss-Reimann and Kunz, "O-glycopeptide synthesis using 9-Fluorenylmethoxycarbonyl (Fmoc)-protected synthetic units," Jan. 1983 *Angew. Chem. Int. Ed.* 22(1):62-63.

Schweizer, "Glycosamino acids: building blocks for combinatorial synthesis—implication for drug discovery," 2002 *Angew. Chem. Int. Ed.*, 41(2):230-253. Available online on Jan. 18, 2002.

Singer et al., "Optimal humanization of 1B4, and anti-CD18 murine monoclonal antibody, is achieved by correct choice of human V-region framework sequences," Apr. 1, 1993 *J. Immunol.* 150(7):2844-2857.

Slovin et al., "Fully synthetic carbohydrate-based vaccines in biochemically relapsed prostate cancer: clinical trial results with α-N-acetylgalactosamine-O-serine/threonine conjugate vaccine," Dec. 1, 2003 *J. Clin. Oncol.* 21(23):4292-4298.

Slovin et al., "Carbohydrate vaccines as immunotherapy for cancer," Aug. 2005 *Immunol. Cell Biol.* 83(4):418-428.

Snijdewint et al., "Antibody-dependent cell-mediated cytotoxicity can be induced by MUC1 peptide vaccination of breast cancer patients," Jul. 1, 2001 *Int. J. Cancer* 93(1):97-106.

Spohn et al., "Synthetic lipopeptide adjuvants and Toll-like receptor 2-structure-activity relationships," Jun. 23, 2004 *Vaccine* 22(19):2494-2499. Available online on Apr. 8, 2004.

Sorensen, "Neutralization epitopes on HIV pseudotyped with HTLV-I," Dec. 1996 *Persp. Drug Disc. Design* 5:154-160.

Springer, "Immunoreactive T and Tn epitopes in cancer diagnostics, prognosis, and immunotherapy," Aug. 1997 *J. Mol. Med.* 75(8):594-602.

"TLR Ligands," datasheet [online]. InvivoGen, San Diego, CA;Copyright date 2008 [retrieved on Apr. 14, 2009]. Retrieved from the Internet: <http://www.invivogen.com/sscat.php?ID=9 &ID_cat=2>; 3 pgs.

Toth et al., "A combined adjuvant and carrier system for enhancing synthetic peptides immunogenicity utilising lipidic amino acids," Jun. 11, 1993 *Tetrahedron Lett.* 34(24):3925-3928.

Toyokuni et al., "Synthetic carbohydrate vaccines: synthesis and immunogenicity of Tn antigen conjugates," Nov. 1994 *Bioorg. & Med. Chem.* 2(11):1119-1132.

Toyokuni et al., "Synthetic vaccines: synthesis of a dimeric Tn antigen-lipopeptide conjugate that elicits immune responses against Tn-expressing glycoproteins," 1994 *J. Am. Chem. Soc.* 116(1):395-396.

Tsubery et al., "The functional association of polymyxin B with bacterial lipopolysaccharide is stereospecific: studies on polymyxin B nonapeptide," Oct. 3, 2000 *Biochemistry* 39(39):11837-11844. Available online on Sep. 8, 2000.

Valiyaveetil et al., "Semisynthesis and folding of the potassium channel KcsA," Aug. 7, 2002 *J. Am. Chem. Soc.* 124(31):9113-9120. Available online on Jul. 11, 2002.

van Duin et al., "Triggering TLR signaling in vaccination," Jan. 2006 *TRENDS Immunol.* 27(1):49-55. Available online on Nov. 23, 2005.

Verheul et al., "Minimal oligosaccharide structures required for induction of immune responses against meningococcal immunotype L1, L2, and L3,7,9 lipopolysaccharides determined by using synthetic oligosaccharide-protein conjugates," Oct. 1991 *Infect. Immun.* 59(10):3566-3573.

Verhoeyen et al., "Reshaping human antibodies: grafting an antilysozyme activity," Mar. 25, 1988 *Science* 239(4847):1534-1536.

Vliegenthart, "Carbohydrate based vaccines," May 22, 2006 *FEBS Lett.* 580(12): 2945-2950. Available online on Mar. 29, 2006.

von Mensdorff-Pouilly et al., "Reactivity of natural and induced human antibodies to MUC1 mucin with MUC1 peptides and N-acetylgalactosamine (GalNAc) peptides," Jun. 1, 2000 *Int. J. Cancer* 86(5):702-712.

Vosseller et al., "Elevated nucleocytoplasmic glycosylation by O-GlcNAc results in insulin resistance associated with defects in Akt activation in 3T3-L1 adipocytes," Apr. 16, 2002 *Proc. Natl. Acad. Sci. U.S.A.* 99(8):5313-5318.

Wang, "Toward oligosaccharide- and glycopeptide-based HIV vaccines," 2006 *Current Opinion in Drug Disc. & Develop.* 9(2):194-206.

Ward et al., "Binding activities of a repertoire of single immunoglobulin variable domains secreted from *Escherichia coli*," Oct. 12, 1989 *Nature* 341(6242):544-546.

Weissmüller et al., "Synthesis of the mitogenic S[2,3-bis(palmitoyloxy)propyl]-N-palmitoylpentapeptide from *Escherichia coli* lipoprotein," May 1983 *Hoppe-Seyler's Z. Physiol. Chem.* 364(5):593-606.

Wells, Lance, "Role of O-GlcNAc in Metabolic Signaling," Grant Abstract, Grant No. 1RO1DK075069-01A1 [online]. National Institute of Diabetes and Digestive and Kidney Diseases, National Institutes of Health, project dates Jan. 1, 2007 to Dec. 31, 2011 [retrieved on Mar. 31, 2009]. Retrieved from the Internet: <http://crisp.cit.nih.gov/crisp/CRISP_LIB.getdoc?textkey=7211834&p_grant_num=1R01DK075069-01A1&p_query=&ticket=91023918 &p_audit_session_id=412710435&p_keywords=>; 2 pgs.

(56) References Cited

OTHER PUBLICATIONS

Wells, Lance, "Role of O-GlcNAc in Metabolic Signaling," Grant Abstract, Grant No. 5RO1DK075069-02 [online]. National Institute of Diabetes and Digestive and Kidney Diseases, National Institutes of Health, project dates Jan. 1, 2007 to Dec. 31, 2011 [retrieved on Mar. 31, 2009]. Retrieved from the Internet: <http://crisp.cit.nih.gov/crisp/CRISP_LIB.getdoc?textkey=7336329&p_grant_num=5R01DK075069-02&p_query=&ticket=91023918&p_audit_session_id=412710435&p_keywords=>; 1 pg.

Wells, Lance, "Role of O-GlcNAc in Metabolic Signaling," Grant Abstract, Grant No. 5RO1DK075069-03 [online]. National Institute of Diabetes and Digestive and Kidney Diseases, National Institutes of Health, project dates Jan. 1, 2007 to Dec. 31, 2011 [retrieved on Mar. 31, 2009]. Retrieved from the Internet: <http://crisp.cit.nih.gov/crisp/CRISP_LIB.getdoc?textkey=7545835&p_grant_num=5R01DK075069-03&p_query=&ticket=91023918&p_audit_session_id=412710435&p_keywords=>; 1 pg.

Wells et al., "Glycosylation of nucleocytoplasmic proteins: signal transduction and O-GlcNAc," Mar. 23, 2001 *Science* 291(5512):2376-2378.

Werling and Jungi, "TOLL-like receptors linking innate and adaptive immune response," Jan. 10, 2003 *Vet. Immunol. Immunopathol.* 91(1):1-12.

Whelan and Hart, "Identification of O-GlcNAc sites on proteins," 2006 *Methods Enzymol.* 415:113-133.

Wiertz et al., "Identification of T cell epitopes occurring in a meningococcal class 1 outer membrane protein using overlapping peptides assembled with simultaneous multiple peptide synthesis," Jul. 1, 19921. *Exp. Med.* 176(1):79-88.

Winter and Harris, "Humanized antibodies," Jun. 1993 *Immunol. Today* 14(6):243-246.

Yang et al., "A new approach for the stereoselective introduction of alpha-glycosides," Poster Abstract [online]. Abstract No. CARB 50, Division of Carbohydrate Chemistry. $229^{th}$ *American Chemical Society (ACS) National Meeting*. San Diego, CA; Mar. 13-17, 2005. Available online [retrieved on Apr. 14, 2009]. Retrieved from the Internet: <http://oasys2.confex.com/acs/229nm/techprogram/>; 1 pg.

Zachara and Hart, "Cell signaling, the essential role of O-GlcNAc," May-Jun. 2006 *Biochim. Biophys. Acta*, 1761(5-6):599-617. Available online on May 6, 2006.

Zeng et al., "Highly immunogenic and totally synthetic lipopeptides as self-adjuvanting immunocontraceptive vaccines," Nov. 1, 2002 *J. Immunol.* 169(9):4905-4912.

Zhang et al., "Immune sera and monoclonal antibodies define two configurations for the sialyl Tn tumor antigen," Aug. 1, 1995 *Cancer Res.* 55(15):3364-3368.

Zhang et al., "O-GlcNAc modification in en endogenous inhibitor of the proteasome," Dec. 12, 2003 *Cell* 115(6):715-725. Published on Dec. 11, 2003.

Zhang et al., "Modulation of innate immune responses with synthetic lipid a derivatives," 2007 *J. Am. Chem. Soc.* 129:5200-5216. Available online on Mar. 29, 2007.

\* cited by examiner

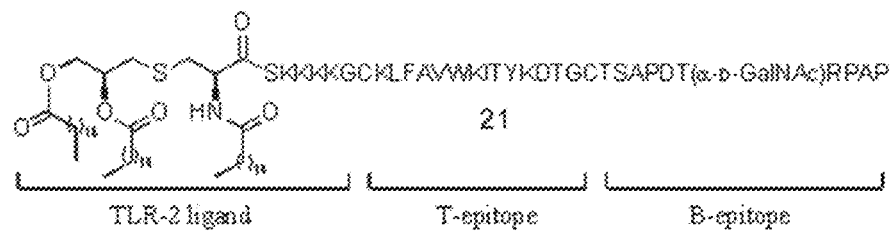
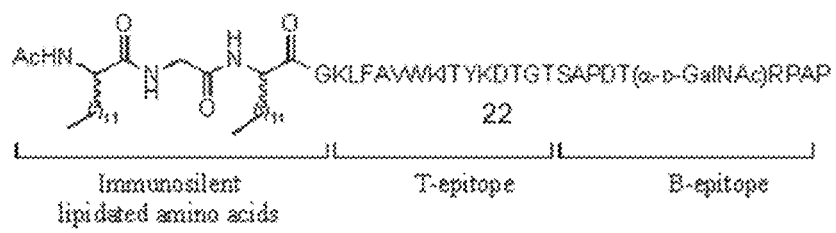
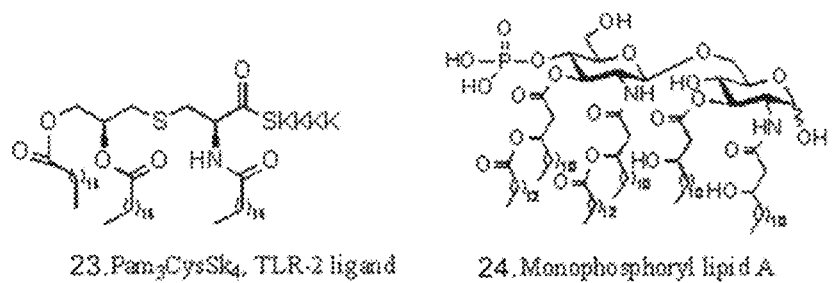
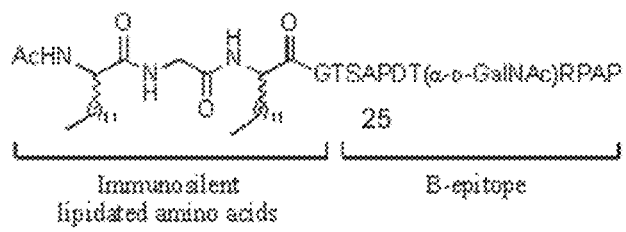
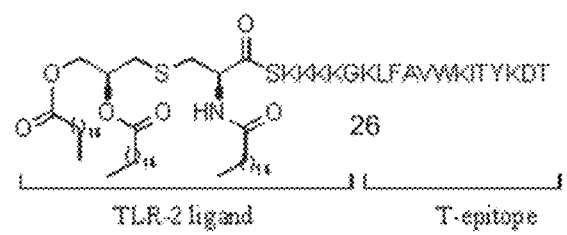
Fig. 5

Compound 22
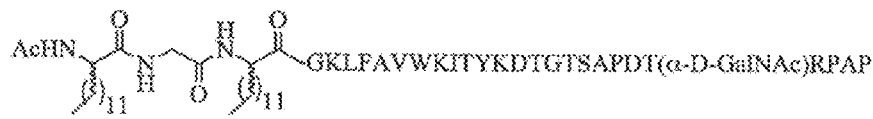
HPLC chromatogram:
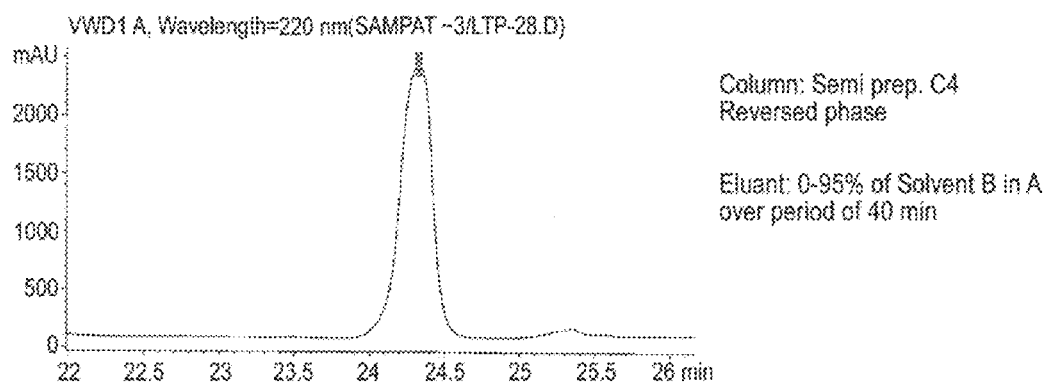
Column: Semi prep. C4
Reversed phase
Eluant: 0-95% of Solvent B in A
over period of 40 min
MALDI-ToF spectra:
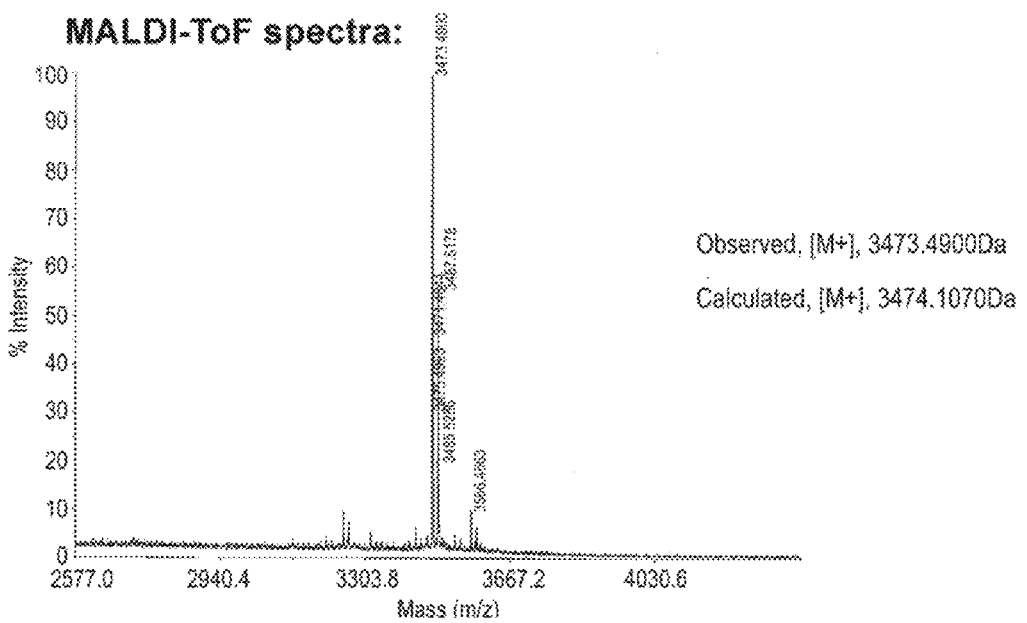
Observed, [M+], 3473.4900Da
Calculated, [M+], 3474.1070Da
*Fig. 10*

Compound 23
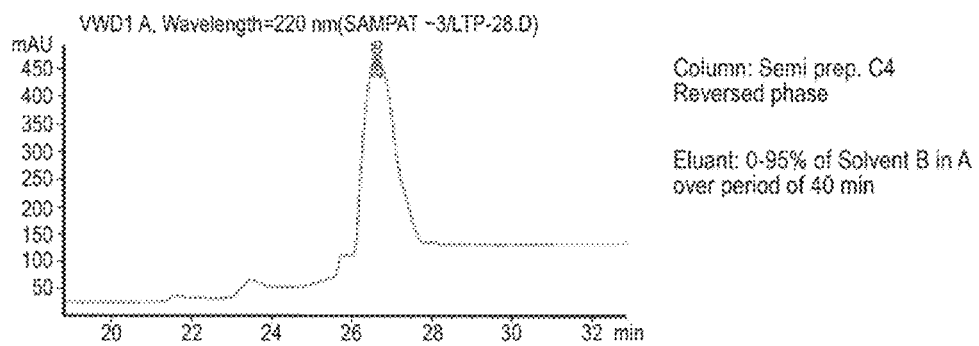
HPLC chromatogram:
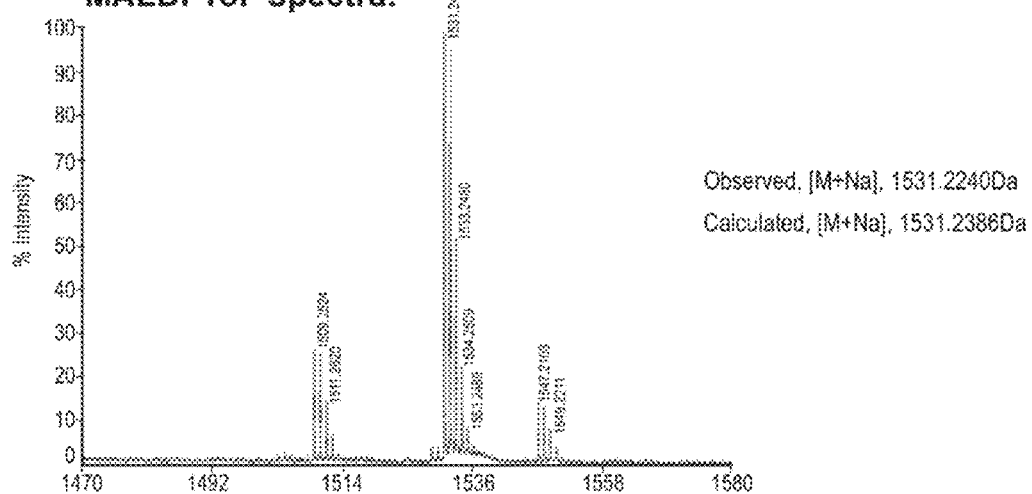
Column: Semi prep. C4
Reversed phase
Eluant: 0-95% of Solvent B in A
over period of 40 min
MALDI-ToF spectra:
Observed, [M+Na], 1531.2240Da
Calculated, [M+Na], 1531.2386Da
*Fig. 11*

Compound 25
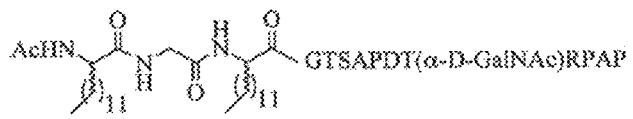
HPLC chromatogram:
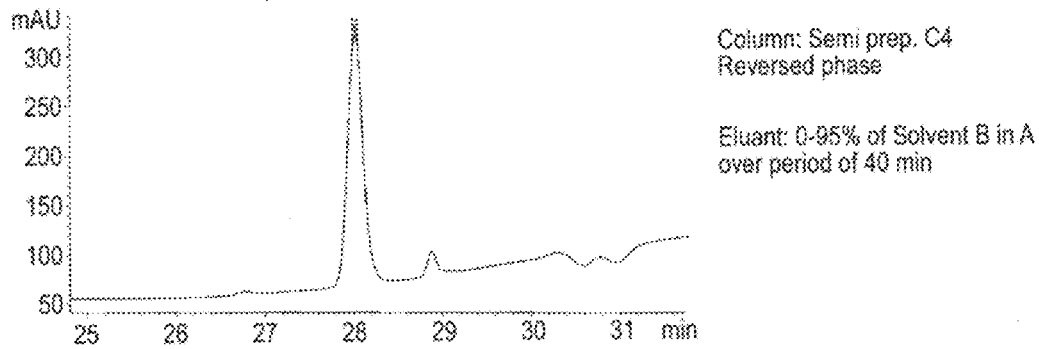
Column: Semi prep. C4
Reversed phase
Eluant: 0-95% of Solvent B in A over period of 40 min
MALDI-ToF spectra:
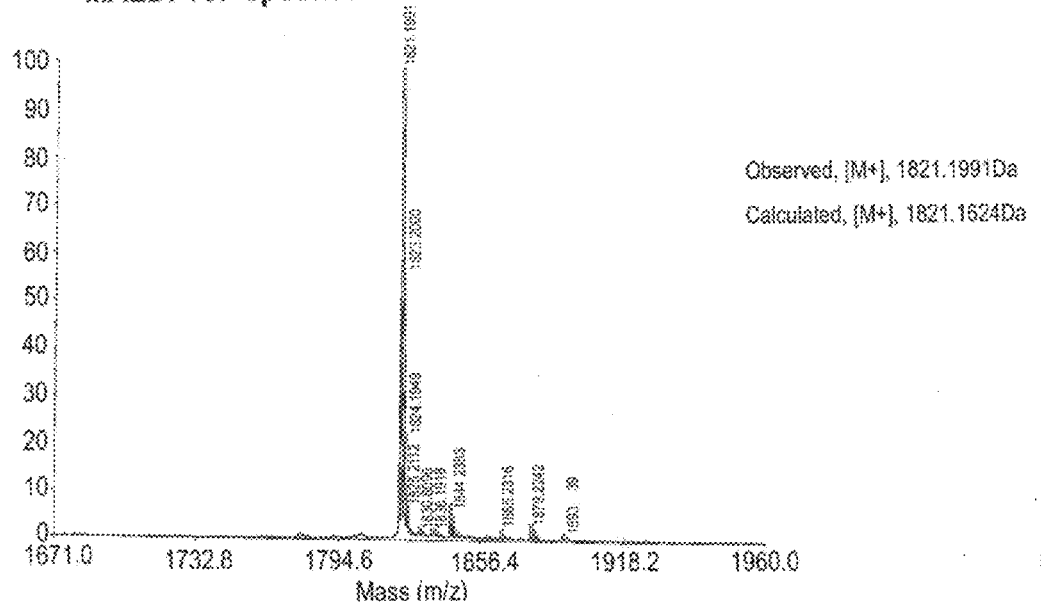
Observed, [M+], 1821.1991Da
Calculated, [M+], 1821.1624Da
*Fig. 12*

Compound 26
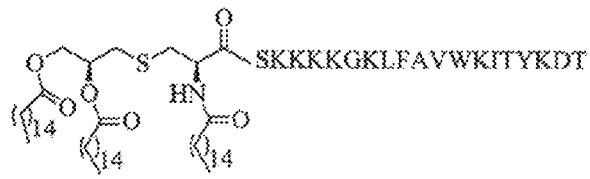
HPLC chromatogram:
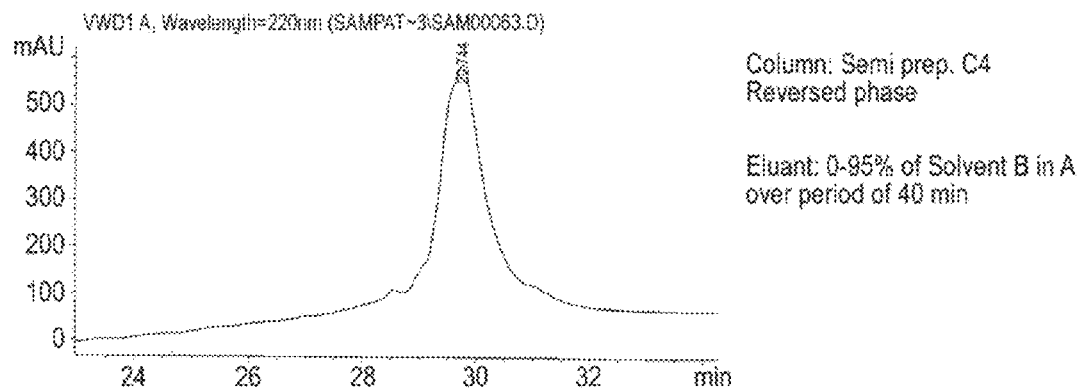
Column: Semi prep. C4 Reversed phase
Eluant: 0-95% of Solvent B in A over period of 40 min
MALDI-ToF spectra:
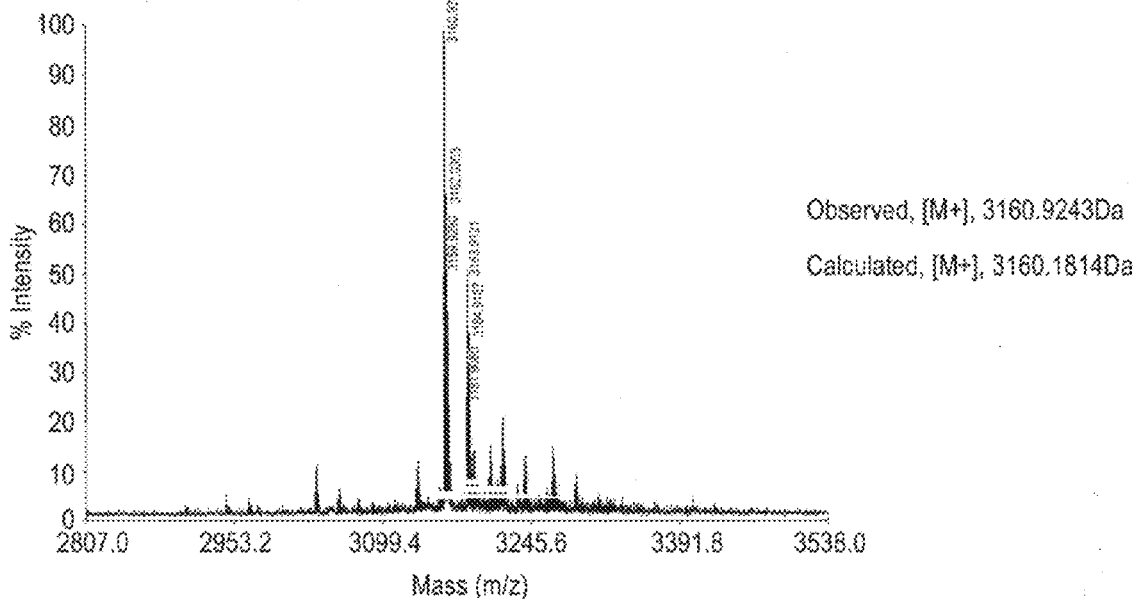
Observed, [M+], 3160.9243Da
Calculated, [M+], 3160.1814Da
*Fig. 13*

Compound 27
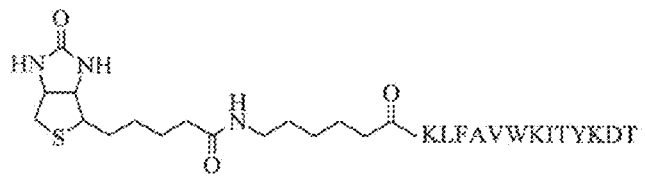
HPLC chromatogram:
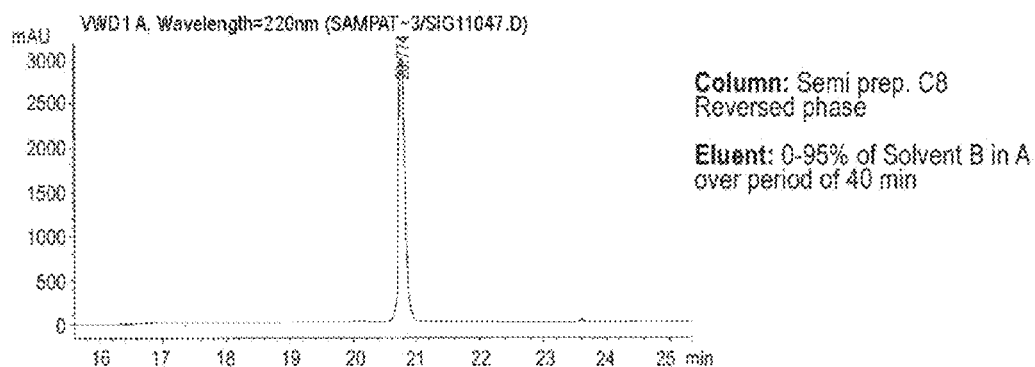
Column: Semi prep. C8 Reversed phase
Eluent: 0-95% of Solvent B in A over period of 40 min
MALDI-ToF spectra:
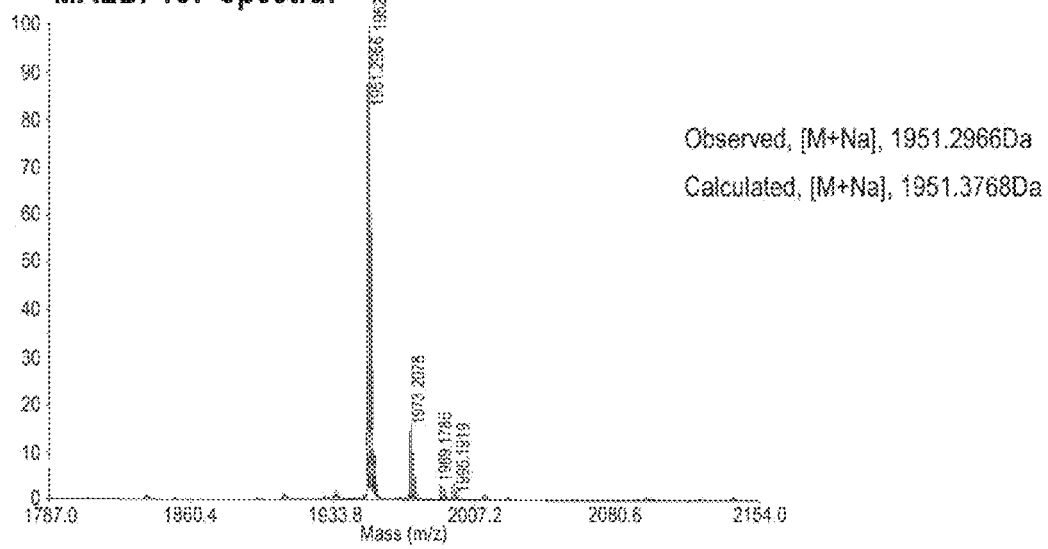
Observed, [M+Na], 1951.2966Da
Calculated, [M+Na], 1951.3768Da
*Fig. 14*

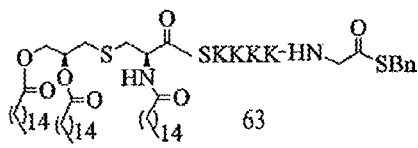
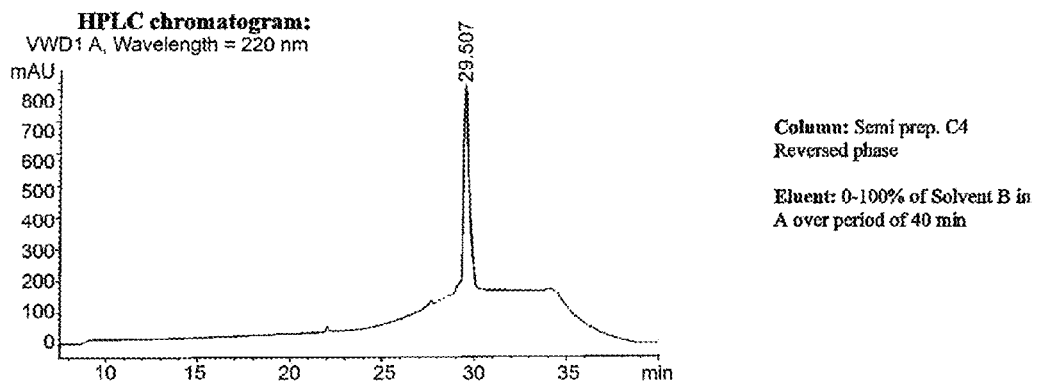
Column: Semi prep. C4
Reversed phase
Eluent: 0-100% of Solvent B in A over period of 40 min
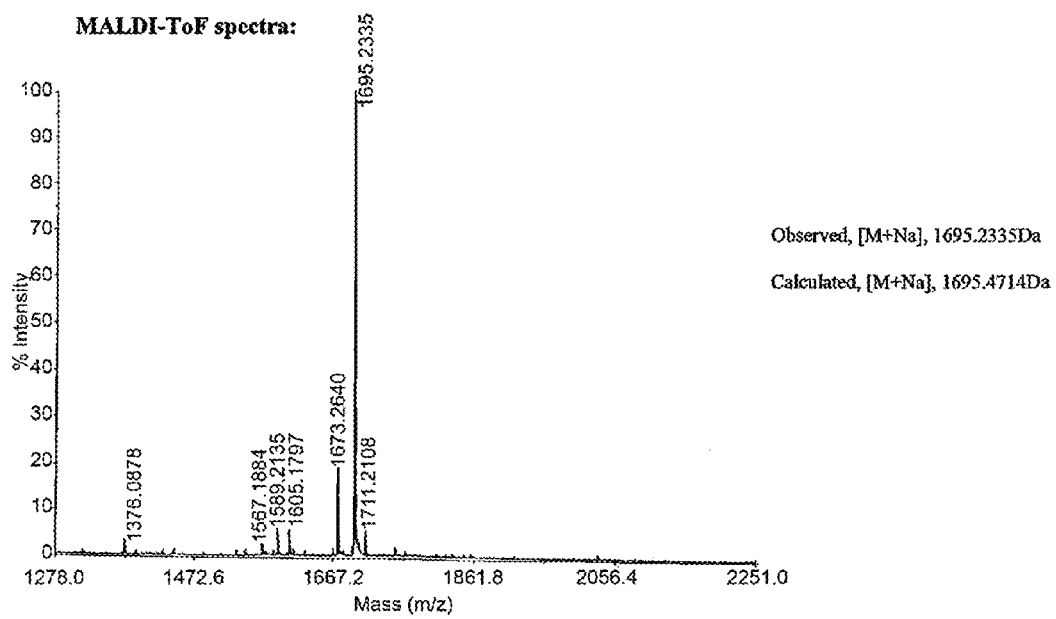
Observed, [M+Na], 1695.2335Da
Calculated, [M+Na], 1695.4714Da
*Fig. 25*

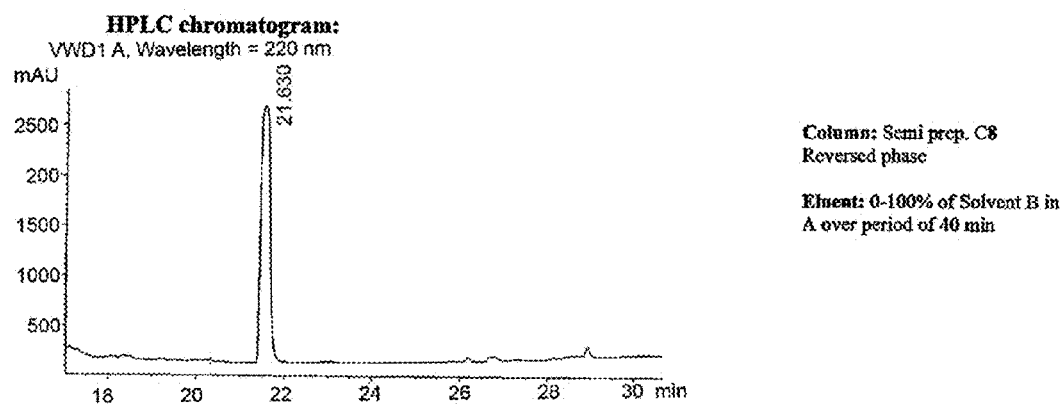
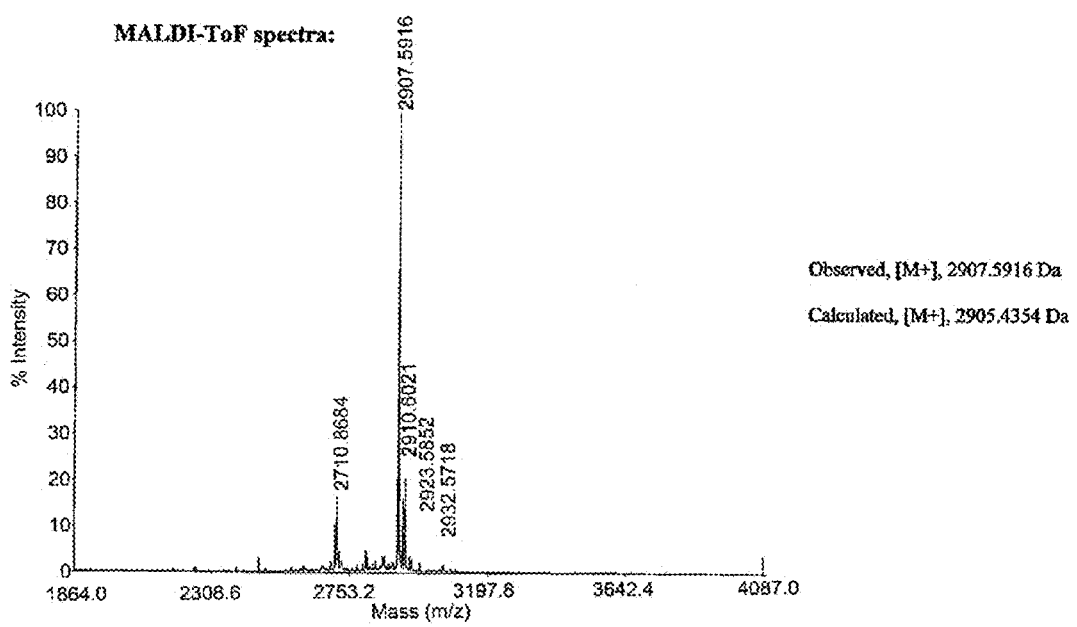
Fig. 26

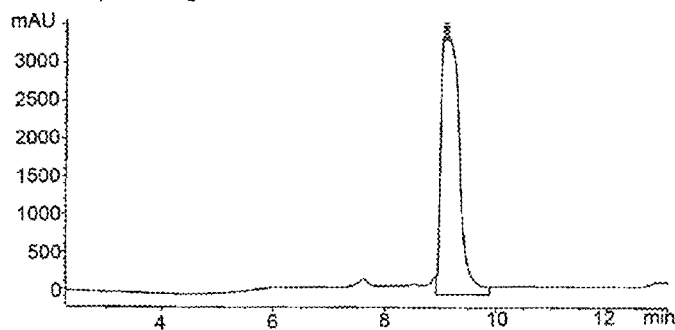
66
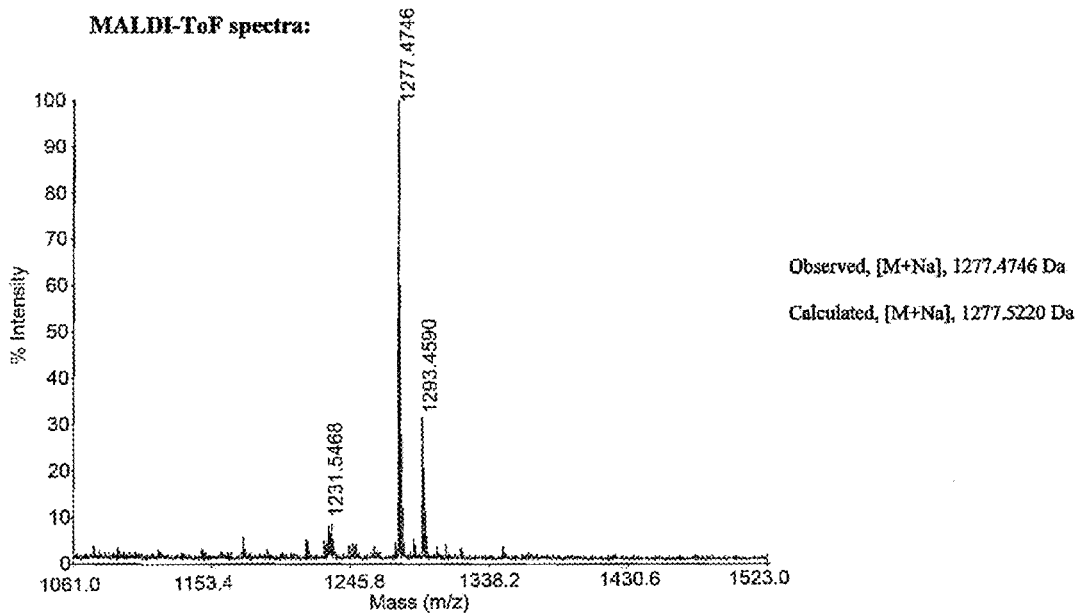
*Fig. 28*

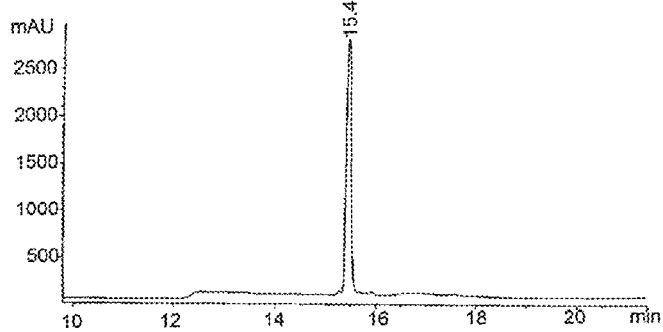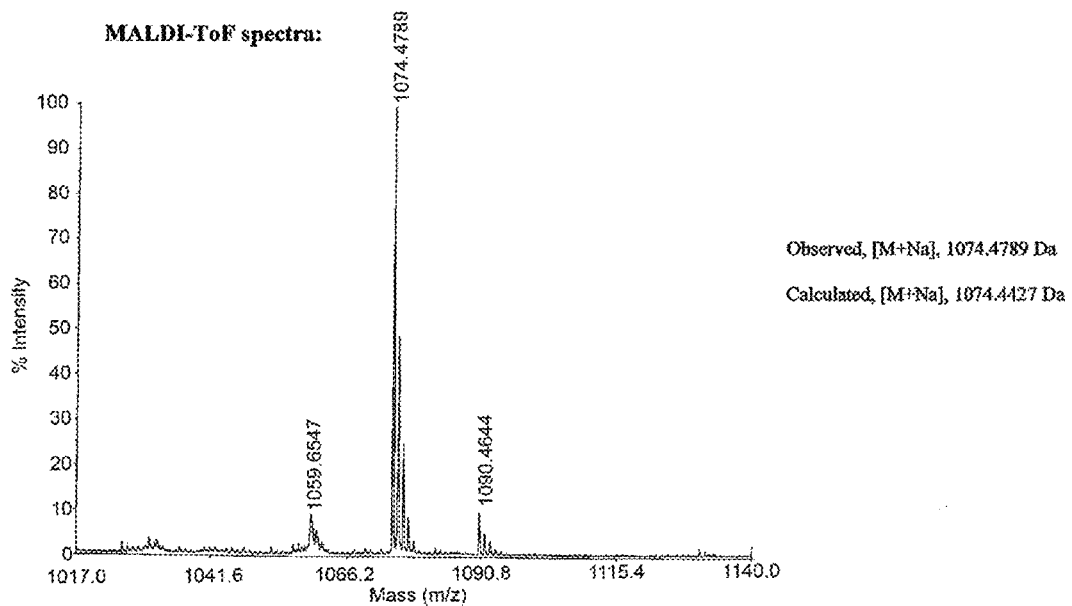
Fig. 29

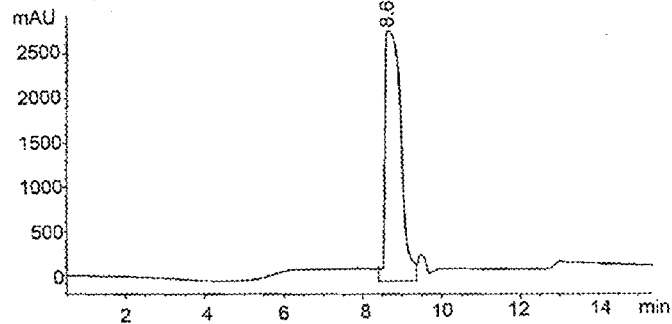
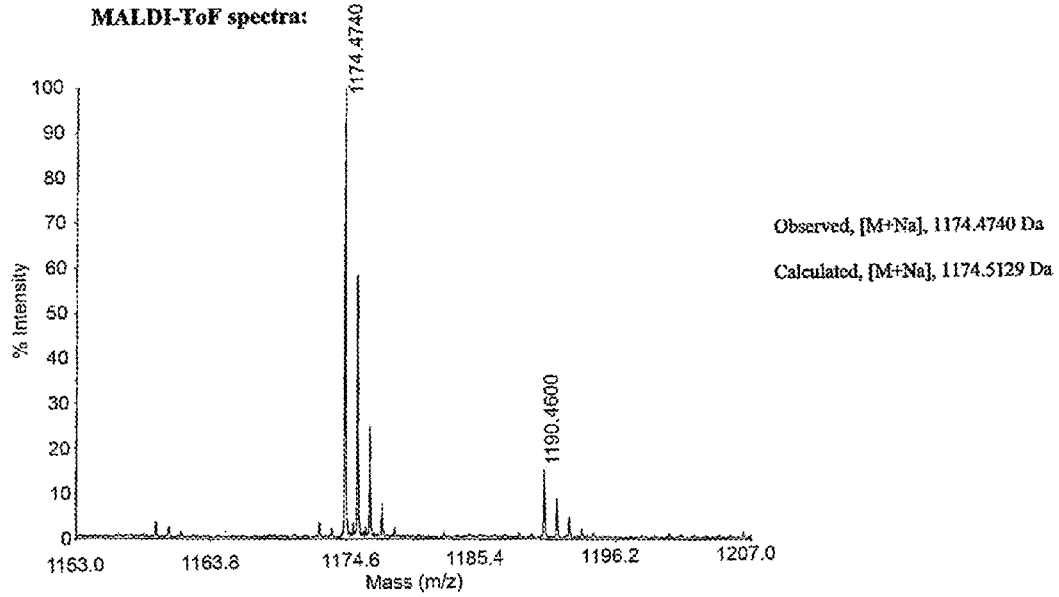
*Fig. 30*

GSTPVSSANM

69

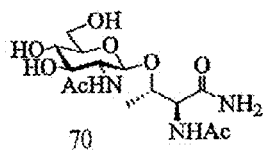
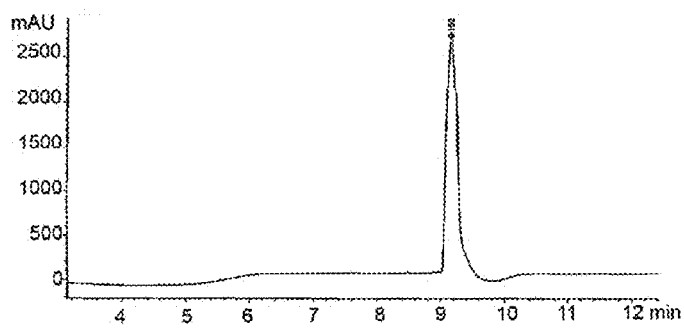
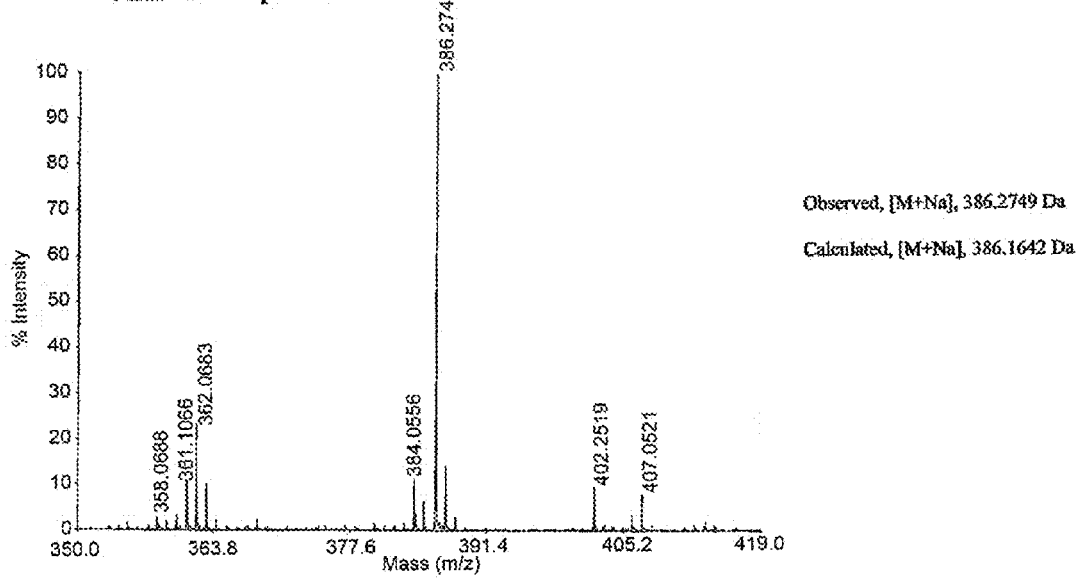
Fig. 32

SEQUENCE LISTING

```
<160> NUMBER OF SEQ ID NOS: 19

<210> SEQ ID NO 1
<211> LENGTH: 15
<212> TYPE: PRT
<213> ORGANISM: artificial
<220> FEATURE:
<223> OTHER INFORMATION: helper T peptide

<400> SEQUENCE: 1

Gln Tyr Ile Lys Ala Asn Ser Lys Phe Ile Gly Ile Thr Glu Leu
1               5                   10                  15

<210> SEQ ID NO 2
<211> LENGTH: 20
<212> TYPE: PRT
<213> ORGANISM: artificial
<220> FEATURE:
<223> OTHER INFORMATION: helper T peptide
```

-continued

```
<400> SEQUENCE: 2

Tyr Ala Phe Lys Tyr Ala Arg His Ala Asn Val Gly Arg Asn Ala Phe
1               5                   10                  15

Glu Leu Phe Leu
            20

<210> SEQ ID NO 3
<211> LENGTH: 13
<212> TYPE: PRT
<213> ORGANISM: artificial
<220> FEATURE:
<223> OTHER INFORMATION: helper T peptide

<400> SEQUENCE: 3

Lys Leu Phe Ala Val Trp Lys Ile Thr Tyr Lys Asp Thr
1               5                   10

<210> SEQ ID NO 4
<211> LENGTH: 15
<212> TYPE: PRT
<213> ORGANISM: artificial
<220> FEATURE:
<223> OTHER INFORMATION: tetanus toxin peptide

<400> SEQUENCE: 4

Val Ser Ile Asp Lys Phe Arg Ile Phe Cys Lys Ala Asn Pro Lys
1               5                   10                  15

<210> SEQ ID NO 5
<211> LENGTH: 16
<212> TYPE: PRT
<213> ORGANISM: artificial
<220> FEATURE:
<223> OTHER INFORMATION: tetanus toxin peptide

<400> SEQUENCE: 5

Leu Lys Phe Ile Ile Lys Arg Tyr Thr Pro Asn Asn Glu Ile Asp Ser
1               5                   10                  15

<210> SEQ ID NO 6
<211> LENGTH: 16
<212> TYPE: PRT
<213> ORGANISM: artificial
<220> FEATURE:
<223> OTHER INFORMATION: tetanus toxin peptide

<400> SEQUENCE: 6

Ile Arg Glu Asp Asn Asn Ile Thr Leu Lys Leu Asp Arg Cys Asn Asn
1               5                   10                  15

<210> SEQ ID NO 7
<211> LENGTH: 21
<212> TYPE: PRT
<213> ORGANISM: artificial
<220> FEATURE:
<223> OTHER INFORMATION: tetanus toxin peptide

<400> SEQUENCE: 7

Phe Asn Asn Phe Thr Val Ser Phe Trp Leu Arg Val Pro Lys Val Ser
1               5                   10                  15

Ala Ser His Leu Glu
            20

<210> SEQ ID NO 8
<211> LENGTH: 20
```

```
<212> TYPE: PRT
<213> ORGANISM: Neisseria meningitidis

<400> SEQUENCE: 8

Tyr Ala Phe Lys Tyr Ala Arg His Ala Asn Val Gly Arg Asn Ala Phe
1               5                   10                  15

Glu Leu Phe Leu
            20

<210> SEQ ID NO 9
<211> LENGTH: 18
<212> TYPE: PRT
<213> ORGANISM: Plasmodium falsiparum

<400> SEQUENCE: 9

Glu Lys Lys Ile Ala Lys Met Glu Lys Ala Ser Ser Val Phe Asn Val
1               5                   10                  15

Asn Asn

<210> SEQ ID NO 10
<211> LENGTH: 5
<212> TYPE: PRT
<213> ORGANISM: artificial
<220> FEATURE:
<223> OTHER INFORMATION: amino acid sequence modified by O-GlcNac

<400> SEQUENCE: 10

Thr Pro Val Ser Ser
1               5

<210> SEQ ID NO 11
<211> LENGTH: 10
<212> TYPE: PRT
<213> ORGANISM: artificial
<220> FEATURE:
<223> OTHER INFORMATION: peptide component of glycopeptide

<400> SEQUENCE: 11

Gly Ser Thr Pro Val Ser Ser Ala Asn Met
1               5                   10

<210> SEQ ID NO 12
<211> LENGTH: 11
<212> TYPE: PRT
<213> ORGANISM: artificial
<220> FEATURE:
<223> OTHER INFORMATION: peptide conjugated to BSA

<400> SEQUENCE: 12

Cys Gly Ser Thr Pro Val Ser Ser Ala Asn Met
1               5                   10

<210> SEQ ID NO 13
<211> LENGTH: 10
<212> TYPE: PRT
<213> ORGANISM: artificial
<220> FEATURE:
<223> OTHER INFORMATION: peptide component of glycopeptide

<400> SEQUENCE: 13

Gly Ser Thr Pro Val Ser Ser Ala Asn Met
1               5                   10

<210> SEQ ID NO 14
<211> LENGTH: 54
```

```
<212> TYPE: DNA
<213> ORGANISM: artificial
<220> FEATURE:
<223> OTHER INFORMATION: oligonucleotide primer

<400> SEQUENCE: 14
ccccatgtat ccatatgacg tcccagacta tgccgcgtct ccgtgggca acgt        54

<210> SEQ ID NO 15
<211> LENGTH: 74
<212> TYPE: DNA
<213> ORGANISM: artificial
<220> FEATURE:
<223> OTHER INFORMATION: oligonucleotide primer

<400> SEQUENCE: 15
ggggacaagt ttgtacaaaa aagcaggctg gatgatgtat ccatatgacg tcccagacta    60
tgccgcgtct ccg                                                      74

<210> SEQ ID NO 16
<211> LENGTH: 70
<212> TYPE: DNA
<213> ORGANISM: artificial
<220> FEATURE:
<223> OTHER INFORMATION: oligonucleotide primer

<400> SEQUENCE: 16
ggggaccact ttgtacaaga aagctgggtt ctatgctgac tcagtgactt caacgggctt    60
aatcatgtgg                                                          70

<210> SEQ ID NO 17
<211> LENGTH: 54
<212> TYPE: DNA
<213> ORGANISM: artificial
<220> FEATURE:
<223> OTHER INFORMATION: oligonucleotide primer

<400> SEQUENCE: 17
ccccatgtat ccatatgacg tcccagacta tgccgtgcag aaggagagtc aagc        54

<210> SEQ ID NO 18
<211> LENGTH: 74
<212> TYPE: DNA
<213> ORGANISM: artificial
<220> FEATURE:
<223> OTHER INFORMATION: oligonucleotide primer

<400> SEQUENCE: 18
ggggacaagt ttgtacaaaa aagcaggctg gatgatgtat ccatatgacg tcccagacta    60
tgccgtgcag aagg                                                     74

<210> SEQ ID NO 19
<211> LENGTH: 50
<212> TYPE: DNA
<213> ORGANISM: artificial
<220> FEATURE:
<223> OTHER INFORMATION: oligonucleotide primer

<400> SEQUENCE: 19
ggggaccact ttgtacaaga aagctgggtt cacaggctcc gaccaagtat              50
```

GLYCOPEPTIDE AND USES THEREOF

CONTINUING APPLICATION DATA

This application is a continuation of U.S. patent application Ser. No. 13/002,180, filed Aug. 5, 2011, which is the national stage entry of International Application PCT/US2009/003944, with an international filing date of Jul. 2, 2009, which claims the benefit of U.S. Provisional Application Ser. No. 61/197,386, filed Oct. 27, 2008, and is continuation-in-part of U.S. patent application Ser. No. 12/217,376, filed on Jul. 3, 2008 (now issued as U.S. Pat. No. 7,820,797), which claims the benefit of U.S. Provisional Application Ser. No. 61/127,710, filed May 15, 2008, and is also a continuation-in-part of International Application PCT/US2007/000158, with an international filing date of Jan. 3, 2007, which in turn claims the benefit of U.S. Provisional Application Ser. Nos. 60/755,881, filed Jan. 3, 2006; 60/796,769, filed May 2, 2006; and 60/809,272, filed May 30, 2006; each of which is incorporated herein by reference in its entirety.

STATEMENT OF GOVERNMENT RIGHTS

This invention was made with government support under Grant No CA88986 awarded by the National Institute of Health. The government has certain rights in the invention.

SEQUENCE LISTING

This application contains a Sequence Listing electronically submitted via EFS-Web to the United States Patent and Trademark Office as an ASCII text filed entitled "235-00800131_SequenceListing_ST25.txt" having a size of 5 kilobytes and created on Nov. 18, 2013. The information contained in the Sequence Listing is incorporated by reference herein.

BACKGROUND

A large number of tumor-associated carbohydrate antigens (TACA) are expressed on human cancer cells in the form of glycolipids and glycoproteins. A common feature of oncogenic transformed cells is the over-expression of oligosaccharides, such as Globo-H, Lewis$^Y$, and Tn antigens. Numerous studies have shown that this abnormal glycosylation can promote metastasis and hence it is strongly correlated with poor survival rates of cancer patients.

The differential expression that is characteristic of these tumor-associated carbohydrate antigens renders them attractive targets for immunotherapy and the development of cancer vaccines. Recently, several elegant studies have attempted to capitalize on the differential expression of tumor-associated carbohydrates for the development of cancer vaccines (e.g., Raghupathi, Cancer Immunol. 1996, 43, 152-157; Musselli et al., J. Cancer Res. Clin. Oncol. 2001, 127, R20-R26; Sabbatini et al., Int. J. Cancer, 2000, 87, 79-85; Lo-Man et al., Cancer Res. 2004, 64, 4987-4994; Kagan et al., Immunol. Immunother. 2005, 54, 424-430).

Carbohydrate antigens are also abundant on the surface the human immunodeficiency virus (HIV), the causative agent of acquired immune deficiency syndrome (AIDS). Hepatitis C virus (HCV) is also known to contain carbohydrate antigens.

For most immunogens, including carbohydrates, antibody production depends on the cooperative interaction of two types of lymphocytes, B-cells and helper T-cells. Carbohydrates alone, however, cannot activate helper T-cells and therefore are characterized by poor immunogenicity. The formation of low affinity IgM antibodies and the absence of IgG antibodies manifest this limited immunogenicity. It has proven difficult to overcome the immunotolerance that characterizes these antigens.

In an effort to activate helper T cells, researchers have conjugated carbohydrate antigens to a foreign carrier protein, e.g. keyhole limpet hemocyanin (KLH) or detoxified tetanus toxoid (TT). The carrier protein enhances the presentation of the carbohydrate to the immune system and supplies T-epitopes (typically peptide fragments of 12-15 amino acids) that can activate T-helper cells.

However, conjugation of carbohydrates to a carrier protein poses several new problems. The conjugation chemistry is difficult to control, resulting in conjugates with ambiguities in composition and structure that may affect the reproducibility of an immune response. In addition, the foreign carrier protein may elicit a strong B-cell response, which in turn may lead to the suppression of an antibody response against the carbohydrate epitope. The latter is particularly a problem when self-antigens are employed such as tumor-associated carbohydrates. Also, linkers employed for conjugating carbohydrates to proteins can themselves be immunogenic, leading to epitope suppression. See also McGeary et al., for a review of lipid and carbohydrate based adjuvant/carriers in vaccines (J. Peptide Sci. 9 (7): 405-418, 2003).

Not surprisingly, several clinical trials with carbohydrate-protein conjugate cancer vaccines failed to induce sufficiently strong helper T-cell responses in all patients. Therefore, alternative strategies need to be developed for the presentation of tumor associated carbohydrate epitopes that will result in a more efficient class switch to IgG antibodies. These strategies may prove useful as well for the development of vaccines based on other carbohydrate epitopes, particularly those from pathogenic viruses such as HIV and HCV.

SUMMARY OF THE INVENTION

The present invention provides a glycolipopeptide, also referred to herein as a lipidated glycopeptide, for use in immunotherapy, as well as pharmaceutical compositions containing such glycolipopeptide and methods of making and using such glycolipopeptide. In a preferred embodiment, the glycolipopeptide of the invention is fully synthetic.

The glycolipopeptide preferably contains at least 2 epitopes: a B-epitope and a T-epitope, as well as a lipid component. The glycolipopeptide is thus able to elicit both a humoral response to the B-epitope and a cellular immune response to T-epitope. In a preferred embodiment, the glycolipopeptide of the invention advantageously combines features from a B-epitope glycan or glycopeptide and a T-epitope peptide derived from glycoproteins of mammalian (preferably human or murine) or microbial origin.

Lipidation confers several additional advantages to the glycolipopeptide. It helps the glycolipopeptides self assemble into vesicles, and may also facilitate the incorporation of the immunogen into a liposome which in turn can improve the presentation of the immunogen to the immune system. Additionally, the lipid component serves as a built-in adjuvant. Cellular uptake of the glycopeptide is also facilitated by the lipidation. Cytokine production is also enhanced by inclusion of the lipid component.

Accordingly, in one aspect, the invention provides a glycolipopeptide containing at least one carbohydrate component that includes all or part of a B-epitope; at least one peptide component that includes all or part of a T-epitope; and at least one lipid component. The carbohydrate component and the peptide component may be heterologous with respect to each other or they may be homologous with respect to each other. The glycolipopeptide of the invention may include a glycopeptide that includes all or part of both the B-epitope and the T-epitope.

The carbohydrate component of the glycolipopeptide can include a glycoconjugate, for example, a glycosylated protein, a glycosylated peptide (also referred to herein as a glycopeptide) a glycosylated lipid, a glycosylated amino acid, a DNA or an RNA. The B-epitope of the carbohydrate component may be from a microorganism, such as a virus, a bacterium, a fungus, and a protozoan. Exemplary viruses as sources for the B-epitope include human immunodeficiency virus and hepatitis C virus, without limitation. The B-epitope can therefore constitute all or part of a viral antigen, such as a viral antigen from human immunodeficiency virus or hepatitis C virus. Alternatively or additionally, the B-epitope can constitute all or part of a self-antigen. For example, the B-epitope can be one that is overexpressed on a cancer cell. An exemplary self-antigen is MUC-1 glycopeptide. Another example of a glycopeptide that can constitute the carbohydrate component of the glycolipopeptide of the invention is a β-N-acetylglucosamine (β-O-GlcNAc) modified peptide. In another embodiment, the carbohydrate component of the glycolipopeptide includes a heparin fragment or a heparan sulfate fragment.

The peptide component of the glycolipopeptide, which includes a T-epitope, preferably includes a helper T-epitope.

The lipid component of the glycolipopeptide is preferably an antigenic, immunogenic, or otherwise immunostimulatory lipid. For example, the lipid component can include a Toll-like receptor (TLR) ligand, such as a PamCys-type lipid. Examples of a PamCys-type lipid include $Pam_2Cys$, $Pam_3Cys$, $Pam_2CysSK_n$ and $Pam_3CysSK_n$, wherein n=0, 1, 2, 3, 4 or 5. A particularly preferred lipid component includes $Pam_3CysSK_4$. In another preferred embodiment, the lipid component binds to a Toll-like receptor and facilitates internalization of the glycolipopeptide by a target cell. Exemplary lipid components can be found, for example, in Scheme 8 hereinbelow. The lipid may serve as an internal (covalently linked) adjuvant. Preferably, the lipid component includes a TLR agonist, i.e., a TLR ligand that has a stimulatory effect on a Toll-like receptor.

Optionally, the glycolipopeptide of the invention includes at least one linker component. The linker component may link one or more of the carbohydrate component, peptide component and/or lipid component to each other or to a different component or structure.

A particularly preferred embodiment of the glycolipopeptide is one that contains at least one carbohydrate component that includes a self-antigen having a B-epitope, for example a MUC-1 glycopeptide; at least one peptide component comprising a T-epitope, preferably a helper T-epitope; and at least one lipid component, for example a Toll-like receptor ligand (TLR ligand). In another particularly preferred embodiment, the glycolipopeptide of the invention includes at least one carbohydrate component that has a B-epitope; at least one peptide component that has a helper T-epitope; and at least one lipid component that binds to a Toll-like receptor and facilitates uptake of the glycolipopeptide by a target cell that includes the Toll-like receptor; wherein the carbohydrate component and the peptide component are heterologous with respect to each other. In another particularly preferred embodiment, the glycolipopeptide includes at least one carbohydrate component that includes a self-antigen that has a B-epitope; at least one peptide component that has a helper T-epitope; and at least one lipid component that binds to a Toll-like receptor, i.e., a TLR ligand. Advantageously, the TLR ligand may facilitate uptake of the glycolipopeptide by a target cell that includes the Toll-like receptor.

In another aspect, the invention provides a pharmaceutical composition. In one embodiment, the pharmaceutical composition includes a glycolipopeptide of the invention, without limitation. Optionally, the pharmaceutical composition contains plurality of glycopeptides, which may include glycolipopeptides having different or the same B-epitopes, having different or the same T-epitopes and/or having different or the same lipid components. In another embodiment, the pharmaceutical composition includes an antibody against a glycolipopeptide of the invention, without limitation. The antibody can be a monoclonal or polyclonal antibody, and may be a humanized antibody. Techniques for humanizing antibodies are well known in the art.

Optionally, the pharmaceutical composition contains a liposome. Formulations with liposomes, micelles, or other lipid vesicles may facilitate delivery of the glycopeptide to a subject in need thereof. The glycolipopeptide may be covalently or noncovalently incorporated into the liposome, micelle or other lipid vesicle.

The pharmaceutical composition preferably includes a pharmaceutically acceptable carrier. In one embodiment, the pharmaceutical composition does not contain an external adjuvant. In another embodiment, the pharmaceutical composition contains an external adjuvant. An example of an external adjuvant is QS-21.

Advantageously, the pharmaceutical composition of the invention can be used as a vaccine, for example to treat or prevent an infection, disease or disorder. Additionally, the glycolipopeptide of the invention can be used for the manufacture of a medicament to treat or prevent an infection, disease or disorder.

Accordingly, in another aspect, the invention provides method for treating or preventing an infection, disease or disorder in a subject that involves administering a pharmaceutical composition of the invention to a subject in need thereof. Inclusion of QS-21 as an external adjuvant may skew the immune response of the subject toward a Th1 response, compared to a comparable pharmaceutical composition that does not include QS-21. The infection, disease or disorder that is treated or prevented may be one that is caused by a microorganism, such as a virus, a bacterium, a fungus, and a protozoan. Viral infections that can be treated or prevented include, without limitation, those caused a human immunodeficiency virus or a hepatitis C virus. Alternatively, the infection, disease or disorder that is treated or prevented can include cancer, a precancerous condition, or an autoimmune disease, such as diabetes type II.

In another aspect, the invention includes a method for making the glycolipopeptide of the invention. The carbohydrate component, the peptide component and the lipid component are synthetically linked, for example by using chemical or in vitro enzymatic methods.

In yet another aspect, the invention provides a method for identifying a Toll-like receptor (TLR) ligand. A Toll-like receptor ligand is useful for inclusion in a glycolipopeptide vaccine of the invention. The method includes contacting a candidate compound with a target cell containing a TLR, and determining whether the candidate compound binds to the TLR. Optionally, the method also includes determining whether the candidate compound is internalized by the target cell. In a preferred embodiment, the candidate compound includes a lipid, and the TLR ligands thus identified are useful as the lipid component for the glycolipopeptide of the invention. Accordingly, another embodiment of the glycolipopeptide of the invention includes at least one carbohydrate component having a B-epitope; at least one peptide component having a helper T-epitope; and at least one lipid component identified using the method of identifying a TLR ligand as described herein.

In another embodiment, the glycolipopeptide of the invention includes at least one carbohydrate component comprising a B-epitope; at least one peptide component comprising a T-epitope; and at least one lipid component; wherein the carbohydrate component comprises a saccharide selected from the group consisting of N-acetylglucosamine (GlcNAc) or N-acetylgalactoseamine (GalNAc) or mannose. In one embodiment, the saccharide is O-linked, S-linked or N-linked to the glycolipopeptide. Preferably, the saccharide comprises β-N-acetylglucosamine (β-O-GlcNAc). In another embodiment, carbohydrate component of the glycolipopeptide includes a saccharide that includes a glycosaminoglycan or fragment thereof. Examples of glycosaminoglycans include heparin, heparan sulfate, chondroitin sulfate, dermatan sulfate, keratan sulfate and hyaluronan. The carbohydrate component may include a glycopeptide comprising the saccharide. The carbohydrate component may include a self-antigen. The lipid component of the glycolipopeptide may include a Toll-like receptor (TLR) ligand.

In another aspect, the invention provides a polyclonal or monoclonal antibody against the glycolipopeptide of the invention, as well as hybridoma cells and cell lines that produce said antibody. Humanized antibodies are encompassed by the invention. Exemplary hybridoma cell lines include hybridoma 1F5.D6, hybridoma 9D1.E4, hybridoma 5H11.H6, and hybridoma 18B10.C7. The monoclonal antibodies produced by these hybridoma cell lines are also included in the invention.

Also included in the invention is a polyclonal or monoclonal antibody that competes with a monoclonal antibody described herein for binding to glycolipopeptide 52, as well as a polyclonal or monoclonal antibody that binds to glycolipopeptide 52.

Also included in the invention is a method for making an antibody of the invention. In one embodiment, a glycolipopeptide of the invention is injected into a mammal, and at least one antibody that binds to the glycolipopeptide is isolated from the mammal. Alternatively, cells, for example spleen or lymph node cells, can be isolated from the mammal and fused with myeloma cells to form hybridomas. At least one hybridoma that produces an antibody that binds to the glycolipopeptide is selected, and the antibody is isolated. Antibodies made using any of the methods of the invention are also included in the invention, as is use of a glycolipopeptide of the invention to produce a polyclonal or monoclonal antibody that binds the glycolipopeptide.

Also included in the invention is an antibody produced by immunizing a mammal or a mammalian cell with an immunogenic glycopeptide of the invention. Antibodies to the glycopeptide of the invention can also be produced using commonly available techniques such as phage display. Preferably, the antibody produced is an IgG antibody that binds a broad spectrum of glycoproteins. The carbohydrate component of the glycolipopeptide used to immunize the mammal may include, without limitation, a saccharide selected from the group consisting of N-acetylglucosamine (GlcNAc) or N-acetylgalactoseamine (GalNAc) or mannose, or a saccharide comprising a glycosaminoglycan or fragment thereof. The lipid component of the glycolipopeptide used to immunize the mammal may include a Toll-like receptor (TLR) ligand.

Preferably, the monoclonal or polyclonal antibody of the invention is an IgG antibody; more preferably, it is an antibody that binds a broad spectrum of glycoproteins.

The invention further provides for use of a glycolipopeptide or antibody of the invention, without limitation, for the manufacture of a medicament to treat or prevent an infection, disease or disorder.

In another aspect, the invention provides a kit, for example a diagnostic kit or a kit for laboratory research use, that includes an antibody of the invention, for example a monoclonal antibody that binds to a glycolipopeptide of the invention, without limitation, along with packaging and instructions for use. The kit optionally also includes a second antibody that binds to the primary antibody. Either or both of the primary or secondary antibodies is optionally conjugated to a detectable label.

The invention further provides a method for detecting, diagnosing or monitoring an infection, disease or disorder in a subject. A biological sample, such as a body fluid or tissue from the subject, is contacted with an antibody of the invention; and binding of the antibody to a component in the biological sample is detected. The antibody selected for use in the method can be one that is known to bind to a biomolecule that is associated with infection, disease or disorder. Binding of the antibody to a sample component is indicative of the presence of the infection, disease or disorder in the subject. Optionally the method further includes quantitating the level of antibody binding to the sample component; quantitating the level of antibody binding to components in a comparable non-diseased sample; and comparing the binding levels; wherein a change in antibody binding in the biological sample compared to the non-diseased sample is indicative of the presence of the infection, disease or disorder in the subject.

The invention further includes a method for detecting a glycosylated protein. A biological sample is contacted with an antibody of the invention, for example a monoclonal antibody that binds to a glycolipopeptide of the invention; and binding of the antibody to the protein is detected. Optionally the method includes identifying the protein.

The invention further includes method for identifying a protein associated with a disease state. A first biological sample associated with a disease state is contacted with an antibody of the invention; and a second biological sample associated with different disease state or no disease is also contacted with the antibody. Binding of said antibody to glycosylated proteins in the first and second samples is detected, and glycosylated proteins that are enriched in one sample compared to the other are detected. A difference in the amount of a glycosylated protein in the two samples is indicative of a protein associated with a disease state. Optionally the method includes identifying the protein associated with a disease state.

Unless otherwise specified, "a," "an," "the," and "at least one" are used interchangeably and mean one or more than one.

Figure 3:
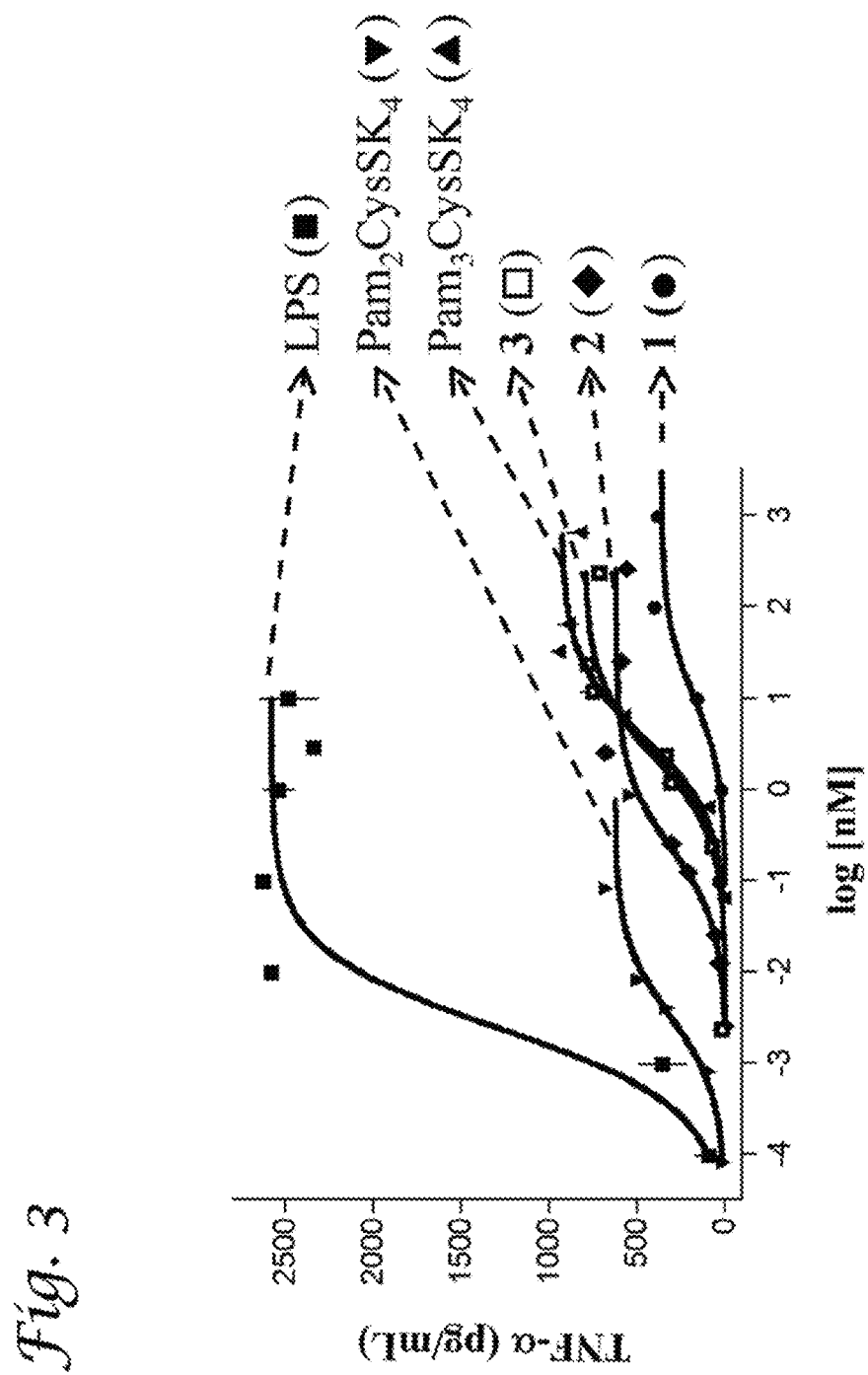

FIG. 3 shows TNF-α production by murine macrophages after stimulation with LPS and synthetic compounds. Murine RAW γNO(−) cells were incubated for 5.5 hours with increasing concentrations of *E. coli* LPS (■), 1 (●), Pam$_2$CySSK$_4$ (▼), 2 (◆), Pam$_3$CySSK$_4$ (▲), or 3 (□) as indicated.

Figure 4:
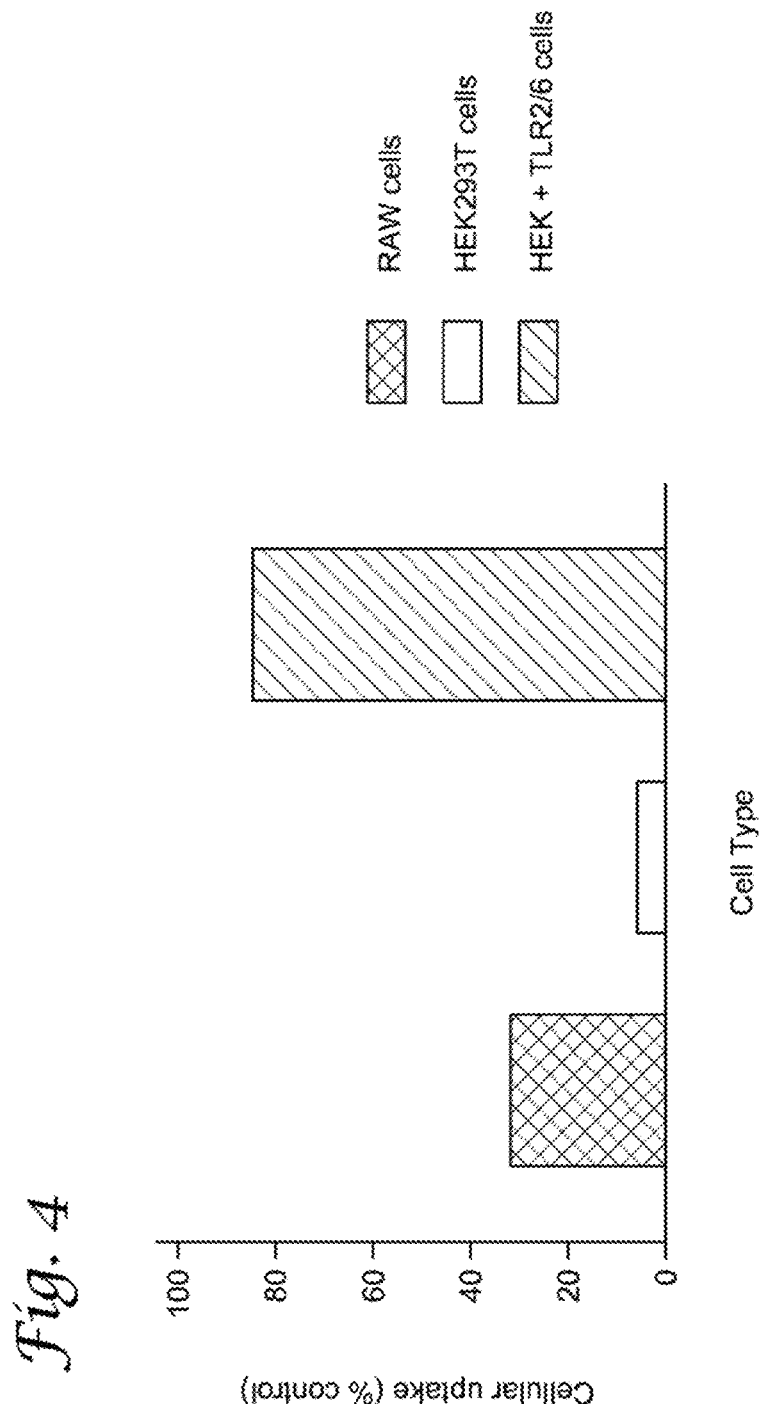

FIG. 4 shows the effect of TLR ligand on cellular uptake.

FIG. 5 shows the chemical structures of synthetic antigens.

Figure 6:
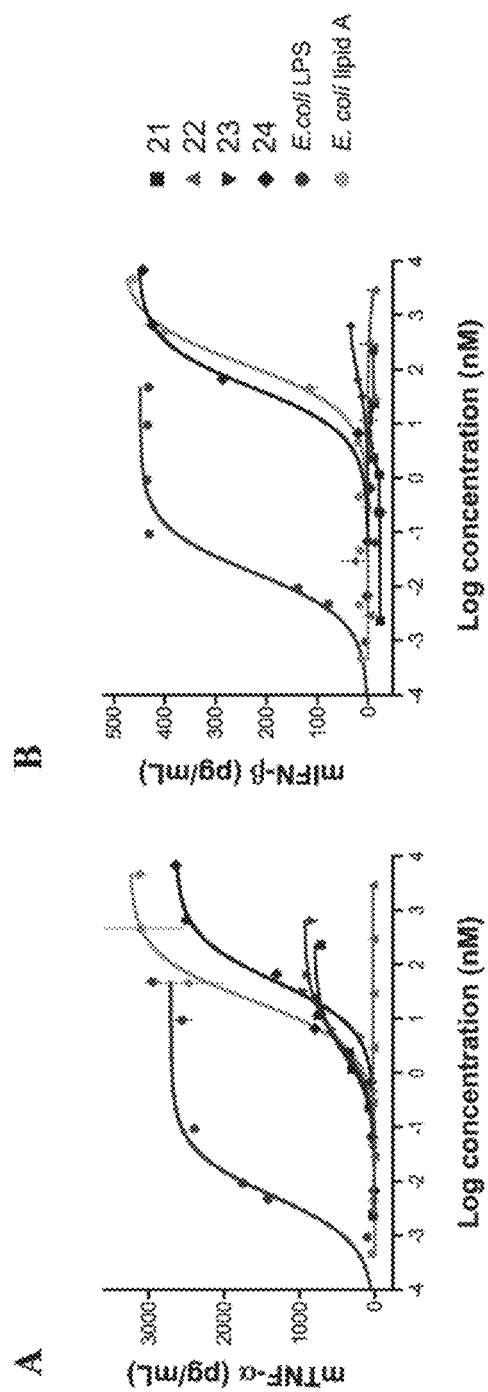

FIG. 6 shows TNF-α and IFN-β production by murine macrophages after stimulation with synthetic compounds 21-24, *E. coli* LPS, and *E. coli* lipid A. Murine 264.7 RAW γNO(−) cells were incubated for 5.5 h with increasing concentrations of 21-24, *E. coli* LPS, or *E. coli* lipid A as indicated. TNF-α (A) and IFN-β (B) in cell supernatants were measured using ELISAs. Data represent mean values±SD (n=3).

Figure 7:
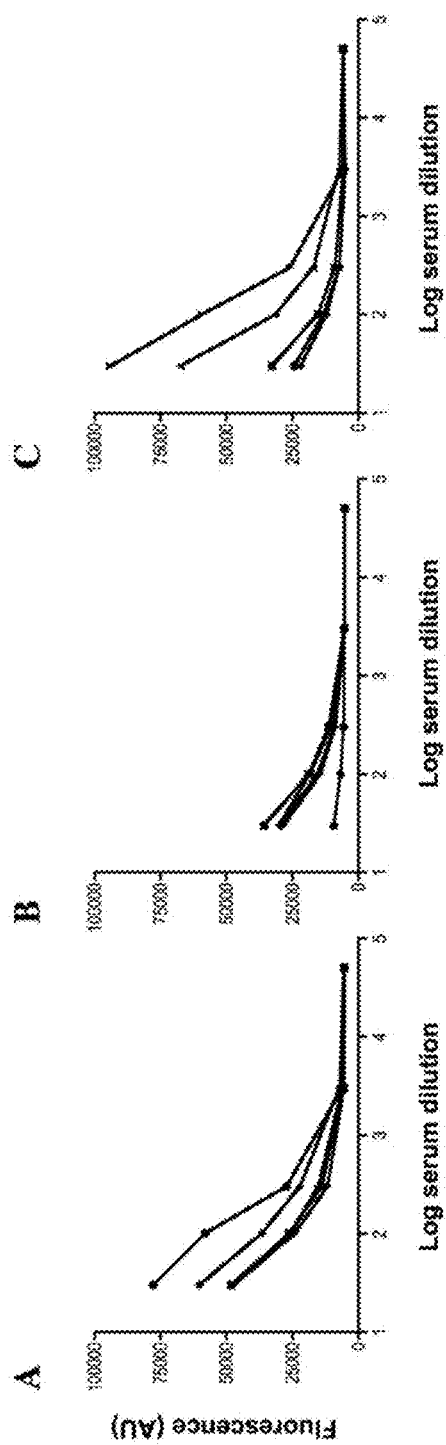

FIG. 7 shows cell recognition analysis for specific anti-MUC1 antibodies. Reactivity of sera was tested on MCF7 cells. Serial dilutions of serum samples after 4 immunizations with 21 (A), 22/23 (B), or 22/24 (C) were incubated with MCF7 cells. After incubation with FITC-labeled anti-mouse IgG antibody, the fluorescence intensity was assessed in cell lysates. No fluorescence over background was observed with pre-immunization sera and incubation of the serum samples with control SK-MEL-28 cells (shown in FIG. 9). AU indicates arbitrary fluorescence units.

Figure 8:
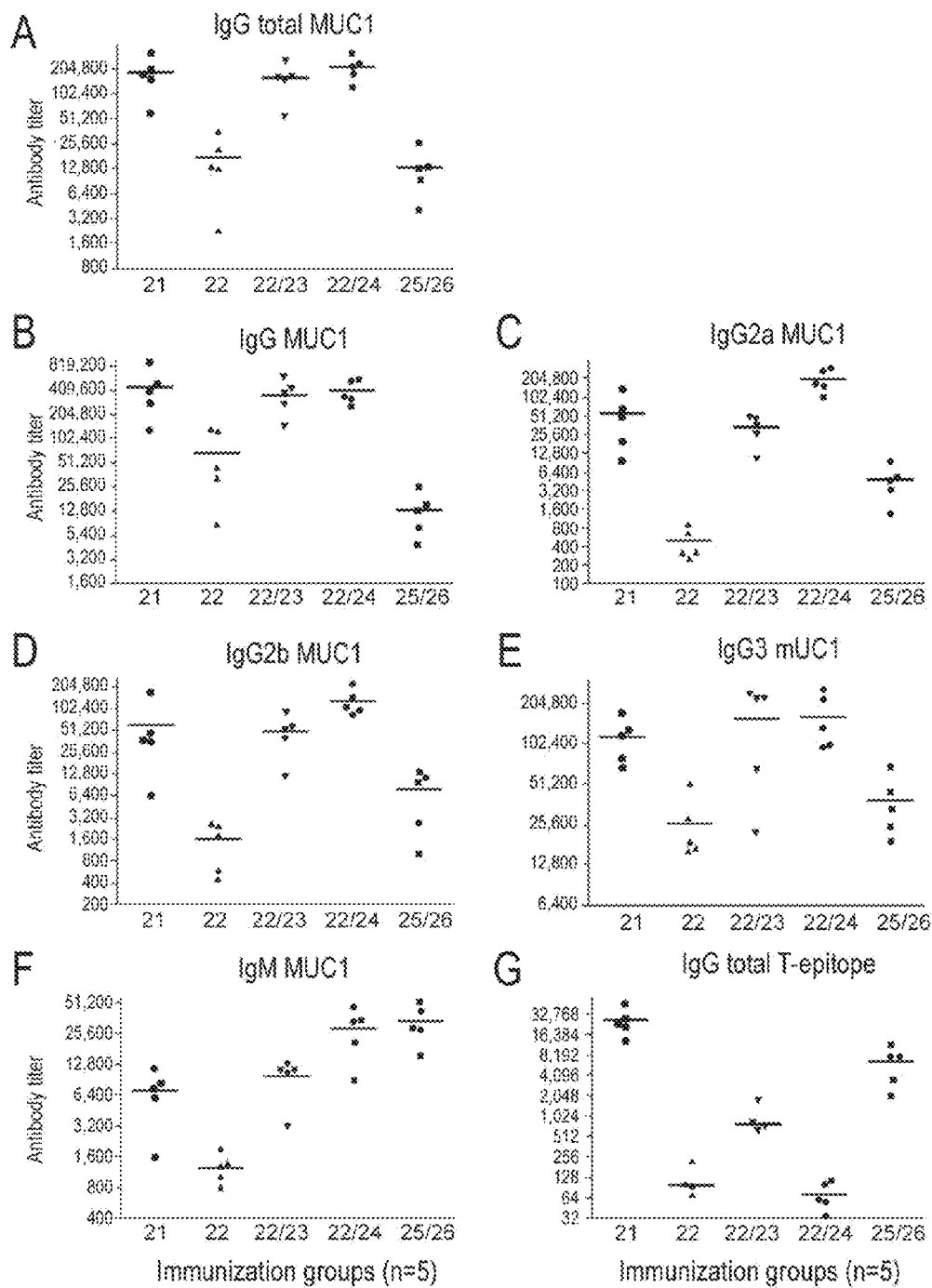

FIG. 8 shows ELISA anti-MUC1 and anti-T-epitope antibody titers after 4 immunizations with 21, 22, 22/23, 22/24 and 25/26. ELISA plates were coated with BSA-MI-MUC-1 conjugate (A-F) or neutravidin-biotin-T-epitope (G) and titers were determined by linear regression analysis, plotting dilution vs. absorbance. Titers were defined as the highest dilution yielding an optical density of 0.1 or greater over that of normal control mouse sera. Each data point represents the titer for an individual mouse after 4 immunizations and the horizontal lines indicate the mean for the group of five mice.

Figure 9:
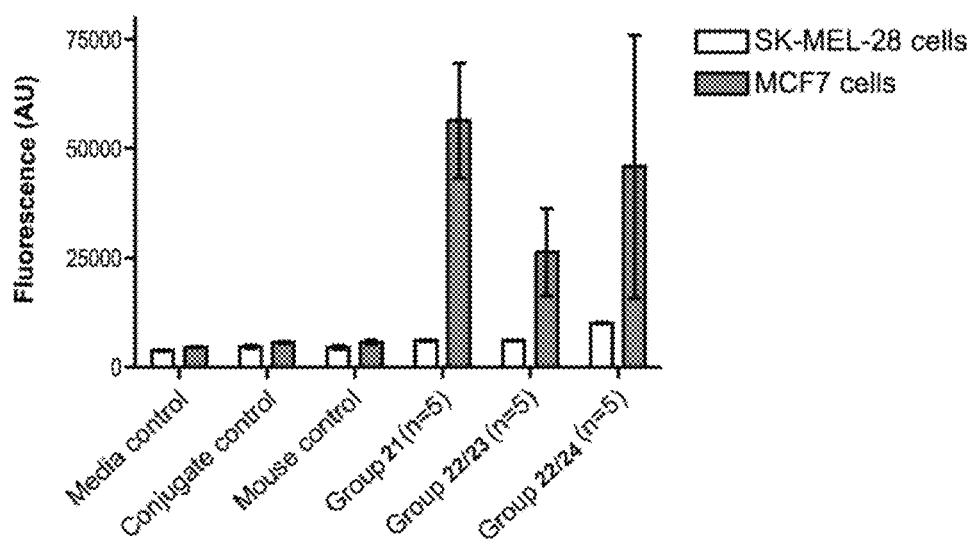

FIG. 9 shows cell recognition analysis for specific anti-MUC-1 antibodies. Reactivity of sera was tested on MCF7 and SK-MEL-28 cells. Serum samples (1:30 diluted) after 4 immunizations with 21, 22/23, or 22/24 were incubated with MCF7 and SK-MEL-28 cells. After incubation with FITC-labeled anti-mouse IgG antibody, the fluorescence intensity was assessed in cell lysates. Also shown are media, conjugate, and mouse (normal control mouse sera) controls. Data represent mean values±SD. AU indicates arbitrary fluorescence units.

FIG. 10 shows compound 22.

FIG. 11 shows compound 23.

FIG. 12 shows compound 25.

FIG. 13 shows compound 26.

FIG. 14 shows compound 27.

Figure 15:
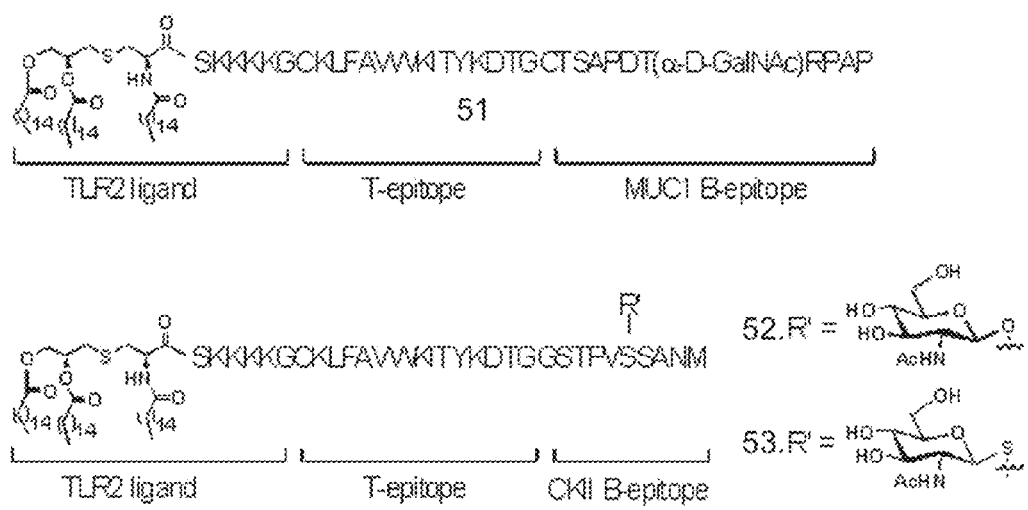

FIG. 15 shows the structure of fully synthetic three-component immunogens.

Figure 16:
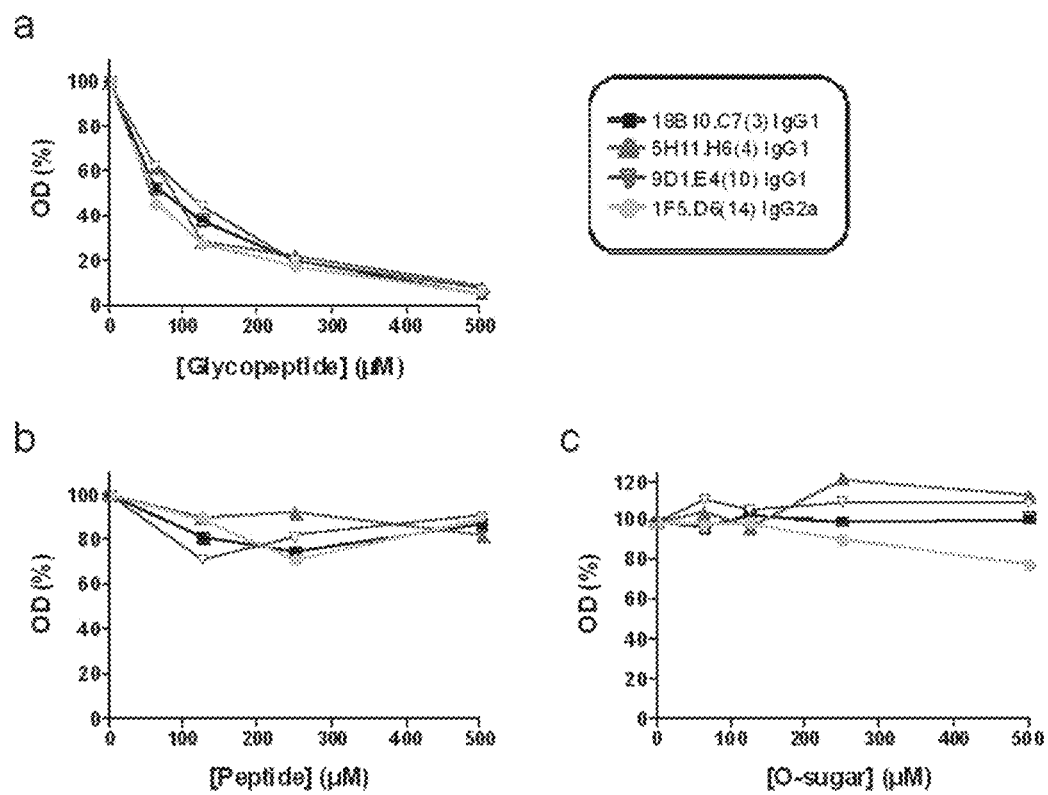

FIG. 16 shows competitive inhibition of monoclonal antibody binding to GSTPVS(β-O-GlcNAc)SANM (68) by the corresponding glycopeptide, peptide and sugar. ELISA plates were coated with BSA-MI-CGSTPVS(β-O-GlcNAc) SANM (BSA-MI-66) conjugate. MAbs, diluted to obtain in the absence of an inhibitor an OD of approximately 1 in the ELISA, were first mixed with (a) glycopeptide 68 (GSTPVS (β-O-GlcNAc)SANM), (b) peptide 69 (GSTPVSSANM; SEQ ID NO:11) or (c) sugar 70 (β-O-GlcNAc-Ser) (0-500 µM final concentration) and then applied to the coated microtiter plate. OD values were normalized for the OD values obtained with monoclonal antibody alone (0 µM inhibitor, 100%).

Figure 17:
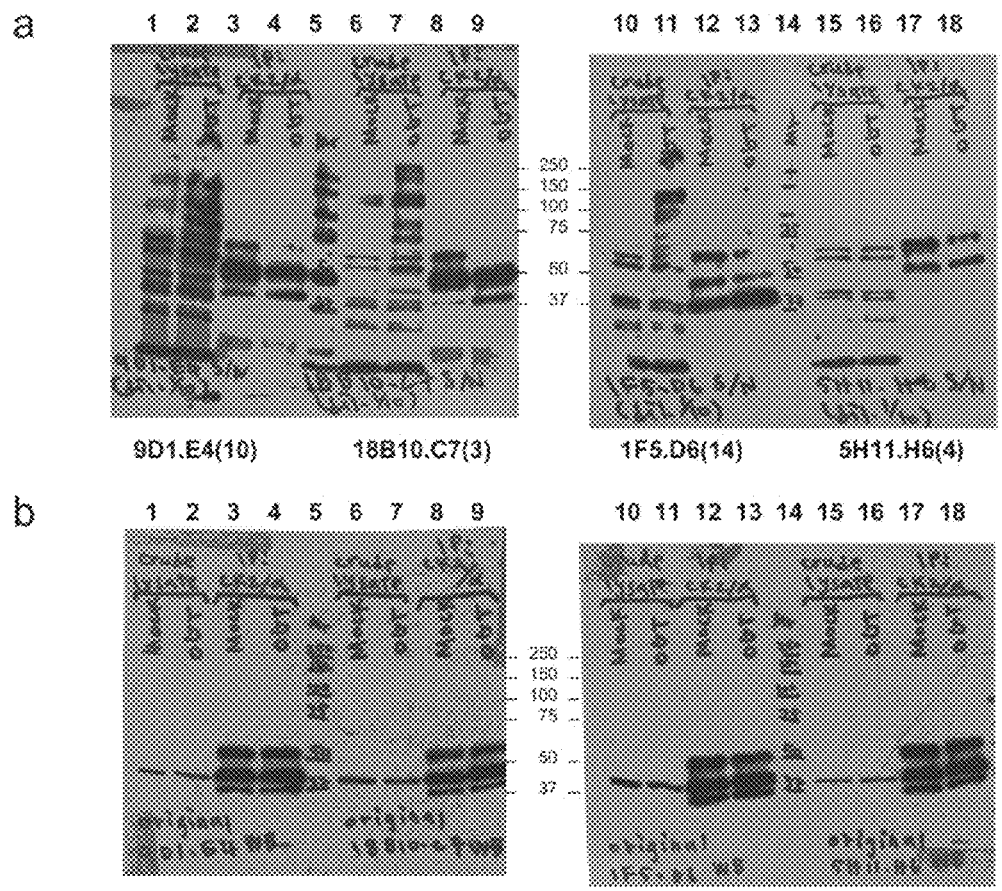

FIG. 17 shows Western blots of cell lysates and immunoprecipitated samples. HEK293TN cells were transiently transfected with an OGT plasmid or mock transfected. (a) Cell lysates of mock transfected cells (lanes 1, 6, 10 and 15) and OGT overexpressing cells (lanes 2, 7, 11 and 16) and immunoprecipitated samples using rabbit polyclonal CK2II alpha antibody of mock transfected cell lysates (lanes 3, 8, 12 and 17) and OGT overexpressing cells lysates (lanes 4, 9, 13 and 18) were resolved by SDS-PAGE (10%), transferred to PVDF membranes and probed with cell culture supernatants (1:10 diluted) of monoclonal antibody clones 9D1.E4 (10) (lanes 1-4), 18B10.C7(3) (lanes 6-9), 1F5.D6(14) (lanes 10-13 and 5H11.H6(4) (lanes 15-18). As secondary antibody an anti-mouse IgG antibody linked to peroxidase was used. (b) The blots of (a) were stripped and reprobed with rabbit polyclonal anti-CKII antibody and an anti-rabbit IgG antibody linked to peroxidase as secondary antibody was used. Blots were visualized with ECL substrate by exposing on film.

Figure 18:
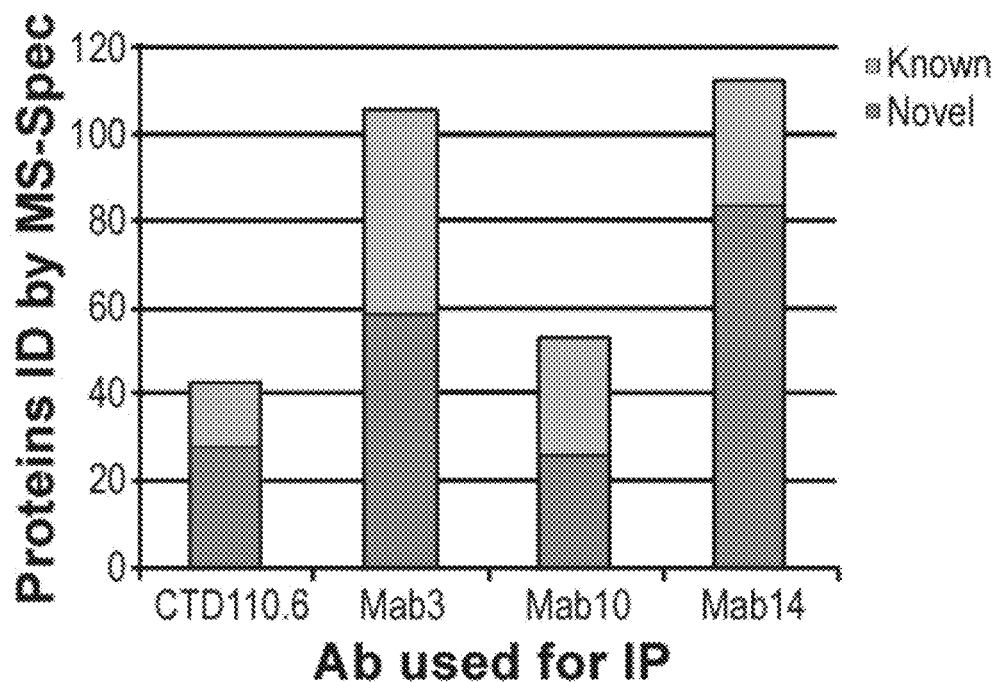

FIG. 18 shows a large-scale immunoprecipitation of O-GlcNAc modified proteins by Mab3, 10 and 14 as well as CTD 110.6 from HEK29T cells treated with PUGNAc. Following Lys-C digestion, samples were subject to ESI (CID-pseudo neutral loss) analysis. Results were filtered at 1% false recovery rate and proteins appeared in mock IP were subtracted from the final list.

Figure 19:
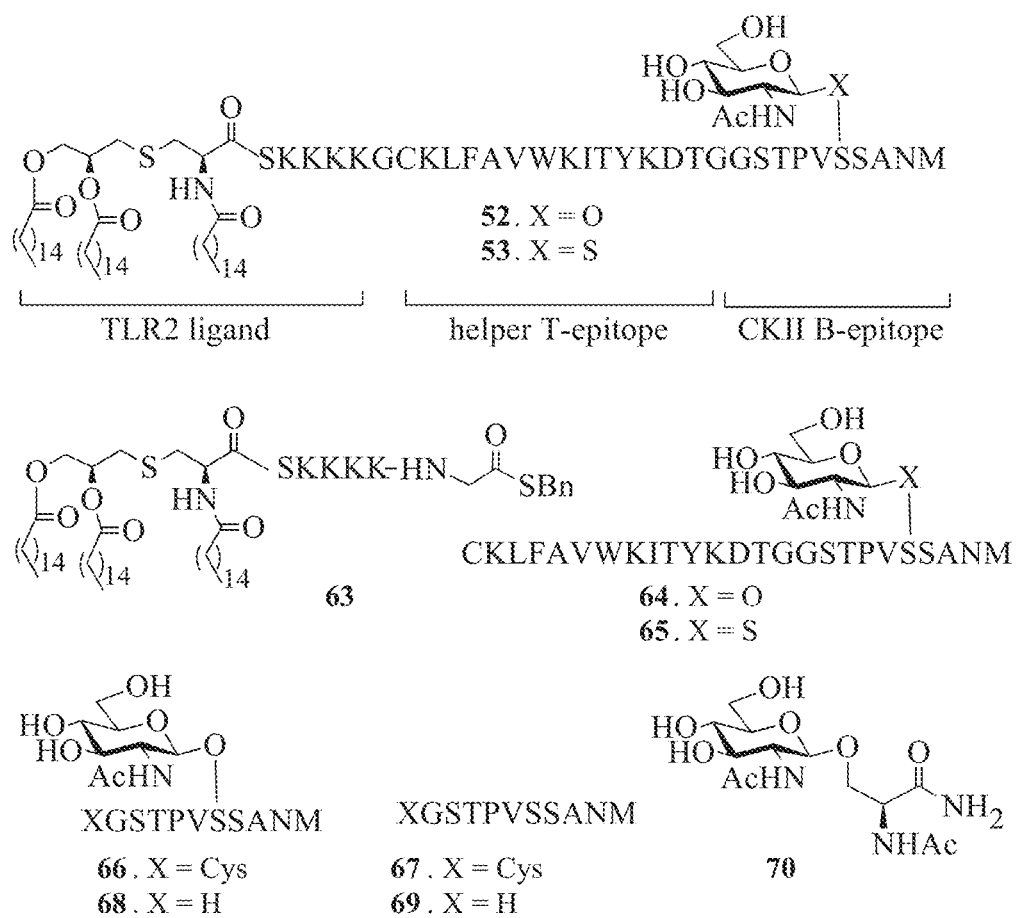

FIG. 19 shows the structures of fully synthetic three-component immunogens 52 and 53 and the reagents 63-65 for their preparation. Compounds 66-70 were employed for ELISA and inhibition ELISA.

Figure 20:
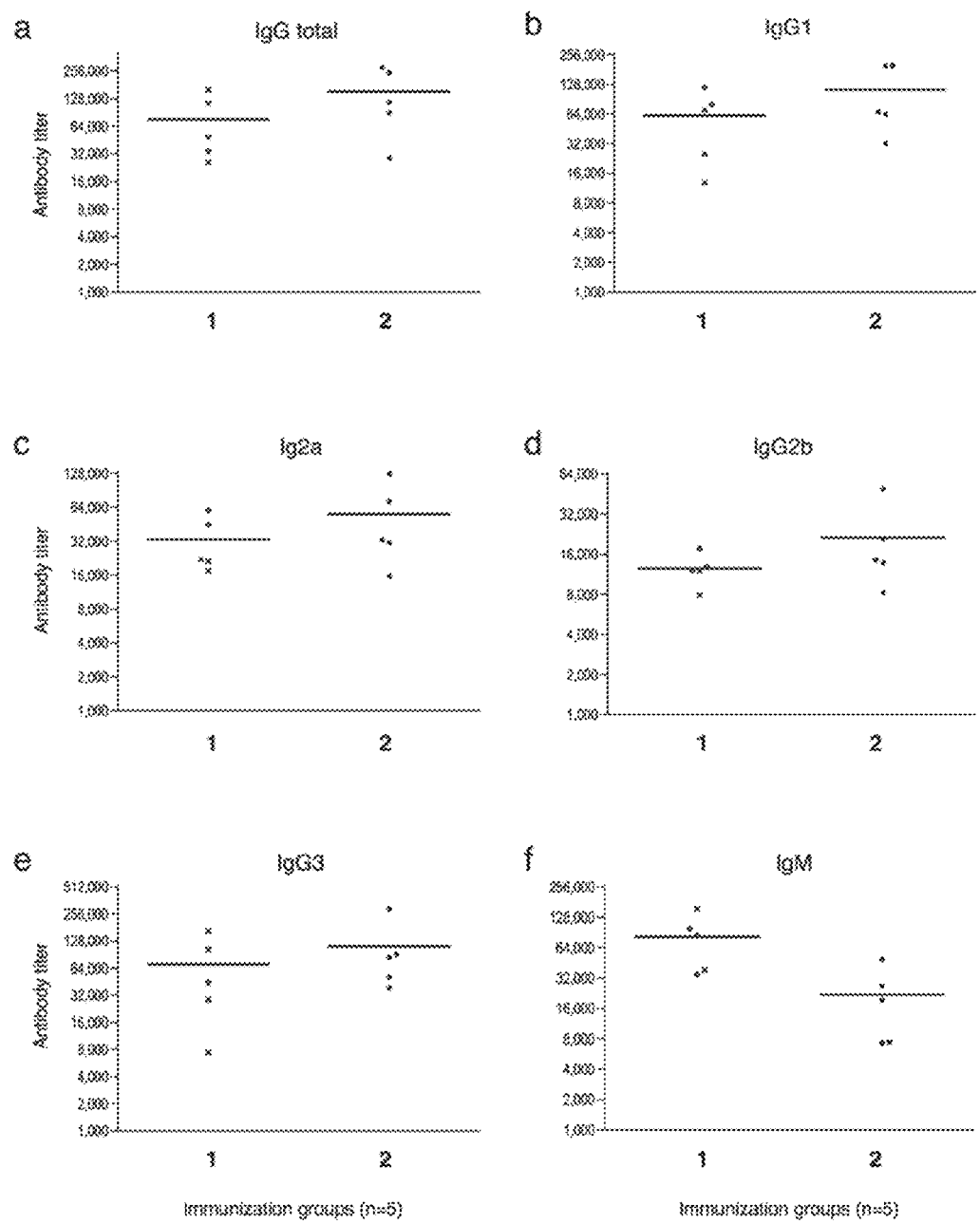

FIG. 20 shows ELISA anti-GSTPVS(β-O-GlcNAc) SANM (68) antibody titers after 4 immunizations with 52 and 53. ELISA plates were coated with BSA-MI-GSTPVS (β-O-GlcNAc) SANM (BSA-MI-66) conjugate and (a) IgG total, (b) IgG1, (c) IgG2a, (d) IgG2b, (e) IgG3 and (f) IgM titers were determined by linear regression analysis, plotting dilution vs. absorbance. Titers were defined as the highest dilution yielding an optical density of 0.1 or greater over that of normal control mouse sera. Each data point represents the titer for an individual mouse after 4 immunizations and the horizontal lines indicate the mean for the group of five mice.

Figure 21:
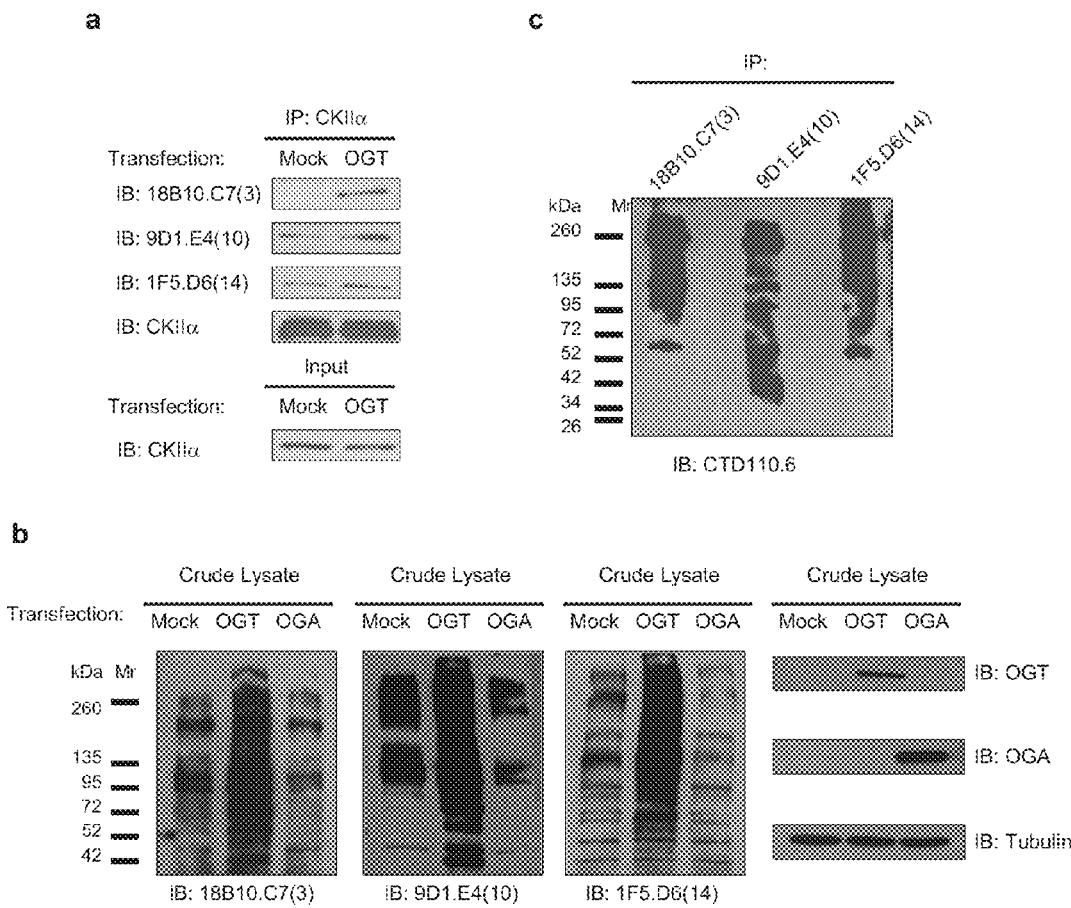

FIG. 21 shows immunoblotting of three monoclonal antibodies. (a) CKII α subunit was immunoprecipitated from HEK293T cells with or without OGT overexpression. Eluates were resolved by SDS-PAGE and immunoblotted with MAbs 18B10.C7(3), 9D1.E4(10) and 1F5.D6(14). A band corresponding to CKII α subunit was detected with signal intensity correlated with O-GlcNAc status. All blots were stripped and reprobed with antibody against CKII α subunit (only one representative blot is shown here). Also, equal amount of CKII a subunit was present in the input regardless of the status of O-GlcNAc levels. (b) HEK293T lysates with low (OGA overexpression), median (Mock transfection) and high (OGT overexpression) levels of O-GlcNAc modification were exposed to MAbs 18B10.C7(3), 9D1.E4(10) and 1F5.D6(14) respectively. The signals obtained mirror the corresponding 0-GlcNAc status in each sample. Immunoblots against OGT, OGA and tubulin are also shown. While equal loading of tubulin was detected in all samples, higher OGA and OGT protein levels were detected with lysates from OGA and OGT transfection. Note: Endogenous OGT and OGA levels do appear after longer exposure. (c) O-GlcNAc proteins were immunoprecipitated from HEK293T cells treated with PUGNAc (an OGA inhibitor), resolved by SDS-PAGE and subjected to CTD110.6 (an IgM isotype O-GlcNAc specific antibody) blotting. Cross-reactivity of MAbs 18B10.C7(3), 9D1.E4(10) and 1F5.D6(14) with CTD110.6, albeit distinct in pattern, were detected.

Figure 22:
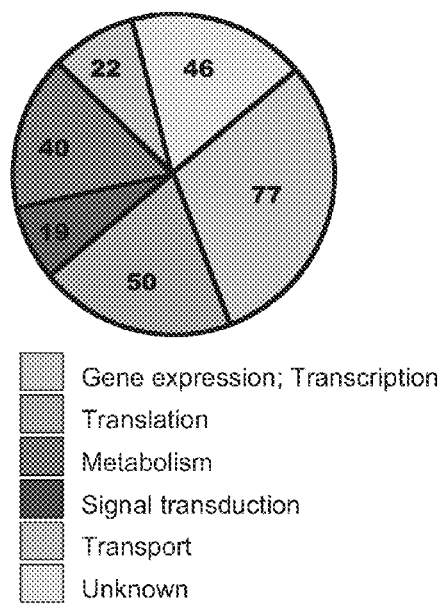

FIG. 22 shows application of MAbs for O-GlcNAc-omics. (a) Number of O-GlcNAc modified proteins pulled down with different MAbs. 254 proteins were assigned to be O-GlcNAc modified in the combination of all MAbs, where 191 appeared to be novel. (b) Distribution of 0-GlcNAc modified proteins based on their biological process categorized in HPRD.

Figure 23:
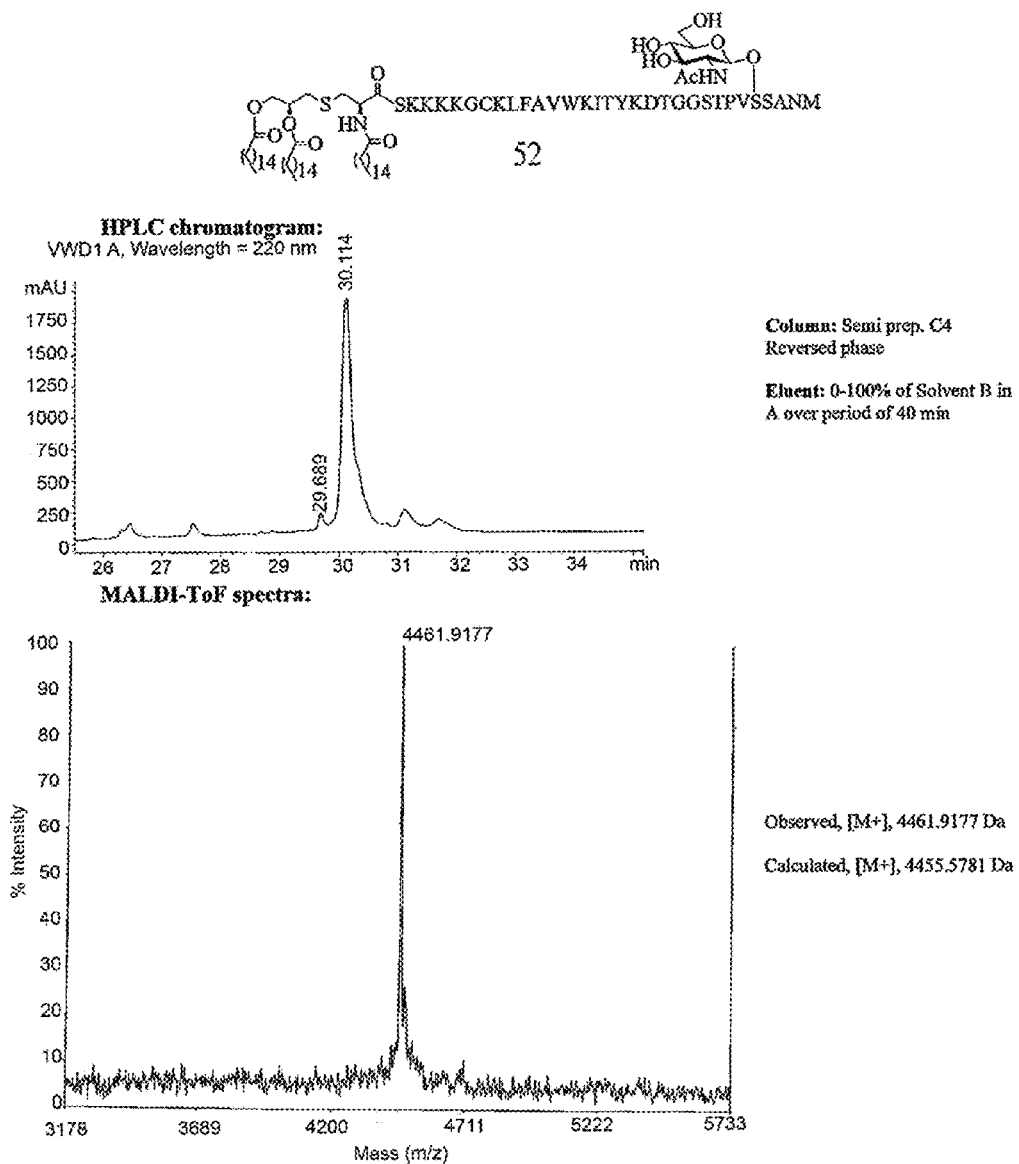
Figure 24:
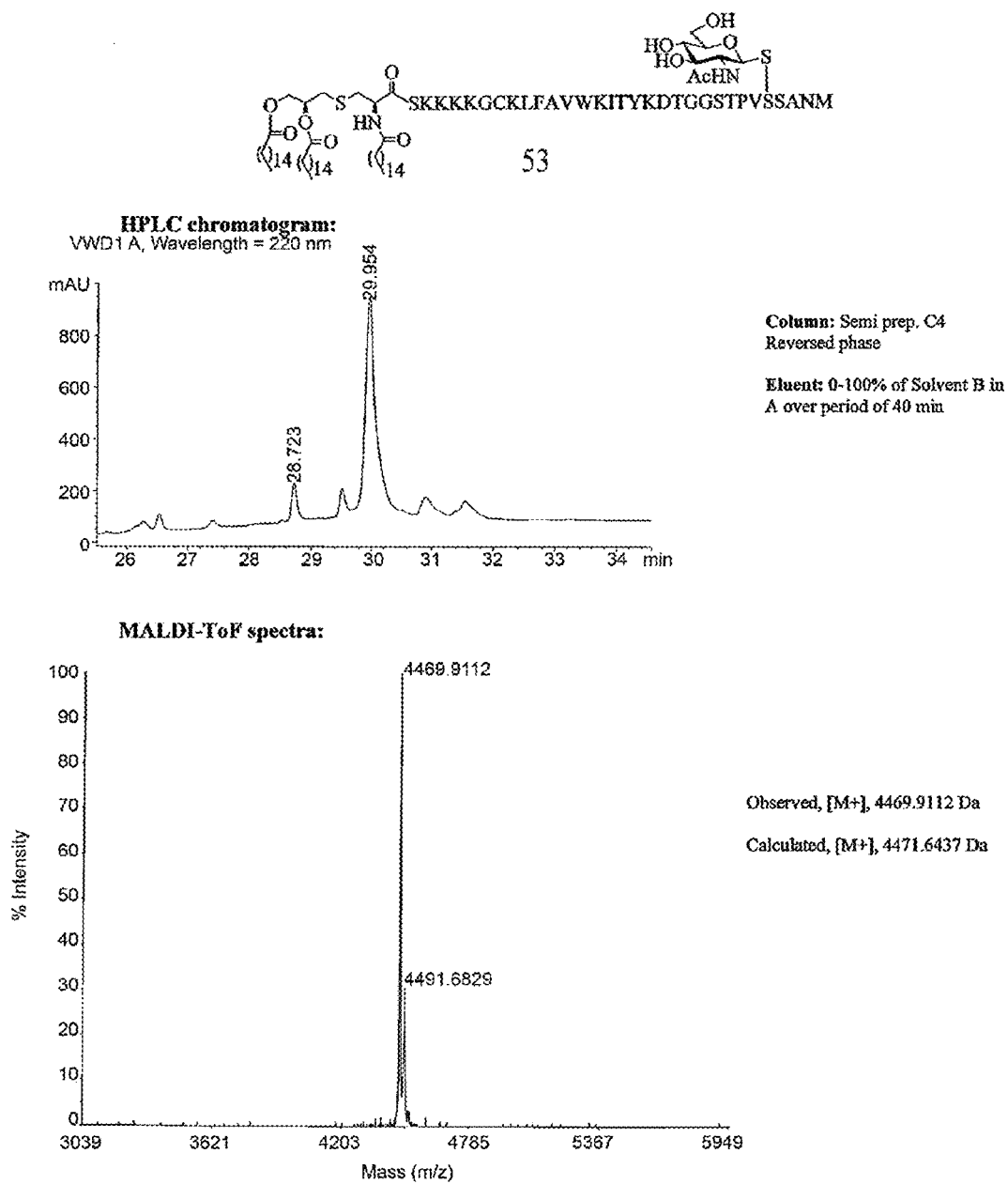
Figure 27:
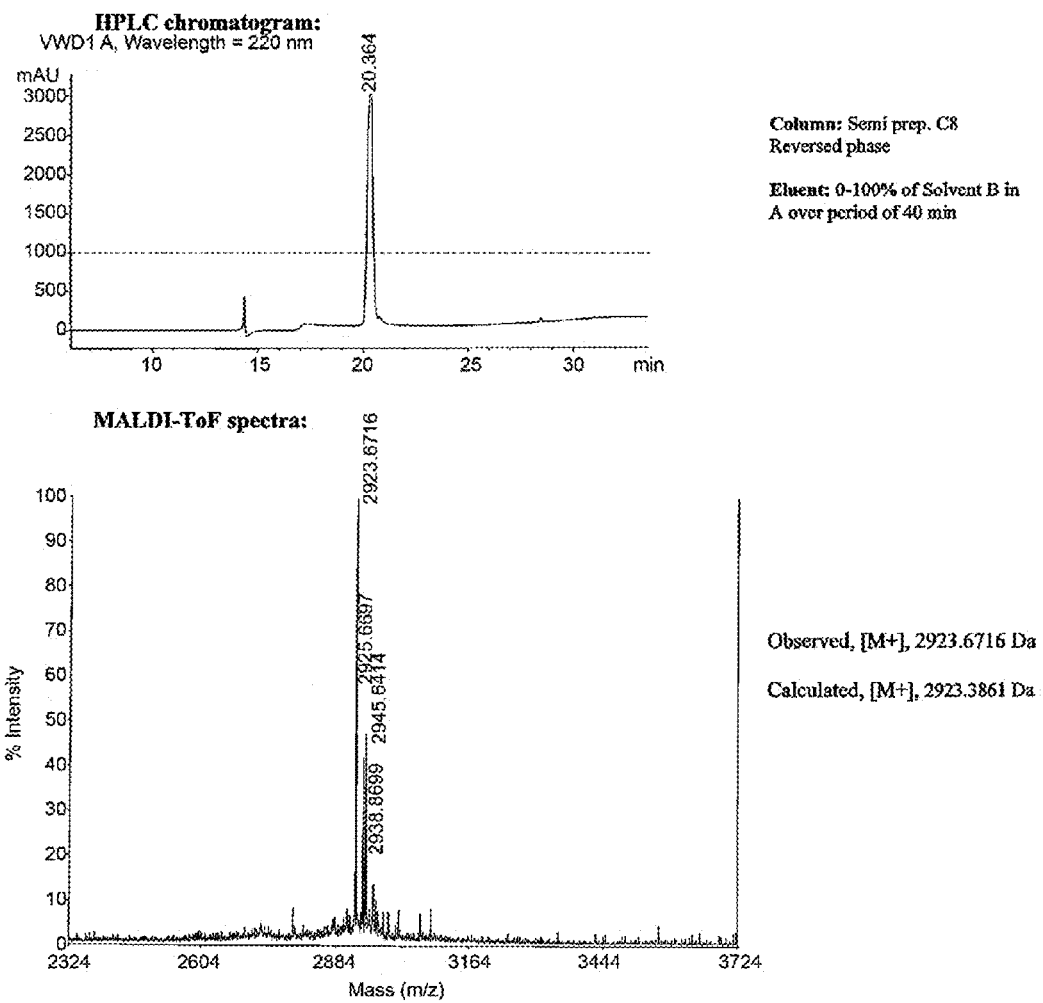
Figure 31:
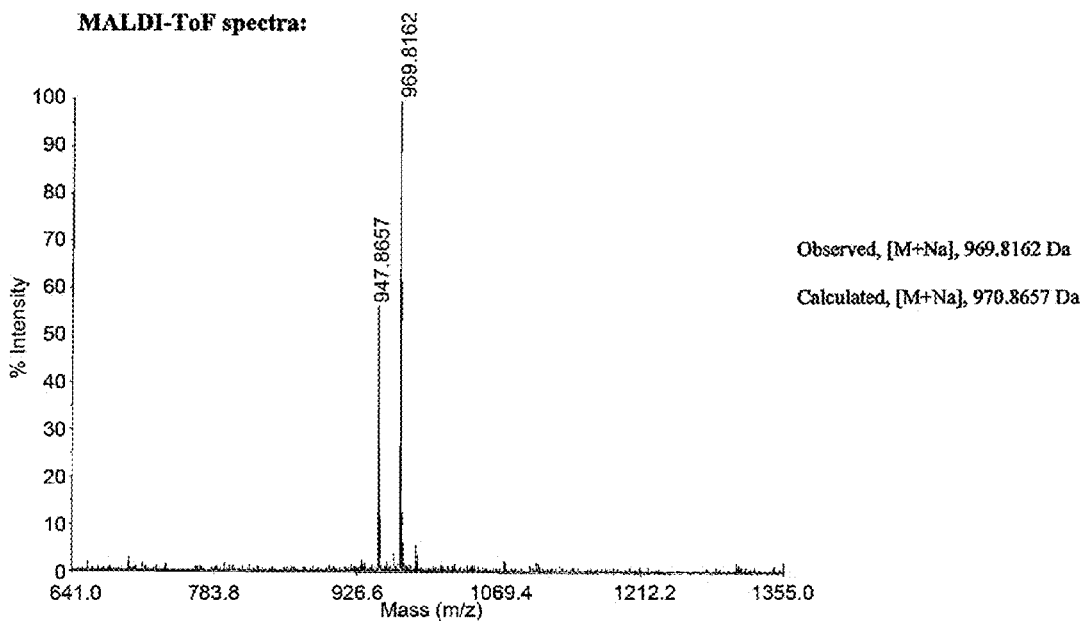

FIG. 23 shows compound 52.
FIG. 24 shows compound 53.
FIG. 25 shows compound 63.
FIG. 26 shows compound 64.
FIG. 27 shows compound 65.
FIG. 28 shows compound 66.
FIG. 29 shows compound 67; SEQ ID NO: 12.
FIG. 30 shows compound 68.
FIG. 31 shows compound 69; SEQ ID NO: 11.
FIG. 32 shows compound 70.

Figure 33:
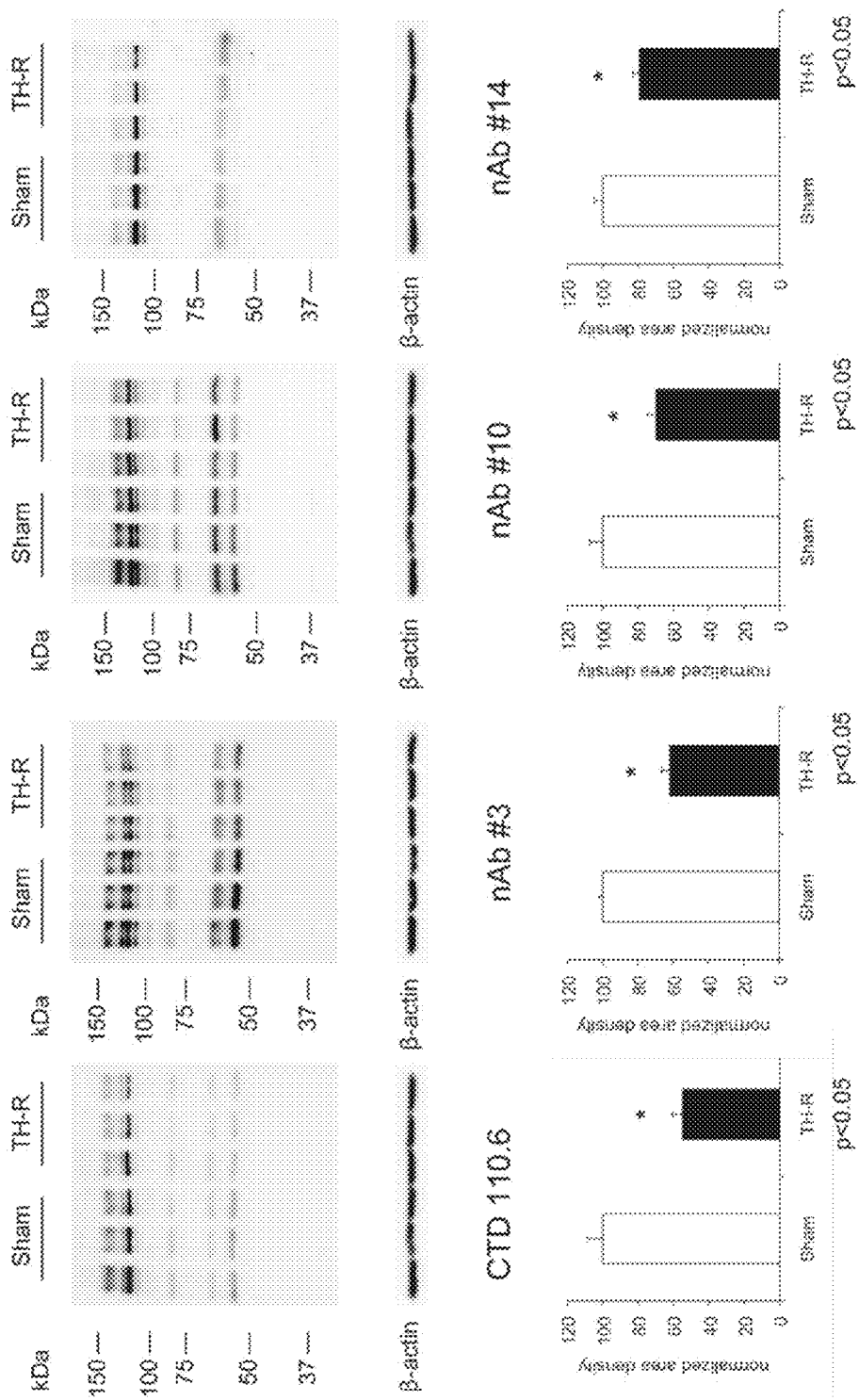

FIG. 33 shows Western blots in rat liver samples 24 hours after trauma-hemorrhage and resuscitation. Protein samples were prepared using T-PER lysis, Laemmli buffer, and 5% β-mercaptoethanol. 25 μg protein was loaded in each lane and antibody binding was visualized using enhanced chemiluminescence. Livers subjected to trauma-hemorrhage and resuscitation demonstrated significantly lower overall hepatic O-GlcNAc levels 24 hrs compared to sham controls.

Figure 34:
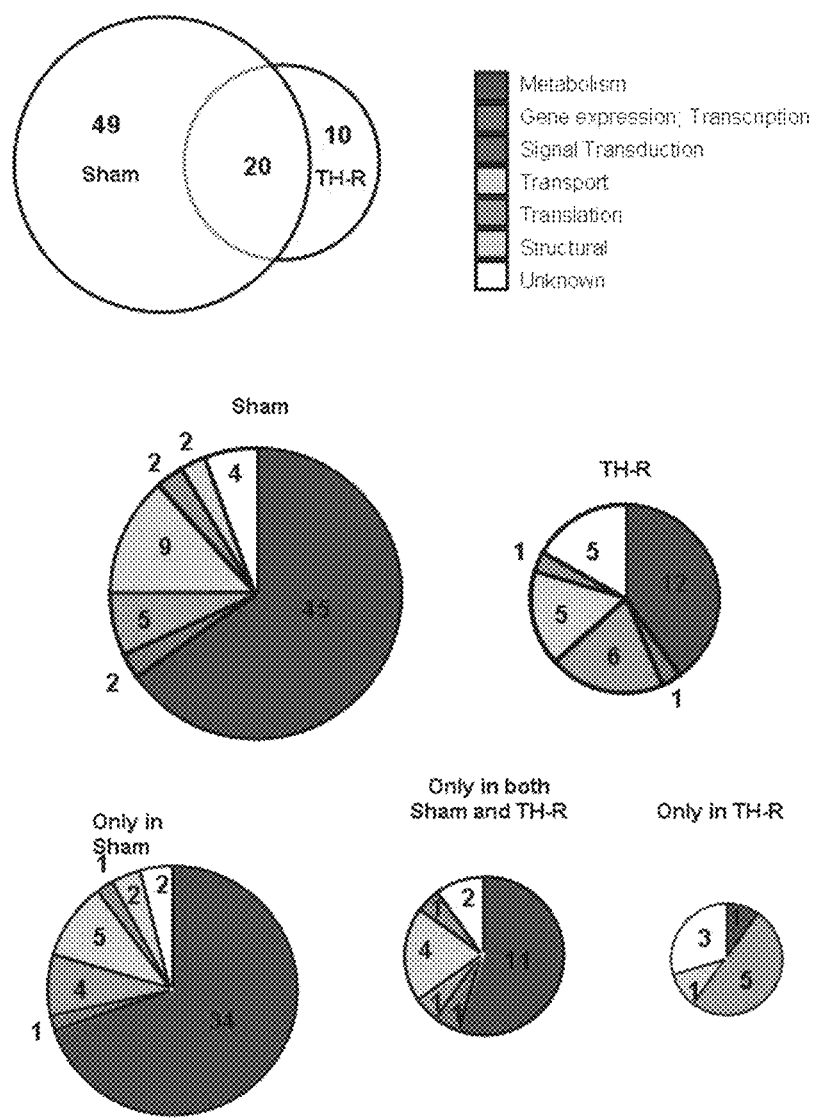

FIG. 34 shows show the distribution of the identified O-GlcNAc proteins according to function. In the control (sham) group, 96 O-GlcNAc modified proteins were identified. In the in trauma-hemorrhage and resuscitated group, 30 different O-GlcNAc modified proteins were identified.

DESCRIPTION OF ILLUSTRATIVE EMBODIMENTS

The glycolipopeptide of the invention includes at least one B-epitope, at least one T-epitope, and a lipid component. In a preferred embodiment, the glycolipopeptide consists essentially of three main components: at least one carbohydrate component that contains a B-epitope; at least one peptide component that contains a helper T-epitope; and at least one lipid component. Exemplary carbohydrate, peptide and lipid components are described herein and also, for example, in references cited herein, including Koganty et al., US Patent Publication 20060069238, published Mar. 30, 2006; see also Koganty et al., Drug Disc. Today, 1 (5): 190-198, 1996. The three components are covalently linked, either directly or indirectly, to form a single glycolipopeptide molecule. Indirect linkage involves the use of an optional linker component "L" to link two or more of the main components together. The three main components can be linked together (directly or indirectly) in any order. For example, the lipid and carbohydrate component can each be covalently linked to the peptide component to form the glycolipopeptide. Alternatively, the lipid component and the peptide component can each be covalently linked to the carbohydrate component. Likewise, the carbohydrate component and the peptide component can each be covalently linked to the lipid component. Or, all three components can be linked such that each of the three components is covalently linked to each of the other two components. Intermolecular crosslinking is also possible, as described in more detail below.

In a preferred embodiment, the glycolipopeptide of the invention contains one carbohydrate component, one peptide component, and one lipid component. In another embodiment, the glycolipopeptide contains a plurality of carbohydrate components, which may be the same, or may be different. Likewise, in another embodiment, the glycolipopeptide contains a plurality of peptide components, which may be the same, or may be different. Further, in another embodiment, the glycolipopeptide contains a plurality of lipid components, which may be the same, or may be different. Thus, various embodiments of the glycolipopeptide of the invention may contain one or more carbohydrate components, one or more peptide components, and/or one or more lipid components. For example, the concept of "multiple antigenic glycopeptides" (Bay et al., U.S. Pat. No. 6,676,946, Jan. 13, 2004, Bay et al.; WO 98/43677, published Oct. 8, 1998, Bay et al.) can be adapted for use in the present invention. High antigen density can be achieved using a core, for example a poly-lysine core, to which extended peptidic "arms" (the peptide component of the glycolipopeptide of the invention) are attached, which peptidic arms display the carbohydrate antigen components of the glycolipopeptide in clustered presentation. The lipid component of the glycolipopeptide can likewise extend from the lysine core, particularly in embodiments wherein the peptide component is attached to the lysine core via a nonterminal amino acid. High antigen density can also be achieved by using a liposome as a delivery vehicle, as exemplified in Examples II and III. Additionally or alternatively, the glycolipopeptides can be optionally cross-linked to form a multi-molecular complex, thereby increasing the antigen density.

The various carbohydrate, peptide and lipid components of the glycolipopeptide can be structurally derived from or based on, and/or can mimic, those found in naturally occurring biological molecules. The glycolipopeptide components preferably contain molecular structures or parts of structures (including epitopes) that are identical to or similar to those found in a living organism. Typically, while the components of the glycolipopeptide are derived from, are structurally based on, and/or mimic naturally occurring structures, they are prepared synthetically, using chemical or in vitro enzymatic methods, for example. In some embodiments, epitopes that are formed in the naturally occurring antigen from molecular elements that are close in space but distant from each other in terms of chemical bonding can be formed in the glycolipopeptide of the invention by a different chemical structure (with different bonding order or pattern) that forms the same or a similar epitope.

The three component glycolipopeptide of the invention can be viewed as cassette, wherein the carbohydrate component, the peptide component, and the lipid component are each independently selected for inclusion in the glycolipopeptide. Any combination (i.e., mixing and matching) of carbohydrate component, peptide component and lipid component as described herein to form a glycolipopeptide is encompassed by the invention.

Carbohydrate Component

The carbohydrate component of the glycolipopeptide can be any component that contains a carbohydrate. Examples of suitable carbohydrate components include oligosaccharides, polysaccharides and monosaccharides, and glycosylated biomolecules (glycoconjugates) such as glycoproteins, glycopeptides, glycolipids, glycosylated amino acids, DNA, or RNA. Glycosylated peptides (glycopeptides) and glycosylated amino acids, which contain one or more carbohydrate moieties as well as a peptide or amino acid, are particularly preferred as the carbohydrate component of the glycolipopeptide of the invention. An example of a glycopeptide is CD52, which is expressed on virtually all human lymphocytes and believed to play an important role in the human immune system. An example of a glycosylated amino acid is the Tn antigen. It should be understood that when the carbohydrate component is a glycopeptide, the peptide part of the glycopeptide optionally includes a T-epitope as well as a B-epitope and thus may serve as a peptide component of the glycolipopeptide. A glycopeptide that contains both a T-epitope and a B-epitope is sometimes referred to as possessing a "B-T" epitope or a "T-B" epitope. The B-epitope and the T-epitope present on the glycolipopeptide of the invention may or may not overlap.

The carbohydrate component of the glycolipopeptide of the invention includes a carbohydrate that contains one or more saccharide monomers. For example, the carbohydrate can include a monosaccharide, a disaccharide or a trisaccharide; it can include an oligosaccharide or a polysaccharide. An oligosaccharide is a oligomeric saccharide that contains two or more saccharides and is characterized by a well-defined structure. A well-defined structure is characterized by the particular identity, order, linkage positions (including branch points), and linkage stereochemistry ($\alpha$, $\beta$) of the monomers, and as a result has a defined molecular weight and composition. An oligosaccharide typically contains about 2 to about 20 or more saccharide monomers. A polysaccharide, on the other hand, is a polymeric saccharide that does not have a well defined structure; the identity, order, linkage positions (including brand points) and/or linkage stereochemistry can vary from molecule to molecule. Polysaccharides typically contain a larger number of monomeric components than oligosaccharides and thus have higher molecular weights. The term "glycan" as used herein is inclusive of both oligosaccharides and polysaccharides, and includes both branched and unbranched polymers. When the carbohydrate component contains a carbohydrate that has three or more saccharide monomers, the carbohydrate can be a linear chain or it can be a branched chain. In a preferred embodiment, the carbohydrate component contains less than about 15 saccharide monomers; more preferably in contains less than about 10 saccharide monomers.

The carbohydrate component of the glycolipopeptide includes a carbohydrate that contains a B-epitope. It should be understood that the carbohydrate may be coextensive with the B-epitope, or the carbohydrate may be inclusive of the B-epitope, or the carbohydrate may include only part of the B-epitope (i.e., the B-epitope may additionally encompass other parts of the glycolipopeptide such as the peptide component, the lipid component, and/or the linker component). An example of a glycopeptide that includes a B-epitope is the glycosylated peptide MUC-1. Thus, a carbohydrate or carbohydrate component that "comprises" a B-epitope is to be understood to mean a carbohydrate or carbohydrate component that encompasses all or part of a B-epitope that is present on the glycolipopeptide.

The B-epitope can be a naturally occurring epitope or a non-naturally occurring epitope. Preferably, two or more saccharide monomers of the carbohydrate interact to form a conformational epitope that serves as the B-epitope. A B-epitope is an epitope recognized by a B cell. Any antigenic carbohydrate that contains a B-epitope can be used as the carbohydrate component, without limitation.

Non-naturally occurring carbohydrates that can be used as components of the glycolipopeptide of the invention include glycomimetics, which are molecules that mimic the shape and features of a sugar such as a monosaccharide, disaccharide or oligosaccharide (see, e.g., Barchi, Current Pharmaceutical Design, 6(4):485-501 (March 2000); Martinez-Grau et al., Chemical Society Reviews, 27(2):155-162 (1998); Schweizer, Angewandte Chemie-International Edition, 41(2):230-253 (2002)). Glycomimetics can be engineered to supply the desired B-epitope and potentially provide greater metabolic stability.

In another embodiment, the carbohydrate component contains all or part of a self-antigen. Self-antigens are antigens that are normally present in an animal's body. They can be regarded as "self-molecules," e.g., the molecules present in or on the animal's cells, or proteins like insulin that circulate in the animal's blood. An example of a self-antigen is a carbohydrate-containing component derived from a cancer cell of the animal, such as a tumor-associated carbohydrate antigen (TACA). Typically, such self-antigens exhibit low immunogenicity. Examples include tumor-related carbohydrate B-epitope such as Le$^y$ antigen (a cancer related tetrasaccharide; e.g., Fuc$\alpha$(1,2)-Gal$\beta$(1,4)-[Fuc$\alpha$(1,3)]-GlcNAc); Globo-H antigen (e.g., L-Fuc$\alpha$(1,2)-Gal$\beta$(1,3)-GalNAc$\beta$(1,3)-Gala(1,4)-Gal$\beta$(1,4)-Glu); T antigen (e.g., Gal$\beta$(1,3)-GalNAc$\alpha$-O-Ser/Thr); STn antigen (sialyl Tn, e.g., NeuAc$\alpha$(2,6)-GalNAc$\alpha$-O-Ser/Thr); and Tn antigen (e.g., $\alpha$-GalNAc-O-Ser/Thr). Another example of a self-antigen is a glycopeptide derived from the tandem repeat of the breast tumor-associated MUC-1 of human polymorphic epithelial mucin (PEM), an epithelial mucin (Baldus et al., Crit. Rev. Clin. Lab. Sci., 41(2):189-231 (2004)). A MUC-1 glycopeptide comprises at least one Tn and/or sialyl Tn (sialyl $\alpha$-6 GalNAc, or "STn") epitope; preferably linked to a threonine (T-Tn or T-STn).

Structures of exemplary tumor-associated carbohydrate antigens (TACA) that can be used as a component of the glycolipopeptide include, without limitation, the structures shown in Schemes 1 and 2.

Scheme 1

Tn, STn, and TF antigens

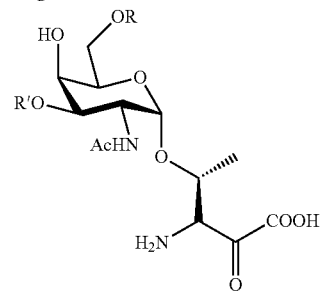

1. R = H, R' = H

2. R =
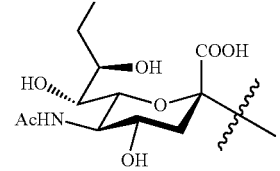
R' = H

3. R = H, R' =
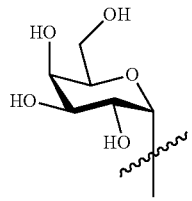

-continued

Tn3, STn3, and TF3

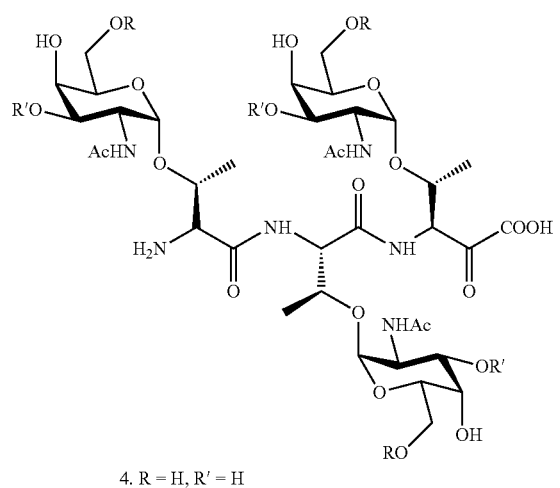

4. R = H, R' = H

5. R = 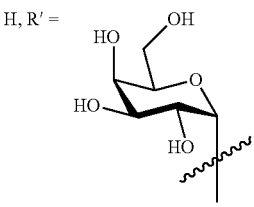 R' = H

6. R = H, R' = 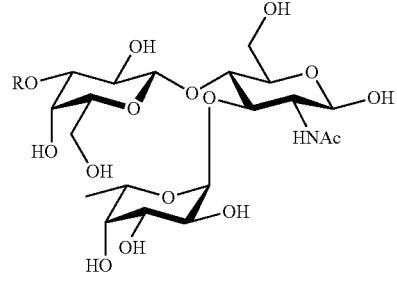

-continued

MUC-1 with Tn, STn, and TF

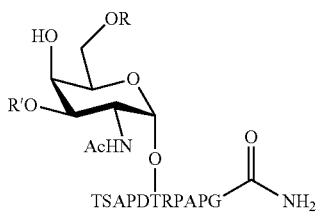

7. R = H, R' = H

8. R = 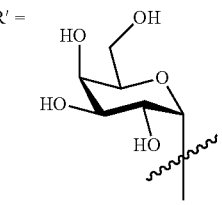 R' = H

9. R = H, R' = 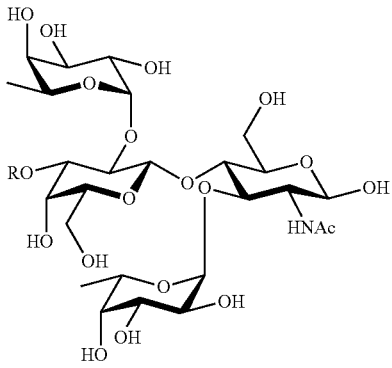

It should be noted that the Tn, STn, and TF structures shown in Scheme 1 (monomeric, trimeric, clustered) are all shown with a threonine residue. The corresponding serine analogues are also suitable structures. In the case of Tn3, STn3, TF3 and their respective clusters, all possible homo- and hetero-analogues with differences in the threonine/serine composition of the backbone are included.

Scheme 2

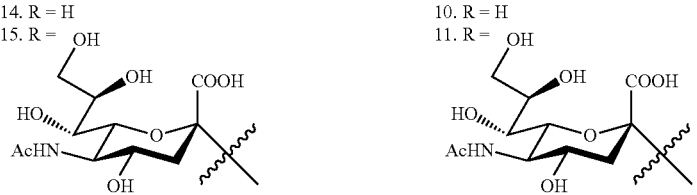

Lewis<sup>x</sup> and SLewis<sup>x</sup>

14. R = H
15. R = OH

Lewis<sup>y</sup> and SLewis<sup>y</sup>

10. R = H
11. R = OH

-continued
Lewis$^y$-lactose and SLewis$^y$-lactose
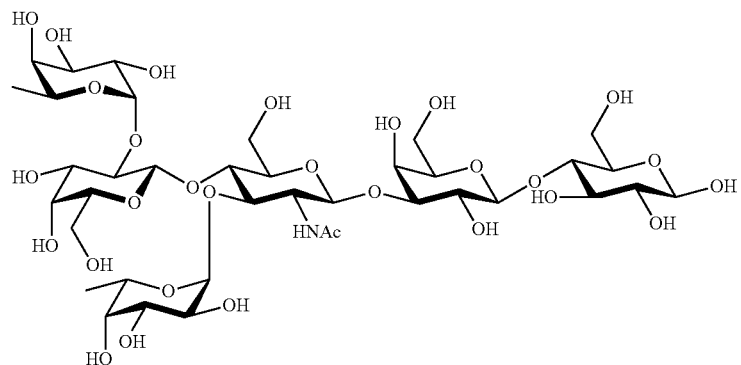
12. R = H
13. R = 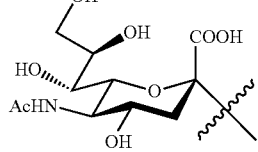
Lewis$^y$-Lewis$^x$ dimer
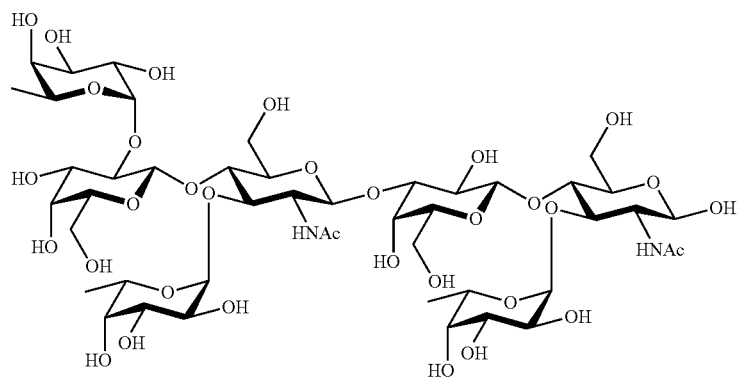
The KH-1 antigen
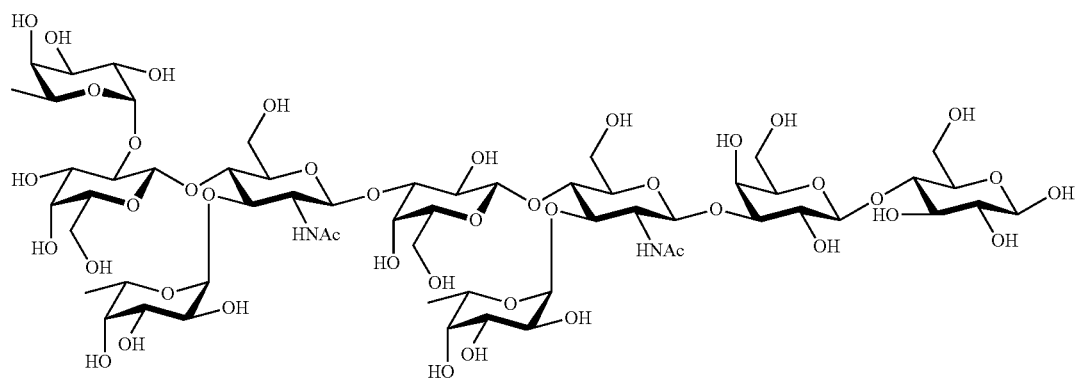

Another self-antigen for use in the carbohydrate component of the glycolipopeptide is a glycopeptide that includes an amino acid or peptide covalently linked to a monosaccharide. Preferably the monosaccharide is N-acetylglucosamine (GlcNAc) or N-acetylgalactoseamine (GalNAc). A preferred glycopeptide self-antigen is a β-N-acetylglucosamine (β-O-GlcNAc) modified peptide. Preferably the monosaccharide is O-linked to a serine or a threonine of the polypeptide. Also suitable for use as a self-antigen are the related thiol (S-linked) and amine (N-linked) analogues, some examples of which are described in Example VIII. The monosaccharide is preferably linked to the peptide via a beta (β) linkage but it may be an alpha (α) linkage. In a particularly preferred embodiment, the carbohydrate component of the glycolipopeptide of the invention (which may be coextensive with the peptide component when formulated as a glycopeptide) contains a TPVSS (SEQ ID NO:10) amino acid sequence modified by O-GlcNAc. Examples of a carbohydrate that contains a β-GlcNAc modified glycopeptide as a B-epitope are shown as compounds 52 (O-linked) and 53 (S-linked) in FIG. 15; see Example VIII.

In another embodiment, the carbohydrate component contains all or part of a carbohydrate antigen (typically a glycan) from a microorganism, preferably a pathogenic microorganism, such as a virus (e.g., a carbohydrate present on gp120, a glycoprotein derived from the HIV virus), a Gram-negative or Gram-positive bacterium (e.g., a carbohydrate derived from *Haemophilus influenzae, Streptococcus pneumoniae*, or *Neisseria meningitides*), a fungus (e.g., a 1,3-β-linked glucan) a parasitic protozoan (e.g., a GPI-anchor found in protozoan parasites such as *Leishmania* and *Trypanosoma brucei*), or a helminth. Preferably, the microorganism is a pathogenic microorganism.

An exemplary glycan from viral pathogens, Man9 from HIV-1 gp120, is shown in Scheme 3.

Scheme 3

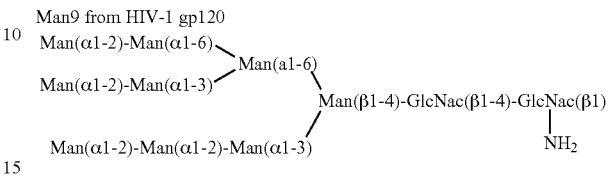

Exemplary HIV carbohydrate and glycopeptide antigens are described in Wang et al., Current Opinion in Drug Disc. & Develop., 9(2): 194-206 (2006), and include both naturally occurring HIV carbohydrates and glycopeptides, as well as synthetic carbohydrates and glycopeptides based on naturally occurring HIV carbohydrates and glycopeptides.

Exemplary HCV carbohydrate and glycopeptide antigens are described in Koppel et al. Cellular Microbiology 2005; 7(2):157-165 and Goffard et al. *J. of Virology* 2005; 79(13): 8400-8409, and include both naturally occurring HCV carbohydrates and glycopeptides, as well as synthetic carbohydrates and glycopeptides based on naturally occurring HCV carbohydrates and glycopeptides.

Exemplary glycans from bacterial pathogens are shown in Scheme 4.

Scheme 4

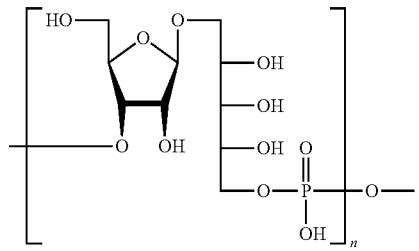

*Haemophilus influenzae* Type b, CPS repeating unit

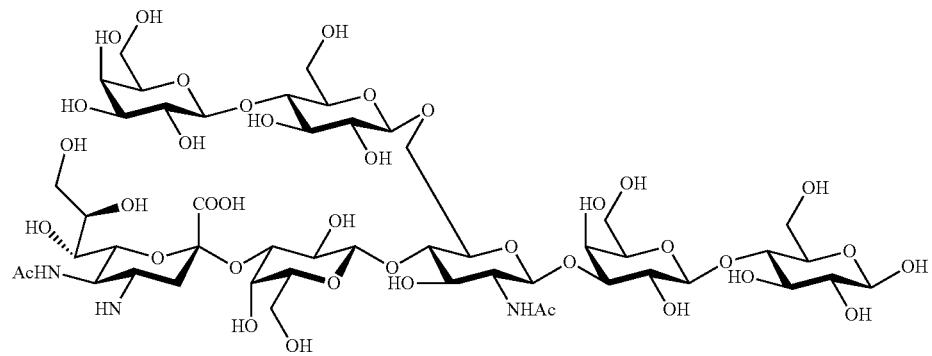

Group B type III *Streptococcus*

Cell-wall Carbohydrates from *Bacillus anthracis*, Ames, Sterne, Pasteur

Core-oligosaccharide
R = attachment O-chain
*Francisella tularencis*, Core region and O-side chain repeating unit Repeating unit of O-chain
(R = extension point)

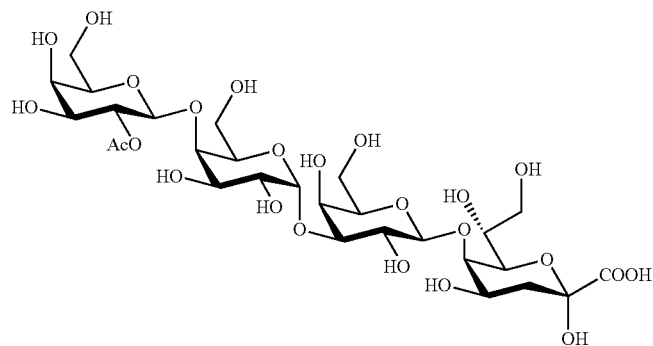
*Burkholdaria psuedomallei*, exo-polysaccharide
Exemplary glycans from protozoan pathogens are shown in Scheme 5.
Scheme 5
ethanolamine phosphate
6|
Man(α1-2)-Man(α1-2)-Man(α1-6)-Man(α1-4)-GlcNAc(α1-6)-myo-Inositol
*Plasmodium falsiparum*, Malaria parasite
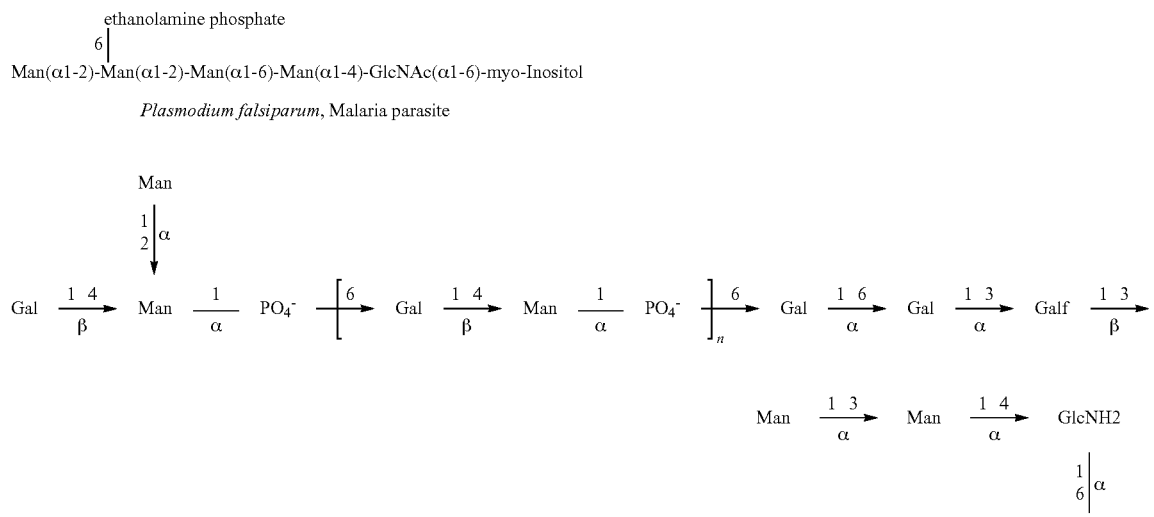
*Leishmania* species antigenic glycan
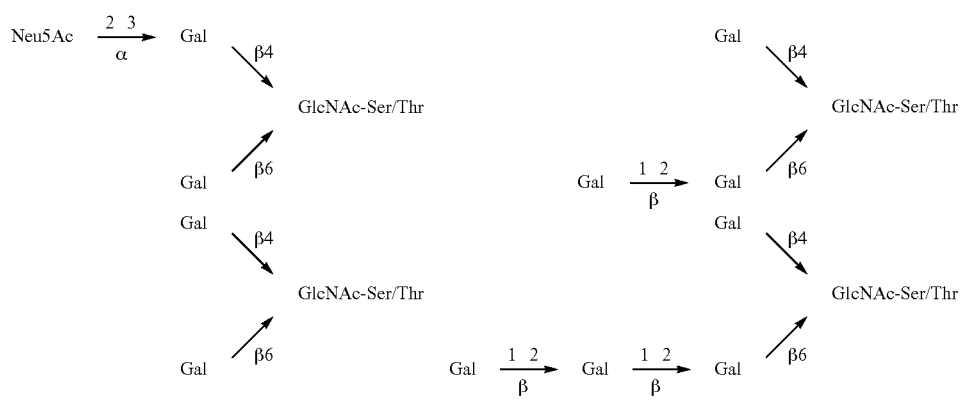
*Trypanozoma cruzi*

-continued
Scheme 6

An exemplary glycan from a fungal pathogen is shown in Scheme 6. *Cryptococcus neoformans* Capsular polysaccharide

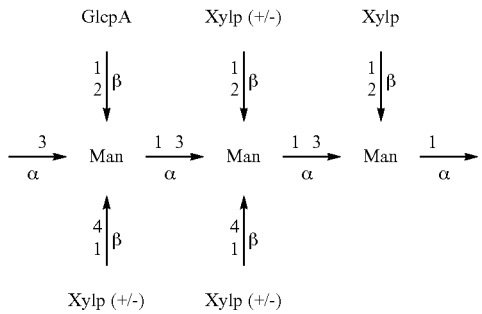

An exemplary glycan from helminth pathogen is shown in Scheme 7.

Scheme 7

*Schistosoma*

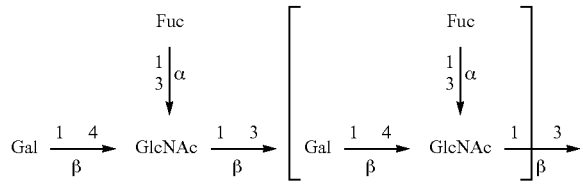

It will be appreciated by one of skill in the art that while numerous antigenic carbohydrate structures are known, many more exist, since only a small fraction of the antigenic or immunogenic carbohydrates have been identified thus far. Examples of the many carbohydrate antigens discovered thus far can be found in Kuberan et al., Curr. Org. Chem, 4, 653-677 (2000); Ouerfelli et al., Expert Rev. Vaccines 4(5):677-685 (2005); Hakomori et al., Chem. Biol. 4, 97-104 (1997); Hakomori, Acta Anat. 161, 79-90 (1998); Croce and Segal-Eiras, Drugs of Today 38(11):759-768 (2002); Mendonca-Previato et al., Curr Opin. Struct. Biol. 15(5):499-505 (2005); Jones, Anais da Academia Brasileira de Ciencias 77(2):293-324 (2005); Goldblatt, J. Med. Microbiol. 47(7):563-567 (1998); Diekman et al., Immunol. Rev., 171: 203-211, 1999; Nyame et al., Arch. Biochem. Biophys., 426 (2): 182-200, 2004; Pier, Expert Rev. Vaccines, 4 (5): 645-656, 2005; Vliegenthart, FEBS Lett., 580 (12): 2945-2950, Sp. Iss., 2006; Ada et al., Clin. Microbiol. Inf., 9 (2): 79-85, 2003; Fox et al., J. Microbiol. Meth., 54 (2): 143-152, 2003; Barber et al., J. Reprod. Immunol., 46 (2): 103-124, 2000; and Sorensen, Persp. Drug Disc. Design, 5: 154-160, 1996. Any antigenic carbohydrate derived from a mammal or from an infectious organism can be used as the carbohydrate component of the glycolipopeptide of the invention, without limitation.

Peptide Component

The peptide component of the glycolipopeptide includes a T-epitope, preferably a helper T epitope. The peptide component can be any peptide-containing structure, and can contain naturally occurring and/or non-naturally occurring amino acids and/or amino acid analogs (e.g., D-amino acids). The peptide component may be from a microorganism, such as a virus, a bacterium, a fungus, and a protozoan. The T-epitope can therefore constitute all or part of a viral antigen. Alternatively or additionally, the T-epitope can be from a mammal, and optionally constitutes all or part of a self-antigen. For example, the T-epitope can be part of a glycopeptide that is overexpressed on a cancer cell. When the peptide component of the glycolipopeptide of the invention is a glycopeptide, the peptide component may also include all or part of the B-epitope, as described elsewhere herein. More generally, it should be understood that the peptide component of the glycolipopeptide may be coextensive with the T-epitope, or the peptide component may be inclusive of the T-epitope, or the peptide component may include only part of the T-epitope (i.e., the T-epitope may additionally encompass other parts of the glycolipopeptide such as the carbohydrate component, the lipid component, and/or the linker component). Thus, a peptide or peptide component that "comprises" a T-epitope is to be understood to mean a peptide or peptide component that encompasses all or part of a T-epitope that is present on the glycolipopeptide.

Preferably peptide component contains fewer than about 20 amino acids and/or amino acid analogs. Examples of peptide components include the universal helper T peptide, QYIKANSKFIGITEL ("QYI") (SEQ ID NO:1), the universal helper T peptide YAFKYARHANVGRNAFELFL ("YAF") (SEQ ID NO:2), the murine helper T peptide KLFAVWKITYKDT ("KLF") (SEQ ID NO:3) derived from polio virus, and pan-DR binding (PADRE) peptides (PCT WO 95/07707; Alexander et al., Immunity 1:751-761 (1994); Alexander et al., J. Immunol. 2000 Feb. 1; 164(3): 1625-33; U.S. Pat. No. 6,413,935 (Sette et al., Jul. 2, 2002)).

Preferred immunogenic peptide components for use in the glycolipopeptide of the invention include universal (degenerate or "promiscuous") helper T-cell peptides, which are peptides that are immunogenic in individuals of many major histocompatibility complex (MHC) haplotypes. Numerous universal helper T-cell peptide structures are known; however, it should be understood that additional universal T-epitopes, including some with similar or even higher potency, will be identified in the future, and such peptides are well-suited for use as the peptide component the glycolipopeptide of the invention.

Exemplary T-cell peptides for use in the glycolipopeptide include, without limitation: Synthetic, nonnatural PADRE peptide, DAla-Lys-Cha-Val-Ala-Ala-Trp-Thr-Leu-Lys-Ala-Ala-DA1a, including all the analogues described by J Alexander et al. in Immunity, Vol. 1, 751-761, 1994;

Peptides derived from tetanus toxin, e.g., (TT830-843) QYIKANSKFIGITEL (SEQ ID NO:1), (TT1084-1099)

VSIDKFRIFCKANPK (SEQ ID NO:4), (TT1174-1189)
LKFIIKRYTPNNEIDS (SEQ ID NO:5), (TT1064-1079)
IREDNNITLKLDRCNN (SEQ ID NO:6), and (TT947-967)
FNNFTVSFWLRVPKVSASHLE (SEQ ID NO:7);

Peptides derived from polio virus, e.g., KLFAVWKI-TYKDT (SEQ ID NO:3);

Peptides derived from *Neisseria meningitidis*, e.g., YAFKYARHANVGRNAFELFL (SEQ ID NO:8); and Peptides derived from *P. falsiparum* CSP, e.g., EKKIAK-MEKASSVFNVNN (SEQ ID NO:9).

The peptide component of the glycolipopeptide contains a T-epitope. A T-epitope is an epitope recognized by a T cell. The T-epitope can elicit a CD4+ response, thereby stimulating the production of helper T cells; and/or it can elicit a CD8+ response, thereby stimulating the production of cytotoxic lymphocytes. Preferably, the T-epitope is an epitope that stimulates the production of helper T cells (i.e., a helper T-cell epitope or Th-epitope), which in turn makes possible a humoral response to the B-epitope supplied by the carbohydrate component of the glycolipopeptide of the invention.

It should be understood that the glycolipopeptide of the invention can contain multiple T-epitopes, which may be the same or different. Further, T-epitopes may be present on the carbohydrate component and/or the lipid component (e.g., in embodiments that include glycopeptides and/or glycolipids as the carbohydrate and/or lipid components) in addition to, or in place of, the peptide component.

In one embodiment, the B-epitopes and the T-epitopes are homologous; that is, they are derived from the same organism. For example, in a glycolipopeptide suitable for use as a vaccine against a microbial pathogen, the T-epitope in addition to the B-epitope may be epitopes that are present in the microbial pathogen. In another embodiment, the B-epitopes and the T-epitopes are heterologous; that is, they are not derived from the same organism. For example, a glycolipopeptide suitable for use as an anti-cancer vaccine may have a B-cell epitope from a cancer cell, but a T-cell epitope from a bacterium or virus.

Lipid Component

It was originally postulated that a glycopeptide having just two main components, i.e., a carbohydrate component and a peptide component, would be effective to elicit an immune response in an animal. The helper T-cell epitope was expected to induce a T-cell dependent immune response, resulting in the production of IgG antibodies against a tumor-related carbohydrate B-epitope such as Le$^y$ and Tn. However, in some applications, the two component vaccine was not found to be very effective. It was postulated that the B-cell and helper T-cell epitopes lack the ability to provide appropriate "danger signals" for dendritic cell (DC) maturation. To remedy this problem, a lipid component was included in the compound, resulting in the glycolipopeptide of the invention.

The lipid component can be any lipid-containing component, such as a lipopeptide, fatty acid, phospholipid, steroid, or a lipidated amino acids and glycolipids such as Lipid A derivatives. Preferably, the lipid component is non-antigenic; that is, it does not elicit antibodies directed against specific regions of the lipid component. However, the lipid component may and preferably does serve as an immunoadjuvant. The lipid component can serve as a carrier or delivery system for the multi-epitopic glycolipopeptide. It assists with incorporation of the glycolipopeptide into a vesicle or liposome to facilitate delivery of the glycolipopeptide to a target cell, and it enhances uptake by target cells, such as dendritic cells. Further, the lipid component stimulates the production of cytokines.

One class of preferred lipid components for use in the glycolipopeptide of the invention comprises molecular ligands of the various Toll-like receptors (TLRs). There are many known subclasses of Toll-like receptors (e.g., TLR1, TLR2, TRL3, TLR4, TLR5, TLR6, TLR7, TLR8, TLR9, TLR10, TLR11, TLR12, TLR13, TLR14, TLR15 and TLR16). See Roach et al., PNAS 2005, 102:9577-9582, for a review of the relationships between and evolution of Toll-like receptors; and Duin et al., TRENDS Immunol., 2006, 27:49-55, for a discussion of TLR signaling in vaccination. Particularly preferred are lipid components that interact with TLR2 and TLR4. TLR2 is involved in the recognition of a wide array of microbial molecules from Gram-positive and Gram-negative bacteria, as well as mycoplasma and yeast. TLR2 ligands include lipoglycans, lipopolysaccharides, lipoteichoic acids and peptidoglycans. TLR4 recognizes Gram-negative lipopolysaccharide (LPS) and lipid A, its toxic moiety. TLR ligands are widely available commercially, for example from Apotech and InvivoGen. Preferably, the lipid component is a TLR ligand that facilitates uptake of the glycolipopeptide by antigen presenting cells (see Example III).

Suitable lipids for use as the lipid component of the glycolipopeptide of the invention include PamCys-type lipid structures, such as those derived from Pam$_3$Cys (S—[(R)-2,3-dipalmitoyloxy-propyl]-N-palmitoyl-(R)-cysteine) and Pam$_2$Cys (S—[(R)-2,3-dipalmitoyloxy-propyl]-(R)-cysteine), which lacks the N-palmitoyl group of Pam$_3$Cys. Pam$_3$Cys and Pam$_2$Cys are derived from the immunologically active N-terminal sequence of the principal lipoprotein of *Escherichia coli*. This class of lipids also includes Pam$_3$CysSK$_4$ (N-palmitoyl-S—[(R)-2,3-bis(palmitoyloxy)-propyl]-(R)-cysteinyl-(S)-seryl-(S)-lysine-(S)-lysine-(S)-lysine-(S)-lysyne) and Pam$_2$CysSK$_4$ (S—[(R)-2,3-bis(palmitoyloxy)-propyl]-(R)-cysteinyl-(S)-seryl-(S)-lysine-(S)-lysine-(S)-lysine-(S)-lysyne), which lacks the N-palmitoyl group of Pam$_3$CysSK4; it should be understood that the number of lysines in these structures can be 0, 1, 2, 3, 4, 5 or more (i.e., K$_n$ where n=0, 1, 2, 3, 4, 5 or more).

Another preferred class of lipids includes Lipid A (LpA) type lipids, such as Lipid As derived from *E. coli, S. typhimurium* and *Neisseria meningitidis*. The Lipid As can be attached to the carbohydrate component (containing a B-epitope) of the glycolipopeptide and/or to the peptide component (containing a T-epitope) through a linker that is connected, for example, to the anomeric center or anomeric phosphate, the C-4' phosphate or the C-6' position. The phosphates can be modified, for example, to include one or more phosphate ethanolamine diesters. Exemplary Lipid A derivatives are described in, for example, Caroff et al., Microbes Infect. 4, 915-926 (2002); Raetz et al., Annu Rev. Biochem. 71, 635-700 (2002); and Dixon et al., J. Dent. Res. 84, 584-595 (2005).

Below, in Scheme 8, are exemplary immunogenic lipids for the incorporation into the glycolipopeptide of the invention. The first structure in the first row is Pam$_3$CysSK$_n$; the second structure in the first row is Pam$_2$CysSK$_n$; and the last 4 structures are Lipid A derivatives.

Scheme 8

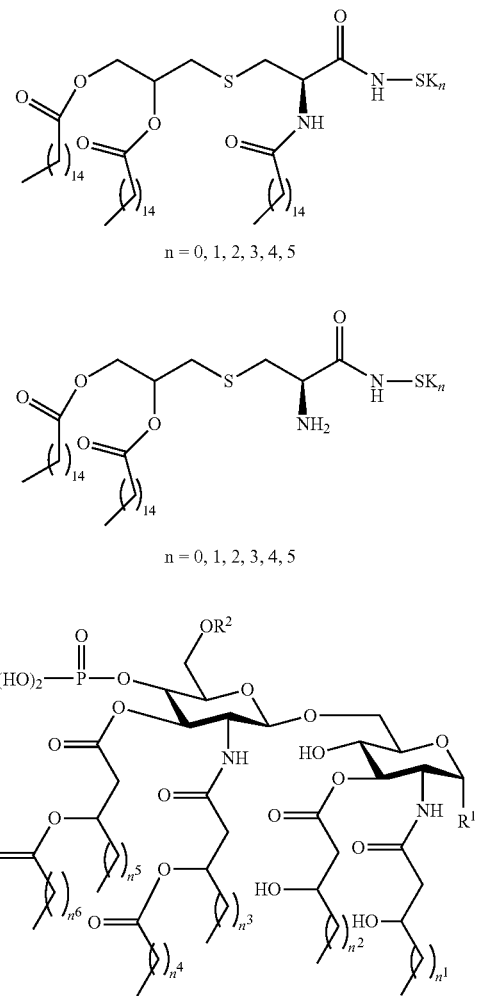

n = 0, 1, 2, 3, 4, 5

$R^1 = OP(O)(OH)_2$, or $R^1 = H$; $R^2 =$ or KDO
$n^1, n^2, n^3, n^4, n^5, n^6, = 8, 9, 10, 11, 12, 13, 14, 15, 16, 17$ or $18$

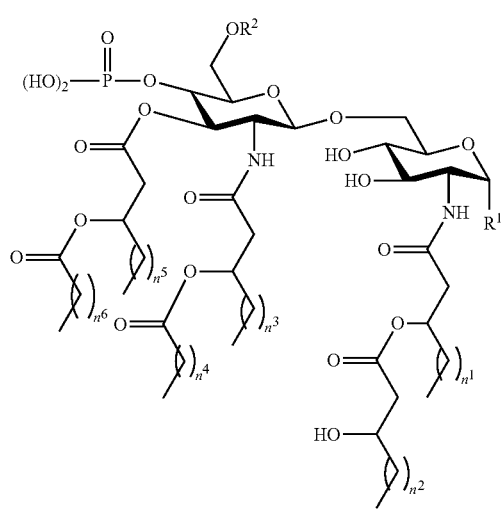

$R = OP(O)(OH)_2$, or $R = H$; $R^2 =$ or KDO
$n^1, n^2, n^3, n^4, n^5, n^6, = 8, 9, 10, 11, 12, 13, 14, 15, 16, 17$ or $18$

-continued

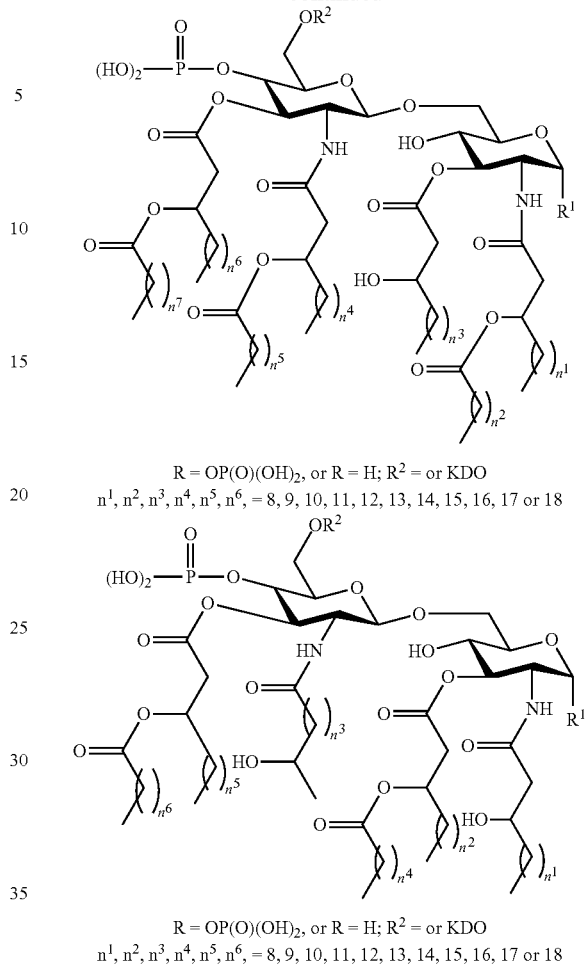

$R = OP(O)(OH)_2$, or $R = H$; $R^2 =$ or KDO
$n^1, n^2, n^3, n^4, n^5, n^6, = 8, 9, 10, 11, 12, 13, 14, 15, 16, 17$ or $18$ $R = OP(O)(OH)_2$, or $R = H$; $R^2 =$ or KDO
$n^1, n^2, n^3, n^4, n^5, n^6, = 8, 9, 10, 11, 12, 13, 14, 15, 16, 17$ or $18$

Lipids that are structurally based on Pam$_3$Cys are particularly preferred for use as the lipid component. Pam$_3$Cys is derived from the immunologically active N-terminal sequence of the principal lipoprotein of *Escherichia coli*. These lipopeptides are powerful immunoadjuvants. Recent studies have shown that Pam$_3$Cys exerts its activity through the interaction with Toll-like receptor-2 (TLR2).

Without being bound by theory, it is believed that interaction between the lipid component and a TLR results in the production of pro-inflammatory cytokines and chemokines, which, in turn, stimulates antigen-presenting cells (APCs), and thus, initiating helper T cell development and activation. Covalent attachment of the TLR ligand to the B- and T-epitopes ensures that cytokines are produced at the site where the vaccine interacts with immune cells. This leads to a high local concentration of cytokines facilitating maturation of relevant immune cells. The lipopeptide promotes selective targeting and uptake by antigen presenting cells and B-lymphocytes. Additionally, the lipopeptide facilitates the incorporation of the glycolipopeptide into liposomes. Liposomes have attracted interest as vectors in vaccine design due to their low intrinsic immunogenicity, thus, avoiding undesirable carrier-induced immune responses.

Optional Linker

One or more linkers ("L") are optionally used for assembly of the three components of the glycolipopeptide. In one embodiment, the linker is a bifunctional linker that has functional groups in two different places, preferably at a first and second end, in order to covalently link two of the three components together. A bifunctional linker can be either homofunctional (i.e., containing two identical functional groups) or heterofunctional (i.e., containing two different functional groups). In another embodiment, the linker is trifunctional (hetero- or homo-) and can link all three components of the glycolipopeptide together. A suitable functional group has reactivity toward or comprises any of the following: amino, alcohol, carboxylic acid, sulfhydryl, alkene, alkyne, azide, thioester, ketone, aldehyde, or hydrazine. An amino acid, e.g., cysteine, can constitute a linker.

Bifunctional linkers are exemplified in Scheme 9.

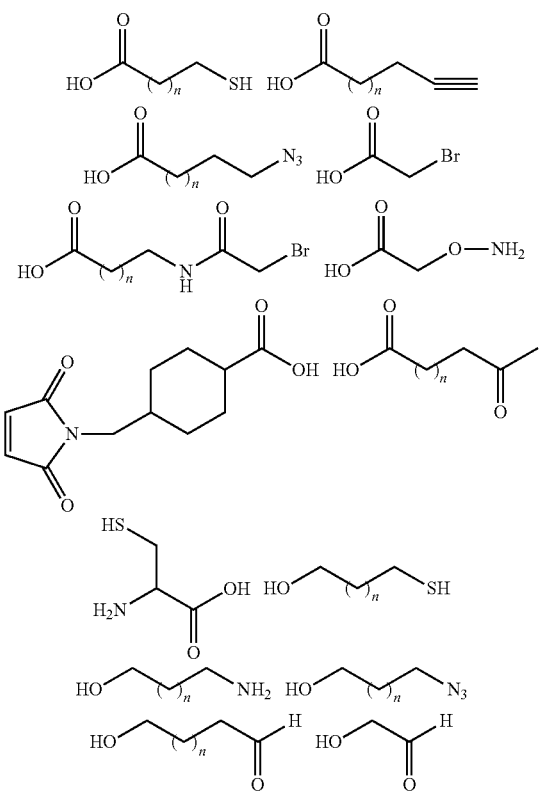

n = 1, 2, 3 ...

Figure 1:
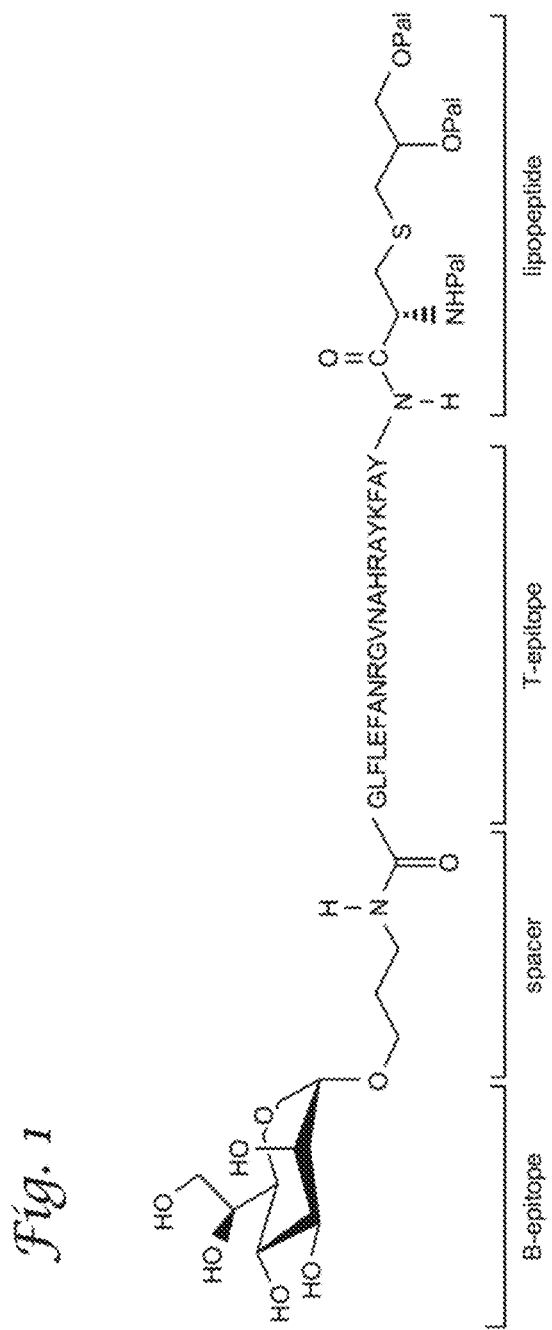
FIG. 1 shows an exemplary glycolipopeptide of the invention.

FIG. 1 shows an exemplary fully synthetic glycolipopeptide of the invention containing a carbohydrate-based B-epitope, a peptide T-epitope and a lipopeptide. The compound shown in FIG. 1 contains a L-glycero-D-mannoheptose sugar that acts as a B-epitope, the peptide sequence YAFKYARHANVGRNAFELFL (SEQ ID NO:2) that has been identified as a MHC class II restricted recognition site for human T-cells and is derived from an outer-membrane protein of *Neisseria meningitidis*, and the lipopeptide S-2-3 [dipalmitoyloxy]-(R/S)-propyl-N-palmitoyl-R-Cysteine (Pam$_3$Cys). As noted elsewhere herein, lipopeptide Pam$_3$Cys and the related compound Pam$_3$CysSK$_4$ are highly potent B-cell and macrophage activators.

Methods of making the glycolipopeptide, as exemplified in the Examples, are also encompassed by the invention. Preferably, the method for making the glycolipopeptide utilizes chemical synthesis, resulting in a fully synthetic glycolipopeptide. In embodiments that make use of one or more linkers, the optional linker component is functionalized so as to facilitate covalent linkage of one of the main components to another of the main components. For example, the linker can be functionalized at each end with a thiol-reactive group, such as maleimide or bromoacetyl, and the components to be joined are modified to include reactive thiols. Other options for ligation chemistry include Native Chemical Ligation, the Staudinger Ligation and Huisgen ligation (also known as "Click Chemistry"). Example II illustrates how the carbohydrate component, in that case an oligosaccharide, and the peptide component can be functionalized with a thiol-containing linker. Preferably, the linker component, if used, is nonantigenic.

The glycolipopeptide of the invention is capable of generating an immune response in a mammal. The glycolipopeptide is antigenic, in that it can generate a humoral response, resulting in the activation of B cells and production of antibodies (immunoglobulins) such as IgM. Additionally, the glycolipopeptide is immunogenic, in that it can generate a cellular response; for example, it facilitates the activation of T cells, particularly helper T cells which are also instrumental in the generation of a more complex antibody response that includes the production of IgG. Ultimately, the immune response elicited in the animal includes the production of anti-carbohydrate antibodies.

In another aspect, the glycolipopeptide of the invention is used to produce a polyclonal or monoclonal antibody that recognizes either or both of the carbohydrate component and the peptide component. The invention encompasses the method of making said antibodies, as well as the antibodies themselves and hybridomas that produce monoclonal antibodies of the invention.

The immunogenic glycolipopeptide of the invention for use in the production an antibody can contain any carbohydrate component described herein, without limitation. Preferably it contains, as its carbohydrate component, a glycopeptide. The glycopeptide includes a glycosylated peptide sequence that includes a carbohydrate moiety, such as a saccharide. The saccharide can be a monosaccharide, an oligosaccharide or a polysaccharide. Preferably, the carbohydrate component of the glycolipopeptide used to generate the antibodies contains a self-antigen as described above. Advantageously, even if carbohydrate component, e.g., the glycopeptide, is poorly antigenic (such as a self-antigen), covalent attachment of the carbohydrate component to the peptide component and the lipid component produces a remarkably immunogenic glycolipopeptide.

Antibodies of the invention that bind to the glycolipopeptide preferably bind to a B-epitope that includes the saccharide moiety and, in a preferred embodiment, at least part of the peptide that forms the glycopeptide. A preferred antibody binds to the glycopeptide used as the carbohydrate component, but does not bind to the deglycosylated peptide or to the saccharide residue alone. The selectivity of an antibody for the glycopeptide can be determined using, for example, the methods set forth in Examples VIII and X.

When used to generate antibodies, the glycolipopeptide of the invention successfully generates high affinity IgG antibodies. This is especially surprising and unexpected for embodiments of the glycolipopeptide having a poorly antigenic carbohydrate component, such as a self-antigen. The polyclonal or monoclonal antibody is thus preferably an IgG isotype antibody. Without being bound by theory, it is believed that the glycolipopeptide of the invention is a superior antigen (compared to the non-lipidated glycopeptide) because it stimulates local production of cytokines, upregulates co-stimulatory proteins, enhances uptake by macrophages and dendritic cells and/or avoids epitope suppression.

Antibodies of the invention include but are not limited to those that recognize B-epitopes that contain O-GlcNAc, O-GalNAc, O-mannose, or other saccharide modifications. Other B-epitopes that may be recognized by the antibodies of the invention include those that contain fragments of glycosaminoglycans such as heparin, heparan sulfate, chondroitin sulfate, dermatan sulfate, keratan sulfate, hyaluronan, and generally any glycosaminoglycan. In the case of a glycosaminoglycan formed by repeating disaccharide units, the B-epitope may contain one or more disaccharide unit. B-epitopes recognized by the antibodies of the invention may contain pentose, hexose or other sugar moieties including acids, including but not limited to glucuronic acid, iduronic acid, hyaluronic acid, glucose, galactose, galactosamine, glucosamine and the like. The antibodies of the invention are preferably produced using, as an immunogen, the glycolipopeptide of the invention wherein the carbohydrate component contains the B-epitope of interest. Analogues of naturally occurring B-epitopes, such as those containing N-linked or S-linked structures or glycomimetics, can be used as the carbohydrate component, for example to make the glycolipopeptide immunogen more metabolically stable.

The antibodies produced using the glycolipopeptide of the invention advantageously include high affinity IgG antibodies that recognize a broad spectrum of glycoproteins. Thus, even though antibodies produced using the glycolipopeptide of the invention as an immunogen are specific for the glycopeptide used as the carbohydrate component, they may bind to a broad spectrum of glycoproteins. An antibody with relatively broad selectivity for glycosylated peptides or proteins containing a B-epitope component of interest is referred to herein as a "pan-specific" antibody. A polyclonal or monoclonal antibody of the invention may be either pan-specific or site-specific. An antibody that is pan-specific, as the term is used herein, is one that specifically recognizes a selected B-epitope, for example a B-epitope that contains O-GlcNAc, but that has a relatively broad selectivity for proteins and peptides containing the B-epitope. A pan-specific antibody is thus able to bind multiple different glycosylated proteins or peptides that contain the B-epitope of interest, although it does not necessarily bind all glycosylated proteins or peptides that contain the selected B-epitope. See, for example, Tables 8-11 in Examples IX and X which show binding selectivity for several pan-specific monoclonal antibodies, including the monoclonal antibodies produced by hybridoma cell lines 1F5.D6 (Mab14), 9D1.E4 (Mab10), 18B10.C7 (Mab3) and the commercially available monoclonal IgM antibody CTD110.6 (Covance Research Products, Inc.). A site-specific antibody, on the other hand, typically shows greater selectivity for a particular individual glycosylated protein or peptide.

Without intending to be being bound by theory, the different glycoproteins recognized by the pan-specific antibodies of the invention may share a substantially similar or identical (glyco)peptide sequence (i.e., primary sequence) or a substantially similar secondary or tertiary structure at the glycosylation site, thereby resulting in a broad spectrum of binding targets being recognized by the antibody. A secondary or tertiary epitope structure shared by the O-GlcNAc modified glycoproteins to which an antibody binds may advantageously be maintained in the glycolipopeptide immunogen, as evidenced by the successful production of IgG antibodies that recognize the broad spectrum of glycoproteins.

Preferably, the antibody of the invention binds to a plurality of glycosylated proteins or peptides having an epitope comprising O-GlcNAc, O-GalNAc, or other saccharide modifications, but does not detectably bind a protein or peptide that does not contain the saccharide. More preferably, the antibody binds to a protein or peptide having an epitope comprising O-GlcNAc, O-GalNAc, or other saccharide modifications, but does not detectably bind the same protein or peptide that does not contain O-GlcNAc, O-GalNAc, or other saccharide modifications.

An example of a preferred polyclonal or monoclonal antibody is one that binds to a glycopeptide that contains an O-GlcNAc monosaccharide residue. In a particularly preferred embodiment, the antibody has a relatively broad selectivity for O-GlcNAc modified proteins. For example, many proteins of interest have a TPVSS (SEQ ID NO:10) sequence modified by 0-GlcNAc, and a preferred monoclonal antibody recognizes this and/or similar glycosylated peptide sequences. Examples of preferred monoclonal antibodies specific for O-GlcNAc modified sequences include the monoclonal antibodies produced by hybridoma cell lines 1F5.D6, 9D1.E4, 18B10.C7 and 5H11.H6. These monoclonal antibodies were produced using compounds 52 and/or 53 as an immunogen. Thus, in one embodiment, the antibody of the invention binds to the carbohydrate component of compound 52 or of compound 53. Hybridoma cell lines 1F5.D6, 9D1.E4 and 18B10.C7 were deposited with the American Type Culture Collection (ATCC), 10801 University Blvd., Manassas, Va., 20110-2209, USA, on Jul. 1, 2008, and assigned ATCC deposit numbers PTA-9339, PTA-9340, and PTA-9341, respectively. The invention encompasses the hybridoma cell lines as well as the monoclonal antibodies they produce.

Another example of a preferred polyclonal or monoclonal antibody is one that binds to a heparan sulfate fragment.

It is to be understood that any carbohydrate or glycopeptide of clinical significance or interest can be incorporated as the carbohydrate and/or peptide component of the glycolipopeptide of the invention and used to generate polyclonal and monoclonal antibodies according to the method of the invention. Such carbohydrates and peptides include those of medical and veterinary interest, as well as those with other commercial or research applications. It should be understood that the monoclonal and polyclonal antibodies of the invention are not limited to those that recognize any particular ligand but include, without limitation and by way of example only, antibodies against any type of tumor associated carbohydrate antigen (TACA) and against any saccharides derived from any microorganism.

To recapitulate, use of the glycolipopeptide of the invention to make monoclonal antibody of the invention is surprisingly effective in producing monoclonal IgG antibodies having high affinity for their carbohydrate or glycopeptide antigen, even when the antigens are poorly antigenic. This opens the door for the creation of antibodies useful to study, diagnose and treat immune-related diseases or diseases having autoimmune or inflammatory components including cancer, diabetes type II, allergies, asthma, Crohn's disease, Alzheimer's disease, muscular dystrophy, microbial infections and the like. Monoclonal antibodies of the invention that recognize O-GlcNAc-modified glycoproteins, for example, are far superior to commercially available antibodies such CTD110.6 (Covance Research Products, Inc.; see Examples VIII, IX and X). The glycolipopeptide of the invention can be assembled using a modular synthesis, wherein the lipid, peptide and carbohydrate component are selected according to the desired application. Moreover, the glycolipopeptide of the invention is a remarkably effective antigen for use in producing pan-specific antibodies, particularly pan-specific monoclonal IgG antibodies that recognize glycosylated peptides and proteins that contain an O-linked monosaccharide such as O-GlcNAc.

The antibodies of the invention and those created by the method of the invention are important research tools for the identification and characterization of proteins, peptides and other biomolecules associated with various disease states. For example, the pan-specific antibodies of the invention can be used to pull down glycoproteins from complex biological samples, as shown in Examples VIII through XI below. This method can be used to detect and identify proteins not heretofore known to be identified with a particular disorder or disease state, thereby identifying potential therapeutic or diagnostic targets. In one embodiment, an antibody of the invention can be contacted with a biological sample under conditions that enable the antibody to bind to a plurality of glycosylated proteins or glycosylated peptides and detecting antibody-protein binding. Optionally the method may include isolating the glycosylated proteins or glycosylated peptides. The method may further include identifying one or more of the proteins or peptides within the plurality of glycosylated proteins or glycosylated peptides. The identification of glycosylated proteins and peptides may provide an opportunity to explore the role of glycosylation and its biological implications in various biological processes. For example, glycosylation of proteins or peptides may be involved in a number of biological processes including, but not limited to, transcription, translation, signal transduction, the ubiquitin pathway, anterograde trafficking of intracellular vesicles and post-translational modifications (e.g. SUMOylation and phosphorylation). Methods for identifying a protein or peptide are well known in the art and may include, without limitation, techniques such as mass spectrometry and Edman degradation. Examples of proteins or peptides that may be glycosylated are exemplified in Tables 8-11, and 13.

The pan-specific antibody of the invention may also be used to identify proteins or peptides having altered glycosylation in a disease state. O-GlcNAc modifications are associated with a variety of disease states. For example, an increase of O-GlcNAc modifications in skeletal muscle and pancreas glycopeptides correlates with development of Type II Diabetes while a reduction in O-GlcNAc modifications in neural glycopeptides correlates with the onset of Alzheimer's disease (Dias and Hart; Mol. BioSyst. 3:766-772 (2007)). Therefore, detection of changes in the levels of O-GlcNAc modifications may be used as a diagnostic or prognostic tool. Additionally, the glycosylation state of the proteins or peptides listed in Tables 8-11 and 13 may be correlated with disease state. A method for identifying proteins or peptides having altered glycosylation that is correlated with disease state includes incubating an antibody of the present invention with a first biological sample of a known disease state and incubating the antibody with a second biological sample of a non-diseased state under conditions enabling the antibody to bind to a plurality of glycosylated proteins and peptides within the first sample and to a plurality of glycosylated proteins and peptides within the second sample, independently isolating the glycosylated proteins and glycosylated peptides from the samples, and identifying the glycosylated proteins and glycosylated peptides. The method may further include comparing the identified glycosylated proteins and glycosylated peptides in the first sample to the glycosylated proteins and glycosylated peptides in the second sample wherein a protein or peptide that demonstrates a change in glycosylation state between first and second samples is indicative of the glycosylated protein or a glycosylated peptide being associated with a disease state. Correlations between glycosylation and disease state include the disease state having increased or decreased glycosylation relative to the non-diseased state. In addition, the disease state may exhibit glycosylation while the non-disease state shows complete absence of glycosylation or conversely, the disease state may show complete absence of glycosylation while the non-disease exhibits the presence of glycosylation. In each example, the protein or peptide is considered to have differential or altered glycosylation in the disease state. Methods of using the antibody of the invention to detect the presence or overexpression glycosylation and to detect changes in the level of glycosylation have been previously described.

The antibodies of the invention are broadly useful in diagnostic or therapeutic applications as described in more detail elsewhere herein. Comparative analysis can be done on two or more different biological samples. For example, large scale immunoprecipitation can be performed on samples before and after a treatment intervention, or over time to monitor the progression of disease, or to compare normal samples with samples from patients suspected of suffering from a disease, infection or disorder characterized by changes in protein glycosylation.

In one embodiment, the present invention includes methods to diagnose the presence of a disease state in a subject. The method includes incubating a biological sample from the subject with an antibody of the present invention and detecting binding of the antibody to a protein or peptide having differential glycosylation in the disease state. Methods of detecting antibody binding have been previously described. In cases where glycosylation is completely absent in the disease state, a lack of binding of the antibody to the protein or peptide is indicative of subject having the disease state. In cases where glycosylation is present in the disease state but completely absent in the non-disease state, binding of the antibody to the protein or peptide is indicative of the presence of the disease state in the subject. Optionally, the method may further include incubating a second, non-diseased, biological sample with an antibody of the invention, detecting binding of the antibody to a protein or peptide, and comparing antibody binding in the first and second samples.

Additionally, for protein and peptides where glycosylation is present in both the disease state and the non-disease state, but is altered (i.e. increased or decreased) in the disease state, the method may further include quantitating the level of antibody binding in the first sample, quantitating the level of antibody binding in the second, non-diseased sample, and comparing the binding levels. A change in antibody binding in the first sample compared to the non-diseased sample is indicative of the presence of the infection, disease or disorder in the subject.

For preparation of an antibody of the present invention, any technique which provides for the production of antibody molecules by continuous cell lines in culture may be used. For example, the hybridoma technique originally developed by Kohler and Milstein (256 Nature 495-497 (1975)) may be used. See also Ausubel et al., Antibodies: a Laboratory Manual, (Harlow & Lane eds., Cold Spring Harbor Lab.

1988); Current Protocols in Immunology, (Colligan et al., eds., Greene Pub. Assoc. & Wiley Interscience N.Y., 1992-1996).

The present invention also provides for a hybridoma cell line that produces a monoclonal antibody, preferably one that has a high degree of specificity and affinity toward its antigen. The present invention further includes variants and mutants of the hybridoma cell lines, such as those described in Example VIII. Such cell lines can be produced artificially using known methods and still have the characteristic properties of the starting material. For example, they may remain capable of producing the antibodies according to the invention or derivatives thereof, and secreting them into the surrounding medium. Optionally, the hybridoma cell lines may occur spontaneously. Clones and sub-clones of hybridoma cell lines are to be understood as being hybridomas that are produced from the starting clone by repeated cloning and that still have the main features of the starting clone.

Antibodies can be elicited in an animal host by immunization with the glycolipopeptide of the invention, or can be formed by in vitro immunization (sensitization) of immune cells. The antibodies can also be produced in recombinant systems in which the appropriate cell lines are transformed, transfected, infected or transduced with appropriate antibody-encoding DNA. Alternatively, the antibodies can be constructed by biochemical reconstitution of purified heavy and light chains.

Once an antibody molecule has been produced by an animal, chemically synthesized, or recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In addition, the antibodies of the present invention or fragments thereof can be fused to heterologous polypeptide sequences known in the art to facilitate purification.

In a preferred embodiment, the monoclonal antibody recognizes and/or binds to an antigen present on the carbohydrate component or the peptide component of the glycolipopeptide of the invention. In a particularly preferred embodiment, the monoclonal antibody binds to an antigen present on a selected feature of the carbohydrate component. An example of a selected feature would include the modification on a glycopeptide such as O-GlcNAc. Other modifications include, but are not limited to, GalNAc and other saccharide modifications.

The term "antibody" is used in the broadest sense and specifically covers monoclonal antibodies (including full length monoclonal antibodies) and antibody fragments so long as they exhibit the desired biological activity. "Antibody fragments" comprise a portion of a full length antibody, generally the antigen binding or variable region thereofxamples of antibody fragments include, but are not limited to Fab, Fab', and Fv fragments; diabodies; linear antibodies; and single-chain antibody molecules. The term "monoclonal antibody" as used herein refers to antibodies that are highly specific, being directed against a single antigenic site. The term "antibody" as used herein also includes naturally occurring antibodies as well as non-naturally occurring antibodies, including, for example, single chain antibodies, chimeric, bifunctional and humanized antibodies, as well as antigen-binding fragments thereof. Such non-naturally occurring antibodies can be constructed using solid phase peptide synthesis, can be produced recombinantly or can be obtained, for example, by screening combinatorial libraries consisting of variable heavy chains and variable light chains as described by Huse et al. (Science 246:1275-1281 (1989)). These and other methods of making functional antibodies are well known to those skilled in the art (Winter and Harris, Immunol. Today 14:243-246 (1993); Ward et al., Nature 341:544-546 (1989); Harlow and Lane, supra, 1988); Hilyard et al., Protein Engineering: A practical approach (IRL Press 1992); Borrabeck, Antibody Engineering, 2d ed. (Oxford University Press 1995)).

In all mammalian species, antibody peptides contain constant (i.e., highly conserved) and variable regions, and, within the latter, there are the complementarity determining regions (CDRs) and the so-called "framework regions" made up of amino acid sequences within the variable region of the heavy or light chain but outside the CDRs. Preferably the monoclonal antibody of the present invention has been humanized. As used herein, the term "humanized" antibody refers to antibodies in which non-human (usually from a mouse or a rat) CDRs are transferred from heavy and light variable chains of the non-human immunoglobulin into a variable region designed to contain a number of amino acid residues found within the framework region in human IgG. Similar conversion of mouse/human chimeric antibodies to a humanized antibody has been described before. General techniques for cloning murine immunoglobulin variable domains are described, for example, by the publication of Orlandi et al., Proc. Nat'l Acad. Sci. USA 86: 3833 (1989), which is incorporated by reference in its entirety. Techniques for producing humanized MAbs are described, for example, by Jones et al., Nature 321: 522 (1986), Riechmann et al., Nature 332: 323 (1988), Verhoeyen et al., Science 239: 1534 (1988), and Singer et al., J. Immun. 150: 2844 (1993), each of which is hereby incorporated by reference.

Methods of using the monoclonal antibody that recognizes and/or binds to a component of the glycolipopeptide are also encompassed by the invention. Uses for the monoclonal antibody of the invention include, but are not limited to, diagnostic, therapeutic, and research uses. In a preferred embodiment, the monoclonal antibody can be used for diagnostic purposes. Because O-GlcNAc modifications are associated with a variety of disease states, detection of changes in the levels of O-GlcNAc modifications may be interpreted as early indicators of the onset of such diseases. For example, an increase in O-GlcNAc modifications in skeletal muscle and pancreas glycopeptides correlates with development of Type II Diabetes while a reduction in O-GlcNAc modifications in neural glycopeptides correlates with the onset of Alzheimer's disease (Dias and Hart, Mol. BioSyst. 3:766-772 (2007); Lefebvre et al., Exp. Rev. Proteomics 2(2):265-275 (2005)). Therefore, identifying an increase in the amount of O-GlcNAc in a sample of skeletal muscle tissue relative to a non-disease control sample may be indicative of development of Type II Diabetes.

It should be understood that the monoclonal and polyclonal antibodies of the invention are not limited to those that recognize any particular ligand but include, without limitation and by way of example only, antibodies against any type of tumor associated carbohydrate antigen (TACA) and against any saccharides derived from any microorganism. The antibodies of the invention are broadly useful in diagnostic or therapeutic applications.

Antibodies of the invention can be used to detect the presence or overexpression of a specific protein or a specific modification. Techniques for detection are known to the art and include but are not limited to Western blotting, dot blotting, immunoprecipitation, agglutination, ELISA assays, immunoELISA assays, tissue imaging, mass spectrometry, immunohistochemistry, and flow cytometry on a variety of tissues or bodily fluids, and a variety of sandwich assays. See, for example, U.S. Pat. No. 5,876,949, hereby incorporated by reference.

In order to detect changes in the level of O-GlcNAc modified glycopeptides, monoclonal antibodies of the invention may be labeled covalently or non-covalently with any of a number of known detectable labels, such as fluorescent, radioactive, or enzymatic substances, as is known in the art. Alternatively, a secondary antibody specific for the monoclonal antibody of the invention is labeled with a known detectable label and used to detect the O-GlcNAc-specific antibody in the above techniques.

Preferred detectable labels include chromogenic dyes. Among the most commonly used are 3-amino-9-ethylcarbazole (AEC) and 3,3'-diaminobenzidine tetrahydrochloride (DAB). These can be detected using light microscopy. Also preferred are fluorescent labels. Among the most commonly used fluorescent labeling compounds are fluorescein isothiocyanates (e.g. FITC and TRITC), Idotricarbocyanines (e.g. Cy5 and Cy7), rhodamine, phycoerythrin, phycocyanin, allophycocyanin, o-phthaldehyde and fluorescamine. Chemiluminescent and bioluminescent compounds such as luminol, isoluminol, theromatic acridinium ester, imidazole, acridinium salt, oxalate ester, luciferin, luciferase, and aequorin may also be used. When the fluorescent-labeled antibody is exposed to light of the proper wavelength, its presence can be detected due to its fluorescence. Also preferred are radioactive labels. Radioactive isotopes which are particularly useful for labeling the antibodies of the present invention include $^3H$, $^{125}I$, $^{131}I$, $^{35}S$, $^{32}P$, and $^{14}C$. The radioactive isotope can be detected by such means as the use of a gamma counter, a scintillation counter, or by autoradiography. Enzymes which can be used to detectably label antibodies and which can be detected, for example, by spectrophotometric, fluorometric, or visual means include, but are not limited to, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase, and acetylcholinesterase. Other methods of labeling and detecting antibodies are known in the art and are within the scope of this invention.

Because it is antigenic and immunogenic, the glycolipopeptide of the invention is well-suited for use in an immunotherapeutic pharmaceutical composition. The invention thus includes pharmaceutical compositions that include a glycolipopeptide of the invention as well as a pharmaceutically acceptable carrier. In a preferred embodiment, the pharmaceutical composition contains liposomes, for example phospholipid-based liposomes, and the glycolipopeptide is incorporated into liposomes as a result of noncovalent interactions such as hydrophobic interactions. Alternatively, the glycolipopeptide can be covalently linked to a component of the liposome. The liposome formulation can include glycolipopeptides that have the same or different B-epitopes; the same or different T-cell epitopes; and/or the same or different lipid components.

The glycolipopeptide of the invention is readily formulated as a pharmaceutical composition for veterinary or human use. The pharmaceutical composition optionally includes excipients or diluents that are pharmaceutically acceptable as carriers and compatible with the glycolipopeptide. The term "pharmaceutically acceptable carrier" refers to a carrier(s) that is "acceptable" in the sense of being compatible with the other ingredients of a composition and not deleterious to the recipient thereof or to the glycolipopeptide. Suitable excipients include, for example, water, saline, dextrose, glycerol, ethanol, or the like and combinations thereof. In addition, if desired, the pharmaceutical composition may contain minor amounts of auxiliary substances such as wetting or emulsifying agents, pH buffering agents, salts, and/or adjuvants which enhance the effectiveness of the immune-stimulating composition. For oral administration, the glycolipopeptide can be mixed with proteins or oils of vegetable or animal origin. Methods of making and using such pharmaceutical compositions are also included in the invention.

The pharmaceutical composition of the invention can be administered to any subject including humans and domesticated animals (e.g., cats and dogs). In a preferred embodiment, the pharmaceutical composition is useful as a vaccine and contains an amount of glycolipopeptide effective to induce an immune response in a subject. Dosage amounts, schedules for vaccination and the like for the glycolipopeptide vaccine of the invention are readily determinable by those of skill in the art. The vaccine can be administered to the subject using any convenient method, preferably parenterally (e.g., via intramuscular, intradermal, or subcutaneous injection) or via oral or nasal administration. The useful dosage to be administered will vary, depending on the type of animal to be vaccinated, its age and weight, the immunogenicity of the attenuated virus, and mode of administration.

Inclusion of an adjuvant, such as alum or QS-21, in the pharmaceutical composition is optional. However, it has been found that as long as the three main components of the glycolipopeptide are covalently linked, an adjuvant is not needed in order to effectively generate an immune response in an animal. Moreover, the inclusion of QS-21 may skew the immune response, resulting in a change in the relative amounts Th1 and Th2 T cells produced (see Example III). QS-21 can be included as an adjuvant in the pharmaceutical composition when, for example, a shift toward a Th1 response is desired, as opposed to a bias toward a Th2 response that is observed in the absence of QS-21.

As noted, the pharmaceutical composition is useful as a vaccine. The vaccine can be a prophylactic or protective vaccine, administered before or after contact with a pathogen but prior to the development of infection or disease. Likewise, the vaccine can be a therapeutic vaccine, administered after infection with a pathogen, or the development of a disease or disorder such as cancer, precancerous conditions, or autoimmune disease. Thus vaccines that include a glycolipopeptide as described herein, including antimicrobial (e.g., anti-viral or anti-bacterial) and anti-cancer vaccines, are encompassed by the present invention. Cancers that can be effectively treated or prevented include, but are not limited to, prostate cancer, bladder cancer, colon cancer and breast cancer.

The glycolipopeptide of the invention can also be used in passive immunization methods. For example, the glycolipopeptide can be administered to a host animal such as a rabbit, mouse, rat, chicken or goat to generate antibody production in the host animal. Protocols for raising polyclonal antibodies in host animals are well known. The T-epitope or T-epitopes included in the glycolipopeptide optionally are selected to be the same as or similar to the corresponding T-epitope of the host animal in which the antibody is raised. The antibodies are isolated from the animal, then administered to a mammalian subject, preferably a human subject, prophylactically or therapeutically to treat or prevent disease or infection. Monoclonal antibodies against the glycolipopeptide of the invention can be isolated from hybridomas prepared in accordance with standard laboratory protocols; they can also be produced using recombinant techniques such as phage display. Such antibodies are also useful for passive immunization. Optionally, the anti-glycolipopeptide monoclonal antibodies are human antibodies or humanized antibodies. The B-epitope or B-epitopes included in the glycolipopeptide used to create the polyclonal or monoclonal antibodies is selected with reference to the intended purpose of treatment. The invention encompasses polyclonal and monoclonal anti-glycolipopeptide antibodies, as well as methods for making and using them.

Accordingly, also provided by the invention is a pharmaceutical composition that includes the monoclonal or polyclonal antibody of the invention as well as a pharmaceutically acceptable carrier. Preferably the monoclonal antibody is a humanized antibody. Humanized antibodies are more preferable for use in therapies of human diseases or disorders because the humanized antibodies are much less likely to induce an immune response, particularly an allergic response, when introduced into a human host. As noted, the pharmaceutical composition optionally includes excipients or diluents that are pharmaceutically acceptable as carriers and are compatible with the monoclonal antibody and can be administered to any subject including humans and domesticated animals (e.g. cats and dogs). Methods of making and using such a pharmaceutical composition are also included in this invention.

A common feature of oncogenic transformed cells is the over-expression of oligosaccharides, such as Globo-H, Lewis$^Y$, and Tn antigens. Optionally, the pharmaceutical composition of the invention that includes the monoclonal or polyclonal antibody of the invention as well as a pharmaceutically acceptable carrier may be useful in targeting a tumor comprising oncogenic transformed cells over-expressing such oligosaccharides. For example, an antibody conjugated to a chemotherapeutic molecule may be used to deliver the chemotherapeutic molecule to the tumor.

Another pharmaceutical composition of the invention may include a compound (e.g. an antibody, ligand, small molecule, or peptide) that can affect the activity of a protein listed in Tables 8-11 or 13 as well as a pharmaceutically acceptable carrier. The effect of the compound on the protein may include, without limitation, agonizing, antagonizing, inhibiting, or enhancing the normal biological process of the protein. Preferably, the compound is an antibody than binds to an epitope on the protein that includes an O-glycosylation site. Preferably, the O-glycosylation site is an O-GlcNAc site. Numerous studies have shown that this abnormal glycosylation can promote metastasis and hence it is strongly correlated with poor survival rates of cancer patients. Thus, the ability to affect the activity of an abnormally glycosylated protein may enable the prevention of the abnormal activity.

As noted elsewhere herein, it has been surprisingly found that covalent attachment of a Toll-like receptor (TLR) ligand to a glycopeptide comprising a carbohydrate component (containing a B epitope) and a peptide component (containing a T-epitope) enhances uptake and internalization of the glycopeptide by a target cell (see Example III). TLR ligands thus identified that are characterized as lipids are preferred lipid components for use in the glycolipopeptide of the invention. The invention thus further provides a method for identifying TLR ligands, preferably lipid ligands, that includes contacting a candidate compound with a target cell containing a Toll-like receptor (TLR), and determining whether the candidate compound binds to the TLR (i.e., is a TLR ligand). Preferably, the candidate compound is internalized by the target cell through the TLR. Lipid-containing TLR ligands identified by binding to a TLR and, optionally, by internalization into the target cell are expected to be immunogenic and are well-suited for use as the lipid component of the glycolipopeptide of the invention. The invention therefore also encompasses glycolipopeptides which include, as the lipid component(s), one or more lipid-containing TLR ligands identified using the method of the invention.

The present invention also includes a diagnostic kit. The kit provided by the invention can contain an antibody of the invention, preferably a monoclonal antibody, and a suitable buffer (such as Tris, phosphate, carbonate, etc.), thus enabling the kit user to identify O-GlcNAc modifications. The user can then detectably label the antibodies as desired. Alternatively, the kit provided by the invention can contain the antibody in solution, preferably frozen in a quenching buffer, or in powder form (as by lyophilization). The antibody, which may be conjugated to a detectable label, or unconjugated, is included in the kit with buffers that may optionally also include stabilizers, biocides, inert proteins, e.g., serum albumin, or the like. Generally, these materials will be present in less than 5% wt. based on the amount of active antibody, and usually present in total amount of at least about 0.001% wt. based again on the antibody concentration. Optionally, the kit may include an inert extender or excipient to dilute the active ingredients, where the excipient may be present in from about 1% to 99% wt. of the total composition. In a preferred embodiment, the antibody provided by the kit is detectably labeled such that bound antibody is detectable. The detectable label can be a radioactive label, an enzymatic label, a fluorescent label, or the like. Optionally, the kit may contain an unconjugated monoclonal antibody of the invention and further contain a secondary antibody capable of binding to the primary antibody. Where a secondary antibody capable of binding to the primary antibody is employed in an assay, this will usually be present in a separate vial. The secondary antibody is typically conjugated to a detectable label and formulated in an analogous manner with the antibody formulations described above. The kit will generally also include packaging and a set of instructions for use.

EXAMPLES

The present invention is illustrated by the following examples. It is to be understood that the particular examples, materials, amounts, and procedures are to be interpreted broadly in accordance with the scope and spirit of the invention as set forth herein.

Example I

Towards a Fully Synthetic Carbohydrate-Based Anti-Cancer Vaccine: Synthesis and Immunological Evaluation of a Lipidated Glycopeptide Containing the Tumor-Associated Tn-Antigen In this Example, a fully synthetic candidate cancer vaccine, composed of a tumor associated Tn-antigen, a peptide T-epitope and the lipopeptide Pam$_3$Cys was prepared by a combination of polymer-supported and solution phase chemistry. Incorporation of the glycolipopeptide into liposomes gave a formulation that was able to elicit a T-cell dependent antibody response in mice.

A common feature of oncogenic transformed cells is the over-expression of oligosaccharides, such as Globo-H, Lewis$^Y$, and Tn antigens (Lloyd, Am. J Clin. Pathol. 1987, 87, 129; Feizi et al., Trends in Biochem. Sci. 1985, 10, 24-29; Springer, J. Mol. Med. 1997, 75, 594-602; Hakomori, Acta Anat. 1998, 161, 79-90). Numerous studies have shown that this abnormal glycosylation can promote metastasis (Sanders et al., Mol. Pathol. 1999, 52, 174-178) and hence its expression is strongly correlated with poor survival rates of cancer patients.

Several elegant studies have exploited the differential expression of tumor-associated carbohydrates for the development of cancer vaccines (Ragupathi, Cancer Immunol. 1996, 43, 152-157; Musselli et al., J Cancer Res. Clin. Oncol. 2001, 127, R20-R26). The inability of carbohydrates to activate helper T-lymphocytes has complicated, however, their use as vaccines (Kuberan et al., Current Organic Chemistry 2000, 4, 653-677). For most immunogens, including carbohydrates, antibody production depends on the cooperative interaction of two types of lymphocytes, B-cells and helper T-cells (Jennings et al., Neoglycoconjugates, preparation and application, Academic, San Diego, 1994). Saccharides alone cannot activate helper T-cells and therefore have a limited immunogenicity. The formation of low affinity IgM antibodies and the absence of IgG antibodies manifest this limited immunogenicity.

In order to overcome the T-cell independent properties of carbohydrates, past research has focused on the conjugation of saccharides to a foreign carrier protein (e.g. Keyhole Limpet Hemocyanin (KLH) detoxified tetanus toxoid). In this approach, the carrier protein enhances the presentation of the carbohydrate to the immune system and provides T-epitopes (peptide fragments of 12-15 amino acids) that can activate T-helper cells.

However, the conjugation of carbohydrates to a carrier protein poses several problems. In general, the conjugation chemistry is difficult to control, resulting in conjugates with ambiguities in composition and structure, which may affect the reproducibility of an immune response (Anderson et al., J. Immunol. 1989, 142, 2464-2468). In addition, the foreign carrier protein can elicit a strong B-cell response, which may lead to the suppression of an antibody response against the carbohydrate epitope. The latter is a greater problem when self-antigens are employed such as tumor-associated carbohydrates. Also linkers for the conjugation of carbohydrates to proteins can be immunogenic, leading to epitope suppression (Buskas et al., Chem. Eur. J. 2004, 10, 3517-3523). Not surprisingly, several clinical trials with carbohydrate-protein conjugate cancer vaccines failed to induce sufficiently strong helper T-cell responses in all patients (Sabbatini et al., Int. J. Cancer 2000, 87, 79-85). Therefore, alternative strategies need to be developed for the presentation of tumor associated carbohydrate epitopes that will result in a more efficient class switch to IgG antibodies (Keil et al., Angew. Chem. Int. Ed. 2001, 40, 366-369; Angew. Chem. 2001, 113, 379-382; Toyokuni et al., Bioorg. & Med. Chem. 1994, 2, 1119-1132; Lo-Man et al., Cancer Res. 2004, 64, 4987-4994; Kagan et al., Cancer Immunol. Immunother. 2005, 54, 424-430; Reichel et al., Chem. Commun. 1997, 21, 2087-2088).

Here we report the synthesis and immunological evaluation of a structurally well-defined fully synthetic anti-cancer vaccine candidate (compound 9) that constitutes the minimal structural features required for a focused and effective T-cell dependent immune response. The vaccine candidate is composed of the tumor-associated Tn-antigen, the peptide T-epitope YAFKYARHANVGRNAFELFL (YAF) (SEQ ID NO:2), and the lipopeptide S—[(R)-2,3-dipalmitoyloxypropyl]-N-palmitoyl-(R)-cysteine (Pam$_3$Cys). The Tn-antigen, which will serve as a B-epitope, is over-expressed on the surface of human epithelial tumor-cells of breast, colon, and prostate. This antigen is not present on normal cells, and thus rendering it an excellent target for immunotherapy. To overcome the T-cell independent properties of the carbohydrate antigen, the YAF peptide was incorporated. This 20 amino acid peptide sequence is derived from an outer-membrane protein of *Neisseria meningitides* and has been identified as a MHC class II restricted site for human T-cells (Wiertz et al., J. Exp. Med. 1992, 176, 79-88). It was envisaged that this helper T-cell epitope would induce a T-cell dependent immune response resulting in the production of IgG antibodies against the Tn-antigen. The combined B-cell and helper T-cell epitope lacks the ability to provide appropriate "danger signals" (Medzhitov et al., Science 2002, 296, 298-300) for dendritic cell (DC) maturation. Therefore, the lipopeptide Pam$_3$Cys, which is derived from the immunologically active N-terminal sequence of the principal lipoprotein of *Escherichia coli* (Braun, Biochim. Biophys. Acta 1975, 415, 335-377), was incorporated. This lipopeptide has been recognized as a powerful immunoadjuvant (Weismuller et al., Physiol. Chem. 1983, 364, 593) and recent studies have shown that it exerts its activity through the interaction with Toll-like receptor-2 (TLR-2) (Aliprantis et al., Science 1999, 285, 736-73). This interaction results in the production of pro-inflammatory cytokines and chemokines, which, in turn, stimulates antigen-presenting cells (APCs), and thus, initiating helper T cell development and activation (Werling et al., Vet. Immunol. Immunopathol. 2003, 91, 1-12). The lipopeptide also facilitates the incorporation of the antigen into liposomes. Liposomes have attracted interest as vectors in vaccine design (Kersten et al., Biochim. Biophys. Acta 1995, 1241, 117-138) due to their low intrinsic immunogenicity, thus, avoiding undesirable carrier-induced immune responses.

The synthesis of target compound 9 requires a highly convergent synthetic strategy employing chemical manipulations that are compatible with the presence of a carbohydrate, peptide and lipid moiety. It was envisaged that 9 could be prepared from spacer containing Tn-antigen 7, polymer-bound peptide 1, and S[2,3-bis(palmitoyloxy)propyl]-N-Fmoc-Cys (Pam$_2$FmocCys, 2, (Metzger et al., Int. J. Peptide Protein Res. 1991, 38, 545-554)). The resin-bound peptide 1 was assembled by automated solid-phase peptide synthesis using Fmoc protected amino acids in combination with the hyper acid-sensitive HMPB-MBHA resin and 2-(1H-benzotriazole-1-yl)-oxy-1,1,3,3-tetramethyluronium hexafluorophosphate/1-hydroxybenzotriazole (HBTU/HOBt) (Knorr et al., Tetrahedron Lett. 1989, 30, 1927-1930) as the activation cocktail (Scheme 10). The HMPB-MBHA resin was selected because it allows the cleavage of a compound from the resin without concomitant removal of side-chain protecting groups. This feature was important because side-chain functional groups of aspartic acid, glutamic acid and lysine would otherwise interfere with the incorporation of the Tn-antigen derivative 7. Next, the Pam$_2$FmocCys derivative 2 was manually coupled to the N-terminal amine of peptide 1 using PyBOP (Martinez et al., J. Med. Chem. 1988, 28, 1874-1879) and HOBt in the presence of DIPEA in a mixture of DMF and dichloromethane to give the resin-bound lipopeptide 3. The Fmoc group of 3 was removed under standard conditions and the free amine of the resulting compound 4 was coupled with palmitic acid in the presence of PyBOP and HOBt to give the fully protected and resin-bound lipopeptide 5. The amine of the Pam$_2$Cys moiety was palmitoylated after coupling with 1 to avoid racemization of the cysteine moiety. Cleavage of compound 5 from the resin was achieved with 2% TFA in dichloromethane followed by the immediate neutralization with 5% pyridine in methanol. After purification by LH-20 size exclusion chromatography, the C-terminal carboxylic acid of lipopeptide 6 was coupled with the amine of Tn-derivative 7, employing DIC/HOAt/DIPEA (Carpino, J. Am. Chem. Soc 1993, 115, 4397-4398) as coupling reagents to give, after purification by Sephadex LH-20 size-exclusion chromatography, fully protected lipidated glycopeptide 8 in a yield of 79%. Mass spectrometric analysis by MALDI-TOF showed signals at m/z 5239.6 and 5263.0, corresponding to [M+H]$^+$ and [M+Na]$^+$, respectively. Finally, the side-chain protecting groups of 8 were removed by treatment with 95% TFA in water using 1,2-ethanedithiol (EDT) as a scavenger. It was found that the alternative use of triisopropyl silane (TIS) resulted in the formation of unidentified by-products. The target compound 9 was purified by size-exclusion chromatography followed by RP-HPLC using a Synchropak C4 column. MALDI mass analysis of 9 showed a signal at m/z 3760.3 corresponding to [M+Na]$^+$.

Scheme 10.

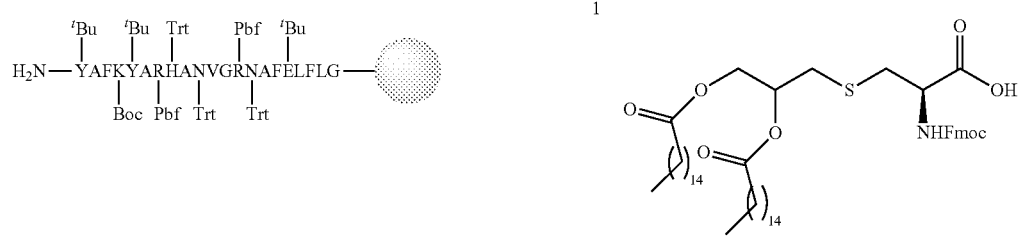

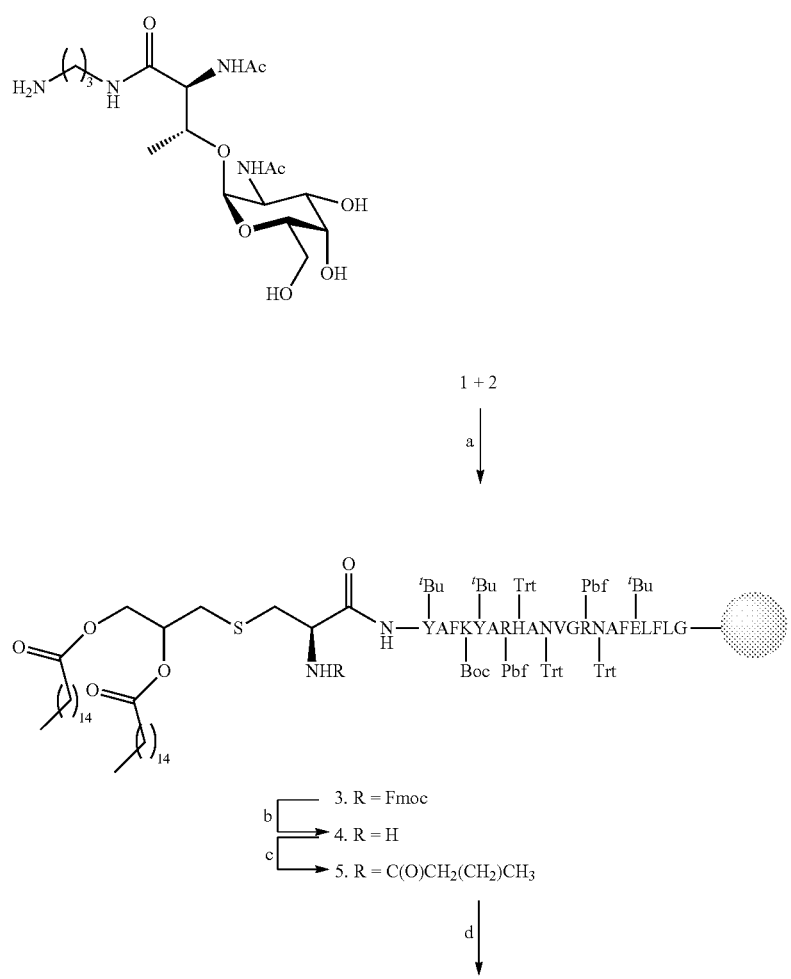

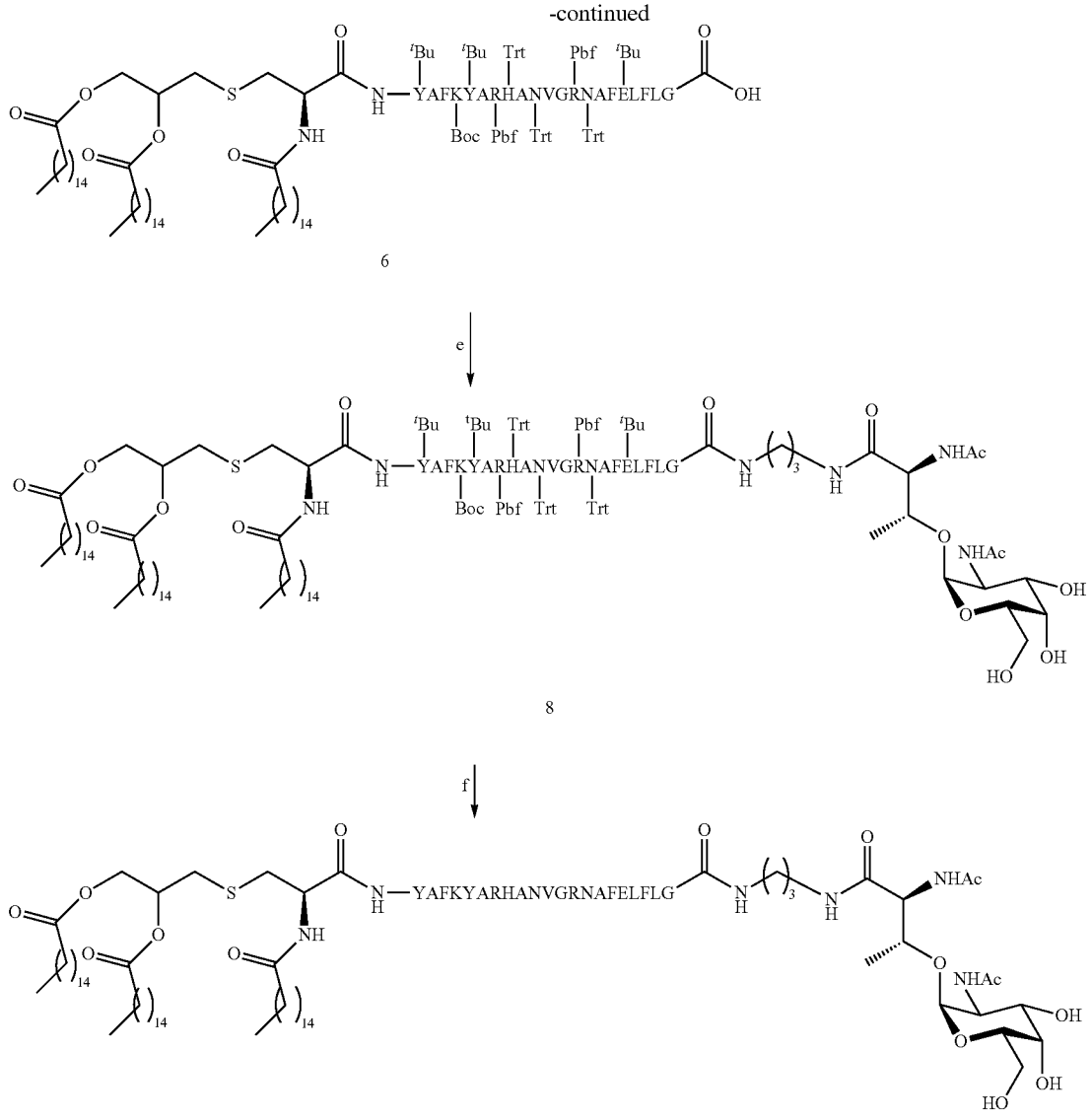

a) PyBOP, HOBt, DIPEA, DMF/DCM (5/1, v/v);
b) piperidine/DMF (1/5, v/v);
c) CH$_3$(CH$_2$)$_{14}$COOH, PyBOP, HOBt, DMF/DCM (1/5, v/v);
d) 2% TFA in DCM;
e) 7, DIC, HOAt, DIPEA, DMF/DCM (2/1, v/v), 79%;
f) TFA/H$_2$O/EDT (95/2.5/2.5, v/v/v), 79%.

Next, the compound 9 was incorporated into phospholipid-based liposomes. Thus, after hydration of a lipid-film containing 9, cholesterol, phosphatidylcholine and phosphatidylethanolamine, small uni-lamellar vesicles (SUVs) were prepared by extrusion through 100 nm Nuclepore® polycarbonate membranes. Transmission electron microscopy (TEM) by negative stain confirmed that the liposomes were uniformly sized with an expected diameter of approximately 100 nm (see FIG. 1 of Buskas et al., Angew. Chem. Int. Ed. 2005, 44, 5985-5988). The liposome preparations were analyzed for N-acetyl galactosamine content by hydrolysis with TFA followed by quantification by high pH anion exchange chromatography. Concentrations of approximately 30 μg/mL of GalNAc were determined, which corresponded to an incorporation of approximately 10% of the starting compound 9.

Groups of five female BALB/c mice were immunized subcutaneously at weekly intervals with freshly prepared liposomes containing 0.6 μg carbohydrate. To explore the adjuvant properties of the built-in lipopeptide Pam$_3$Cys, the antigen-containing liposomes were administered with or without the potent saponin immuno-adjuvant QS-21 (Antigenics Inc., Lexington, Mass.). Anti-Tn antibody titers were determined by coating microtiter plates with a BSA-Tn conjugate and detection was accomplished with anti-mouse IgM or IgG antibodies labeled with alkaline phosphatase. As can be seen in Table 1, the mice immunized with the liposome preparations elicited IgM and IgG antibodies against the Tn-antigen (Table 1, entries 1 and 2). The presence of IgG antibodies indicated that the helper T-epitope peptide of 9 had activated helper T-lymphocytes.

Furthermore, the observation that IgG antibodies were raised by mice which were only immunized with liposomes (group 1) indicated that the built-in adjuvant Pam$_3$Cys had triggered appropriate signals for the maturation of DCs and their subsequent activation of helper T-cells. However, the mice which received the liposomes in combination with QS-21 (group 2), elicited higher titers of anti Tn-antibodies. This stronger immune response may be due to a shift from a mixed Th1/Th2 to a Th1 response (Moore et al., Vaccine 1999, 17, 2517-2527).

TABLE 1

ELISA anti-Tn antibody titers[a] after 4 immunizations with the glycolipopeptide/liposome formulation.

| Entry | Group | IgM Titers | IgG Titers |
|---|---|---|---|
| 1. | 1. Pam$_3$Cys-YAF-Tn | 250 | 1410 |
| 2. | 2. Pam$_3$Cys-YAF-Tn + QS-21 | 170 | 2675 |

[a]ELISA plates were coated with a BSA-BrAc-Tn conjugate. All titers are means for a group of five mice. Titers were determined by regression analysis, plotting log$_{10}$ dilution vs. absorbance. The titers were calculated to be the highest dilution that gave 0.1 or higher than the absorbance of normal saline mouse sera diluted 1:100.

The results presented herein provide, for the first time, a proof-of-principle for the use of lipidated glycopeptides as a minimal subunit vaccine. It is to be expected that several improvements can be made. For example, it has been found that a clustered presentation of the Tn-antigen is a more appropriate mimetic of mucins, and hence antibodies raised against this structure recognize better Tn-antigens expressed on cancer cells (Nakada et al., J. Biol. Chem. 1991, 266, 12402-12405; Nakada et al., Proc. Natl. Acad. Sci. USA 1993, 90, 2495-2499; Reddish et al., Glycoconj. J. 1997, 14, 549-560; Reis et al., Glycoconj. J. 1998, 15, 51-62). The Th-epitope employed in this study is known to be a MHC class II restricted epitope for humans. Thus, a more efficient class-switch to IgG antibodies may be expected when a murine Th-epitope is employed. On the other hand, compound 9 is a more appropriate vaccine candidate for use in humans. A recent report indicated that Pam$_2$Cys is a more potent immunoadjuvant than Pam$_3$Cys (Jackson et al., Proc. Nat. Acad. Sci. USA 2004, 101, 15440-15445). It has also been suggested that the Pam$_2$Cys adjuvant has improved solubility properties (Zeng et al., J. Immunol. 2002, 169, 4905-4912), which is a problematic feature of compound 9. Studies addressing these issues are ongoing.

This work is reported in Buskas et al., *Angew. Chem. Int. Ed.* 2005, 44, 5985-5988.

Supporting Information

Reagents and General Experimental Procedures.

Amino acids and resins were obtained from Applied Biosystems and NovaBiochem; DMF from EM science; and NMP from Applied Biosystems. Phosphatidylethanolamine (PE), cholesterol, phosphatidylcholine (PC; egg yolk), and phosphatidylglycerol (PG; egg yolk) were from purchased from Sigma-Aldrich and Fluka. All other chemicals were purchased from Aldrich, Acros, and Fluka and used without further purification. All solvents employed were of reagent grade and dried by refluxing over appropriate drying agents. TLC was performed using Kieselgel 60 F$_{254}$ (Merck) plates, with detection by UV light (254 nm) and/or by charring with 8% sulfuric acid in ethanol or by ninhydrine. Column chromatography was performed on silica gel (Merck, mesh 70-230). Size exclusion column chromatography was performed on Sephadex LH-20. Extracts were concentrated under reduced pressure at ≤40° C. (water bath). An Agilent 1100 series HPLC system equipped with an autosampler, UV-detector and fraction-collector and a Synchropak C4 column 100×4.6 mm RP with a flow rate of 1 mL/min was used for analysis and purifications. Positive ion matrix assisted laser desorption ionization time of flight (MALDI-TOF) mass spectra were recorded using an HP-MALDI instrument using gentisic acid as a matrix. $^1$H NMR and $^{13}$C NMR spectra were recorded on a Varian Inova300 spectrometer, a Varian Inova500 spectrometer, and a Varian Inova600 spectrometer all equipped with Sun workstations. $^1$H spectra recorded in CDCl$_3$ were referenced to residue CHCl$_3$ at 7.26 ppm or TMS, and $^{13}$C spectra to the central peak of CDCl$_3$ at 77.0 ppm. Assignments were made using standard 1D experiments and gCOSY/DQCOSY, gHSQC and TOCSY 2D experiments.

Lipopeptide 6.

Compound 1 was synthesized on HMPB-MBHA resin (maximum loading, 0.1 mmol). The synthesis of peptide 1 was carried out on an ABI 433A peptide synthesizer equipped with a UV-detector using Fmoc-protected amino acids and 2-(1H-benzotriazole-1-yl)-oxy-1,1,3,3-tetramethyluronium hexafluorophosphate (HBTU)/1-hydroxybenzotriazole (HOBt) as the coupling reagents. Single coupling steps were performed with conditional capping as needed. After completion of the synthesis of peptide 1, the remaining steps were performed manually. N-Fluorenylmethoxycarbonyl-S-(2,3-bis(palmitoyloxy)-(2R-propyl)-(R)-cysteine 2 (120 mg, 0.13 mmol) was dissolved in DMF (5 mL) and PyBOP (0.13 mmol), HOBt (0.13 mmol), and DIPEA (0.27 mmol) were added. After premixing for 2 min., DCM (1 mL) was added and the mixture was added to the resin. The coupling step was performed twice. Upon completion of the coupling, as determined by the Kaiser test, the N-Fmoc group was cleaved using 20% piperidine in DMF (5 mL). Palmitic acid (77 mg, 0.3 mmol) was coupled to the free amine as described above using PyBop (0.3 mmol), HOBt (0.3 mmol) and DIPEA (0.6 mmol) in DMF. The resin was thoroughly washed with DMF and DCM and dried under vacuum for 4 h. The fully protected lipopeptide 6 was released from the resin by treatment with 2% trifluoroacetic acid in DCM (2.5 mL) for 2 min. The mixture was filtered into 5% pyridine in methanol solution (5 mL). The procedure was repeated and fractions containing the lipopeptide were pooled and concentrated to dryness. The crude product was purified by size-exclusion chromatography (LH-20, DCM/MeOH, 1:1) to give lipo-peptide 6 (275 mg, 0.057 mmol) as a white solid: R$_f$=0.57 (DCM/MeOH 9:1); selected NMR data (CDCl$_3$/CD$_3$OD 1/1 v/v 600 MHz): $^1$H, δ 0.48-0.90 (m, 27H, Pam CH$_3$, Leu CH$_3$, Val CH$_3$), 0.96-1.61 (m, Leu CH$_2$, Leu CH, Lys CH$_2$, $^t$Bu CH$_3$, Boc CH$_3$, Ala CH$_3$, Arg CH$_2$), 1.18 (br s, 72H, Pam CH$_2$), 1.95, 1.99 (s, 4×3H, Pbf CH$_3$C), 2.36, 2.41, 2.44 (s, 6×3H, Pbf CH$_3$), 2.48 (s, 2×2H, Pbf CH$_2$) 2.65-2.73 (m, 6H, S—CH$_2$-glyceryl, His CH$_2$, Cys$^β$), 3.47 (m, 2H, Gly$^α$), 3.57 (m, 2H, Gly$^α$), 4.06 (m, 1H, S-glyceryl-CH$_2{}^b$O), 4.32 (m, 1H, S-glyceryl-CH$_2{}^a$O), 3.65-4.39 (m, 17H, Phe$^α$, Ala$^α$, His$^α$, Lys$^α$, Val$^α$, Asn$^α$, Glu$^α$, Tyr$^α$, Arg$^α$), 4.45 (m, 1H, Cys$^α$), 5.06 (m, 1H, S-glyceryl-CH), 6.72-7.39 (m, 70H, His CH, Tyr aromat, Phe aromat, Trt aromat), 7.48-8.29 (m, NH). MALDI-MS calcd for C$_{269}$H$_{373}$N$_{33}$O$_{42}$S$_3$ [M+Na] m/z=4860.22. found 4860.31.

Protected glycolipopeptide 8.

A solution of lipopeptide 6 (22 mg, 4.6 µmol), HOAt (6.3 mg, 46 µmol), and DIC (7 µL, 46 µmol) in DCM/DMF (2/1 v/v, 1.5 mL) was stirred under argon atm. at ambient temperature for 15 min. Compound 7 (8 mg, 19 µmol) and DIPEA (14 µL, 92 µmol) in DMF (1.5 mL) was added to the stirred mixture of lipopeptide and the reaction was kept at room temperature for 18 h. The mixture was diluted with toluene and concentrated to dryness under reduced pressure. Purification of the residue by size-exclusion chromatography (LH-20, DCM/MeOH 1:1) gave compound 8 (19 mg, 79%) as a white solid: selected NMR data (CDCl$_3$/CD$_3$OD 1/1 v/v 600 MHz): $^1$H, δ 0.60-0.90 (m, 27H, Pam CH$_3$, Leu CH$_3$, Val CH$_3$), 0.96-1.61 (m, Leu CH$_2$, Leu CH, Lys CH$_2$, $^t$Bu CH$_3$, Boc CH$_3$, Ala CH$_3$, Arg CH$_2$), 1.18 (br s, 72H, Pam CH$_2$), 1.94, 1.98, 1.99, 2.00 (s, 6×3H, Pbf CH$_3$C, HNAc CH$_3$), 2.36, 2.41, 2.45 (s, 6×3H, Pbf CH$_3$), 2.48 (s, 2×2H, Pbf CH$_2$), 3.42-4.31 (m, Phe$^\alpha$, Ala, Lys, Val, Asp, Glu, Tyr, Arg, Gly, Leu, His, Asn CH$_2$, Tyr CH$_2$, Phe CH$_2$, Arg CH$_2$), 3.71 (H-3), 3.88 (H-4) 4.06 (S-glyceryl-CH$_2$$^\beta$O), 4.20 (t, 1H, H-2), 4.32 (m, 1H, S-glyceryl-CH$_2$$^\alpha$O), 4.42 (m, 1H, Cys$^\alpha$), 4.82 (d, 1H, H-1, J=3.68 Hz), 5.06 (m, 1H, S-glyceryl-CH), 6.72-7.39 (m, 70H, His CH, Tyr aromat, Phe aromat, Trt aromat), 7.48-8.29 (m, NH). MALDI-MS calcd for C$_{286}$H$_{403}$N$_{37}$O$_{49}$S$_3$ [M+Na] m/z=5262.67. found 5262.99.

Glycolipopeptide 9.

Compound 8 (12 mg, 2.3 µmol) in a deprotection cocktail of TFA/H$_2$O/ethane-1,2-dithiol (95:2.5:2.5, 3 mL) was stirred at room temperature for 1 h. The solvents were removed under reduced pressure and the crude compound was first purified by a short size-exclusion LH-20 column (DCM/MeOH 1:1) and the then by HPLC using a gradient of 0-100% acetonitrile in H$_2$O (0.1% TFA) to give, after lyophilization, compound 9 (6.8 mg, 79%) as a white solid: selected NMR data (CDCl$_3$/CD$_3$OD 600 MHz): $^1$H, δ 0.74-0.96 (m, 27H, Pam CH$_3$, Leu CH$_3$, Val CH$_3$), 1.11-2.35 (Leu CH$_2$, Leu CH, sp CH$_2$, Lys CH$_2$, Glu CH$_2$, Ala CH$_3$, Val CH, Asp CH$_2$), 1.29 (br S, 72H, Pam CH$_2$), 2.43-3.87 (Ala$^\alpha$, Gly$^\alpha$, S-glyceryl-OCH$_2$, Cys$^\beta$, H-2, H-3, H-4, H-5, H-6), 4.05-4.73 (m, Cys$^\alpha$, Phe$^\alpha$, Tyr$^\alpha$, His$^\alpha$, Leu$^\alpha$, Lys$^\alpha$, Asp$^\alpha$, Val$^\alpha$, Arg$^\alpha$, Glu$^\alpha$, H-1), 5.12 (m, 1H, S-glyceryl-CH), 6.64-6.71 (dd+dd, 2H, His CH, NH), 6.86-7.12 (dd+dd 2H, His CH, NH) 7.16-8.23 (m, Tyr aromat, Phe aromat, NH). HR-MALDI-MS calcd for C$_{186}$H$_{297}$N$_{37}$O$_{41}$S [M+Na] m/z=3760.1911. found 3760.3384.

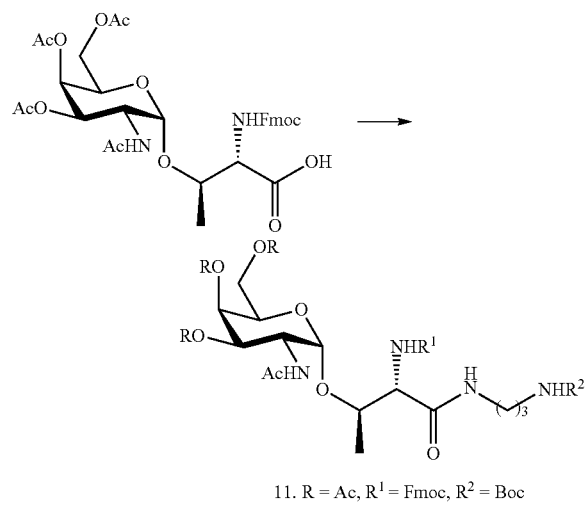

11. R = Ac, R$^1$ = Fmoc, R$^2$ = Boc

Tn Derivative 11.

Compound 10 was dissolved in DMF (10 mL) and di-isopropylcarbodiimide (DIC) (82 µL, 0.53 mmol) and HOAt (216 mg, 1.58 mmol) were added. After stirring for 15 min., 3-(N-(tert.butyloxycarbonyl)-amino)propanol (111 mg, 0.63 mmol) was added and the reaction was kept at ambient temperature for 15 h. The mixture was concentrated to dryness under reduced pressure and the residue was purified by silica gel column chromatography (0-5% MeOH in DCM) and LH-20 size-exclusion chromatography (DCM/MeOH 1:1) to give compound 11(363 mg, 83%). R$_f$=0.63 (DCM/MeOH 9:1); [α]$_D$+4.4 (c 1.0 mg/mL, CH$_2$Cl$_2$); NMR data (CDCl$_3$, 500 MHz): $^1$H, δ 1.27 (d, 3H, CH$_3$ Thr), 1.43 (s, 9H, $^t$Bu CH$_3$), 1.46-1.61 (m, 2H, CH$_2$), 1.99 (s, 3H, CH$_3$Ac), 2.05 (s, 6H, CH$_3$Ac), 2.06 (s, 3H, CH$_3$Ac), 2.17 (s, 3H, CH$_3$Ac), 3.17-3.27 (m, 3H, CH$_2$, CH$_{2a}$), 3.48-3.50 (m, 1H, CH$_{2b}$), 4.07-4.28 (m, 6H, H-6, H-5, Thr$^\alpha$, Thr$^\beta$, CH Fmoc), 4.43-4.51 (m, 2H, CH$_2$ Fmoc), 4.62 (dd, 1H, H-2), 4.89 (br t, 1H, NH), 5.04-5.11 (m, 2H, H-1, H-3), 5.41 (d, 1H, H-4), 5.75 (br d, 1H, NH T), 6.81 (br d, 1H, NH GalNAc), 7.17-7.79 (m, 8H, aromatic H); $^{13}$C (CDCl$_3$, 75 MHz) δ17.19, 20.92, 20.99, 21.09, 23.30, 28.55, 30.69, 35.87, 36.92, 47.43, 47.77, 58.57, 62.36, 67.47, 68.68, 77.46, 80.08, 99.88, 120.25, 125.34, 127.35, 128.00, 128.76, 129.13, 141.55, 143.94, 144.01, 156.51, 157.52, 169.68, 170.66, 170.94, 170.99.

HR-MALDI-MS calcd for C$_{41}$H$_{54}$N$_4$O$_{14}$ [M+Na] m/z=849.3535. found 849.3391.

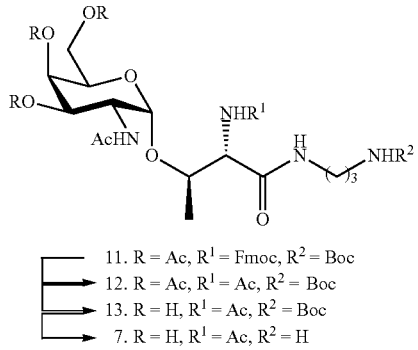

11. R = Ac, R$^1$ = Fmoc, R$^2$ = Boc
12. R = Ac, R$^1$ = Ac, R$^2$ = Boc
13. R = H, R$^1$ = Ac, R$^2$ = Boc
7. R = H, R$^1$ = Ac, R$^2$ = H Tn Derivative 7.

A solution of compound 11 (194 mg, 0.24 mmol) in 20% piperidine in DMF (5 mL) was stirred at ambient temperature for 1 h. The mixture was concentrated to dryness and the residue was treated with pyridine/acetic anhydride (3:1, 5 mL) for 2 h. The reaction mixture was diluted with toluene and concentrated to dryness. The residue was dissolved in dichloromethane and washed with 1M HCl and sat. aq. NaHCO$_3$, dried with MgSO$_4$, filtered and concentrated. Purification of the residue by size-exclusion chromatography (LH-20, DCM/MeOH 1:1) furnished compound 12 (167 mg, 91%): NMR data (CDCl$_3$, 300 MHz): $^1$H, δ 1.24 (d, 1H, Thr CH$_3$), 1.42 (s, 9H, $^t$Bu CH$_3$), 1.55-1.59 (m, 2H, NHCH$_2$CH$_2$CH$_2$NH), 1.95, 2.02, 2.03, 2.12, 2.14 (s, 15H, CH$_3$Ac), 3.13-3.23 (m, 3H, CH$_2$+CH$_{2a}$), 3.36-3.41 (m, 1H, CH$_{2b}$), 4.03-4.12 (m, 2H), 4.19-4.23 (m, 2H, Thr$^\beta$), 4.54-4.61 (m, H-2, Thr$^\alpha$), 4.88 (m, 1H, NH), 4.96 (s, 1H, J=3.57 Hz, H-1), 5.07 (dd, 1H, H-3), 5.35 (d, 1H, H-4), 6.43 (br S, 1H, NH), 6.72 (br S, 1H, NH). MALDI-MS calcd for C$_{28}$H$_{46}$N$_4$O$_{13}$ [M+Na] m/z=669.296. found 669.323. Compound 12 was deprotected by stirring with 5% hydrazine-hydrate in methanol (5 mL) at room temperature for 35 min. The reaction mixture was diluted with toluene and concentrated. The residue was co-evaporated twice with toluene. Purification by silica gel column chromatography (DCM/MeOH 5:1) yielded 13 (119 mg, 89%): NMR data (CD$_3$OD, 300 MHz): $^1$H, δ 1.26 (d, 3H, Thr CH$_3$), 1.43 (s, 9H, $^t$Bu $CH_3$), 1.57-1.63 (m, 2H, $NHCH_2CH_2CH_2NH$), 2.06, 2.10 (s, 2×3H NHAc), 2.12-3.09 (m, 2H, $CH_2$), 3.15 (m, 2H, $CH_2$), 3.31 (br s, 2H, H-6), 3.68-3.76 (m, 2H, H-3, H-5), 3.88 (d, 1H, H-4), 4.22-4.26 (m, 2H, H-2, $Thr^\beta$), 4.46 (m, 1H, $Thr^\alpha$), 4.84 (d, 1H, H-1), 6.60 (br m, 1H, NH), 7.50 (br d, 1H, NH). MALDI-MS calcd. for $C_{22}H_{40}N_4O_{10}$ [M+Na] m/z=543.264. found 543.301. A solution of 13 in trifluoro acetic acid (4 mL) was stirred under an argon atmosphere at ambient temperature for 45 min. The reaction mixture was then diluted with DCM and concentrated to dryness. The crude product was purified by column chromatography (Iatro beads, $EtOAc/MeOH/H_2O$ 2:2:1→$MeOH/H_2O$ 1:1). After concentration of the pooled fractions, the solid was lyophilized from $H_2O$ to give compound 7 (91 mg, 0.21 mmol, 95%) as a white powder. $R_f$=0.17 (EtOAc/MeOH/$H_2O$ 6:3:1); $[\alpha]_D$ –37 (c 1.0 mg/mL, $H_2O$); NMR data ($D_2O$, 300 MHz): $^1H$, δ 1.15 (d, 3H, J=6.3 Hz, Thr $CH_3$), 1.73-1.77 (m, 2H, $CH_2$), 1.95 (s, 3H, NHAc), 2.04 (s, 3H, NHAc), 2.82-2.87 (m, 2H, $CH_2$), 3.11-3.15 (m, 1H, $CH_{2a}$), 3.22-3.26 (m, 1H, $CH_{2b}$), 3.65 (m, 2H, H-6), 3.76 (dd, 1H, J=2.9, 11.2 Hz, H-3), 3.87 (d, 1H, J=2.9 Hz, H-4), 3.92 (t, 1H, H-5), 3.99 (dd, 1H, J=3.41, 11.2 Hz, H-2), 4.28-4.30 (m, 1H, $Thr^\beta$), 4.32 (d, 1H, J=2.4 Hz, $Thr^\alpha$) 4.78 (d, 1H, J=3.56 Hz, J=3.9 Hz, H-1), 7.97 (br d, 1H, NH), 8.17 (br t, 1H, NH), 8.27 (br d, 1H, NH); $^{13}C$ ($D_2O$, 75 MHz), δ 18.17 Thr $CH_3$), 21.93, 22.33 (2×NAc) 26.98 ($CH_2$), 36.55 ($CH_2$), 37.22 ($CH_2$), 49.98 (C-6), 58.30 (C-3), 61.46 (C-4), 67.76 (C-5), 68.65 (C-2), 71.54 (C-$Thr^\beta$), 74.60)(C-$Thr^\alpha$, 98.60 (C-1), 172.09, 174.37, 175.18 (3×C=O, NHAc). HR-MALDI-MS calcd for $C_{17}H_{32}N_4O_8$ [M+Na] m/z=443.2118. found 443.2489.

Liposome Preparation.

Liposomes were prepared from PC, PG, cholesterol, and the glycolipopeptide 9 (15 μmol, molar ratio 65:25:50:10). The lipids were dissolved in DCM/MeOH (3/1, v/v) under an atmosphere of argon. The solvent was then removed by passing a stream of dry nitrogen gas, followed by further drying under high vacuum for one hour. The resulting lipid film was suspended in 1 mL 10 mM Hepes buffer, pH 6.5, containing 145 mM NaCl. The solution was vortexed on a shaker (250 rpm), under Ar atmosphere at 41° C. for 3 hours. The liposome suspension was extruded ten-times through 0.6 μm, 0.2 μm and 0.1 μm polycarbonate membranes (Whatman, Nuclepore®, Track-Etch Membrane) at 50° C. to obtain SUV.

Immunizations.

Groups of five mice (female BALB/c, 6 weeks) were immunized subcutaneously on days 0, 7, 14 and 21 with 0.6 μg of carbohydrate-containing liposomes and 10 μg of the adjuvant QS-21 in each boost. The mice were bled on day 28 (leg-vein) and the sera were tested for the presence of antibodies.

ELISA.

96-well plates were coated over night at 4° C. with Tn-BSA, (2.5 μg $mL^{-1}$) in 0.2 M borate buffer (pH 8.5) containing 75 mM sodium chloride (100 μL) per well). The plates were washed three times with 0.01 M Tris buffer containing 0.5% TWEEN 20% and 0.02% sodium azide. Blocking was achieved by incubating the plates 1 h at room temperature with 1% BSA in 0.01 M phosphate buffer containing 0.14 M sodium chloride. Next, the plates were washed and then incubated for 2 h at room temperature with serum dilutions in phosphate buffered saline. Excess antibody was removed and the plates were washed three times. The plates were incubated with rabbit anti-mouse IgM and IgG Fcγ fragment specific alkaline phosphatase conjugated antibodies (Jackson ImmunoResearch Laboratories Inc., West Grove, Pa.) for 2 h at room temperature. Then, after the plates were washed, enzyme substrate (p-nitrophenyl phosphate) was added and allowed to react for 30 min before the enzymatic reaction was quenched by addition of 3 M aqueous sodium hydroxide and the absorbance read at dual wavelengths of 405 and 490 nm. Antibody titers were determined by regression analysis, with $log_{10}$ dilution plotted against absorbance. The titers were calculated to be the highest dilution that gave two times the absorbance of normal mouse sera diluted 1:120.

Example II

Non-Covalently Linked Diepitope Liposome Preparations

In a first set of experiments, the tumor-related carbohydrate B-epitope and the universal T-epitope peptide were incorporated separately into preformed liposomes to form a diepitopic construct. Additionally, the lipopeptide $Pam_3Cys$ was incorporated into the liposome with the expectation that it would function as a built-in adjuvant, and thus circumvent the necessity of using an additional external adjuvant, such as QS-21.

The liposomes were prepared from lipid anchors carrying two different thiol-reactive functionalities, maleimide and bromoacetyl, at their surface. The $Pam_3Cys$ adjuvant was also incorporated into the preformed liposome and included a maleimide functionality. Conveniently, the maleimide and the bromoacetyl group show a marked difference in their reactivity towards sulfhydryl groups. The maleimide reacts rapidly with a sulfhydryl compound at pH 6.5, whereas the bromoacetyl requires slightly higher pH 8-9 to react efficiently with a thiol compound.

By exploiting this difference in reactivity, a diepitope liposome construct carrying the cancer related $Le^y$ tetrasaccharide and the universal T helper peptide QYIKANSK-FIGITEL (QYI) (SEQ ID NO:1) was prepared (Scheme 11). For the conjugation to the thiol-reactive anchors, both the oligosaccharide and the peptide were functionalized with a thiol-containing linker. The two-step consecutive conjugation to preformed liposomes has a great advantage: it is a very flexible approach that makes it easy to prepare liposomes carrying an array of different carbohydrate B-epitopes. The yield of conjugation, as based on quantitating the carbohydrate and peptide covalently coupled to the vesicles, was high, 70-80% for the oligosaccharide and 65-70% for the peptide, and the results were highly reproducible.

It is important to note that in these first diepitope liposome constructs, the carbohydrate B-epitope and peptide T-epitope are not themselves joined together by covalent linkages, but rather are held in proximity by their respective lipid anchors to which they are conjugated, and by hydrophobic interactions. It has been shown in several reports in the literature regarding vaccine candidates with pathogen-related peptide B-epitopes that this approach is successful leading to good titers of both IgM and specific IgG antibodies. These studies also indicate that the built-in adjuvant $Pam_3Cys$ is sufficient to induce a proper immune response.

However, in our study with the tumor-related carbohydrate B-epitope $Le^y$, immunizations of mice using the non-covalently linked diepitope liposome preparation described in this Example resulted in only very low titers of IgM antibodies. No IgG anti-$Le^y$ antibodies were detected. Even more surprising, co-administering the liposomal vaccine candidate with the powerful external adjuvant, QS-21, did not improve the outcome. Additionally, it was found that mice that had been immunized with an un-coated liposome control, i.e. a liposome that carried nothing but the maleimide and bromoacetyl functional groups on the surface, elicited high titers of IgG antibodies as detected by ELISA. More detailed ELISA studies of the anti-sera from this group of mice using a variety of protein conjugates revealed that the mice had responded to and elicited antibodies towards the maleimide linker. Also the anti-sera from the mice immunized with the liposomes coated with the Le$^y$ antigen and the QYI peptide were screened for anti-linker antibodies and it was found that also these mice had elicited IgG antibodies towards the maleimide linker.

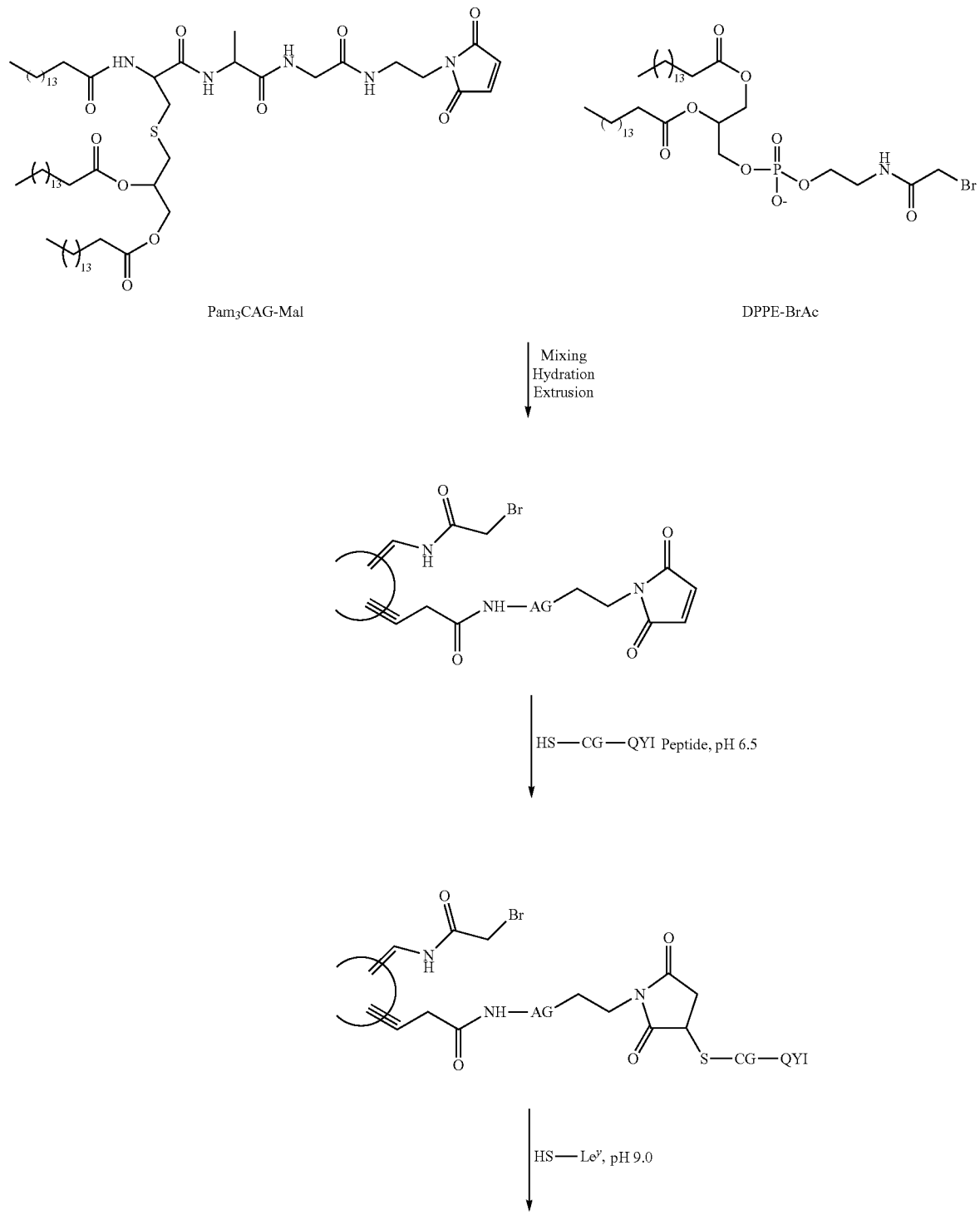

Scheme 11. Non-covalently linked diepitope liposome preparation

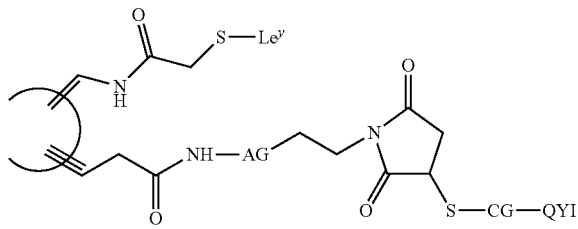

Due to its high reactivity at near neutral pH, the maleimide linker is widely used in conjugation chemistry to reach glyco- and peptide-protein conjugates that are further used in immunization studies. There are commercially available protein conjugation kits (Pierce Endogen Inc.) that utilize the maleimide linker both for the antigenic conjugate and the detection conjugate. Our data show that using these kits can lead to false positive results, especially when working with antigens of low immunogenicity (See T. Buskas, Y. Li and G-J. Boons, Chem. Eur. J., 10:3517-3523, 2004).

To test whether the highly immunogenic maleimide linker suppressed the immune response towards the Le$^y$ tetrasaccharide, we prepared the non-covalent diepitope liposome using only the bromoacetyl linker. In this experiment, the thiol-containing Le$^y$ tetrasaccharide and the universal T helper peptide were conjugated, in separate reactions, to lipids containing the bromoacetyl linker. The conjugated lipids were then mixed together to form lipid vesicles. Administering this new liposome formulation to mice, with or without the external adjuvant QS-21, raised only low titers of anti-Le$^y$ antibodies. Thus, the lack of an effective immune response toward the Le$^y$ tetrasaccharide was not due solely to the immunogenic maleimide linker.

Since the tumor-associated Le$^y$ tetrasaccharide is known to be only weakly immunogenic, we prepared another diepitope liposomal construct where the more immunogenic Tn(cluster) antigen was used as a target B-epitope. However, the same negative results were obtained with this antigen. Again, immunizations of mice resulted in only very low titers of anti-Tn(c) IgM antibodies. Co-administering with QS-21 as an external adjuvant did nothing to enhance the immune response.

From these results we concluded that the non-covalently linked diepitope liposome approach that has proven successful for a range of peptide antigens failed when a tumor-associated carbohydrate antigen of low immunogenicity was used as a B-epitope. Thus, we reasoned that the tumor-associated carbohydrate B-epitope and the helper T-epitope needed to be presented differently to the immune system to evoke a T-cell dependent immune response.

Example III

Covalently Linked Diepitope Liposome Preparations

We speculated that in order to achieve a better presentation of the carbohydrate B-epitope and peptide T-epitope, perhaps they needed to be covalently linked together. To test this idea we synthesized construct 1 (Scheme 12), a structurally well-defined anti-cancer vaccine candidate containing the structural features needed for a focused and effective T-cell dependent immune response. The vaccine candidate is composed of the tumor-associated Tn-antigen, the peptide T-epitope YAFKYARHANVGRNAFELFL (YAF) (SEQ ID NO:2) (*Neisseria meningitides*) and the lipopeptide Pam$_3$Cys. Due to difficulties in the synthesis using the original helper T-epitope peptide QYI, a different universal T-epitope (YAF) that displayed better solubility properties was used in this study.

Compound 1 was synthesized in a highly convergent manner by a combination of solid-phase and solution phase synthesis.

Scheme 12

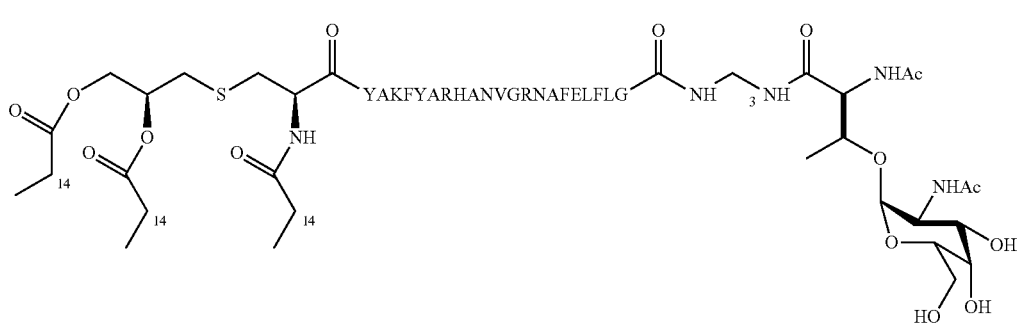

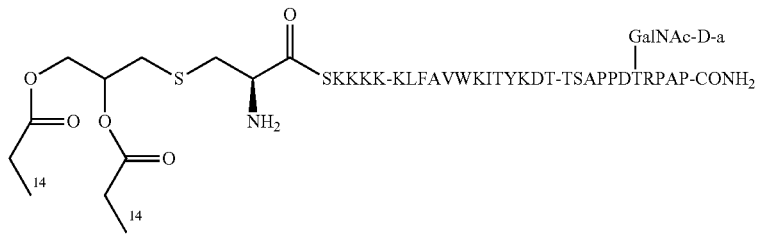

2

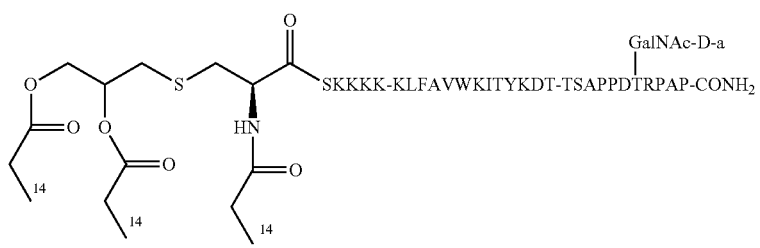

3

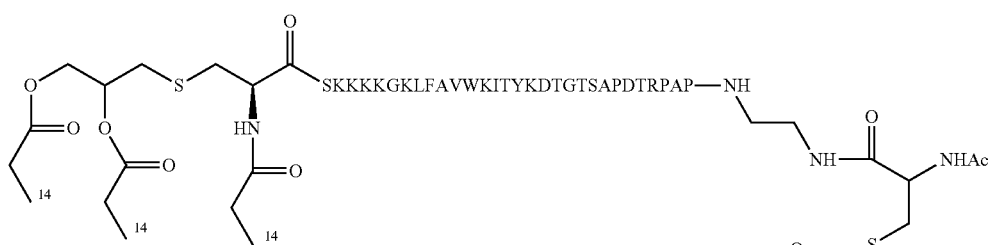

4

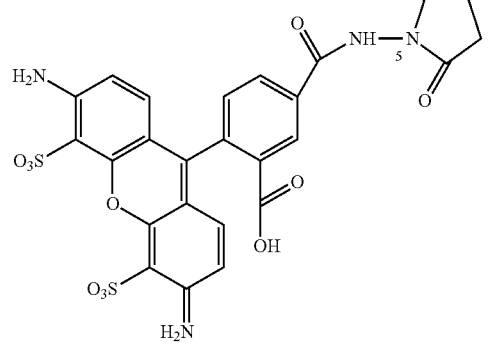

The construct was then incorporated into phospholipid-based liposomes. Compound 1 suffers from low solubility in a range of solvents, which probably is the main reason the incorporation into the liposomes was only 10%.

Mice were immunized with the construct at weekly intervals. To explore the adjuvant properties of the built-in lipopeptide Pam$_3$Cys, the antigen-containing liposomes were administered with (group 2) or without (group 1) the adjuvant QS-21.

As can be seen in Table 1 (Example I), the mice immunized with the liposome preparations elicited both IgM and IgG antibodies against the Tn-antigen (Table 1, entries 1 and 2). The presence of IgG antibodies indicated that the helper T-epitope peptide of 1 had activated helper T-lymphocytes. Furthermore, the observation that IgG antibodies were raised by mice which were immunized with liposomes in the absence of the external adjuvant QS-21 (group 1) indicated that the built-in adjuvant Pam$_3$Cys had triggered appropriate signals for the maturation of DCs and their subsequent activation of helper T-cells. However, the mice which received the liposomes in combination with QS-21 (group 2) elicited higher titers of anti Tn-antibodies. This stronger immune response may be due to a shift from a mixed Th1/Th2 to a Th1 skewed response.

The results provide, for the first time, a proof-of-principle for the use of a lipidated glycopeptide that contains a carbohydrate B-epitope, a helper T-cell epitope and a lipopeptide adjuvant as a minimal, self-contained subunit vaccine. It was also concluded that to evoke a T-cell dependent immune response toward the tumor-associated carbohydrate antigen, it is not enough that the carbohydrate B-epitope and the peptide T-epitope are presented together in a non-covalent manner on the surface of a adjuvant-containing liposome; rather, the entities are preferably covalently joined together. Finally, it was observed that an external adjuvant (QS-21) was not needed when the three components (carbohydrate B-epitope, helper T-cell epitope and lipopeptide) are covalently linked to form the lipidated glycopeptides.

Alternative Glycolipopeptide Components

Several improvements can be made to compound 1. For example, it has been found that antibodies elicited against the Tn-antigen poorly recognize cancer cells. However, clustering (Nakada et al., Proc. Natl. Acad. Sci. USA 1993, 90, 2495-2499; Reddish et al., 1997, 14, 549-560; Zhang et al., Cancer Res. 1995, 55, 3364-3368; Adluri et al., Cancer Immunol. Immunother 1995, 41, 185-192) or presenting the Tn antigen as part of the MUC-1 glycopeptide elicits antibodies with improved binding characteristics (Snijdewint et al., Int. J. Cancer 2001, 93, 97-106 The T-epitope employed in compound 1 is a MHC class II restricted epitope for humans. Thus, a more efficient class-switch to IgG antibodies may be expected when a murine T-epitope is used. Furthermore, it has been found that the lipopeptide $Pam_2Cys$ or $Pam_3CysSK_4$ are more potent immunoadjuvants than $Pam_3Cys$ (Spohn et al., Vaccine 2004, 22, 2494-2499). However, it was not known whether attachment of $Pam_2Cys$ or $Pam_3CysSK_4$ to the T- and B-epitope would affect their efficacies and potencies. Thus, based on these considerations, compounds 2 and 3 (Scheme 12) were designed, which contain the MUC-1 glycopeptide as a B-epitope, the well-documented murine helper T-cell epitope KLFAVWKI-TYKDT (KLF) (SEQ ID NO:3) derived from Polio virus (Leclerc et al., J. Virol. 1991, 65, 711-718) as the T-epitope, and the lipopeptide $Pam_7CysSK_4$ or $Pam_3CysSK_4$, respectively.

Glycolipopeptides 2 and 3 were incorporated into phospholipid-based liposomes as described for compound 1. Surprisingly, the solubility problems that plagued compound 1 were not an issue for compounds 2 and 3. Female BALB/c mice were immunized four times at weekly intervals with the liposome formulations with or without the external adjuvant QS-21 (Kensil et al., J. Immunol. 1991, 146, 431-437). Anti-Muc1 antibody titers were determined by coating microtiter plates with CTSAPDT(αGalNAc)RPAP conjugated to BSA and detection was accomplished with anti-mouse IgG antibodies labeled with alkaline phosphatase. The results are summarized in Tables 2 and 3.

TABLE 2

ELISA anti-MUC-1 antibody titers* after 4 immunizations with the glycolipopeptide/liposome formulations.

| Entry | Group | IgG1 |
|---|---|---|
| 1. | 1. $Pam_2Cys$-MUC-1 | 24,039 |
| 2. | 2. $Pam_2Cys$-MUC-1 + QS-21 | 36,906 |
| 3. | 3. $Pam_3Cys$-MUC-1 | 183,085 |
| 4. | 4. $Pam_3Cys$-MUC-1 + QS-21 | 450,494 |

*ELISA plates were coated with a BSA-BrAc-MUC-1 conjugate. Anti-MUC1 antibody titers are presented as means of groups of five mice. Titers are defined as the highest dilution yielding an optical density of 0.1 or greater over background of blank mouse sera.

TABLE 3

ELISA anti-MUC-1 antibody titers* after 4 immunizations with the glycolipopeptide/liposome formulations.

| Entry | Group | IgG1 | IgG2a | IgG2b | IgG3 |
|---|---|---|---|---|---|
| 1. | 1. $Pam_2Cys$-MUC-1 | 74,104 | 3,599 | 5,515 | 17,437 |
| 2. | 2. $Pam_2Cys$-MUC-1 + QS-21 | 126,754 | 22,709 | 5,817 | 20,017 |
| 3. | 3. $Pam_3Cys$-MUC-1 | 448,023 | 57,139 | 61,094 | 115,131 |
| 4. | 4. $Pam_3Cys$-MUC-1 + QS-21 | 653,615 | 450,756 | 70,574 | 305,661 |

*ELISA plates were coated with a BSA-BrAc-MUC-1 conjugate. Anti-MUC1 antibody titers are presented as means of groups of five mice. Titers are defined as the highest dilution yielding an optical density of 0.1 or greater over background of blank mouse sera.

As can be seen in Table 2, mice immunized with liposomal preparations of compounds 2 and 3 elicited high titers of anti-MUC-1 IgG antibodies. Surprisingly, mice that were immunized with the $Pam_3CysSK_4$-based vaccine elicited higher titers of antibodies than mice immunized with $Pam_2CysSK_4$ derivative. These results are contradictory to reports that have compared adjuvancy of $Pam_2Cys$ and $Pam_3CysSK_4$. Sub-typing of the IgG antibodies (IgG1, IgG2a, IgG2b and IgG3) indicated a bias towards a Th2 immune response (entries 1 and 3, Table 3). Co-administering of the adjuvant QS-21 did not lead to a significant increase of IgG antibody, however, in these cases a mixed Th1/Th2 response was observed (entries 2 and 4, Table 3).

Figure 2:
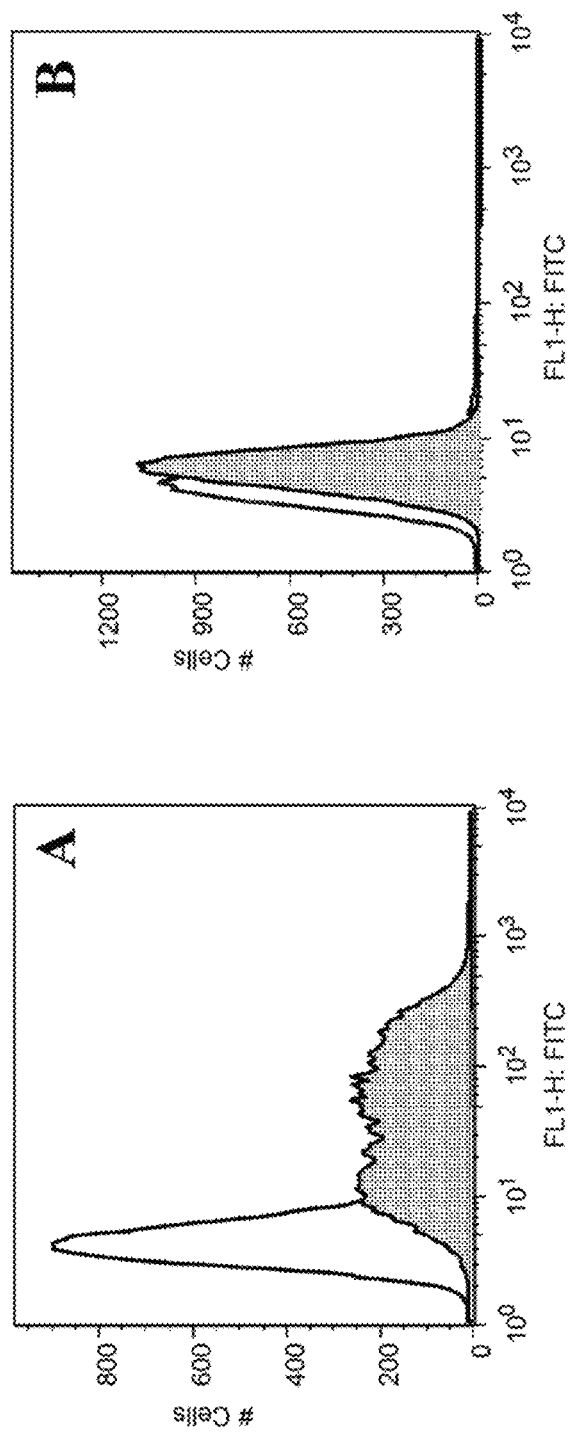
FIG. 2 shows flow cytometry analysis for specific anti-MUC-1 antibodies. Reactivity was tested on MCF-7 (A) and SK-MEL-28 (B) cells. Fluorescence intensity of serum (1:50 diluted) was assessed before (serum control; open peak) and after immunization with 3 (filled peak).

To ensure that the mouse sera were able to recognize native MUC-1 glycopeptide present on cancer cells, the binding of the sera to the MUC-1 expressing MCF-7 human breast cancer cell line was examined. Thus, the cells were treated with a 1:50 diluted sera for 30 minutes after which goat anti-mouse IgG antibodies labeled with FITC was added. The percentage of positive cells and mean fluorescence was determined by flow cytometry analysis. As can be seen in (FIG. 2), the anti-sera reacted strongly with the MUC-1 positive tumor cells whereas no binding was observed for sera obtained from naïve mice. Furthermore, no binding was observed when SK-MEL 28 cell were employed, which do not express the MUC-1 glycopeptide. These results demonstrate that anti-MUC-1 antibodies induced by 3 recognize the native antigen on human cancer cells. Further ELISA studies showed that titers against the T-epitope were very low, showing that no significant epitope suppression had occurred.

The lipopeptide moiety of the three-component vaccine is required for initiating the production of necessary cytokines and chemokines (danger signals) (Bevan, Nat. Rev. Immunol. 2004, 4, 595-602; Eisen et al., Curr. Drug Targets 2004, 5, 89-105; Akira et al., Nat. Immunol. 2001, 2, 675-680; Pasare et al., Immunity 2004, 21, 733-741; Dabbagh et al., Curr. Opin. Infect. Dis. 2003, 16, 199-204; Beutler, Mol. Immunol. 2004, 40, 845-859). The results of recent studies indicate that the lipopeptide initiates innate immune responses by interacting with the Toll-like receptor 2 on the surface of mononuclear phagocytes. After activation, the intracellular domain of TLR-2 recruits the adaptor protein MyD88, resulting in the activation of a cascade of kinases leading to the production of a number of cytokines and chemokines. On the other hand, lipopolysaccharides induce cellular responses by interacting with the Toll-like receptor 4 (TLR4)/MD2, which results in the recruitment of the adaptor proteins MyD88 and TRIF leading to a more complex pattern of cytokine TNF-α secretion is the prototypical measure for activation of the MyD88-dependent pathway, whereas secretion of IFN-β is commonly used as an indicator of TRIF-dependent cellular activation (Akira et al., Nat. Immunol. 2001, 2, 675-680; Beutler, Mol. Immunol. 2004, 40, 845-859).

To examine whether attachment of a glycopeptide containing a T epitope and a B epitope to the TLR ligand affects cytokine production, the efficacy ($EC_{50}$) and potency (maximum responsiveness) of TNF-α and IFN-β secretion induced by compounds 1, 2 and 3 was determined and the results compared with those of $Pam_2CysSK_4$, $Pam_3CysSK_4$ and LPS. Thus, RAW NO⁻ mouse macrophages were exposed over a wide range of concentrations to compounds 1, 2 and 3, $Pam_2CysSK_4$, $Pam_3CysSK_4$ and E. coli 055:B5 LPS. After 5 hours, the supernatants were harvested and examined for mouse TNF-α and IFN-β using commercial or in-house developed capture ELISA assays, respectively.

TABLE 4

$EC_{50}$ and $E_{max}$ values of concentration-response curves of E. coli LPS and synthetic compounds for TNFα production by mouse macrophages (RAW γNO(−) cells).

|  | $EC_{50}$ (nM)* | $E_{max}$ (pg/mL)* |
|---|---|---|
| E. coli LPS | 0.002 | 2585 |
| 1 | 10.230 | 363 |
| $Pam_2CysSK_4$ | 0.003 | 631 |
| 2 | 0.223 | 622 |
| $Pam_3CysSK_4$ | 3.543 | 932 |
| 3 | 2.151 | 802 |

*Values of EC50 and Emax are reported as best-fit values according to Prism (GraphPad Software, Inc). Concentration-response data were analyzed using nonlinear least-squares curve fitting in Prism.

As can be seen in FIG. 3 and Table 4, glycolipopeptide 3 and $Pam_3CysSK_4$ induced the secretion of TNF-α with similar efficacies and potencies indicating that attachment of the B-epitope and T-epitope had no effect on cytokine and chemokine responses. Surprisingly, attachment of the B-epitope and the T-epitope to $Pam_2CysSK_4$ led to a significant reduction in potency and thus in this case the attachment of the B-epitope and the T-epitope led to a reduction in activity. Compound 1 which contains the $Pam_3Cys$ moiety is significantly less active than the compounds 2 and 3, which may explain the poor antigenicity of compound 1. Compounds 1, 2 and 3 did not induce the production of INF-β. Surprisingly, E. coli 055:B5 displayed much larger potencies and efficacies for TNF-α induction compared to compounds 1, 2, 3, and $Pam_3CysSK_4$. In addition, it was able to stimulate the cells to produce INF-β. E. coli LPS is too active resulting in over-activation of the innate immune system, leading to symptoms of septic shock.

It was speculated that in addition to initiating the production of cytokines and chemokines, the lipopeptide may facilitate selective targeting and uptake by antigen presenting cells in a TLR2 dependent manner. To test this hypothesis, compounds 4, which contains a fluorescence label, was administered to RAW NO⁻ mouse macrophages and after 30 minutes the cells were harvested, lysed and the fluorescence measured. To account for possible cell surface binding without internalization, the cells were also trypsinized before lyses and then examination for fluorescence. As can be seen in FIG. 4, a significant quantity of the 4 was internalized whereas a small amount was attached to the cell surface. To determine whether the uptake was mediated by TLR2, the uptake studies were repeated using native HEK297 cell and HEK297 cell transfected with either TLR2 or TLR4/MD2. Importantly, significant uptake was only observed when the cells were transfected with TLR2 indicating that uptake is mediated by this receptor. These studies show that TLR2 facilitates the uptake of antigen, which is an important step in antigen processing and immune responses.

Example IV

Covalent Attachment of the Lipid Component

To establish the importance of covalent attachment of the TLR ligand to the vaccine candidate, compound 5 (Scheme 13) which only contains the B-epitope and the T-epitope was designed and synthesized. Mice were immunized four times at weekly intervals with this compound in the presence of $PAM_3CysSK_4$. Interestingly, the mixture of glycopeptide 5 and the adjuvant $Pam_3CysSK_4$ elicited no- or very low titers of IgG antibodies, demonstrating that covalent attachment of $Pam_3CysSK_4$ to the B-epitope and T-epitope is critical for strong immune responses.

Scheme 13

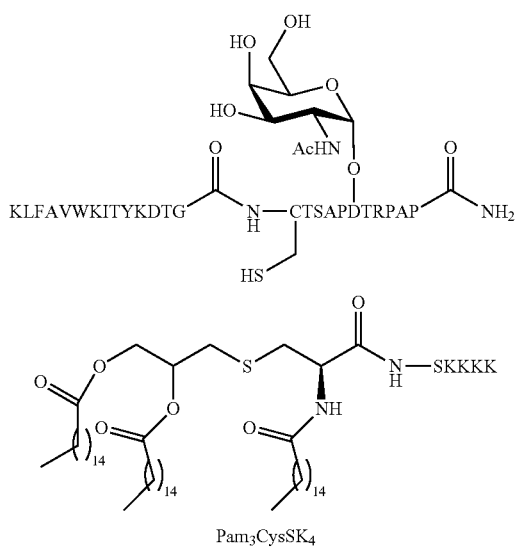

$Pam_3CysSK_4$

Example V

Lipid Component

To determine the importance of lipidation with a ligand of a Toll like receptor, compound 6 (Scheme 14) was designed and synthesized. This compound is composed of the B-epitope and T-epitope linked to non-immunogenic lipidated amino acids. Mice were immunized with a liposomal preparation of compound 6, similar to the procedure employed for compound 1 and 2. Liposomes containing compound 6 induced titers that were significantly lower than those elicited by compound 3, demonstrating that a TLR ligand of the three-component vaccine is important for optimal immune responses.

Scheme 14

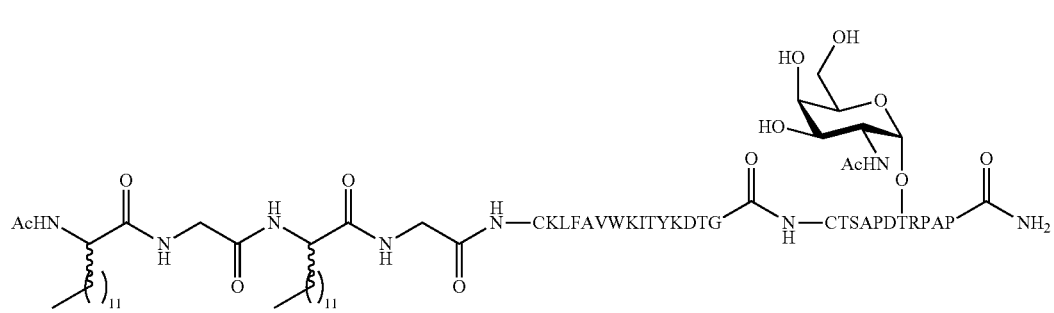

Conclusions

The three-component carbohydrate-based vaccine has a number of distinctive advantages over a traditional conjugate vaccine. For example, the minimal subunit vaccine does not suffer from epitope suppression, a characteristic of carbohydrate-protein conjugates. Apart from providing danger signals, the lipopeptide Pam$_3$CysSK$_4$ also facilitates the incorporation of the antigen into liposomes. A liposomal formulation is attractive because it presents efficiently the antigen to the immune system. A unique feature of the vaccine is that Pam$_3$CysSK$_4$ promotes selective targeting and uptake by antigen presenting cells, T-helper cells and B-lymphocytes, which express Toll loll like receptors (Example III). Finally, a fully synthetic compound has as an advantage that it can be fully characterized, which facilitates its production in a reproducible manner.

Example VI

Increasing the Antigenicity of Synthetic Tumor-Associated Carbohydrate Antigens by Targeting Toll-Like Receptors In this Example, a number of fully synthetic vaccine candidates have been designed, chemically synthesized, and immunologically evaluated to establish strategies to overcome the poor immunogenicity of tumor-associated carbohydrates and glycopeptides and to study in detail the importance of TLR engagement for antigenic responses. Covalent attachment of a TLR2 agonist, a promiscuous peptide T-helper epitope, and a tumor-associated glycopeptide, gives a compound that elicits in mice exceptionally high titers of IgG antibodies which recognize cancer cells expressing the tumor-associated carbohydrate.

The over-expression of oligosaccharides, such as Globo-H, LewisY, and Tn antigens is a common feature of oncogenic transformed cells (Springer, Mol. Med. 1997, 75, 594-602; Hakomori, Acta Anat. 1998, 161, 79-90; Dube, Nat. Rev. Drug Discov. 2005, 4, 477-488). Numerous studies have shown that this abnormal glycosylation can promote metastasis (Sanders, J. Clin. Pathol. Mol. Pathol. 1999, 52, 174-178) and hence the expression of these compounds is strongly correlated with poor survival rates of cancer patients. A broad and expanding body of preclinical and clinical studies demonstrates that naturally acquired, passively administered or actively induced antibodies against carbohydrate-associated tumor antigens are able to eliminate circulating tumor cells and micro-metastases in cancer patients (Livingston, Cancer Immunol. 1997, 45, 10-19; Ragupathi, Cancer Immunol. 1996, 43, 152-157; von Mensdorff-Pouilly, Int. J. Cancer 2000, 86, 702-712; Finn, Nat. Rev. Immunol. 2003, 3, 630-641).

Traditional cancer vaccine candidates composed of a tumor-associated carbohydrate (Globo-H, Lewis$^Y$, and Tn) conjugated to a foreign carrier protein (e.g. KLH and BSA) have failed to elicit sufficiently high titers of IgG antibodies in most patients. It appears that the induction of IgG antibodies against tumor-associated carbohydrates is much more difficult than eliciting similar antibodies against viral and bacterial carbohydrates. This observation is not surprising because tumor associated saccharides are self-antigens and consequently tolerated by the immune system. The shedding of antigens by the growing tumor reinforces this tolerance. In addition, a foreign carrier protein such as KLH can elicit a strong B-cell response, which may lead to the suppression of an antibody response against the carbohydrate epitope. The latter is a greater problem when self-antigens such as tumor-associated carbohydrates are employed. Also, linkers that are utilized for the conjugation of carbohydrates to proteins can be immunogenic leading to epitope suppression (Buskas, Chem. Eur. J. 2004, 10, 3517-3524; Ni, Bioconjug. Chem. 2006, 17, 493-500). It is clear that the successful development of a carbohydrate-based cancer vaccine requires novel strategies for the more efficient presentation of tumor-associated carbohydrate epitopes to the immune system, resulting in a more efficient class switch to IgG antibodies (Reichel, J. Chem. Commun. 1997, 21, 2087-2088; Alexander, J. Immunol. 2000, 164, 1625-1633; Kudryashov, Proc. Natl. Acad. Sci. U.S.A. 2001, 98, 3264-3269; Lo-Man, J. Immunol. 2001, 166, 2849-2854; Jiang, Curr. Med. Chem. 2003, 10, 1423-1439; Jackson, Proc. Natl. Acad. Sci. U.S.A. 2004, 101, 15440-5; Lo-Man, Cancer Res. 2004, 64, 4987-4994; Buskas, Angew. Chem. Int. Ed. 2005, 44, 5985-5988 (Example I); Dziadek, Angew. Chem. Int. Ed. 2005, 44, 7630-7635; Krikorian, Bioconjug. Chem. 2005, 16, 812-819; Pan, J. Med. Chem. 2005, 48, 875-883).

Advances in the knowledge of the cooperation of innate and adaptive immune responses (Pasare, Semin. Immunol. 2004, 16, 23-26; Pashine, Nat. Med. 2005, 11, S63-S68; Akira, Nat. Rev. Immunol. 2004, 4, 499-511; O'Neill, Curr Opin Immunol 2006, 18, 3-9; Lee, Semin Immunol 2007, 19, 48-55; Ghiringhelli, Curr Opin Immunol 2007, 19, 224-31) are offering new avenues for vaccine design for diseases such as cancer, for which traditional vaccine approaches have failed. The innate immune system responds rapidly to families of highly conserved compounds, which are integral parts of pathogens and perceived as danger signals by the host. Recognition of these molecular patterns is mediated by sets of highly conserved receptors, such as Toll-like receptors (TLRs), whose activation results in acute inflammatory responses such as direct local attack against invading pathogens and the production of a diverse set of cytokines Apart from antimicrobial properties, the cytokines and chemokines also activate and regulate the adaptive component of the immune system (Lin, J Clin Invest 2007, 117, 1175-83). In this respect, cytokines stimulate the expression of a number of co-stimulatory proteins for optimum interaction between T-helper cells and B- and antigen presenting cells (APC). In addition, some cytokines and chemokines are responsible for overcoming suppression mediated by regulatory T-cells. Other cytokines are important for directing the effector T-cell response towards a T-helper-1 (Th-1) or T-helper-2 (Th-2) phenotype (Dabbagh, Curr. Opin. Infect. Dis. 2003, 16, 199-204).

Recently, we described a fully synthetic three-component vaccine candidate (compound 21, FIG. 5) composed of a tumor-associated MUC-1 glycopeptide B-epitope, a promiscuous helper T-cell epitope and a TLR2 ligand (Buskas, Angew. Chem. Int. Ed. 2005, 44, 5985-5988 (Example I); Ingale, Nat. Chem. Biol. 2007, 3, 663-667; Ingale, J. Org. Lett. 2006, 8, 5785-5788; Bundle, Nat. Chem. Biol. 2007, 3, 604-606). The exceptional antigenic properties of the three-component vaccine were attributed to the absence of any unnecessary features that are antigenic and may induce immune suppression. It contains, however, all the mediators required for eliciting relevant IgG immune responses. Furthermore, attachment of the TLR2 agonist $Pam_3CysSK_4$ to the B- and T-epitopes ensures that cytokines are produced at the site where the vaccine interacts with immune cells. This leads to a high local concentration of cytokines facilitating maturation of relevant immune cells. Apart from providing danger signals, the lipopeptide $Pam_3CysSK_4$ facilitates the incorporation of the antigen into liposomes and promotes selective targeting and uptake by antigen presenting cells and B-lymphocytes.

To establish the optimal architecture of a fully synthetic three-component cancer vaccine and to study in detail the importance of TLR engagement for antigenic responses, we have chemically synthesized, and immunologically evaluated a number of fully synthetic vaccine candidates. It has been found that a liposomal preparation of compound 22, which is composed of an immunosilent lipopeptide, a promiscuous peptide T-helper epitope, and a MUC-1 glycopeptide, is significantly less antigenic than compound 21, which is modified with a TLR2 ligand ($Pam_3CysSK_4$). However, liposomal preparations of compound 22 with $Pam_3CysSK_4$ (23) or monophosphoryl lipid A (24), which are TLR2 and TLR4 agonists, respectively, elicited titers comparable to compound 21. However, the antisera elicited by mixtures of 22 and 23 or 24 had an impaired ability to recognize cancer cells. Surprisingly, a mixture of compounds 25 and 26, which are composed of a MUC-1 glycopeptide B-epitope linked to lipidated amino acids and the helper T-epitope attached to $Pam_3CysSK_4$, did not raise antibodies against the MUC-1 glycopeptide. Collectively, the results demonstrate that TLR engagement is not essential but greatly enhanced antigenic responses against the tumor-associated glycopeptide MUC-1. Covalent attachment of the TLR agonist to the B- and helper T-epitope is important for antibody maturation for improved cancer cell recognition.

Results and Discussion.
Chemical Synthesis.

Compound 21 (FIG. 5), which contains as B-epitope a tumor-associated glycopeptide derived from MUC-1 (Berzofsky, Nat. Rev. Immunol. 2001, 1, 209-219; Baldus, Crit. Rev. Clin. Lab. Sci. 2004, 41, 189-231; Apostolopoulos, Curr. Opin. Mol. Ther. 1999, 1, 98-103; Hang, Bioorg. Med. Chem. Lett. 2005, 13, 5021-5034), the well-documented murine MHC class II restricted helper T-cell epitope KLFAVWKITYKDT (SEQ ID NO:3) derived from the Polio virus (Leclerc, J. Virol. 1991, 65, 711-718), and the lipopeptide $Pam_3CysSK_4$ (TLR2 agonist) (Spohn, Vaccine 2004, 22, 2494-2499), was previously shown to elicit exceptionally high titers of IgG antibodies in mice (Ingale, Nat. Chem. Biol. 2007, 3, 663-667). Compound 22 has a similar architecture as 21, however, the TLR2 ligand has been replaced by lipidated amino acids (Toth, Tetrahedron Lett. 1993, 34, 3925-3928). The lipidated amino acids do not induce production of cytokines, however, they enable incorporation of the compound into liposomes. Thus, glycolipopeptide 22 is ideally suited to establish the importance of TLR engagement for antigenic responses against tumor-associated glycopeptides. To determine the importance of covalent attachment of the TLR ligand, liposomal preparations of compound 22 and $Pam_3CysSK_4$ (23) or monophosphoryl lipid A (24), which are TLR2 and TRL4 agonists, respectively were employed (Spohn, Vaccine 2004, 22, 2494-2499; Chow, J. Biol. Chem. 1999, 274, 10689-10692). Finally, compounds 25 and 26, which are composed of a MUC-1 glycopeptide B-epitope linked to lipidated amino acids and the helper T-epitope attached to $Pam_3CysSK_4$, were employed to establish the importance of covalent linkage of the B- and helper T-epitope. Compound 21 was prepared as described previously (Ingale, Nat. Chem. Biol. 2007, 3, 663-667; Ingale, Org. Lett. 2006, 8, 5785-5788). Compound 22 was synthesized by SPPS using a Rink amide resin, Fmoc protected amino acids, Fmoc-Thr-($AcO_3$-α-D-GalNAc) (Cato, J. Carbohydr. Chem. 2005, 24, 503-516) and Fmoc protected lipidated amino acid (Gibbons, Liebigs Ann. Chem. 1990, 1175-1183; Koppitz, Hely. Chim. Acta 1997, 80, 1280-1300). The standard amino acids were introduced using 2-(1H-bezotriazole-1-yl)-oxy-1,1,3,3-tetramethyl hexafluorophosphate (HBTU)/N-hydroxybenzotriazole (HOBt) (Knorr, Tetrahedron Lett. 1989, 30, 1927-1930) as an activating reagent, the glycosylated amino acid was installed with O-(7-azabenzotriazol-1-yl)-N,N,N',N'-tetramethyl-uronium hexafluorophosphate (HATU)/1-hydroxy-7-azabenzotriazole (HOAt), and the lipidated amino acids with benzotriazole-1-yl-oxy-tris-pyrrolidino-phosphonium hexafluorophosphate (PyBOP)/HOBt. After completion of the assembly of the glycolipopeptide, the N-terminal Fmoc protecting group was removed using standard conditions and the resulting amine capped by acetylation with acetic anhydride and diisopropylethyl amine (DIPEA) in N-methylpyrrolidone (NMP). Next, the acetyl esters of the saccharide moiety were cleaved with 60% hydrazine in MeOH and treatment with reagent B (TFA, $H_2O$, phenol, triethylsilane, 88/5/5/2, v/v/v/v) resulted in removal of the side chain protecting groups and release of the glycopeptide from the solid support.

Pure compound 22 was obtained after purification of the crude product by precipitation with ice-cold diethyl ether followed by HPLC on a C-4 semi-preparative column. A similar protocol was used for the synthesis of compound 25. Derivative 26 was synthesized by SPPS on a Rink amide resin and after assembly of the peptide, the resulting product was coupled manually with N-fluorenylmethoxycarbonyl-R-(2,3-bis(palmitoyloxy)-(2R-propyl)-(R)-cysteine (Fmoc-$Pam_2Cys$-OH) (Metzger, Int. J. Pept. Protein Res. 1991, 38, 545-554). The N-Fmoc group of the product was removed with 20% piperidine in DMF and the resulting amine was coupled with palmitic acid using and PyBOB, HOBt and DIPEA in DMF. The lipopeptide was treated with reagent B to cleavage it from the resin and to remove side chain protecting groups. The crude product was purified by precipitation with ice-cold diethyl ether followed by HPLC on a C-4 semi-preparative column.

Immunizations and Immunology.

Compounds 21 and 22 were incorporated into phospholipid-based small uni-lamellar vesicles (SUVs) by hydration of a thin film of egg phosphatidylcholine (PC), phosphatidylglycerol (PG), cholesterol (Chol), and compound 21 or 22 (molar ratios: 65/25/50/10) in a HEPES buffer (10 mM, pH 6.5) containing NaCl (145 mM) followed by extrusion through 100 nm Nuclepore® polycarbonate membrane. Groups of five female BALB/c mice were immunized subcutaneously four times at weekly intervals with liposomes containing 3 μg of saccharide. Furthermore, similar liposomes were prepared of a mixture of glycopeptide 22 with 23 or 24 (molar ratios: PC/PG/Choi/22/23 or 24, 65/25/5/5/5) in HEPES buffer and administered four times at weekly intervals prior to sera harvesting. Finally, mice were immunized with a liposomal preparation of compound 25 and 26 (molar ratios: PC/PG/Choi/25/26, 65/25/5/5/5) employing standard procedures.

Anti-MUC-1 antibody titers of anti-sera were determined by coating microtiter plates with the MUC-1 derived glycopeptide TSAPDT(α-D-GalNAc)RPAP conjugated to BSA and detection was accomplished with anti-mouse IgM or IgG antibodies labeled with alkaline phosphatase. Mice immunized with 21 elicited exceptionally high titers of anti-MUC-1 IgG antibodies (Table 5). Sub-typing of the IgG antibodies (IgG1, IgG2a, IgG2b, and IgG3) indicated a bias towards a Th2 immune response. Furthermore, the observed high IgG3 titer is typical of an anti-carbohydrate response. Immunizations with glycolipopeptide 22, which contains lipidated amino acids instead of a TLR2 ligand, resulted in significantly lower titers of IgG antibodies demonstrating that TLR engagement is very important for optimum antigenic responses. However, liposomal preparations of compound 22 with Pam$_3$CysSK$_4$ (23) or monophosphoryl lipid A (24) elicited IgG (total) titers similar to 21. In the case of the mixture of 22 with 23, the immune response was biased towards a Th2 response as evident by high IgG1 and low IgG2a,b titers. On the other hand, the use of monophosphoryl lipid A led to significant IgG1 and IG2a,b responses, and thus this preparation elicited a mixed Th1/Th2 response. Finally, liposomes containing compound 25 and 26 did not induce measurable titers of anti MUC-1 antibodies indicating that the B- and T epitope need to be covalent linked for antigenic responses.

Next, possible antigenic responses against the helper T-epitope were investigated. Thus, streptavidin coated microtiter plates were treated with the helper T-epitope modified with biotin. After the addition of serial dilutions of sera, detection was accomplished with anti-mouse IgM or IgG antibodies labeled with alkaline phosphatase. Interestingly, compound 21 elicited low whereas mixtures of 22 with 23 or 24 elicited no antibodies against the helper T-epitope.

Pam$_3$CysSK$_4$ or monophosphoryl lipid A are employed for initiating the production of cytokines by interacting with TLR2 or TLR4, respectively, on the surface of mononuclear phagocytes (Kawai, Semin. Immunol. 2007, 19, 24-32). After activation with Pam$_3$CysSK$_4$, the intracellular domain of TLR2 recruits the adaptor protein MyD88 resulting in the activation of a cascade of kinases leading to the production of a number of cytokines and chemokines. On the other hand, lipopolysaccharides (LPS) and lipid As induce cellular responses by interacting with the TLR4/MD2 complex, which results in the recruitment of the adaptor proteins MyD88 and TRIF leading to the induction of a more complex pattern of cytokine TNF-α secretion is the prototypical measure for activation of the MyD88-dependent pathway, whereas secretion of IFN-β is commonly used as an indicator of TRIF-dependent cellular activation.

To examine cytokine production, mouse macrophages (RAW γNO(−) cells) were exposed over a wide range of concentrations to compounds 21-24, E. coli 055:B5 LPS and prototypic E. coli bisphosphoryl lipid A (Zhang, J. Am. Chem. Soc. 2007, 129, 5200-5216). After 5.5 h, the supernatants were harvested and examined for mouse TNF-α and IFN-β using commercial or in-house developed capture ELISAs, respectively (FIG. 6). Potencies (EC$_{50}$, concentration producing 50% activity) and efficacies (maximal level of production) were determined by fitting the dose-response curves to a logistic equation using PRISM software. Glycolipopeptide 21 and Pam$_3$CysSK$_4$ (23) induced secretion of TNF-α with similar efficacies and potencies, indicating that attachment of the B- and T-epitopes had no effect on cytokine responses. As expected, none of the compounds induced the production of INF-β. Furthermore, compound 22 did not induce TNF-α and IFN-β secretion, indicating that its lipid moiety is immunosilent. Compound 24 stimulated the cells to produce TNF-α and INF-β but its potency was much smaller than that of E. coli 055:B5 LPS. It displayed a much larger efficacy of TNF-α production compared to compounds 21 and 23. The reduced efficacy of compounds 21 and 23 is probably a beneficial property,

TABLE 5

ELISA anti-MUC1 and anti-T-epitope antibody titers[a] after 4 immunizations with various preparations.

| Immunization[b] | IgG total MUC1 | IgG1 MUC1 | IgG2a MUC1 | IgG2b MUC1 | IgG3 MUC1 | IgM MUC1 | IgG total T-epit. |
|---|---|---|---|---|---|---|---|
| 21 | 177,700 | 398,200 | 49,200 | 37,300 | 116,200 | 7,200 | 23,300 |
| 22 | 13,300 | 44,700 | 300 | 1,800 | 18,600 | 1,300 | 100 |
| 22/23 | 160,500 | 279,800 | 36,200 | 52,500 | 225,600 | 11,000 | 700 |
| 22/24 | 217,400 | 359,700 | 161,900 | 106,000 | 131,700 | 33,400 | 100 |
| 25/26 | 12,800 | 12,700 | 4,800 | 10,100 | 34,400 | 29,000 | 7,600 |

[a]Anti-MUC1 and anti-T-epitope antibody titers are presented as the median for groups of five mice. ELISA plates were coated with BSA-MI-MUC1 conjugate for anti-MUC1 antibody titers or neutravidin-biotin-T-epitope for anti-T-epitope antibody titers. Titers were determined by linear regression analysis, plotting dilution vs. absorbance. Titers are defined as the highest dilution yielding an optical density of 0.1 or greater over that of normal control mouse sera.
[b]Liposomal preparations were employed.
Individual anti-MUC1 titers for IgG total, IgG1, IgG2a, IgG2b, IgG3 and IgM, and anti-T-epitope for IgG total are reported in FIG. 8.

because LPS can over-activate the innate immune system leading to symptoms of septic shock.

Next, the ability of the mouse antisera to recognize native MUC-1 antigen present on cancer cells was established. Thus, serial dilutions of the serum samples were added to MUC-1 expressing MCF-7 human breast cancer cells (Horwitz, Steroids 1975, 26, 785-95) and recognition was established using a FITC-labeled anti-mouse IgG antibody. As can be seen in FIG. 7, anti-sera obtained from immunizations with the three-component vaccine 1 displayed excellent recognition of MUC-1 tumor cell whereas no binding was observed when SK-MEL 28 cells, which do not express the MUC-1 antigen, were employed (FIG. 9).

Although sera obtained from mice immunizations with a mixture of lipidated T-B epitope (22) and $Pam_3CysSK_4$ (23) elicited equally high IgG antibody titers as 21 (table 5), a much-reduced recognition of MCF-7 cells was observed. This result indicates that covalent attachment of the adjuvant $Pam_3CysSK_4$ (23) to the B-T epitope is important for proper antibody maturation leading to improved cancer cell recognition. Immunizations with a mixture of compound 22 and monophosphoryl lipid A (24) led to variable results and two mice displayed excellent, and three modest, recognition of MCF-7 cells.

Discussion

Most efforts aimed at developing carbohydrate-based cancer vaccines have focused on the use of chemically synthesized tumor-associated carbohydrates linked through an artificial linker to a carrier protein (Springer, Mol. Med. 1997, 75, 594-602; Dube, Nat. Rev. Drug Discov. 2005, 4, 477-488; Ouerfelli, Expert Rev. Vaccines 2005, 4, 677-685; Slovin, Immunol. Cell Biol. 2005, 83, 418-428). It has been established that the use of KLH as a carrier protein in combination with the powerful adjuvant QS-21 gives the best results. However, a drawback of this approach is that KLH is a very large and cumbersome protein that can elicit high titers of anti-KLH-antibodies (Cappello, Cancer Immunol Immunother 1999, 48, 483-492), leading to immune suppression of the tumor-associated carbohydrate epitope. Furthermore, the conjugation chemistry is often difficult to control as it results in conjugates with ambiguities in composition and structure, which may affect the reproducibility of immune responses. Also, the linker moiety can elicit strong B-cell responses (Buskas, Chem. Eur. J. 2004, 10, 3517-3524; Ni, Bioconjug. Chem. 2006, 17, 493-500). Not surprisingly, preclinical and clinical studies with carbohydrate-protein conjugates have led to results of mixed merit. For example, mice immunized with a trimeric cluster of Tn-antigens conjugated to KLH (Tn(c)-KLH) in the presence of the adjuvant QS-21 elicited modest titers of IgG antibodies (Kuduk, J. Am. Chem. Soc. 1998, 120, 12474-12485). Examination of the vaccine candidate in a clinical trial of relapsed prostate cancer patients gave low median IgG and IgM antibody titer (Slovin, J. Clin. Oncol. 2003, 21, 4292-4298).

The studies reported herein show that a three-component vaccine, in which a MUC-1 associated glycopeptide B-epitope, a promiscuous murine MHC class II restricted helper T-cell epitope, and a TLR2 agonist (21) are covalently linked, can elicit robust IgG antibody responses. Although covalent attachment of the TLR2 ligand to the T-B glycopeptide epitope was not required for high IgG antibody titers, it was found to be very important for optimal cancer cell recognition. In this respect, liposomes containing compounds 21 or a mixture compound 22 and TLR2 agonist 23 elicited similar high anti-MUC-1 IgG antibody titers. However, antisera obtained from immunizations with 21 recognized MUC-1 expressing cancer cells at much lower sera dilutions than antisera obtained from immunizations with a mixture of 22 and 23. It appears that immunizations with three-component vaccine 21 lead to more efficient antibody maturation resulting in improved cancer cell recognition.

Differences in antigenic responses against the helper T-epitope were also observed. Thus, 21 elicited low titers of IgG antibodies against the helper T-epitope whereas mixtures of 22 with 23 induced no antigenic responses against this part of the candidate vaccine. Thus, the covalent attachment of the TLR2 ligand makes compound 21 more antigenic resulting in low antibody responses against the helper T-epitope.

It was observed that a mixture of compound 22 with 23 or 24 induced similar high titers of total IgG antibodies. However, a bias towards a Th2 response (IgG1) was observed when the TLR2 agonist $Pam_3CysSK_4$ (23) was employed whereas mixed Th1/Th2 responses (IgG2a,b) was obtained when the TLR4 agonist monophosphoryl lipid A (24) was used. The difference in polarization of helper T-cells is probably due to the induction of different patterns of cytokines by TLR2 or TLR4. In this respect, it was previously observed that $Pam_3Cys$ induces lower levels of Th1 inducing cytokines Il-12(p70) and much higher levels of Th2-inducing IL-10 than *E. coli* LPS (Dillon, B. J Immunol 2004, 172, 4733-43). The differences are likely due to the ability of TLR4 to recruit the adaptor proteins MyD88 and Trif whereas TLR2 can only recruit MyD88. The results indicate that the immune system can be tailored in a particular direction by proper selection of an adjuvant, which is significant since different IgG isotypes perform different effector functions.

The results described herein also show that compound 22 alone, which contains an immuno-silent lipopeptide, elicits much lower IgG titers compared to compound 21, which is modified by a TLR2 ligand. In particular, the ability of compound 22 to elicit IgG2 antibodies was impaired. Recent studies employing mice deficient in TLR signaling have cast doubt about the importance of these innate immune receptors for adaptive immune responses (Blander, Nature 2006, 440, 808-812; Gavin, Science 2006, 314, 1936-1938; Meyer-Bahlburg, J Exp Med 2007, 204, 3095-101; Pulendran, N Engl J Med 2007, 356, 1776-8). In this respect, studies with MyD88 deficient mice showed that IgM and IgG1 are largely, but not completely, dependent of TLR signaling whereas the IgG2 isotype is entirely TLR-dependent (Blander, Nature 2006, 440, 808-812). These observations, which are in agreement with the results reported here, were attributed to a requirement of TLR signaling for B-cell maturation. However, another study found that $MyD88^{-/-}/Trif^{lps/lps}$ double knockout mice elicited similar titers of antibodies as wild type mice when immunized with trinitrophenol-hemocyanin (TNP-Hy) or TNP-KLH in the presence or absence of several adjuvants (Gavin, Science 2006, 314, 1936-1938). It was concluded that it might be desirable to exclude TLR agonists from adjuvants. It has been noted that the importance of an adjuvant may depend on the antigenicity of the immunogen (Meyer-Bahlburg, J Exp Med 2007, 204, 3095-101; Pulendran, N Engl J Med 2007, 356, 1776-8). In this respect, proteins conjugates of TNP are highly antigenic and may not require an adjuvant for optimal responses. However, self-antigens such as tumor-associated carbohydrates have low intrinsic antigenicity and the results reported here clearly show that much more robust antibody responses are obtained when a TLR ligand is co-administered. In addition, it is demonstrated here that the architecture of a candidate vaccine is very important for optimal antigenic responses and in particular covalent attachment of a TLR ligand to a T-B epitope led to improved cancer cell recognition.

The failure of a mixture of compounds 25 and 26 to elicit anti-MUC-1 glycopeptide antibodies indicates that covalent attachment of the T- to the B-epitope is needed to elicit antigenic responses. In this respect, activation of B-cells by helper T-cells requires a similar type of cell-cell interaction as for helper T-cell activation by antigen presenting cells. Thus, a protein or peptide-containing antigen needs to be internalized by B-cells for transport to endosomal vesicles, where proteases will digest the protein and some of the resulting peptide fragments will be complexed with class II MHC protein. The class II MHC-peptide complex will then be transported to the cell surface of the B-lymphocyte to mediate an interaction with helper T-cell resulting in a class switch from low affinity IgM to high affinity IgG antibody production. Unlike antigen presenting cells, B-cells have poor phagocytic properties and can only internalize molecules that bind to the B-cell receptor. Therefore, it is to be expected that internalization of the helper T-epitope is facilitated by covalent attachment to the B-epitope (MUC-1 glycopeptide) and as a result covalent attachment of the two epitopes will lead to more robust antigenic responses.

In conclusion, it has been demonstrated that antigenic properties of a fully synthetic cancer vaccine can be optimized by structure-activity relationship studies. In this respect, it has been established that a three-component vaccine in which a tumor-associated MUC-1 glycopeptide B-epitope, a promiscuous helper T-cell epitope and a TLR2 ligand are covalently linked can elicit exceptionally high IgG antibody responses, which have an ability to recognize cancer cells. It is very important that the helper T-epitope is covalently linked to the B-epitope, probably since internalization of the helper T-epitope by B-cells requires the presence of a B-epitope. It has also been shown that incorporation of a TLR agonist is important for robust antigenic responses against tumor associated glycopeptide antigens. In this respect, cytokines induced by the TLR2 ligand are important for maturation of immune cells leading to robust antibody responses. A surprising finding was that improved cancer cell recognition was observed when the TLR2 epitope was covalently attached to the glycopeptide T-B epitope. The result presented here provides important information of the optimal constitution of three-component vaccines and will guide successful development of carbohydrate-based cancer vaccines.

Experimental

Peptide Synthesis

Peptides were synthesized by established protocols on an ABI 433A peptide synthesizer (Applied Biosystems), equipped with a UV-detector using $N^\alpha$-Fmoc-protected amino acids and 2-(1H-bezotriazole-1-yl)-oxy-1,1,3,3-tetramethyl hexafluorophosphate (HBTU)/N-hydroxybenzotriazole (HOBt) (Knorr, Tetrahedron Lett. 1989, 30, 1927-1930) as the activating reagents. Single coupling steps were performed with conditional capping. The following protected amino acids were used: $N^\alpha$-Fmoc-Arg(Pbf)-OH, $N^\alpha$-Fmoc-Asp(O$^t$Bu)-OH, $N^\alpha$-Fmoc-Asp-Thr($\Psi^{Me,Me}$pro)-OH, $N^\alpha$-Fmoc-Ile-Thr($\Psi^{Me,Me}$pro)-OH, $N^\alpha$-Fmoc-Lys(Boc)-OH, $N^\alpha$-Fmoc-Ser($^t$Bu)-OH, $N^\alpha$-Fmoc-Thr($^t$Bu)-OH, and $N^\alpha$-Fmoc-Tyr($^t$Bu)-OH. The coupling of glycosylated amino acid $N^\alpha$-Fmoc-Thr-(AcO$_3$-α-D-GalNAc) 1S (Cato, J. Carbohydr. Chem. 2005, 24, 503-516) was carried out manually using O-(7-azabenzotriazol-1-yl)-N,N,N',N'-tetramethyl-uronium hexafluorophosphate (HATU)/1-hydroxy-7-azabenzotriazole (HOAt) as a coupling agent. The coupling of $N^\alpha$-Fmoc-lipophilic amino acid ($N^\alpha$-Fmoc-D, L-tetradeconic acid) 2S (Gibbons, Liebigs Ann. Chem. 1990, 1175-1183; Koppitz, Hely. Chim. Acta 1997, 80, 1280-1300) and $N^\alpha$-Fmoc-S-(2,3-bis(palmitoyloxy)-(2R-propyl)-(R)-cysteine 3S (Metzger, Int. J. Pept. Protein Res. 1991, 38, 545-554; Roth, Bioconj. Chem. 2004, 15, 541-553), which was prepared from (R)-glycidol, were carried out using benzotriazole-1-yl-oxy-tris-pyrrolidino-phosphonium hexafluorophosphate (PyBOP)/HOBt as coupling agent (See Supporting Information). Progress of the manual couplings was monitored by standard Kaiser test (Kaiser, Anal. Biochem. 1970, 34, 595).

Liposome Preparation:

Egg phosphatidylcholine (PC), phosphatidylglycerol (PG), cholesterol (Chol) and compound 21 or 22 (15 mmol, molar ratios 65:25:50:10) or PC/PG/Chol/22/23 or 24 (15 mmol, molar ratios 60:25:50:10:5) or PC/PG/Chol/25/26 (15 mmol, molar ratios 65:25:50:5:5) were dissolved in a mixture of trifluoroethanol and MeOH (1:1, v/v, 5 mL). The solvents were removed in vacuo to give a thin lipid film, which was hydrated by shaking in HEPES buffer (10 mM, pH 6.5) containing NaCl (145 mM) (1 mL) under argon atmosphere at 41° C. for 3 h. The vesicle suspension was sonicated for 1 min and then extruded successively through 1.0, 0.4, 0.2, and 0.1 μm polycarbonate membranes (Whatman, Nuclepore® Track-Etch Membrane) at 50° C. to obtain SUVs. The GalNAc content was determined by heating a mixture of SUVs (50 μL) and aqueous TFA (2 M, 200 μL) in a sealed tube for 4 h at 100° C. The solution was then concentrated in vacuo and analyzed by high-pH anion exchange chromatography using a pulsed amperometric detector (HPAEC-PAD; Methrome) and CarboPac columns PA-10 and PA-20 (Dionex).

Dose and Immunization Schedule:

Groups of five mice (female BALB/c, age 8-10 weeks; Jackson Laboratories) were immunized four times at weekly intervals. Each boost included 3 μg of saccharide in the liposome formulation. Serum samples were obtained before immunization (pre-bleed) and one week after the final immunization. The final bleeding was done by cardiac bleed.

Serologic Assays:

Anti-MUC-1 IgG, IgG1, IgG2a, IgG2b, IgG3, and IgM antibody titers were determined by enzyme-linked immunosorbent assay (ELISA), as described previously (Buskas, Chem. Eur. J. 2004, 10, 3517-3524). Briefly, ELISA plates (Thermo Electron Corp.) were coated with a conjugate of the MUC-1 glycopeptide conjugated to BSA through a maleimide linker (BSA-MI-MUC-1). Serial dilutions of the sera were allowed to bind to immobilized MUC-1. Detection was accomplished by the addition of phosphate-conjugated anti-mouse IgG (Jackson ImmunoResearch Laboratories Inc.), IgG1 (Zymed), IgG2a (Zymed), IgG2b (Zymed), IgG3 (BD Biosciences Pharmingen), or IgM (Jackson ImmunoResearch Laboratories Inc.) antibodies. After addition of p-nitrophenyl phosphate (Sigma), the absorbance was measured at 405 nm with wavelength correction set at 490 nm using a microplate reader (BMG Labtech). Antibody titers against the T (polio)-epitope were determined as follows. Reacti-bind NeutrAvidin coated and pre-blocked plates (Pierce) were incubated with biotin-labeled T-epitope (10 μg/mL) for 2 h. Next, serial dilutions of the sera were allowed to bind to immobilized T-epitope. Detection was accomplished as described above. The antibody titer was defined as the highest dilution yielding an optical density of 0.1 or greater over that of normal control mouse sera.

Cell Culture:

RAW 264.7 γNO(-) cells, derived from the RAW 264.7 mouse monocyte/macrophage cell line, were obtained from ATCC. The cells were maintained in RPMI 1640 medium with L-glutamine (2 mM), adjusted to contain sodium bicarbonate (1.5 g $L^{-1}$), glucose (4.5 g $L^{-1}$), HEPES (10 mM) and sodium pyruvate (1.0 mM) and supplemented with penicillin (100 u $mL^{-1}$)/streptomycin (100 µg $mL^{-1}$; Mediatech) and FBS (10%; Hyclone). Human breast adenocarcinoma cells (MCF7) (Horwitz, Steroids 1975, 26, 785-95), obtained from ATCC, were cultured in Eagle's minimum essential medium with L-glutamine (2 mM) and Earle's BSS, modified to contain sodium bicarbonate (1.5 g $L^{-1}$), non-essential amino acids (0.1 mM) and sodium pyruvate (1 mM) and supplemented with bovine insulin (0.01 mg $mL^{-1}$; Sigma) and FBS (10%). Human skin malignant melanoma cells (SK-MEL-28) were obtained from ATCC and grown in Eagle's minimum essential medium with L-glutamine (2 mM) and Earle's BSS, adjusted to contain sodium bicarbonate (1.5 g $L^{-1}$), non-essential amino acids (0.1 mM) and sodium pyruvate (1 mM) and supplemented with FBS (10%). All cells were maintained in a humid 5% $CO_2$ atmosphere at 37° C.

TNF-α and IFN-β Assays.

RAW 264.7 γNO(-) cells were plated on the day of the exposure assay as 2×10⁵ cells/well in 96-well plates (Nunc) and incubated with different stimuli for 5.5 h in the presence or absence of polymyxin B. Culture supernatants were collected and stored frozen (-80° C.) until assayed for cytokine production. Concentrations of TNF-α were determined using the TNF-α DuoSet ELISA Development kit from R&D Systems. Concentrations of IFN-β were determined as follows. ELISA MaxiSorp plates were coated with rabbit polyclonal antibody against mouse IFN-β (PBL Biomedical Laboratories). IFN-β in standards and samples was allowed to bind to the immobilized antibody. Rat anti-mouse IFN-β antibody (USBiological) was then added, producing an antibody-antigen-antibody "sandwich". Next, horseradish peroxidase (HRP) conjugated goat anti-rat IgG (H+L) antibody (Pierce) and a chromogenic substrate for HRP 3,3',5,5'-tetramethylbenzidine (TMB; Pierce) were added. After the reaction was stopped, the absorbance was measured at 450 nm with wavelength correction set to 540 nm. Concentration-response data were analyzed using nonlinear least-squares curve fitting in Prism (GraphPad Software, Inc.). These data were fit with the following four parameter logistic equation: $Y=E_{max}/(1+(EC_{50}/X)^{Hill\ slope})$, where Y is the cytokine response, X is the concentration of the stimulus, $E_{max}$ is the maximum response and $EC_{50}$ is the concentration of the stimulus producing 50% stimulation. The Hill slope was set at 1 to be able to compare the $EC_{50}$ values of the different inducers. All cytokine values are presented as the means±SD of triplicate measurements, with each experiment being repeated three times.

Evaluation of Materials for Contamination by LPS:

To ensure that any increase in cytokine production was not caused by LPS contamination of the solutions containing the various stimuli, avidly binds to the lipid A region of LPS, thereby preventing LPS-induced cytokine production (Tsubery, Biochemistry 2000, 39, 11837-44). TNF-α and IFN-β concentrations in supernatants of cells preincubated with polymyxin B (30 µg $mL^{-1}$; Bedford Laboratories) for 30 min before incubation with E. coli O55:B5 LPS for 5.5 h showed complete inhibition, whereas preincubation with polymyxin B had no effect on TNF-α synthesis by cells incubated with the synthetic compounds 21 and 23. Therefore, LPS contamination of the latter preparations was inconsequential.

Cell Recognition Analysis by Fluorescence Measurements:

Serial dilutions of pre- and post-immunization sera were incubated with MCF7 and SK-MEL-28 single-cell suspensions for 30 min on ice. Next, the cells were washed and incubated with goat anti-mouse IgG γ-chain specific antibody conjugated to fluorescein isothiocyanate (FITC; Sigma) for 20 min on ice. Following three washes and cell lysis, cell lysates were analyzed for fluorescence intensity (485 ex/520 em) using a microplate reader (BMG Labtech). Data points were collected in triplicate and are representative of three separate experiments.

Example VII

Synthesis of Compounds

General Methods:

Fmoc-L-amino acid derivatives and resins were purchased from NovaBioChem and Applied Biosystems; peptide synthesis grade N, N-dimethylformamide (DMF) from EM Science; and N-methylpyrrolidone (NMP) from Applied Biosystems. Egg phosphatidylcholine (PC), phosphatidylglycerol (PG), cholesterol (Chol), and monophosphoryl lipid A (MPL-A) were obtained from Avanti Polar Lipids. EZ-Link® NHS-Biotin reagent (succinimidyl-6-(biotinamido) hexanoate) was obtained from Pierce. All other chemical reagents were purchased form Aldrich, Acros, Alfa Aesar, and Fisher Scientific and used without further purification. All solvents employed were reagent grade. Reversed phase high performance liquid chromatography (RP-HPLC) was performed on an Agilent 1100 series system equipped with an auto-injector, fraction-collector, and UV-detector (detecting at 214 nm) using an Agilent Zorbax Eclipse™ C8 analytical column (5 µm, 4.6×150 mm) at a flow rate of 1 mL/min, Agilent Zorbax Eclipse™ C8 semi preparative column (5 µm, 10×250 mm) at a flow rate of 3 mL/min or Phenomenex Jupiter™ C4 semi preparative column (5 µm, 10×250 mm) at a flow rate of 2 mL/min. All runs were performed using a linear gradient of 0-100% solvent B over 40 min (solvent A=5% acetonitrile, 0.1% trifluoroacetic acid (TFA) in water, solvent B=5% water, 0.1% TFA in acetonitrile). Matrix assisted laser desorption ionization time of flight mass spectrometry (MALDI-ToF) mass spectra were recorded on a ABI 4700 proteomic analyzer.

Synthesis of Glycolipopeptide 22:

The synthesis 22 was carried out on a Rink amide resin (28, 0.1 mmol) as described under peptide synthesis in the experimental. The first four amino acids, Arg-Pro-Ala-Pro were coupled on the peptide synthesizer using a standard protocol to obtain 29. After the completion of the synthesis, a manual coupling of 1S (0.2 mmol, 134 mg) was carried out. $N^{\alpha}$-Fmoc-Thr-(AcO₃-α-D-GalNAc) 1S (Cato, J. Carbohydr. Chem. 2005, 24, 503-516) was dissolved in NMP (5 mL) and O-(7-azabenzotriazol-1-yl)-N,N,N',N'-tetramethyluronium hexafluorophosphate (HATU; 0.2 mmol, 76 mg), 1-hydroxy-7-azabenzotriazole (HOAt; 0.2 mmol, 27 mg), and diisopropylethylamine (DIPEA; 0.4 mmol, 70 µL) were added to the solution and the resulting mixture was added to the resin. The coupling reaction was monitored by standard Kaiser test. After 12 h, the resin was washed with NMP (6 mL) and methylene chloride (DCM; 6 mL), and resubjected to the same coupling conditions to ensure complete coupling. The glycopeptide 30 was then elongated on the peptide synthesizer. After the completion of the synthesis, the resin was thoroughly washed with NMP (6 mL), DCM (6 mL) and methanol (MeOH; 6 mL) and dried in vacuo. The resin was then swelled in DCM (5 mL) for 1 h and the rest of the couplings were carried out manually. Next, $N^\alpha$-Fmoc-lipophilic amino acid ($N^\alpha$-Fmoc-D,L-tetradeconic acid) 2S (Gibbons, Liebigs Ann. Chem. 1990, 1175-1183; Koppitz, Helv. Chim. Acta 1997, 80, 1280-1300) (0.3 mmol, 139 mg) dissolved in NMP (5 mL), benzotriazole-1-yl-oxy-tris-pyrrolidino-phosphonium hexafluorophosphate (PyBOP; 0.3 mmol, 156 mg), HOBt (0.3 mmol, 40 mg) and DIPEA (0.4 mmol, 67 µL) were premixed for 2 min., and then added to the resin. The coupling reaction was monitored by the Kaiser test and was complete after standing for 8 h. The $N^\alpha$-Fmoc group was cleaved using piperidine (20%) in DMF (6 mL). $N^\alpha$-Fmoc-Gly-OH (0.3 mmol, 90 mg) dissolved in NMP (5 mL), PyBOP (0.3 mmol, 156 mg), HOBt (0.3 mmol, 40 mg), and DIPEA (0.4 mmol, 67 µL) were premixed for 2 min, and were then added to the resin. The coupling reaction was monitored by Kaiser test and was complete after standing for 4 h. The $N^\alpha$-Fmoc group was cleaved using piperidine (20%) in DMF (6 mL). One more cycle of coupling of 2S (0.3 mmol, 139 mg) was carried out as described above using PyBOP (0.3 mmol, 156 mg), HOBt (0.3 mmol, 40 mg), and DIPEA (0.4 mmol, 67 µL) in NMP (5 mL). Finally, the $N^\alpha$-Fmoc group was cleaved using piperidine (20%) in DMF (6 mL) and the resulting free amino group was acetylated by treatment of the resin with $Ac_2O$ (10%) and DIPEA (5%) in NMP (5 mL) for 10 min. The resin was washed thoroughly with NMP (5 mL×2), DCM (5 mL×2), and MeOH (5 mL×2), and dried in vacuo. The resin was swelled in DCM (5 mL) for 1 h, treated with hydrazine (60%) in MeOH[4,5] (10 mL) for 2 h, thoroughly washed with NMP (5 mL×2), DCM (5 mL×2), and MeOH (5 mL×2), and dried in vacuo. The resin was swelled in DCM (5 mL) for 1 h and then treated with reagent B (TFA (88%), water (5%), phenol (5%), and TIS (2%), 10 mL) for 2 h. The resin was filtered, washed with neat TFA (2 mL), and the filtrate was then concentrated in vacuo to approximately ⅓ of its original volume. The glycolipopeptide was precipitated using diethyl ether (0° C., 40 mL) and recovered by centrifugation at 3,000 rpm for 15 min. The crude glycolipopeptide was purified by RP-HPLC on a semi preparative C-4 column using a linear gradient of 0-95% solvent B in A over 40 min, and the appropriate fractions were lyophilized to afford 22 (FIG. 10) (57 mg, 16%). $C_{165}H_{267}N_{37}O_{44}$, MALDI-ToF MS: observed, [M+] 3473.4900 Da; calculated, [M+] 3473.1070 Da.

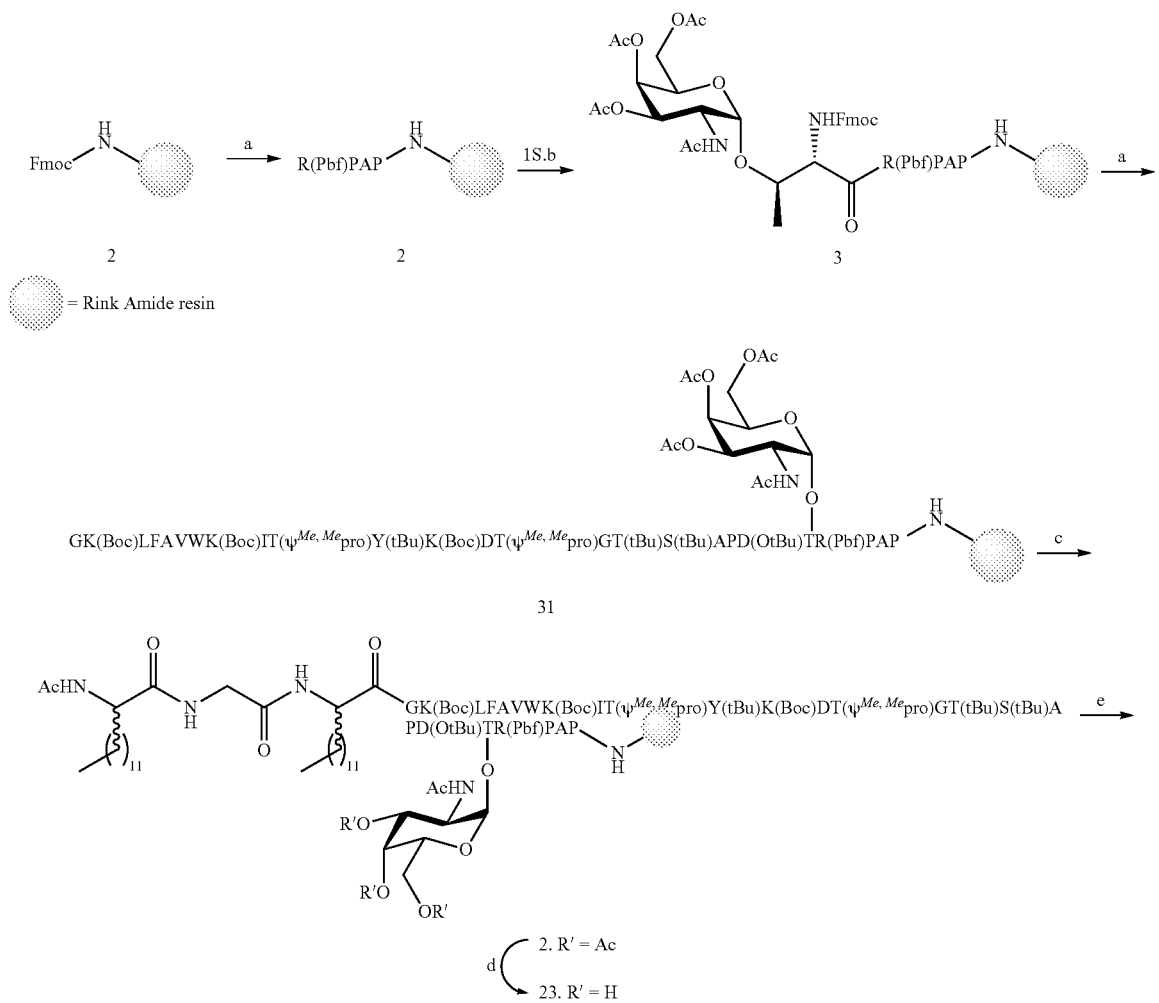

Scheme 15.

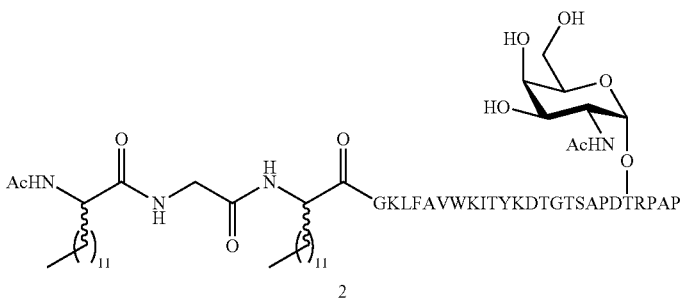

Reagents and conditions:
a) SPPS using Fmoc-chemistry, coupling with HBTU/HOBt in the presence of DIPEA in NMP;
b) 1S, HATU/HOAt, DIPEA, NMP, overnight;
c) i. manula coupling of 2S with PyBOP/HOBt in the presence of DIPEA in NMP; ii. 20% piperidine in DMF; iii. manual coupling of 1S with PyBOP/HOBt in the presence of DIPEA in NMP; iv. 20% piperidine in DMF; v. manual coupling of 2S with PyBOP/HOBt in the presence of DIPEA in NMP; vi. 20% piperidine in DMF; vii. 10% Ac₂O, 5% DIPEA in NMP for 10 min;
(d) 60% hydrazine in MeOH, 2 h; e) reagent B, TFA, (88%), phenol (5%), water (5%), TIS (2%), 2 h.

Synthesis of Lipopeptide 23:

The synthesis of 23 was carried out on a Rink amide resin (28, 0.1 mmol) as described under peptide synthesis in the experimental. After coupling of the first five amino acids, the lipid portion of the molecule was coupled manually. $N^{\alpha}$-Fmoc-S-(2,3-bis(palmitoyloxy)-(2R-propyl)-(R)-cysteine, 3S (Metzger, Int. J. Pept. Protein Res. 1991, 38, 545-554; Roth, Bioconj. Chem. 2004, 15, 541-553) (0.3 mmol, 267 mg) was dissolved in DMF (5 mL) and PyBOP (0.3 mmol, 156 mg), HOBt (0.3 mmol, 40 mg), and DIPEA (0.4 mmol, 67 μL) were added to the solution. After 2 min the reaction mixture was added to the resin. The coupling reaction was monitored by the Kaiser test and was complete after standing for 12 h. Next, the $N^{\alpha}$-Fmoc group was cleaved using piperidine (20%) in DMF (6 mL) to obtain 36. Palmitic acid (0.3 mmol, 77 mg) was coupled to the free amine of 36 as described above using PyBOP (0.3 mmol, 156 mg), HOBt (0.3 mmol, 40 mg), and DIPEA (0.4 mmol, 67 μL) in DMF. The resin was washed thoroughly with DMF (5 mL×2), DCM (5 mL×2), and MeOH (5 mL×2) and then dried in vacuo. The resin was swelled in DCM (5 mL) for 1 h and then treated with TFA (95%), water (2.5%), and TIS (2.5%) (10 mL) for 2 h at room temperature. The resin was filtered and washed with neat TFA (2 mL). The filtrate was then concentrated in vacuo to approximately ⅓ of its original volume. The lipopeptide was precipitated using diethyl ether (0° C.; 30 mL) and recovered by centrifugation at 3000 rpm for 15 min. The crude lipopeptide was purified by RP-HPLC on a semi preparative C-4 column using a linear gradient of 0 to 95% solvent B in solvent A over a 40 min period and the appropriate fractions were lyophilized to afford 23 (FIG. 11) (40 mg, 26%). $C_{81}H_{156}N_{11}O_{12}S$, MALDI-ToF MS: observed [M+Na], 1531.2240 Da; calculated [M+Na], 1531.1734 Da.

Scheme 16.

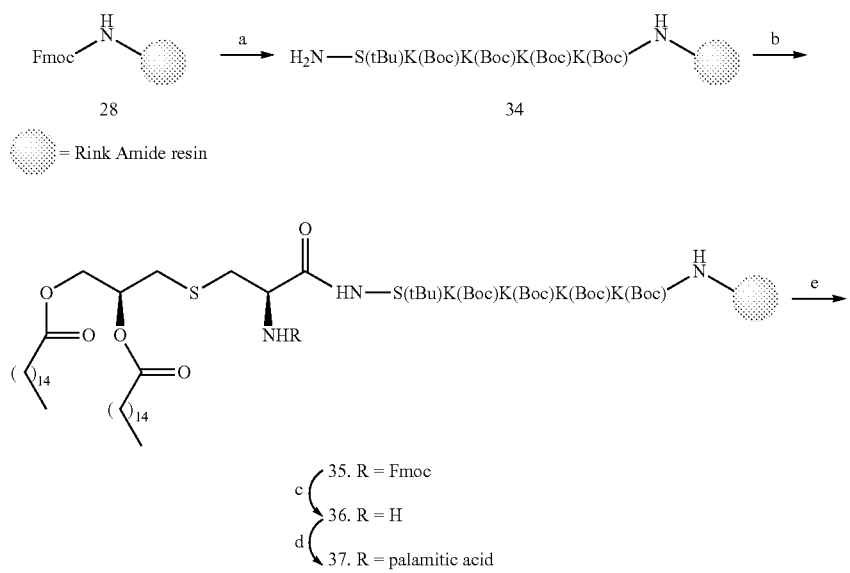

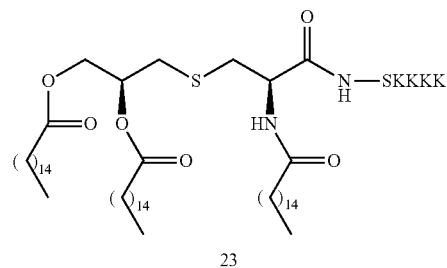

23

Reagents and conditions:
a) SPPS using Fmoc-chemistry, coupling with HBTU/HOBt in the presence of DIPEA in NMP;
b) manual coupling of 3S by PyBOP/HOBt activation in the presence of DIPEA in DMF;
c) piperidine (20%) in DMF;
d) coupling of palmitic acid by PyBOP/HOBt activation in the presence of DIPEA in DMF;
e) TFA (95%), water (2.5%), TIS (2.5%), 2 h.

20

Synthesis of Glycolipopeptide 25:

The synthesis 25 was carried out on a Rink amide resin (28, 0.1 mmol) as described under peptide synthesis in the experimental. The first four amino acids, Arg-Pro-Ala-Pro were coupled on the peptide synthesizer using a standard protocol to obtain 29. After the completion of the synthesis, a manual coupling was carried out using 1S (0.2 mmol, 134 mg). 1S was dissolved in NMP (5 mL) and HATU (0.2 mmol, 76 mg), HOAt (0.2 mmol, 27 mg), and DIPEA (0.4 mmol, 70 µL) were added and the resulting mixture was added to the resin. The coupling reaction was monitored by standard Kaiser test. After 12 h, the resin was washed with NMP (6 mL) and DCM (6 mL), and re-subjected to the same coupling conditions to ensure complete coupling. Glycopeptide 30 was then elongated on the peptide synthesizer. After the completion of the synthesis, the resin was thoroughly washed with NMP (6 mL), DCM (6 mL), and MeOH (6 mL) and dried in vacuo. The resin was then swelled in DCM (5 mL) for 1 h and the rest of the peptide sequence was completed manually. 2S (0.3 mmol, 139 mg) was dissolved in NMP (5 mL) and PyBOP (0.3 mmol, 156 mg), HOBt (0.3 mmol, 40 mg), and DIPEA (0.4 mmol, 67 µL) were added to the solution. After 2 min, the mixture was added to the resin. The coupling reaction was monitored by standard Kaiser test and was complete after standing for 8 h. Next, the $N^\alpha$-Fmoc group was cleaved using piperidine (20%) in DMF (6 mL). $N^\alpha$-Fmoc-L-glycine (0.3 mmol, 90 mg) was dissolved in NMP (5 mL) and premixed with PyBOP (0.3 mmol, 156 mg), HOBt (0.3 mmol, 40 mg), and DIPEA (0.4 mmol, 67 µL) for 2 min before the reaction mixture was added to the resin. The coupling reaction was monitored by Kaiser test and was complete after standing for 4 h. The $N^\alpha$-Fmoc group was cleaved using piperidine (20%) in DMF (6 mL). One more cycle of coupling of 2S (0.3 mmol, 139 mg) was carried out as described above using PyBOP (0.3 mmol, 156 mg), HOBt (0.3 mmol, 40 mg), and DIPEA (0.4 mmol, 67 µL) in NMP (5 mL). Finally, the $N^\alpha$-Fmoc group was cleaved using piperidine (20%) in DMF (6 mL) and the resulting free amino group was acetylated using $Ac_2O$ (10%) and DIPEA (5%) in NMP (5 mL) for 10 min. The resin was washed thoroughly with NMP (5 mL×2), DCM (5 mL×2), and MeOH (5 mL×2), and dried in vacuo. The resin was swelled in DCM (5 mL) for 1 h, treated with hydrazine (60%) in MeOH (10 mL) for 2 h, washed thoroughly with NMP (5 mL×2), DCM (5 mL×2) and MeOH (5 mL×2) and dried in vacuo. The resin was swelled in DCM (5 mL) for 1 h after which it was treated with reagent B (TFA (88%), water (5%), phenol (5%), and TIS (2%), 10 mL) for 2 h. The resin was filtered, washed with neat TFA (2 mL) and the filtrate was then concentrated in vacuo to approximately ⅓ of its original volume. The glycolipopeptide was precipitated using diethyl ether (0° C.; 40 mL) and recovered by centrifugation at 3,000 rpm for 15 min. The crude glycolipopeptide was purified by RP-HPLC on a semi preparative C-4 column using a linear gradient of 0-95% solvent B in A over 40 min, and the appropriate fractions were lyophilized to afford 5 (FIG. 12) (35 mg, 19%). $C_{84}H_{145}N_{19}O_{255}$ MALDI-ToF MS: observed, [M+] 1821.1991 Da; calculated, [M+] 1821.1624 Da.

Scheme 17.

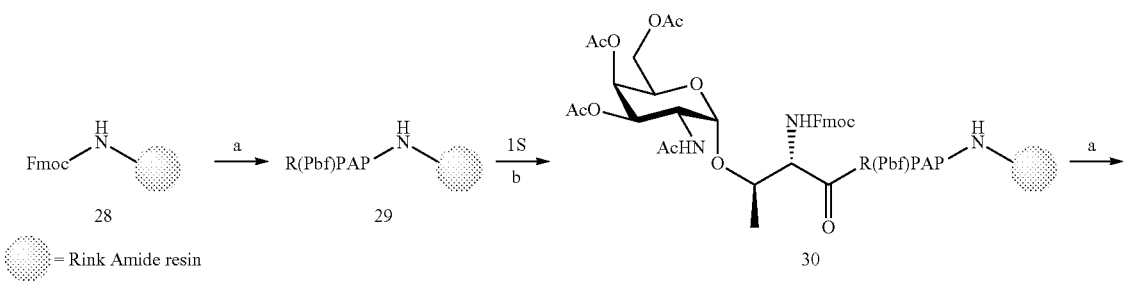

-continued

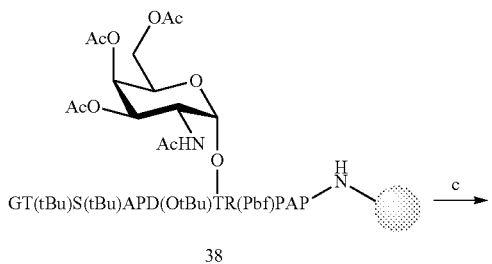

38

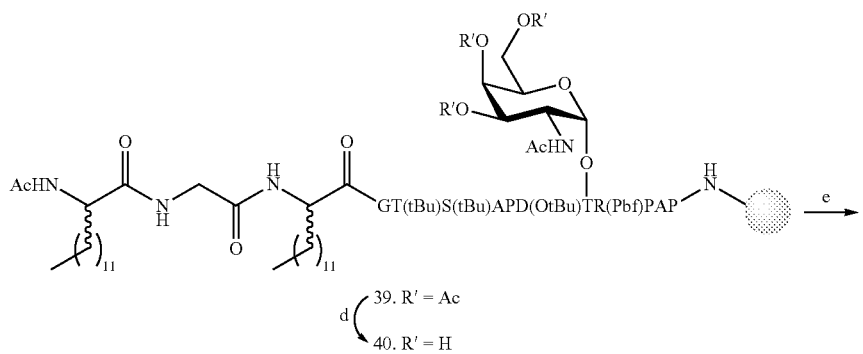

d ( 39. R' = Ac
   40. R' = H

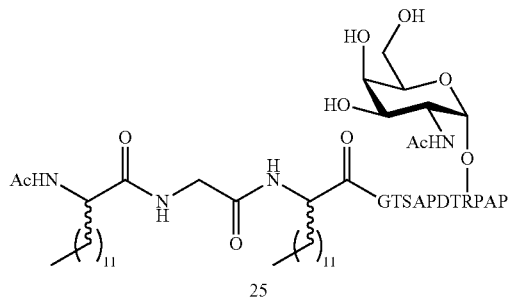

25

Reagents and conditions:
a) SPPS using Fmoc-chemistry, coupling with HBTU/HOBt in the presence of DIPEA in NMP;
b) 1S, HATU/HOAt, DIPEA, NMP, overnight;
c) i. manual coupling of 2S with PyBOP/HOBt in the presence of DIPEA in NMP; ii. 20% piperidine in DMF; iii. manual coupling of N$^\alpha$-Fmoc-Gly-OH with PyBOP/HOBt in the presence of DIPEA in NMP; iv. 20% piperidine in DMF; v. manual coupling of 2S with PyBOP/HOBt in the presence of DIPEA in NMP; vi. 20% piperidine in DMF; vii. 10% Ac$_2$O, 5% DIPEA in NMP for 10 min;
(d) 60% hydrazine in MeOH, 2 h;
e) reagent B, TFA (88%), phenol (5%), water (5%), TIS (2%), 2 h.

Synthesis of Lipopeptide 26:

The synthesis of 26 was carried out on a Rink amide resin (28, 0.1 mmol). After the assembly of the peptide by using standard SPPS, the lipid portion of the molecule was coupled manually. 3S (0.3 mmol, 267 mg) was dissolved in DMF (5 mL) and PyBOP (0.3 mmol, 156 mg), HOBt (0.3 mmol, 40 mg), and DIPEA (0.4 mmol, 67 µL) were added to the solution. After activation of 3S for 2 min the reaction mixture was added to the resin. The coupling reaction was monitored by the Kaiser test and was complete after standing for 12 h. The N-Fmoc group was cleaved using piperidine (20%) in DMF (6 mL) to obtain 43. Palmitic acid (77 mg, 0.3 mmol) was coupled to the free amine of 43 as described above using PyBOP (0.3 mmol, 156 mg,), HOBt (0.3 mmol, 40 mg), and DIPEA (0.4 mmol, 67 µL) in DMF. The resin was washed thoroughly with DMF (5 mL×2), DCM (5 mL×2), and MeOH (5 mL×2) and then dried in vacuo. The resin was swelled in DCM (5 mL) for 1 h, treated with reagent B (TFA (88%), water (5%), phenol (5%), and TIS (2%), 10 mL) for 2 h, filtered and washed with neat TFA (2 mL). The filtrate was then concentrated in vacuo to approximately ⅓ of its original volume, and the lipopeptide was precipitated using diethyl ether (0° C.; 30 mL) and recovered by centrifugation at 3000 rpm for 15 min. The crude lipopeptide was purified by RP-HPLC on a semi preparative C-4 column using a linear gradient of 0-95% solvent B in A over a 40 min., and the appropriate fractions were lyophilized to afford 26 (FIG. 13) (57 mg, 18%). $C_{162}H_{278}N_{29}O_{31}S$, MALDI-ToF MS: observed, [M+] 3160.9423 Da; calculated, [M+] 3160.1814 Da.

Scheme 18.

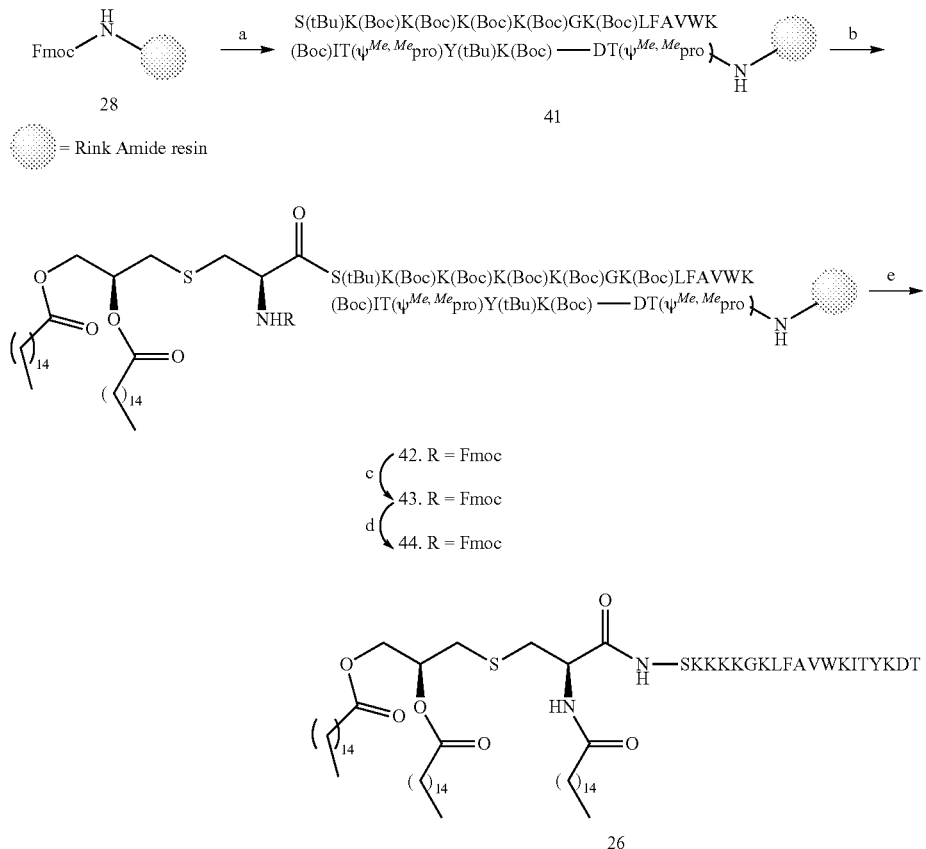

Reagents and conditions:
a) SPPS using Fmoc-chemistry, coupling with HBTU/HOBt in the presence of DIPEA in NMP;
b) manual coupling of 3S, PyBOP, HOBt in the presence of DIPEA in DMF;
c) piperidine in DMF;
d) manual coupling of palmitic acid, PyBOP, HOBt in the presence of DIPEA in DMF;
e) reagent B, TFA (88%), phenol (5%), water (5%), TIS (2%), 2 h.

Synthesis of Biotin-T-Epitope Peptide 27:

The synthesis of 27 was carried out on a Rink amide resin (28, 0.1 mmol) as described in the general method. After the completion of synthesis the resin was washed thoroughly with DMF (5 mL×2), DCM (5 mL×2), and MeOH (5 mL×2) and then dried in vacuo. The resin was swelled in DCM (5 mL) for 1 h. Next, a mixture of EZ-Link® NHS-Biotin reagent (succinimidyl-6-(biotinamido)hexanoate) (0.2 mmol, 90 mg) and DIPEA (0.2 mmol, 36 µL) in DMF (5 mL) was added to the resin. The coupling was monitored by standard Kaiser test and was complete within 8 h. The resin was washed thoroughly with DMF (5 mL×2), DCM (5 mL×2), and MeOH (5 mL×2) and then dried in vacuo. The resin was swelled in DCM (5 mL) for 1 h and treated with reagent B (TFA (88%), water (5%), phenol (5%), and TIS (2%), 15 mL) for 2 h at room temperature. The resin was filtered and washed with neat TFA (2 mL). The filtrate was concentrated in vacuo to approximately ⅓ of its original volume. The peptide was precipitated using diethyl ether (0° C.; 30 mL) and recovered by centrifugation at 3,000 rpm for 15 min. The crude peptide was purified by RP-HPLC on a semi preparative C-8 column using a linear gradient of 0 to 95% solvent B in solvent A over a 40 min period and the appropriate fractions were lyophilized to afford 27 (FIG. 14) (60% based on resin loading capacity). $C_{95}H_{147}N_{21}O_{21}S$, MALDI-ToF MS: observed [M+], 1951.2966 Da; calculated [M+], 1951.3768 Da.

Scheme 19.

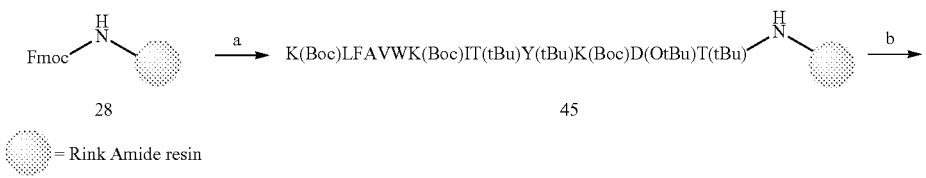

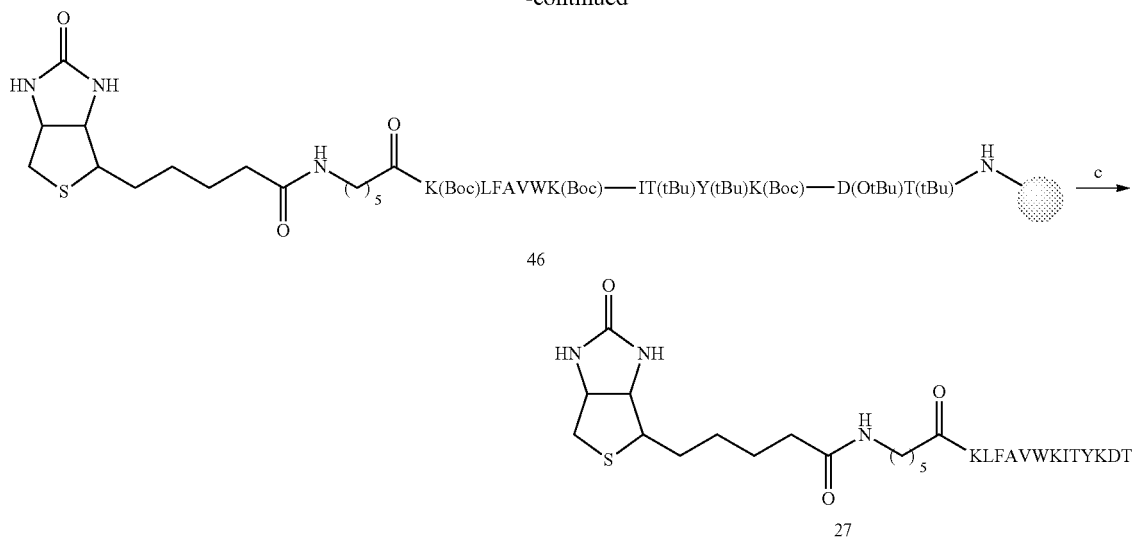

Reagents and conditions:
a) SPPS using Fmoc-chemistry, coupling with HBTU/HOBt in the presence of DIPEA in NMP;
b) manual coupling of succinimidyl-6-(biotinamido) hexonate in the presence of DIPEA in DMF;
c) reagent B, TFA (88%), Phenol (5%), water (5%), TIS (2%), 2 h.

Example VIII

Monoclonal Antibodies Against Carbohydrates and Glycopeptides by Using Fully Synthetic Three-Component Immunogens Glycoconjugates are the most functionally and structurally diverse molecules in nature and it is now well established that protein- and lipid-bound saccharides play essential roles in many molecular processes impacting eukaryotic biology and disease. Examples of such processes include fertilization, embryogenesis, neuronal development, hormone activities, the proliferation of cells and their organization into specific tissues. Remarkable changes in the cell-surface carbohydrates occur with tumor progression, which appears to be intimately associated with metastasis. Furthermore, carbohydrates are capable of inducing a protective antibody response and this immunological reaction is a major contributor to the survival of the organism during infection.

The inability of saccharides to activate helper T-lymphocytes has complicated their development as vaccines. For most immunogens, including carbohydrates, antibody production depends on the cooperative interaction of two types of lymphocytes, the B-cells and helper T-cells (Jennings, Neoglyconjugates: Preparation and Applications 325-371 (Academic Press, Inc., 1994); Kuberan, Curr. Org. Chem. 2000, 4, 653-677). Saccharides alone cannot activate helper T-cells and therefore have a limited immunogenicity as manifested by low affinity IgM antibodies and the absence of IgG antibodies. In order to overcome the T-cell independent properties of carbohydrates, past research has focused on the conjugation of saccharides to a foreign carrier protein (e.g. Keyhole Limpet Hemocyanin (KLH) detoxified tetanus toxoid) (Jennings, Neoglyconjugates: Preparation and Applications 325-371 (Academic Press, Inc., 1994); Kuberan, Curr. Org. Chem. 2000, 4, 653-677; Jones, An. Acad. Bras. Cienc. 2005, 77, 293-324). In this approach, the carrier protein enhances the presentation of the carbohydrate to the immune system and provides T-epitopes (peptide fragments of 12-15 amino acids) that can activate T-helper cells. As a result, a class switch from low affinity IgM to high affinity IgG antibodies is accomplished. This approach has been successfully applied for the development of a conjugate vaccine to prevent infections with *Haemophilus influenzae*.

Carbohydrate-protein conjugate candidate vaccines composed of more demanding carbohydrate antigens, such as tumor associated carbohydrate and glycopeptides, have failed to elicit high titers of IgG antibodies. These results are not surprising because tumor-associated saccharides are of low antigenicity, because they are self-antigens and consequently tolerated by the immune system. The shedding of antigens by the growing tumor reinforces this tolerance. In addition, foreign carrier proteins such as KLH and BSA and the linker that attach the saccharides to the carrier protein can elicit strong B-cell responses, which may lead to the suppression of antibody responses against the carbohydrate epitope (Buskas, Chem. Eur. J. 2004, 10, 3517-3524; Ni, Bioconjug. Chem. 2006, 17, 493-500). It is clear that the successful development of carbohydrate-based cancer vaccines requires novel strategies for the more efficient presentation of tumor-associated carbohydrate epitopes to the immune system, resulting in a more efficient class switch to IgG antibodies (Reichel, Chem. Commun. 1997, 21, 2087-2088; Alexander, J. Immunol. 2000, 164, 1625-1633; Kudryashov, Proc. Natl. Acad. Sci. U.S.A. 2001, 98, 3264-3269; Lo-Man, J. Immunol. 2001, 166, 2849-2854; Jiang, Curr. Med. Chem. 2003, 10, 1423-1439; Jackson, Proc. Natl. Acad. Sci. U.S.A. 2004, 101, 15440-5; Lo-Man, Cancer Res. 2004, 64, 4987-4994; Buskas, Angew. Chem. Int. Ed. 2005, 44, 5985-5988 (Example I); Dziadek, Angew. Chem. Int. Ed. 2005, 44, 7624-7630; Krikorian, Bioconjug. Chem. 2005, 16, 812-819; Pan, J. Med. Chem. 2005, 48, 875-883).

We have found that a three-component vaccine composed of a TLR2 agonist, a promiscuous peptide T-helper epitope and a tumor-associated glycopeptide, can elicit in mice exceptionally high titers of IgG antibodies that can recognize cancer cells expressing the tumor-associated carbohydrate (see compound 21, FIG. 5, Example VI and compound 51, FIG. 15) (Ingale, Nat. Chem. Biol. 2007, 3, 663-667). The superior properties of the vaccine candidate are attributed to the local production of cytokines, upregulation of co-stimulatory proteins, enhanced uptake by macrophages and dendritic cells and avoidance of epitope suppression.

We expect that the three-component immunogen technology of the invention can be used to generate monoclonal antibodies (MAbs) for poorly antigenic carbohydrates and glycopeptides. We have initially focused on MAbs against β-N-acetylglucosamine (β-O-GlcNAc) modified peptides (Wells, Science 2001, 291, 2376-2378; Whelan, Methods Enzymol. 2006, 415, 113-133; Zachara, Biochim. Biophys. Acta, 2006, 1761, 599-617; Dias and Hart, Mol. Biosyst. 2007, 3, 766-772; Hart, Nature 2007, 446, 1017-1022; Lefebvre, Exp. Rev. Proteomics 2005, 2, 265-275). Myriad nuclear and cytoplasmic proteins in metazoans are modified on Ser and Thr residues by the monosaccharide β-O-GlcNAc. The rapid and dynamic change in O-GlcNAc levels in response to extracellular stimuli suggests a key role for O-GlcNAc in signal transduction pathways. Modulation of O-GlcNAc levels has profound effects on the functioning of cells, in part mediated through a complex interplay between O-GlcNAc and O-phosphate. Recently, O-GlcNAc has been implicated in the etiology of type II diabetes, the regulation of stress response pathways and in the regulation of the proteasome. Progress in this exciting field of research is seriously hampered by the lack of reagents such as appropriate MAbs. In this respect, only one poorly performing IgM MAb with relative broad specificity (Comer, Anal. Biochem. 2001, 293, 169-177) is commercially available (Covance Research Products Inc).

We have designed and synthesized compound 52 (FIG. 15), which contains as a B-epitope a β-GlcNAc modified glycopeptide derived from casein kinase II (CKII) (Kreppel, J. Biol. Chem. 1999, 274, 32015-32022), the well-documented murine MHC class II restricted helper T-cell epitope KLFAVWKITYKDT (SEQ ID NO:3) derived from the polio virus and the inbuilt adjuvant $Pam_3CysSK_4$. In addition, compound 53 was prepared which has an artificial thio-linked GlcNAc moiety, which was expected to have better metabolic stability. Compounds 52 and 53 were incorporated into phospholipid-based small uni-lamellar vesicles (SUVs) by hydration of a thin film of the synthetic compounds, egg phosphatidylcholine, phosphatidylglycerol and cholesterol in a HEPES buffer (10 mM, pH 6.5) containing NaCl (145 mM) followed by extrusion through a 100 nm Nuclepore® polycarbonate membrane. Groups of five female BALB/c mice were immunized intra-peritoneal four times at weekly intervals with liposomes containing 3 μg of saccharide.

Anti-glycopeptide antibody titers were determined by coating microtiter plates with CGSTPVS(β-O-GlcNAc)SANM conjugated to maleimide (MI) modified BSA and detection was accomplished with anti-mouse IgG antibodies labeled with alkaline phosphatase. As can be seen in Table 6, compounds 52 and 53 elicited excellent titers of anti-MUC1 IgG antibodies. Furthermore, no significant difference in titer was observed between the O- and S-linked saccharide derivatives.

TABLE 6

ELISA anti-GSTPVS(β-O-GlcNAc)SANM(68) titers[a] after 4 immunizations with two different preparations

| Immunization[b] | IgG total | IgG1 | IgG2a | IgG2b | IgG3 | IgM |
|---|---|---|---|---|---|---|
| O-GlcNAc 52[c] | 76,500 | 61,400 | 33,200 | 12,500 | 69,400 | 81,900 |
| S-GlcNAc 53[d] | 151,600 | 111,800 | 55,600 | 21,300 | 111,700 | 21,900 |

[a]Anti-GSTPVS(β-O-GlcNAc)SANM (68) antibody titers are presented as the mean of groups of five mice. ELISA plates were coated with BSA-MI-GSTPVS(β-O-GlcNAc)SANM (BSA-MI-66) conjugate and titers were determined by linear regression analysis, plotting dilution vs. absorbance. Titers are defined as the highest dilution yielding an optical density of 0.1 or greater over that of normal control mouse sera.
[b]Liposomal preparations were employed.
[c]O-GlcNAc 52; $Pam_3CysSK_4$G-C-KLFAVWKITYKDT-G-GSTPVS(β-O-GluNAc)SANM.
[d]S-GlcNAc 53; $Pam_3CysSK_4$G-C-KLFAVWKITYKDT-G-GSTPVS(β-S-GluNAc)SANM.
A statistically significant difference was observed between 52 versus 53 for IgM titers (P = 0.0327).
Individual titers for IgG total, IgG1, IgG2a, IgG2b, IgG3 and IgM are reported in FIG. 20.

Next, spleens of two mice immunized with the O-linked glycolipopeptide 52 were harvested and standard hybridoma culture technology gave seven IgG1, seven IgG2a, two IgG2b and fourteen IgG3 producing hybridoma cell lines (Table 7). The ligand specificity of the resulting MAbs was investigated using ELISA and inhibition ELISA. All MAbs recognized CGSTPVS(13-O-GlcNAc)SANM linked to BSA whereas only a small number recognized the peptide CGSTPVSSANM (SEQ ID NO:12) conjugated to BSA. Furthermore, the interaction of nineteen MAbs with BSA-MI-CGSTPVS(β-O-GlcNAc)SANM could be inhibited with the glycopeptide GSTPVS(β-O-GlcNAc)SANM.

TABLE 7

Monoclonal antibodies against GSTPVS(β-O-GlcNAc)SANM.

| Fusion | Cell Line | ELISA coating: glycopeptide[a] | Isotype | Titer Isotype[b] | Inhibition with O-GlcNAc glycopeptide[c] | ELISA coating: peptide[d] |
|---|---|---|---|---|---|---|
| Mouse #1 | 1D3.D6(1) | + | IgG1 | 38,000 | − | − |
| | 3C1.E8(2) | + | | 38,000 | ++ | − |
| | 18B10.C7(3) | + | | 19,000 | +++ | − |
| | 5H11.H6(4) | + | | 6,000 | +++ | + |
| | 6G3.A5(5) | + | IgG2a | 17,000 | +++ | − |
| | 7A3.G8.F7(6) | + | | 9,000 | − | − |

TABLE 7-continued

Monoclonal antibodies against GSTPVS(β-O-GlcNAc)SANM.

| Fusion | Cell Line | ELISA coating: glycopeptide[a] | Isotype | Titer Isotype[b] | Inhibition with O-GlcNAc glycopeptide[c] | ELISA coating: peptide[d] |
|---|---|---|---|---|---|---|
|  | 13F10.G6(7) | + | IgG2b | NA[e] | − | + |
|  | 11D6.C1(8) | + | IgG3 | 29,000 | +++ | − |
|  | 1H2.F2(27) | + |  | NA | +++ | + |
| Mouse #4 | 7B8.F5(9) | + | IgG1 | 38,000 | + | − |
|  | 9D1.E4(10) | + |  | 38,000 | +++ | − |
|  | 16B9.F1(11) | + |  | 38,000 | ++ | − |
|  | 1D5.C1(12) | + | IgG2a | 3,000 | +++ | − |
|  | 1E5.H3(13) | + |  | <500 |  | − |
|  | 1F5.D6(14) | + |  | 4,000 | +++ | − |
|  | 8G11.D6(22) | + |  | 2,000 | +++ | − |
|  | 14D9.D4(23) | + |  | 17,000 | + | − |
|  | 3G5.A2(15) | + | IgG2b | 15,000 | + | − |
|  | 1E9.E3(16) | + | IgG3 | 14,000 | +++ | − |
|  | 2A8.F3(17) | + |  | 7,000 | + | − |
|  | 2D5.E6(18) | + |  | 7,000 | − | − |
|  | 5F6.G4(19) | + |  | 14,000 | +++ | − |
|  | 7B3.A3(20) | + |  | 14,000 | +++ | − |
|  | 8C3.H2(24) | + |  | 7,000 | − | − |
|  | 11C6.E5(25) | + |  | 14,000 | + | − |
|  | 16E2.A3(26) | + |  | 14,000 | − | − |
|  | 6B5.A8(21) | + |  | <500 |  | + |
|  | 1D7.B4(28) | + |  | <500 |  | + |
|  | 6A5.H1.C6(29) | + |  | <500 |  | + |
|  | 8F12.A6.C5(30) | + |  | 14,000 | +++ | + |

[a]ELISA plates were coated with BSA-MI-CGSTPVS(β-O-GlcNAc)SANM (BSA-MI-66) conjugate and supernatants of the different cell lines were screened undiluted.
[b]ELISA plates were coated with BSA-MI-CGSTPVS(β-O-GlcNAc)SANM (BSA-MI-66) conjugate and titers were determined by linear regression analysis, plotting dilution vs. absorbance. Titers are defined as the highest dilution yielding an optical density of 0.1 or greater over that of background.
[c]ELISA plates were coated with BSA-MI-CGSTPVS(β-O-GlcNAc)SANM (BSA-MI-66) conjugate and inhibition by GSTPVS(β-O-GlcNAc)SANM (68) was determined: −, +, ++ and +++ indicate no inhibition approximately 50% at 500 μM and complete inhibition at 500 μM, respectively.
[d]ELISA plates were coated with BSA-MI-CGSTPVSSANM (BSA-MI-67) conjugate and supernatants of the different cell lines were screened undiluted.
[e]NA indicates not analyzed.

Hybridoma cell lines 1F5.D6, 9D1.E4 and 18B10.C7 were deposited with the American Type Culture Collection (ATCC), 10801 University Blvd., Manassas, Va., 20110-2209, USA, on Jul. 1, 2008, and assigned ATCC deposit numbers PTA-9339, PTA-9340, and PTA-9341, respectively. It is nonetheless to be understood that the written description herein is considered sufficient to enable one skilled in the art to fully practice the present invention. Moreover, the deposited embodiment is intended as a single illustration of one aspect of the invention and is not to be construed as limiting the scope of the claims in any way.

Four hybridomas (18B10.C7(3), 5H11.H6(4), 9D1.E4 (10), 1F5.D6(14)) were cultured at a one-liter scale and the resulting antibodies purified by saturated ammonium sulfate precipitation followed by Protein G column chromatography to yield, in each case, approximately 10 mg of IgG. The selectivity of the MAbs was investigated by inhibition ELISA using microtiter plates coated with BSA-MI-CGSTPVS(β-O-GlcNAc)SANM and glycopeptide, peptide and β-O-GlcNAc-Ser as inhibitors. As can be seen in FIG. 16, each MAb was strongly inhibited by the glycopeptide whereas no or very little inhibition was observed with peptide and β-O-GlcNAc-Ser. These results show that the MAbs require carbohydrate and peptide (glycopeptide) for binding.

Although CKII is an abundant protein, only a small portion is glycosylated with O-GlcNAc. Therefore, HEK293 cells were transfected with O-GlcNAc-transferase (OGT, enzyme that adds O-GlcNAc) and cell lysates analyzed by Western blotting using the four MAbs as primary antibody and anti-mouse IgG labeled with HRP as secondary antibody and the results were compared with mock-transfected HEK293 cells. Furthermore, CKII was immuno-precipitated with a rabbit polyclonal CKII alpha antibody followed by analysis by Western blotting using the four MAbs (FIG. 17a). In addition, the blots were stripped and examined with a commercial anti-CKII antibody (FIG. 17b). In the case of MAbs 9D1.E4(10), 18B10.C7(3) and 1F5D6(14), CKII (a band at ~42 kDa) was detected after immuno-precipitation and as expected a stronger response was measured in samples transfected with OGT (lanes 3 vs. 4, 8 vs. 9 and 12 vs. 13). Interestingly, multiple bands were observed in cell lysates developed with MAbs 9D1.E4(10), 18B10.C7(3) and 1F5D6(14) (lanes 1, 6 and 10), which were more pronounced in lysates of cells over-expressing OGT (lanes 2, 7 and 11). Furthermore, additional bands were observed when OGT was overexpressed. Thus, it appears that these MAbs have a relatively broad selectivity for O-GlcNAc modified proteins. Although no consensus sequence for 0-GlcNAc has been identified, many proteins have a TPVSS (SEQ ID NO:10) sequence modified by O-GlcNAc and it is probable that the MAbs recognize this or similar glycosylated peptide sequence.

Example IX

Identification of O-GlcNAc Modified Proteins

Large-scale immunoprecipitation (IP) was performed using monoclonal IgG antibodies Mab3, Mab10, and Mab14 produced by hybridomas 18B10.C7, 9D1.E4, and 1F5.D6, respectively, as well as the commercially available monoclonal IgM antibody CTD110.6 that was isolated from HEK29T cells treated with PUGNAc (Covance Research Products, Inc.). The establishment of the hybridomas and characterization of the antibodies derived therefrom are described in Example VIII. Following Lys-C digestion, samples were subjected to electron spray ionization (ESI) mass spectrometry (Collision induced dissociation (CID)-pseudo neutral loss) analysis. Results were filtered at 1% false recovery rate and proteins that appeared in mock IP control experiments were subtracted from the final list (FIG. 18; Table 8). As shown in Table 8, monoclonal IgG antibodies demonstrate much higher affinity for O-GlcNAc than the commercially available IgM antibody.

TABLE 8

O-GlcNAc modified proteins identified by immunoprecipitation

| | | pulled down with | | | |
|---|---|---|---|---|---|
| Protein | Abbreviation | CTD110.6 | Mab3 | Mab10 | Mab14 |
| Acyl-CoA-binding domain-containing protein 7 | ACBD7 | | 1 | | |
| Apoptotic chromatin condensation inducer 1 (Apoptotic chromatin condensation inducer in the nucleus) | ACIN1 | | | | 1 |
| Actin-like protein 6A | ACTL6A | | | | 1 |
| Adenosylhomocysteinase (S-adenocylhomocysteine hydrolase) | AHCY | | 1 | | |
| Aldolase A, Fructose-bisphosphate (Fructose-bisphosphate aldolase A) | ALDOA | | 1 | | |
| Archaelysin family metallopeptidase 2 (Archaemetzincin-2) | AMZ2 | | 1 | | |
| Annexin A1 | ANXA1 | | | 1 | |
| Apolipoprotein D | APOD | | 1 | | |
| AT-rich interactive domain-containing protein 1A (SWI-like) (Chromatin remodeling factor p250) | ARID1A | | | | 1 |
| Additional sex combs like 1 | ASXL1 | | | | 1 |
| Additional sex combs like 2 (KIAA1685) | ASXL2 | | | | 1 |
| Atrophin 1 | ATN1 | | | | 1 |
| Ataxin-2 | ATXN2 | | | | 1 |
| Ataxin-2-like protein | ATXN2L | 1 | 1 | | 1 |
| HLA-B associated transcript 2 (Large proline-rich protein BAT2) | BAT2 | | 1 | | |
| BAT2 domain containing 1 (BAT2-iso) | BAT2D1 | 1 | 1 | 1 | 1 |
| Protein Chromosome 14 open reading frame 166 (CGI-99) | C14orf166 | | 1 | 1 | 1 |
| Protein Chromosome 14 open reading frame 166 (CGI-99) | C14orf166 | 1 | | 1 | |
| Calmodulin-like protein 5 | CALML5 | | | 1 | |
| Capping protein (actin filament) muscle Z-line, beta | CAPZB | | 1 | | |
| Coactivator-associated arginine methyltransferase 1 (Histone-arginine methyltransferase 1) | CARM1 | | | | 1 |
| Cell cycle association protein 1 (Caprin-1; Cytoplasmic activation/proliferation-associated protein-1) | CARPIN1 | | 1 | 1 | |
| Cell division cycle and apoptosis regulator protein 1 | CCAR1 | | 1 | | 1 |
| Cysteine conjugate-beta lyase 2 (RNA-binding motif protein X-linked-like 1) | CCBL2 | | | 1 | 1 |
| Cyclin-K | CCNK | | | | 1 |
| Chaperonin containing TCP1, subunit 8 (theta) | CCT8 | | 1 | | |
| Cofilin-1 | CFL1 | | 1 | 1 | |
| Protein capicua homolog | CIC | | | | 1 |
| Cold-inducible RNA-binding protein (A18hnRNP) | CIRBP | 1 | 1 | 1 | |
| Clathrin light chain B | CLTB | 1 | | | |
| Cdc2-related kinase, arginine/serine rich (Cell division cycle 2-related protein kinase 7) | CRKRS | | | | 1 |
| Cold shock domain-containing E1, RNA binding (N-ras upstream gene protein) | CSDE1 | | 1 | | |
| Casein kinase II subunit alpha' | CSNK2A2 | | | | 1 |
| Casein kinase 2, beta polypeptide | CSNK2B | | | | 1 |
| Aspartyl-tRNA synthetase, cytoplasmic | DARS | | | | 1 |
| Dermcidin precursor | DCD | | 1 | | |
| DEAD (Asp-Glu-Ala-Asp) box poplypeptide 1 (ATP-dependent RNA helicase DDX1) | DDX1 | | 1 | | 1 |
| DEAD (Asp-Glu-Ala-Asp) box poplypeptide 5 (Probable ATP-dependent RNA helicase DDX5) | DDX5 | | | 1 | |
| DEAD (Asp-Glu-Ala-Asp) box polypeptide 21 (Nucleolar RNA helicase 2) | DDX21 | | 1 | | |
| Death-inducer obliterator 1 | DIDO1 | | | | 1 |
| DnaJ (Hsp40) homolog subfamily A member 1 | DNAJA1 | 1 | 1 | | 1 |
| DnaJ (Hsp40) homolog subfamily A member 2 | DNAJA2 | 1 | | | 1 |
| Dopey family member 1 | DOPEY1 | | | 1 | |
| Histone-lysine N-methyltransferase, H3 lysine-79 specific (DOT1-like) | DOT1L | | | | 1 |
| Destrin (actin depolymerizing factor) | DSTN | | 1 | | |
| Eukaryotic translation initiation factor 3 subunit G | EIF3G | | 1 | | |
| Eukaryotic translation initiation factor 3 subunit I (subunit 2) | EIF3I | | 1 | | |
| Eukaryotic translation initiation factor 3 subunit J (subunit 1) | EIF3J | | | | 1 |
| Glutamyl-prolyl-tRNA synthetase (EPRS protein) | EPRS | | 1 | | |
| Endoplasmic reticulum protein ERp29 precursor | ERP29 | | 1 | 1 | |
| Ewing sarcoma breakpoint region 1 (RNA-binding protein EWS) | EWSR1 | 1 | 1 | | 1 |
| Exosome component 1 (3'-5' exoribonuclease CSL4 homolog; Exosomal core protein CSL4) | EXOSC1 | | 1 | | |
| Fatty acid-binding protein, brain | FABP7 | | 1 | | |
| Family with sequence similarity 98, member B (Protein FAM98) | FAM98B | | 1 | | 1 |
| Four and a half LIM domains 1 | FHL1 | | | | 1 |
| Four and a half LIM domains protein 2 - | FHL2 | | 1 | | |

TABLE 8-continued

O-GlcNAc modified proteins identified by immunoprecipitation

| Protein | Abbreviation | CTD110.6 | Mab3 | Mab10 | Mab14 |
|---|---|---|---|---|---|
| Far upstream element-binding protein 1 | FUBP1 | | 1 | | |
| Ras GTPase-activating protein-binding protein (SH3 domain) 1 | G3BP1 | | | | 1 |
| Ras GTPase-activating protein-binding (SH3 domain) protein 2 | G3BP2 | | | | 1 |
| Guanine nucleotide-binding protein subunit beta 2-like 1 (Proliferation-inducing gene 21) | GNB2L1 | | 1 | | |
| Glutathione S-transferase P | GSTP1 | | 1 | 1 | 1 |
| Glycogenin-1 | GYG1 | 1 | | | |
| Histone H1.5 (Histone cluster 1, H1b) | H1B | | | | 1 |
| Histone H1x | H1FX | | 1 | | |
| H2A histone family, member J | H2AFJ | | 1 | | |
| Host cell factor C1 | HCFC1 | 1 | 1 | 1 | 1 |
| Histidine triad nucleotide-binding protein 1 (Protein kinase C-interacting protein 1) | HINT1 | | 1 | | |
| High-mobility group box 1 - *Homo sapiens* (Human) | HMGB1 | | 1 | | |
| Heterogeneous nuclear ribonucleoprotein A0 | hnRNPA0 | | 1 | | 1 |
| Heterogeneous nuclear ribonucleoprotein D (AU-rich element RNA binding protein 1, 37 kDa) | HNRNPD | 1 | 1 | 1 | 1 |
| Heterogeneous nuclear ribonucleoprotein L | HNRNPL | | 1 | | 1 |
| Hypoxanthine-guanine phosphoribosyltransferase 1 (Lesch-Nyhan syndrome) | HPRT1 | | 1 | | |
| HIV-1 Rev binding protein (Nucleoporin-like protein RIP) | HRB | | | | 1 |
| Heat shock 70 kDa protein 1 | HSP70.1 | 1 | 1 | 1 | 1 |
| Heat shock protein 90 kDa alpha (cytosolic), class B member ** pseudogene (Heat shock protein 90Bb) | HSP90AB2P | | 1 | | |
| Heat shock 70 kDa protein 4 | HSPA4 | | 1 | | 1 |
| 60 kDa heat shock protein, mitochondrial precursor | HSPD1 | | 1 | | |
| Hest shock 10 kDa protein 1 (Chaperonin 10; 10 kDa heat shock protein, mitochondrial) | HSPE1 | | 1 | | |
| Interleukin enhancer-binding factor 3, 90 kDa | ILF3 | 1 | 1 | 1 | 1 |
| Inosine-5'-monophosphate dehydrogenase 2 | IMPDH2 | 1 | | | |
| Isochorismatase domain-containing protein 1 | ISOC1 | 1 | | | |
| Uncharacterized protein KIAA1310 | KIAA1310 | | | | 1 |
| Importin subunit beta-1 (Karyopherin) | KPNB1 | | | 1 | |
| Lipocalin 2 (25 kDa alpha-2-microglobulin-related subunit of MMP-9) | LCN2 | | | 1 | |
| Lymphocyte cytosolic protein 1 (L-plastin) | LCP1 | | | 1 | |
| L-lactate dehydrogenase A chain | LDHA | | 1 | | 1 |
| L-lactate dehydrogenase B | LDHB | | 1 | | 1 |
| LIN-54 homolog | LIN54 | | | | 1 |
| Protein LSM12 homolog | LSM12 | | | 1 | 1 |
| Microtubule-associated protein 4 | MAP4 | | 1 | | |
| MBTD1 protein | MBTD1 | 1 | | | |
| Myeloid/lymphoid or mixed-lineage leukemia (Zinc finger protein HRX; Lysine N-methyltransferase 2A) | MLL (HRX | | | | 1 |
| Methylenetetrahydrofolate dehydrogenase (NADP+ dependent) 1 (C-1-tetrahydrofolate synthase, cytoplasmic) | MTHFD1 | | 1 | | |
| v-myb myeloblastosis viral oncogene homolog (avian)-like 2(Myb-related protein B; B-Myb) | MYBL2 | | | | 1 |
| Myosin, heavy chain 9, non-muscle | MYH9 | | 1 | 1 | |
| Myosin, heavy chain 10 (Myosin-10) | MYH10 | | 1 | | 1 |
| N-acetyltransferase 13 | NAT13 | | 1 | 1 | |
| Nucleolin | NCL | | 1 | 1 | 1 |
| Nuclear factor related to kappa-β-binding protein | NFRKB | | | | 1 |
| Nucleophosmin (Nucleolar phosphoprotein B23, numatrin) | NPM1 | 1 | 1 | | |
| Nuclear fragile X mental retardation-interacting protein 2 (FMRP-interacting protein2) | NUFIP2 | | | | 1 |
| Nucleoporin 153 kDa (Nuclear pore complex protein Nup153) | Nup153 | 1 | 1 | 1 | 1 |
| Nucleoporin 214 kDa (Nuclear pore complex protein Nup214) | Nup214 | 1 | 1 | 1 | 1 |
| Nucleoporin 54 kDa | NUP54 | | 1 | 1 | 1 |
| Nucleoporin 62 kDa (Nuclear pore glycoprotein p62) | NUP62 | 1 | 1 | 1 | 1 |
| Nucleoporin 98 kDa (Nuclear pore complex protein Nup98-Nup96 precursor) | NUP98 | 1 | | 1 | 1 |
| Nucleoporin like 1 (Nucleoporin p58/p45) | NUPL1 | 1 | | 1 | 1 |
| O-linked N-acetylglucosamine (GlcNAc) transferase (UDP-N-acetylglucosamine: peptide N-acetylglucosaminyltransferase 110 kDa subunit) | OGT | | | | 1 |
| Poly(A) binding protein, cytoplasmic 1 (Polyadenylate-binding protein 1) | PABPC1 | | 1 | | |
| Poly(A) binding protein, cytoplasmic 4 (inducible form) | PABPC4 | | 1 | | |
| Phosphoribosylaminoimidazole carboxylase, phosphoribosylaminoimidazole succinocarboxamide synthetase (Multifunctional protein ADE2) | PAICS | | 1 | | |
| Poly [ADP-ribose] polymerase 1 | PARP1 | | 1 | | 1 |
| Protein-L-isoaspartate(D-aspartate) O-methyltransferase | PCMT1 | 1 | 1 | | |
| Phosphatidylethanolamine-binding protein 1 | PEBP1 | | 1 | 1 | |
| Profilin-1 | PFN1 | | 1 | 1 | 1 |

TABLE 8-continued

O-GlcNAc modified proteins identified by immunoprecipitation

| Protein | Abbreviation | CTD110.6 | Mab3 | Mab10 | Mab14 |
|---|---|---|---|---|---|
| Polyhomeotic-like protein 3 | PHC3 | | | | 1 |
| PHD finger protein 12 (PHD zinc finger transcription factor) | PHF12 | | | | 1 |
| Pyruvate kinase, muscle (Pyruvate kinase isozymes M1/M2) | PK | | | 1 | |
| POM121 membrane glycoprotein(Nuclear envelope pore membrane protein POM 121) | POM121 | | | | 1 |
| Peptidyl-prolyl cis-trans isomerase A (Cyclophilin A; Cyclosporin A-binding protein) | PPIA | | 1 | 1 | 1 |
| Peptidyl-prolyl cis-trans isomerase B (Cyclophilin B) | PPIB | | 1 | | |
| Peptidyl-prolyl cis-trans isomerase F (Cyclophilin F) | PPIF | | 1 | | |
| Protein phosphatase 1 regulatory subunit 12A | PPP1R12A | | | | 1 |
| Peroxiredoxin-1 | PRDX1 | 1 | 1 | 1 | |
| Proteasome 26S subunit, non-ATPase 1 (26S proteasome non-ATPase regulatory subunit) | PSMD1 | | 1 | | |
| Polypyrimidine tract-binding protein 1(Heterogeneous nuclear ribonucleoprotein1) | PTBP1 | | 1 | | 1 |
| Glutamine and serine-rich protein 1 | QSER1 | | 1 | | 1 |
| RAE1 RNA export 1 homolog (mRNA export factor; mRNA-associated protein mrnp 41) | RAE1 | | | | 1 |
| RAN, member RAS oncogene family(GTP-binding nuclear protein Ran) | RAN | | | | 1 |
| Ran GTPase-activating protein 1 | RANGAP1 | | | | 1 |
| Putative RNA-binding protein 15 | RBM15 | | 1 | | 1 |
| RNA-binding protein 26 | RBM26 | | | | 1 |
| RNA binding motif protein 27 (RNA-binding protein 27) | RBM27 | | | 1 | 1 |
| RNA binding motif protein, X-linked (Heterogeneous nuclear ribonucleoprotein G) | RBMX | | 1 | | |
| Ringer finger protein 2 (E3 ubiquitin-protein ligase RING2) | RNF2 | | | | 1 |
| RNA(guanine-7-)methyltransferase (mRNA cap guanine-N7 methyltransferase) | RNMT | | 1 | | |
| Replication protein A 70 kDa | RPA1 | | 1 | | |
| 60S ribosomal protein L3 | RPL3 | | | | 1 |
| Ribosomal protein L9 | RPL9 | 1 | 1 | 1 | |
| 60S ribosomal protein L10 | RPL10 | | | | 1 |
| 60S ribosomal protein L17 | RPL17 | | | | 1 |
| Ribosomal protein L18a | RPL18A | 1 | | | |
| 60S ribosomal protein L23 | RPL23 | 1 | 1 | | |
| 60S ribosomal protein L23a | RPL23A | 1 | 1 | | 1 |
| 60S ribosomal protein L24 | RPL24 | | 1 | | 1 |
| 60S ribosomal protein L26 | RPL26 | 1 | | | 1 |
| 60S ribosomal protein L27a | RPL27A | 1 | | | |
| Ribosomal protein L28 variant | RPL28 | | 1 | | 1 |
| 60S ribosomal protein L29 | RPL29 | 1 | 1 | | 1 |
| 60S ribosomal protein L31 | RPL31 | 1 | 1 | | |
| 60S ribosomal protein L36a | RPL36A | 1 | | | 1 |
| Ribosomal protein, large P2 (60S acidic ribosomal protein P2) | RPLP2 | | 1 | | |
| 40S ribosomal protein S6 | RPS6 | 1 | | | 1 |
| 40S ribosomal protein S11 - *Homo sapiens* (Human) | RPS11 | 1 | | | 1 |
| 40S ribosomal protein S18 | RPS18 | | | | 1 |
| 40S ribosomal protein S19 | RPS19 | | 1 | | |
| 40S ribosomal protein S20 | RPS20 | 1 | | | 1 |
| 40S ribosomal protein S23 | RPS23 | 1 | 1 | 1 | |
| Ribosomal protein S27 | RPS27 | | 1 | | 1 |
| Ribosomal RNA processing 1 homolog (RRP1-like protein B) | RRP1B | | 1 | | |
| RuvB-like 1 (49 kDa TATA box binding protein-interacting protein) | RUVBL1 | | | | 1 |
| RuvB-like 2 (48 kDa TATA box-binding protein-interacting protein) | RUVBL2 | | 1 | | 1 |
| S100 calcium binding protein A7(Protein S100-A7) | S100A7 | | | 1 | |
| S100 calcium binding protein A8 (Protein S100-A8) | S100A8 | | | 1 | |
| Protein S100-A9 | S100A9 | | | 1 | |
| Scaffold attachment factor B (HSP27 estrogen response element-TATA box-binding protein) | SAFB | | 1 | | |
| Protein SEC 13 homolog | SEC13 | | | 1 | |
| Sec23 homolog A (Protein transport protein Sec23A) | SEC23A | | | | 1 |
| Sec23 homolog B (Protein transport protein Sec23B) | SEC23B | | | 1 | |
| SEC23-interacting protein | SEC23IP | | 1 | | 1 |
| SEC 24 related gene family, member C (Protein transport protein Sec24C) | SEC24C | | | | 1 |
| Protein transport protein Sec31a (SEC31 homolog A) | SEC31A | | | | 1 |
| SET domain containing 1A (Histone-lysine N-methyltransferase, H3 lysine-4 specific SET1) | SETD1A | | | | 1 |
| Splicing factor 1 | SF1 | 1 | | | |
| Splicing factor, proline/glutamine-rich (polypyrimidine tract binding protein associated) | SFPQ | | 1 | | |
| Splicing factor, arginine/serine-rich 3 | SFRS3 | | | | 1 |
| SIN3 homolog, transcription regulator (Paired amphipathic helix protein Sin3b) | SIN3B | | | | 1 |

TABLE 8-continued

O-GlcNAc modified proteins identified by immunoprecipitation

| Protein | Abbreviation | CTD110.6 | Mab3 | Mab10 | Mab14 |
|---|---|---|---|---|---|
| SWI/SNF-related matrix-associated actin-dependent regulator of chromatin subfamily C member 1 | SMARCC1 | | | | 1 |
| Sp1 transcription factor | Sp1 | | | | 1 |
| Snf2-related CREBBP activator protein (KIAA0309 protein) | SRCAP | | | | 1 |
| Signal recognition particle 14 kDa protein | SRP14 | 1 | 1 | | 1 |
| Sjogren syndrome antigen B (Lupus La protein; autoantigen La) | SSB | | 1 | | |
| Serine-threonine kinase receptor-associated protein | STRAP | | 1 | 1 | |
| Transcription elongation regulator 1 | TCERG1 | | | | 1 |
| TRK-fused gene protein (TRKT3 oncogene) | TFG | | | 1 | |
| Triosephosphate isomerase | TPI1 | | | 1 | |
| Thioredoxin | TXN | 1 | 1 | 1 | |
| Ubiquitin-associated protein 2 | UBAP2 | 1 | 1 | 1 | 1 |
| Ubiquitin-associated protein 2-like (Protein NICE-4) | UBAP2L | 1 | 1 | 1 | 1 |
| Vimentin | VIM | | 1 | 1 | |
| WD repeat protein 5 | WDR5 | | | | 1 |
| WD repeat protein 35 | WDR35 | | | | 1 |
| Serine/threonine-protein kinase WNK1(WNK lysine deficient protein kinase 1; Erythrocyte 65 kDa protein) | WNK1 (p65) | 1 | 1 | 1 | 1 |
| WNK lysine deficient protein kinase 3 (Serine/threonine-protein kinase WNK3) | WNK3 | 1 | | 1 | 1 |
| Y box binding protein 1(Nuclease sensitive element-binding protein 1) | YBX1 | | 1 | | 1 |
| YEATS domain-containing protein 2 | YEATS2 | | | | 1 |
| 14-3-3 protein epsilon (tyrosine 3-monooxygenase/tryptophan 5-monooxygenase activation, epsilon polypeptide) | YWHAE | | 1 | | |
| Zinc finger RNA-binding protein (M-phase phosphoprotein homolog) | ZFR | | | | 1 |
| Zyxin | ZYX | | | | 1 |
| Zinc finger ZZ-type-containing protein 3 | ZZZ3 | | | | 1 |

Example X

Generation of O-GlcNAc Specific Monoclonal Antibodies Using a Novel Synthetic Immunogen Combining a fully synthetic three-component immunogen with hybridoma technology led to the generation of O-Gl-cNAc-specific IgG MAbs having a broad spectrum of binding targets. Large-scale shotgun proteomics led to the identification of 254 mammalian O-GlcNAc modified proteins, including a large number of novel glycoproteins. The data imply a role of 0-GlcNAc in transcriptional/translational regulation, signal transduction, the ubiquitin pathway, anterograde trafficking of intracellular vesicles and post-translational modification.

O-glycosylation of serine and threonine of nuclear and cytoplasmic proteins by a single β-N-acetyl-D-glucosamine moiety (β-GlcNAc) is a ubiquitous post-translational modification that is highly dynamic and fluctuates in response to cellular stimuli through the action of the cycling enzymes, O-linked GlcNAc transferase (OGT) and O-GlcNAcase (OGA). This type of glycosylation has been implicated in many cellular processes, frequently via interplay with phosphorylation that can occur on the same amino acid residuel. Importantly, alteration of 0-GlcNAc levels has been linked to the etiology of prevalent human diseases including type II diabetes and Alzheimer's disease (Hart et al., 2007 Nature 446, 1017-1022).

Unlike phosphorylation for which a wide range of pan- and site-specific phospho-antibodies are available, studies of O-GlcNAc modification are hampered by a lack of effective tools for its detection, quantification, and site localization. In particular, only two pan-O-GlcNAc specific antibodies have been described: an IgM pan-O-GlcNAc antibody (CTD 110.6; Comer et al., 2001 Anal. Biochem. 293, 169-177), and an IgG antibody raised against O-GlcNAc modified components of the nuclear pore (RL-2; Snow et al., 1987 J. Cell Biol. 104, 1143-1156) that shows restricted cross-reactivity with O-GlcNAc modified proteins. In fact, multiple studies have shown that O-GlcNAc modified glycoconjugates do not elicit relevant IgG isotype antibodies and thus, the challenge to elicit O-GlcNAc specific IgG antibodies is considerable.

We reasoned that O-GlcNAc-specific antibodies can be elicited by employing a three-component immunogen (compound 52, FIG. 19) composed of an O-GlcNAc containing peptide, which in this study is derived from casein kinase II (CKII) a subunit, (Kreppel and Hart, 1999 J. Biol. Chem. 274, 32015-32022) a well-documented murine MHC class II restricted helper T-cell epitope and a Toll-like receptor-2 (TLR2) agonist as an in-built adjuvant. Such a compound is expected to circumvent immune suppression caused by a carrier protein or linker region of a classical conjugate vaccine; yet it contains all mediators required for eliciting a strong and relevant IgG immune response (Ingale et al., 2007 Nat. Chem. Biol. 3, 663-667). In addition, compound 53 was prepared that has an artificial thio-linked GlcNAc moiety, which has an improved metabolic stability compared to its O-linked counter-part thereby providing additional opportunities to eliciting O-GlcNAc specific antibodies.

Compounds 52 and 53 were readily obtained by liposome-mediated native chemical ligations (Ingale et al., 2006 Org. Lett. 8, 5785-5788) of C-terminal lipopeptide thioester 63 with glycopeptides 64 and 65, respectively (FIG. 19). The starting thioester 63 was assembled on a sulfonamide "safety-catch" linker followed by release by alkylation with iodoacetonitrile and treatment with benzyl mercaptan to give a compound that was deprotected using standard conditions. Compounds 64 and 65 were prepared employing a Rink amide resin, Fmoc protected amino acids and Fmoc-Ser-(AcO3-α-D-GluNAc) or Fmoc-Ser-(1-thio-AcO3-α-D-Glu- NAc), respectively. After completion of the assembly, the acetyl esters were cleaved by treatment with 60% hydrazine in MeOH and the resulting compounds were cleaved from the resin by treatment with reagent K and purified by reverse phase HPLC. Compounds 52 and 53 were incorporated into phospholipid based small unilamellar vesicles (SUVs) followed by extrusion through a 100 nm Nuclepore® polycarbonate membrane. Groups of five female BALB/c mice were immunized intra-peritoneal four times at two-weekly intervals with liposomes containing 3 µg of saccharide. Antiglycopeptide antibody titers were determined by coating microtiter plates with CGSTPVS(β-O-GlcNAc) SANM (66) conjugated to maleimide (MI) modified BSA and detection was accomplished with anti-mouse IgG antibodies labeled with alkaline phosphatase. Compounds 52 and 53 elicited excellent titers of IgG antibodies (Table 6; FIG. 20). Furthermore, no significant difference in IgG titers was observed between the O- and S-linked saccharide derivatives, and therefore further attention was focused on mice immunized with 52.

Spleens of two mice immunized with 52 were harvested and standard hybridoma culture technology gave seven IgG1, seven IgG2a, two IgG2b and fourteen IgG3 producing hybridoma cell lines (Table 7). The ligand specificity of the resulting MAbs was investigated by ELISA. All MAbs recognized CGSTPVS(β-O-GlcNAc)SANM linked to BSA (BSA-MI-66) whereas only a small number recognized the peptide CGSTPVSSANM (SEQ ID NO:12) conjugated to BSA (BSA-MI-67). Furthermore, the interaction of twenty MAbs could be inhibited with the glycopeptide GSTPVS (β-O-GlcNAc)SANM (68), but not with peptide GSTPVS-SANM (SEQ ID NO: 13) (69) or β-O-GlcNAc-Ser (70) demonstrating glycopeptide specificity.

Three hybridomas (18B10.C7(3), 9D1.E4(10), 1F5.D6 (14)) were cultured at a one-liter scale and the resulting antibodies purified by saturated ammonium sulfate precipitation followed by Protein G column chromatography to yield, in each case, approximately 10 mg of IgG. Inhibition ELISA confirmed that the MAbs require carbohydrate and peptide (glycopeptide) for binding (FIG. 16).

To establish the usefulness of the MAbs for immuno detection, CKII α subunit was immunoprecipitated from HEK293T lysates with or without exogenous overexpression of OGT and the eluates were subjected to standard immunoblotting procedures. While equal amounts of CKII α subunit were pulled down, the monoclonal antibodies showed cross-reactivity towards a band corresponding to CKII α subunit with an increased signal for the OGT overexpressed sample supporting GlcNAc-dependence of recognition (FIG. 21a). The latter was supported by the absence of detection when a glycosylated recombinant CKII α subunit expressed in E. coli was employed (data not shown). The specificity of the MAbs was further evaluated in mammalian cell crude extracts by genetically manipulating OGA or OGT levels. Importantly, three distinct global O-GlcNAc levels were observed, in which lysates with OGA, mock and OGT transfection yielded lowest, median and highest modification status, which is in good agreement with the expression levels of the cycling enzymes (FIG. 21b). The results imply that although the epitope was derived from a single protein, the MAbs have a broad spectrum of binding targets. We also compared the immunoblotting profiles of the new MAbs with CTD110.6 (a commercially available pan-O-GlcNAc IgM antibody) after enrichment of O-GlcNAc modified proteins with each of the MAbs (FIG. 21c). The data clearly illustrate that each of the antibodies enrich for CTD110.6 cross-reactive proteins. Immunopurification with CTD110.6 also enriched for proteins that cross-reacted with the three new antibodies upon immunoblotting (data not shown).

Although one gene encodes for OGT and another for OGA in mammals, no obvious primary consensus sequence for O-GlcNAc modification has been identified. A recently reported crystal structure of an OGT homolog (Martinez-Fleites et al., 2008 Nat. Struct. Mol. Biol. 15, 764-765) showed a large groove near the active site and it has been proposed that it may accommodate a diverse set of polypeptide substrates and/or a particular secondary structure. The crystal structure data in conjunction with our findings that all characterized antibodies were pan-O-GlcNAc antibodies indicates that the O-GlcNAc modified regions of polypeptide chains may share a limited number of conserved secondary structures.

Finally, the MAbs were employed for large-scale enrichment of O-GlcNAc modified proteins for shotgun proteomics. Agarose covalently conjugated MAbs were mixed with nucleocytoplasmic proteins extracted from HEK293T cells cultured in the presence of the OGA inhibitor, PUGNAc (Haltiwanger et al., 1998 J. Biol. Chem. 273, 3611-3617). The released proteins were subjected to Lys-C digestion and the recovered peptides and glycopeptides were analyzed by LC-MS/MS on an LTQ-XL. Protein assignments and false-discovery rates (1% at the protein level) were calculated using TurboSequest and ProteoIQ. Proteins were excluded that appeared in control experiments (mixture of Protein A/G PLUS agarose and anti-Mouse IgM agarose) and localization was confirmed with the aid of Human Protein Reference Database (HPRD) and UniProt. Using the three MAbs generated in this study, we identified 254 O-GlcNAc modified proteins, 134 of which are novel (FIG. 22a, Tables 9 and 10). This represents the largest single set of putative O-GlcNAc modified proteins reported to date. A large number of previously characterized O-GlcNAc modified proteins, such as SP1, OGT and nuclear pore protein p62 were found adding confidence to proper assignment and further supports the selectivity of the antibodies for O-GlcNAc modification. However, at this point the possibility that some proteins may have been co-purified due to tight association to O-GlcNAc modified proteins can not be excluded.

TABLE 9

List of enriched known O-GlcNAc proteins.

| SwissProt Number | Gene Name | Protein Name | 18B10.C7(3) | 9D1.E4(10) | 1F5.D6(14) | CTD110.6 | Biological Process | Primary Localization | Alternate Localization | Previously Identified Method (Ref) |
|---|---|---|---|---|---|---|---|---|---|---|
| P18621 | RPL17 | 60 S ribosomal protein L17 | ✓ | | | | Tl | R | No | Click-chemistry-based tagging enrichment, LC-MS/MS (1) |
| Q9H4A3 | WNK1 | Serine/threonine-protein kinase WNK1 (Protein kinase, lysine deficient 1) | ✓ | ✓ | ✓ | | S | C | | Galactose-ketone-biotin enrichment, LC-MS/MS (2) |
| Q12771 | HNRNPS | P37 AUF1 (heterogeneous nuclear ribonucleoprotein D; AU-rich element RNA binding protein 1, 37 kDa | ✓ | | ✓ | | G | C | N | Azido-biotin enrichment, LC-MS/MS (3) |
| P09651 | HNRPA1 | Heterogeneous nuclear ribonucleoprotein A1 | ✓ | | ✓ | ✓ | G | N | C, No | CTD110.6 immunopurify, LC-MS/MS (4) |
| P37198 | NUP62 | Nuclear pore glycoprotein p62 | ✓ | ✓ | ✓ | ✓ | Tp | N | | CTD110.6 immunopurify, LC-MS/MS (5) |
| Q53H29 | — | Nucleoporin 54 kDa variant | ✓ | ✓ | ✓ | ✓ | Tp | N | C | CTD110.6 immunopurify, LC-MS/MS (5) |
| P62937 | PPIA | Peptidyl-prolyl cis-trans isomerase A (cyclophilin A) | ✓ | ✓ | ✓ | ✓ | Tl | C | No | CTD110.6 immunopurify, LC-MS/MS (5) |
| Q14157 | USAP2L | Ubiquitin-associated protein 2-like (Protein NICE-4, KIAA0144) | ✓ | ✓ | ✓ | ✓ | U | N | | CTD110.6 immunopurify, LC-MS/MS (5) |
| P09211 | GSTP1 | Glutathione S-transferase P | ✓ | ✓ | ✓ | | M | C | N | Azido-biotin enrichment, LC-MS/MS (6) |
| P11940 | PABPC1 | Polyadenylate-binding protein 1 | ✓ | ✓ | ✓ | | G | C | N | CTD110.6 immunopurify, LC-MS/MS (4) |
| P10599 | TXN | Thioredoxin | ✓ | | | ✓ | M | C | N | Azido-biotin enrichment, LC-MS/MS (3) |
| P63244 | GNB2L1 | Guanine nucleotide-binding protein subunit beta 2-like 1 (RACK1) | ✓ | | ✓ | | S | C | N, PM | Azido-biotin enrichment, LC-MS/MS (3) |
| P32119 | PROX2 | Peroxiredoxin-2 | ✓ | ✓ | | | M | C | | Azido-biotin enrichment, LG-MS/MS (3) |
| P35580 | MYH10 | Myosin-10 | | ✓ | ✓ | | S | C | PM | Lectin affinity chromatography, LC-MS/MS (7) |
| P60709 | ACTB | Actin, cytoplasmic 1 | ✓ | ✓ | ✓ | | S | C | G, PM, No | Azido-biotin enrichment, LC-MS/MS (3) |
| P34932 | HSPA4 | Heat shock 70 kDa protein 4 | ✓ | ✓ | ✓ | | Tl | C | | Azido-biotin enrichment, LC-MS/MS (3) |
| P14866 | HNRPL | Heterogeneous nuclear ribonucleoprotein L | ✓ | | ✓ | | G | N | No, C | 2DE, CTD110.6 immunoblotting, LC-MS/MS (8) |
| P38159 | RBMX | Heterogeneous nuclear ribonucleoprotein G | ✓ | ✓ | ✓ | ✓ | G | N | No | Hot labeling, HPLC (9) |
| P19338 | NCL | Nucleolin | ✓ | ✓ | | | G | No | N, C, PM | CTD110.6 immunopurify, LC-MS/MS (4) |
| P04075 | ALDOA | Fructose-bisphosphate aldolase A | ✓ | ✓ | | ✓ | M | C | | Lectin affinity chromatography, LC-MS/MS (7) |
| P12268 | IMPDH2 | Inosine-5'-monophosphate dehydrogenase 2 | ✓ | | ✓ | | M | U | No | Azido-biotin enrichment, LC-MS/MS (3) |
| Q23246 | SFPQ | Splicing factor, proline- and glutamine-rich | ✓ | | | ✓ | G | N | No | CTD110.6 immunopurify, LC-MS/MS (4) |
| Q17RM7 | EMSY | EMSY protein | ✓ | ✓ | | | U | U | | Lectin weak affinity chromatography, LC-MS/MS (10) |
| Q15436 | SEC23A | Protein transport protein Sec23A | | ✓ | ✓ | | Tp | C | ER | CTD110.6 immunopurify, LC-MS/MS (5) |
| Q15437 | SEC23B | Protein transport protein Sec23B | | ✓ | ✓ | | Tp | ER | G, C | CTD110.6 immunopurify, LC-MS/MS (5) |
| P35579 | MYH9 | Myosin-9 | ✓ | | | | S | C | No | Lectin affinity chromatography, LC-MS/MS (7) |
| P13639 | EEF2 | Elongation factor 2 | ✓ | | | | Tl | C | No | Click-chemistry-based tagging enrichment, LC-MSIMS (1) |
| P23526 | AHCY | Adenosylhomocysteinase (S-adenosylhomocysteine hydrolase) | ✓ | | | | M | C | | Azido-biotin enrichment; LC-MS/MS (3) |

TABLE 9-continued

List of enriched known O-GlcNAc proteins.

| SwissProt Number | Gene Name | Protein Name | 18B10.C7(3) | 9D1.E4(10) | 1F5.D6(14) | CTD110.6 | Biological Process | Primary Localization | Alternate Localization | Previously Identified Method (Ref) |
|---|---|---|---|---|---|---|---|---|---|---|
| Q92499 | DDX1 | ATP-dependent RNA helicase DDX1 (DEAD box protein retinoblastoma) | ✓ | | | | G | N | No | Azido-biotin enrichment, LC-MS/MS (3) |
| Q15393 | SF3B3 | Splicing factor 3B subunit 3 | ✓ | | | | G | N | C | Azido-biotin enrichment, LC-MS/MS (3) |
| P50990 | CCT8 | T-complex protein 1 subunit theta | ✓ | | | | TI | C | C | Azido-biotin enrichment, LC-MS/MS (3) |
| P61604 | HSPE1 | 10 kDa heat shock protein, mitochondrial | ✓ | | | | TI | M | No | CTD110.6 immunopurify, LC-MS/MS (4) |
| P23528 | CFL1 | Cofilin-1 | ✓ | | | | S | C | N, PM | CTD110.6 immunopurify, LC-MS/MS (5) |
| A4UCT1 | GAPDH | Glyceraldehyde 3-phosphate dehydrogenase | ✓ | | | | M | C | | CTD110.6 immunopurify, LC-MS/MS (5) |
| P08238 | HSP90AB1 | Heat shock protein HSP 90-beta | | | | | S | C | | CTD110.6 immunopurify, LC-MS/MS (5) |
| P60174 | TPI1 | Triosephosphate isomerase | | | | | M | C | | Lectin affinity chromatography, LC-MS/MS (7) |
| P26641 | EEF1G | Elongation factor 1-gamma | | ✓ | | | TI | U | No | Azido-biotin enrichment. LC-MS/MS (3) |
| O43390 | HNRPR | Heterogeneous nuclear ribonucleoprotein R | | ✓ | | | G | N | | CTD110.6 immunopurify, LC-MS/MS (4) |
| P04083 | ANXA1 | Annexin A1 | | ✓ | | | S | PM | C, N | CTD110.6 immunopurify, LC-MS/MS (5) |
| Q14974 | KPNB1 | Importin subunit beta-1 (Karyopherin beta 11) | | ✓ | | | Tp | C | N | CTD110.6 immunopurify, LC-MS/MS (5) |
| P14618 | PKM2 | Pyruvate kinase isozymes M1/M2 | | | | | M | C | No | Lectin affinity chromatography, LC-MS/MS (7) |
| P00338 | LDHA | L-lactate dehydrogenase A chain | | | | | M | C | | Galactose-ketone-biotin enrichment, LC-MS/MS (2) |
| Q6P4R8 | NFRKB | Nuclear factor related to kappa-B-binding protein | | | ✓ | | G | N | | Galactose-ketone-biotin enrichment, LC-MS/MS (2) |
| Q9BYJ9 | YTHDF1 | YTH domain family protein 1 (DACA-1 homolog) | | | ✓ | | U | U | | |
| Q96KR1 | ZFR | Zinc finger RNA-binding protein | | | ✓ | | G | N | No | Galactose-ketone-biotin enrichment, LC-MS/MS (2) |
| A0AVA9 | EPRS | Glutamyl-prolyl-tRNA synthetase | | | ✓ | | TI | C | C, PM, No | Azido-biotin enrichment, LC-MS/MS (3) |
| Q59EJ3 | — | Heat shock 70 kDa protein 1A variant | | | ✓ | | U | U | | Azido-biotin enrichment, LC-MS/MS (3) |
| Q9P215 | LARS | Leucyl-tRNA synthetase, cytoplasmic | | | ✓ | | M | C | C | Azido-biotin enrichment, LC-MS/MS (3) |
| P11831 | SRF | Serum response factor | | | ✓ | | G | N | | Hot labeling, HPLC, Gas chromatography, Edman degradation (11) |
| P08047 | SP1 | Transcription factor Sp1 | | | ✓ | | G | N | N | Hot labeling, HPLC, Gas chromatography, Edman degradation (12) |
| P23396 | RPS3 | 40S ribosomal protein S3 | | | ✓ | | TI | C | C, No | CTD110.6 immunopurify, LC-MS/MS (4) |
| P07910 | HNRPC | Heterogeneous nuclear ribonucleoproteins C1/C2 | | | ✓ | | G | N | | CTD110.6 immunopurify, LC-MS/MS (5) |
| P19784 | CSNK2A2 | Casein kinase II subunit alpha' | | | ✓ | | S | N | | CTD110.6 immunopurify, LC-MS/MS (5) |
| P67870 | CSNK2B | Casein kinase II subunit beta | | | ✓ | | S | N | | CTD110.6 immunopurify, LC-MS/MS (5) |
| Q5SP16 | HSPA1A | Heat shock 70 kDa protein 1A | | | ✓ | | TI | U | | CTD110.6 immunopurify, LC-MS/MS (5) |
| Q9BYG9 | NPM1 | Nucleophosmin/B23.2 | | | ✓ | | TI | N | | CTD110.6 immunopurify, LC-MS/MS (5) |
| O15294 | OGT | UDP-N-acetylglucosamine-peptide N-acetylglucosaminyltransferase 110 kDa subunit | | | | ✓ | G | N | C, M | CTD110.6 immunopurify, LC-MS/MS (5) |
| Q8TE73 | DNAH5 | Dynein, axonemal, heavy polypeptide 5 | | | | ✓ | S | C | | |
| Q02447 | SP3 | Transcription factor Sp3 | | | | ✓ | G | N | No | O-GlcNAc immunoblotting (13) |
| P36578 | RPL4 | 60S ribosomal protein L4 | | | | | TI | R | | Azido-biotin enrichment, LC-MS/MS (3) |
| P49368 | CCT3 | T-complex protein 1 subunit gamma | | | | | TI | C | No | Azido-biotin enrichment, LC-MS/MS (3) |

TABLE 9-continued

List of enriched known O-GlcNAc proteins.

| SwissProt Number | Gene Name | Protein Name | 18B10.C7(3) | 9D1.E4(10) | 1F5.D6(14) | CTD110.6 | Biological Process | Primary Localization | Alternate Localization | Previously Identified Method (Ref) |
|---|---|---|---|---|---|---|---|---|---|---|
| P10809 | HSPD1 | 60 kDa heat shock protein, mitochondrial precursor | | ✓ | | ✓ | Tl | | | 2DE, CTD110.6 immunoblotting, LC-MS/MS (8) |
| P13807 | GYS1 | Glycogen [starch] synthase, muscle | | ✓ | | | M | C | N | O-GlcNAc immunoblotting(14) |

*Abbreviations: G, Gene expression/Transcription: M, Metabolism; S, Signal transduction, Tl, Translation; Tp, Transport U, Unknown; C, Cytoplasm; N, Nucleus; No, Nucleolus; ER, Endoplasmic reticulum; G, Golgi apparatus; Ex, Extracellular.

References
1. Gurcel et al., (2008) Anal Bioanal Chem, 390: 2089-2097.
2. Khidekel et al., (2004) PNAS, 101: 13132-13137.
3. Nandi, et al., (2006)Anal Chem, 78: 452-458.
4. Wang, et al., (2007) MCP, 6: 1365-1379.
5. Wells et al., (2002) MCP, 1: 791-804.
6. Sprung et al., (2005) J Proteome Res. 4: 950-957.
7. Cieniewski-Bernard et al., (2004) MCP, 3: 577-585
8. Park et al., (2007) JBMB, 40: 1058-1068.
9. Soulard et al., (1993) Nucl Acids Res, 21: 4210-4217.
10. Vosseller et al., (2006) MCP, 5: 923-934.
11. Reason et al., (1992) JBC, 267: 16911-16921.
12. Roos at al., (1997) MCB, 17(11): 6472-6480.
13. Yao, et al., (2007) JBC, 282(42): 1038-1045.
14. Parker at al., (2003) JBC. 278: 10022-10027.

TABLE 10

List of enriched novel O-GlcNAc proteins.

| SwissProt Number | Gene Name | Protein Name | 18B10.C7(3) | 9D1.E4(10) | 1F5.D6(14) | CTD110.6 | Biological Process | Primary localization | Alternate localization |
|---|---|---|---|---|---|---|---|---|---|
| P35658 | NUP214 | Nuclear pore complex protein Nup214 | ✓ | | | | Tp | N | |
| P49790 | NUP153 | Nuclear pore complex protein Nup153 | ✓ | | | | Tp | N | |
| Q06687 | RING1 | E3 ubiquitin-protein ligase RING1 | ✓ | | | | G | N | No |
| Q5T6F2 | UBAP2 | Ubiquitin-associated protein 2 | ✓ | | | | U | U | |
| Q9Y520 | BAT2D1 | BAT2-iso (BAT2 domain-containing protein 1; HBxAg transactivated protein 2 | ✓ | | | | U | C | |
| Q9Y6Y8 | SEC23IP | SEC23-interacting protein | ✓ | | ✓ | | Tp | ER | C, N, G |
| Q13151 | HNRPA0 | Heterogeneous nuclear ribonucleoprotein A0 | ✓ | ✓ | ✓ | ✓ | G | N | No |
| Q9GZZ1 | NAT13 | N-acetyltransferase 13 (Mak3) | ✓ | ✓ | | | U | C | |
| Q14011 | CIRBP | Cold-inducible RNA-binding protein | ✓ | | | | S | N | |
| O75821 | EIF3S4 | Eukaryotic translation initiation factor 3 subunit 4 | | | ✓ | ✓ | TI | C | |
| P16402 | HIST1H1D | Histone H1.3 | ✓ | ✓ | ✓ | ✓ | G | R | |
| P26373 | RPL13 | 60 S ribosomal protein L13 | ✓ | | | | U | U | No |
| Q2KHR3 | QSER1 | Glutamine and serine-rich protein 1 (FLJ21924) | ✓ | | | | U | U | |
| Q52LJ0 | FAM98B | Protein FAM98B | ✓ | | ✓ | ✓ | U | C | |
| Q8NC51 | SERBP1 | Plasminogen activator inhibitor 1 RNA-binding protein (SERPINE1 mRNA binding protein 1) | | | ✓ | ✓ | G | C | N |
| P16401 | HIST1H1B | Histone H1.5 | | | ✓ | ✓ | G | N | No |
| P52948 | NUP98 | Nuclear pore complex protein Nup98-Nup96 precursor [Contains: Nuclear pore complex protein Nup98] | | ✓ | | | Tp | N | C |
| P78406 | RAE1 | mRNA export factor (MRNP41) | ✓ | ✓ | ✓ | ✓ | G | N | C |
| Q05BK6 | TFG | TFG protein (TRK-fused gene protein) | ✓ | ✓ | | | S | C | |
| Q5JRG1 | NUPL1 | Nucleoporin like 1 | ✓ | ✓ | ✓ | | U | C | N |
| Q9P2N5 | RBM27 | RNA-binding protein 27 | ✓ | ✓ | ✓ | | U | C | N |
| P07737 | PFN1 | Profilin-1 | ✓ | | ✓ | | S | C | Ex |
| P32969 | RPL9 | 60 S ribosomal protein L9 | ✓ | | ✓ | | TI | R | No |
| Q9Y3F4 | STRAP | Serine-threonine kinase receptor-associated protein | ✓ | | | | S | C | |
| Q8TYH5 | ZZZ3 | Zinc finger ZZ-type-containing protein 3 | | ✓ | | | G | N | |
| Q92522 | H1FX | Histone H1x | | ✓ | | | G | R | No |
| A2A3R5 | RPS6 | Ribosomal protein S6, isoform CRA_a | | | | ✓ | TI | R | |
| P30050 | RPL12 | 60 S ribosomal protein L12 | | | | ✓ | TI | R | |
| P46779 | RPL28 | 60 S ribosomal protein L28 | | | | ✓ | TI | R | |
| P54652 | HSPA2 | Heat shock-related 70 kDa protein 2 | | | | ✓ | TI | C | C, No |
| P63220 | RPS21 | 40 S ribosomal protein S21 | | | ✓ | | G | R | |
| Q15717 | ELAVL1 | ELAV-like protein 1 (Embryonic lethal abnormal vision like 1) | | | ✓ | ✓ | G | N | C, No |
| A1L431 | PPIAL4 | Peptidyl-prolyl cis-trans isomerase A-like 4 (Cyclophilin LC) | | | ✓ | | U | C | |
| P55735 | SEC13 | Protein SEC13 homolog | | | ✓ | ✓ | Tp | ER | |
| Q86X55 | CARM1 | Histone-arginine methyltransferase CARM1 (Coactivator associated arginine methyltransferase 1) | | ✓ | ✓ | | M | N | N, C |
| Q8IX12 | CCAR1 | Cell division cycle and apoptosis regulator protein 1 | | | | ✓ | S | C | |
| O60884 | DNAJA2 | DnaJ homolog subfamily A member 2 | | | | ✓ | TI | C | |
| O14776 | TCERG1 | Transcription elongation regulator 1 | | | ✓ | ✓ | G | N | |
| Q24Q7 | ATXN2 | ATXN2 protein | | | | ✓ | U | U | |
| Q8NCA5 | FAM98A | DKFZP564F0522 protein | | | | ✓ | U | U | N, M |
| Q8WWM7 | ATXN2L | Ataxin-2-domain protein | | | | ✓ | U | N | No |

TABLE 10-continued

List of enriched novel O-GlcNAc proteins.

| SwissProt Number | Gene Name | Protein Name | 18B10.C7(3) | 9D1.E4(10) | 1F5.D6(14) | CTD110.6 | Biological Process | Primary localization | Alternate localization |
|---|---|---|---|---|---|---|---|---|---|
| Q96HA1 | POM121 | POM121 membrane glycoprotein (Nuclear envelop pore membrane protein POM121) | | | ✓ | | Tp | N | ER |
| Q9NX58 | LYAR | Cell growth-regulating nucleolar protein | | | ✓ | ✓ | G | No | |
| A2A3N6 | PIPSL | Novel protein similar to phosphatidylinositol-4-phosphate 5-kinase, type I, alpha (Putative PIP5K1A and PSMD4-like protein) | | | | ✓ | U | C | |
| A2A3R7 | RPS6 | Ribosomal protein S6 | ✓ | | | | Tl | R | |
| A5JHP3 | DCD | Dermcidin isoform 2 | ✓ | | | | U | U | |
| O43148 | RNMT | mRNA cap guanine-N7 methyltransferase | ✓ | | | | G | C | N |
| O75534 | CSDE1 | Cold shock domain-containing protein E1 (Upstream of NRAS) | ✓ | | | | G | C | |
| P00492 | HPRT1 | Hypoxanthine-guanine phosphoribosyltransferase | ✓ | | | | M | C | |
| P02795 | MT2A | Metallothionein-2 | ✓ | | | | U | N | |
| P05387 | RPLP2 | 60 S acidic ribosomal protein P2 | ✓ | | | | Tl | C | C |
| P09429 | HMGB1 | High mobility group protein B1 | ✓ | | | | G | N | No |
| P22234 | PAICS | Multifunctional protein ADE2 [Includes: Phosphoribosylaminoimidazole-succinocarboxamide synthase | ✓ | | | | M | C | C, PM |
| P27694 | RPA1 | Replication protein A 70 kDa DNA-binding subunit V | ✓ | | | | G | N | |
| P30086 | PEBP1 | Phosphatidylethanolamine-binding protein 1 (Raf kinase inhibitor protein) | ✓ | | | | S | C | PM |
| P31689 | DNAJA1 | DnaJ homolog subfamily A member 1 | ✓ | | | | Tl | C | N, No, G |
| P35125 | USP6 | Ubiquitin carboxyl-terminal hydrolase 6 | ✓ | | | | Tl | C | |
| P43487 | RANBP1 | Ran-specific GTPase-activating protein | ✓ | | | | Tp | C | N |
| P48634 | BAT2 | Large proline-rich protein BAT2 (HLA-B associated transcript 2) | ✓ | | | | U | U | |
| P61927 | RPL37 | 60 S ribosomal protein L37 | ✓ | | | | Tl | R | |
| P62633 | CNBP | Cellular nucleic acid-binding protein (Zinc finger protein 9) | ✓ | | | | G | C | ER |
| Q09028 | RBBP4 | Histone-binding protein (Retinoblastoma binding protein 4) | ✓ | | | | G | N | No |
| Q13310 | PABPC4 | Polyadenylate-binding protein 4 | ✓ | | | | Tl | R | |
| Q13347 | EIF3S2 | Eukaryotic translation initiation factor 3 subunit 2 | ✓ | | | | Tl | N | |
| Q14192 | FHL2 | Four and a half LIM domains protein 2 | ✓ | | | | G | C | C, M |
| Q14444 | GPIAP1 | Caprin-1 | ✓ | | | | Tp | PM | |
| Q14684 | KIAA0179 | RRP1-like protein B | ✓ | | | | U | No | |
| Q2M2Y6 | ZNF615 | Zinc Finger protein 615 | ✓ | | | | U | N | |
| Q5JXK1 | FAM135A | Protein FAM135A | ✓ | | | | U | U | |
| Q5RLJ0 | — | CLE | ✓ | | | | Tl | U | |
| Q6BH5 | PPIB | Peptidyl-prolyl cis-trans isomerase B (Cyclophilin B) | | ✓ | | | U | U | |
| Q6ZU10 | FAM79B | Protein FAM79B 9Family with sequence similarity 79, member B) | | ✓ | | | U | N | C, No |
| Q7LBC6 | JMJD1B | JmjC domain-containing histone demethylation protein 2B (Jumonji domain containing 1B) | | ✓ | | | U | N | |
| Q96AE4 | FUBP1 | Far upstream element-binding protein 1 | ✓ | ✓ | | | G | N | C |
| Q9UJV9 | DDX41 | Probable ATP-dependent RNA helicase DDX41 (DEAD Asp-Glu-Ala-Asp box polypeptide 41 | ✓ | | | | G | No | |
| A1L3W5 | SUMO4 | SUMO4 (SMT3 suppressor of mif two 3 homolog 4) | | | | | Tl | N | |
| A2A305 | UBAP2 | Ubiquitin associated protein 2 | | | | | U | U | |
| O60333 | KIF1B | Kinesin-like protein KIF1B | | | | | S | C | M |
| O60506 | SYNCRIP | Heterogenous nuclear ribonucleoprotein Q | | | | | G | C | ER, R, No |
| O95259 | KCNH1 | Potassium voltage-gated channel subfamily H member 1 | | | | | Tp | PM | |
| P05109 | S100A8 | S100 calcium binding protein A8 | | | | | S | C | PM, Ex |
| P06702 | S100A9 | S100 calcium binding protein A9 | | | | | S | C | PM |
| P31151 | S100A7 | S100 calcium binding protein A7 | | | | | S | C | ER, N, PM |
| Q01469 | FABP5 | Fatty acid-binding protein, epidermal | | | | | Tp | C | ER |

TABLE 10-continued

List of enriched novel O-GlcNAc proteins.

| SwissProt Number | Gene Name | Protein Name | 18B10.C7(3) | 9D1.E4(10) | 1F5.D6(14) | CTD110.6 | Biological Process | Primary localization | Alternate localization |
|---|---|---|---|---|---|---|---|---|---|
| Q69YU5 | — | Putative uncharacterized protein DKFZp547P055 | | | | | U | U | |
| Q8IVL0 | NAV3 | Neuron naviogator 3 | | | | | U | N | |
| Q99567 | NUP88 | Nuclear pore complex protein Nup88 | | | | | Tp | N | |
| A0AVI3 | H2BFS | H2B histone family, member S | | | | | G | N | |
| A4D1M5 | LOC401404 | Similar to ribosomal protein S14 | | | ✓ | | Tl | R | |
| O14497 | ARID1A | AT-rich interactive domain-containing protein 1A | | | ✓ | | G | C | N |
| O14974 | PPP1R12A | Protein phosphatase 1 regulatory subunit 12A | | | ✓ | | M | C | PM |
| O15026 | SRCAP | Helicase SRCAP (Transcription activator SRCAP) | | | ✓ | | G | N | |
| O15047 | SETD1A | Histone-lysine N-methyltransferase, H3 lysine-4 specific SET1 | | | ✓ | | S | N | |
| O60907 | TBL1X | F-box-like/WD repeat protein TBL1X (SMAP65) | | | ✓ | | S | N | |
| O75182 | SIN3B | Paired amphipathic helix protein Sin3b | | | ✓ | | G | N | |
| O75528 | TADA3L | Transcriptional adapter 3-like | | | ✓ | | G | C | |
| O75822 | EIF3S1 | Eukaryotic translation initiation factor 3 subunit 1 | | | ✓ | | Tl | C | C, G |
| O75937 | DNAJC8 | DnaJ homolog subfamily C member 8 | | | ✓ | | Tl | No | C |
| O94979 | SEC31A | Protein transport protein Sec31A (SEC31 like 1) | | | ✓ | | Tp | ER | |
| P14174 | MIF | Macrophage migration inhibitory factor | | | ✓ | | S | Ex | |
| P14859 | POU2F1 | Octamer binding transcription factor 1 (POU domain, class 2, transcription factor 1) | | | ✓ | | S | N | |
| P14868 | DARS | Aspartyl-tRNA synthetase, cytoplasmic | | | ✓ | | M | C | C, No |
| P15822 | HIVEP1 | Zinc finger protein 40 (Major histocompatibility complex binding protein 1) | | | ✓ | | G | N | |
| P26599 | PTBP1 | Polypyrimidine tract-binding protein 1 (hnRNPI) | | | ✓ | | G | N | C |
| P49750 | YLPM1 | YLP motif-containing protein 1 (Nuclear protein ZAP) | | | ✓ | | U | N | M |
| P49792 | RANBP2 | E3 SUMO-protein ligase RanBP2 | | | ✓ | | s | N | No |
| P49916 | LIG3 | DNA ligase 3 | | | ✓ | | G | N | C, No |
| P51532 | SMARCA4 | Probable global transcription activator SNF2L4 | | | ✓ | | G | N | C |
| P52594 | HRB | Nucleoporin-like protein RIP | | | ✓ | | Tp | ER | |
| P53992 | SEC24C | Protein transport protein Sec24C | | | ✓ | | G | N | C |
| P54198 | HIRA | Protein HIRA | | | ✓ | | s | N | No |
| P54259 | ATN1 | Atrophin-1 | | | ✓ | | s | C | ER, G |
| P61964 | WDR5 | WD repeat protein 5 | | | ✓ | | s | C | R |
| P61981 | YWHAG | 14-3-3 protein gamma | | | ✓ | | Tl | M | |
| P82914 | MRPS15 | 28 S ribosomal protein S15, mitochondrial precursor | | | ✓ | | Tl | No | |
| Q02878 | RPL6 | 60 S ribosomal protein L6 | | | ✓ | | G | N | C |
| Q03164 | MLL | Zinc finger protein HRX (MLL, Histone-lysine N-methyltransferase HRX) | | | ✓ | | G | N | No |
| Q12830 | BPTF | Nucleosome-remodeling factor subunit (Fetal Alzheimer antigen) | | | ✓ | | G | C | C, N, PM |
| Q13185 | CBX3 | Chromobox protein homolog 3 (Modifier 2 protein) | | | ✓ | | s | N | No |
| Q13283 | G3BP1 | Ras GTPase-activating protein-binding protein 1 | | | ✓ | | G | C | C |
| Q13547 | HDAC1 | Histone deacetylase 1 | | | ✓ | | Tl | C | M |
| Q14119 | VVEZF1 | Vascular endothelial zinc finger 1 | | | ✓ | | s | N | |
| Q14978 | NOLC1 | Nucleolar phosphoprotein p130 | | | ✓ | | U | N | |
| Q15046 | KARS | Lysyl-tRNA synthetase | | | ✓ | | G | N | |
| Q32M68 | LIN54 | Protein lin54-homolog | | | | | | | |
| Q504R3 | — | Putative uncharacterized protein | | | | | | | |
| Q58EY4 | SMARCC1 | SWI/SNF related, matrix associated, actin dependent regulator of chromatin, subfamily c, member 1 | | | | | | | |
| Q59FT6 | — | C5ODA006YC23 variant | | | ✓ | | U | U | |

TABLE 10-continued

List of enriched novel O-GlcNAc proteins.

| SwissProt Number | Gene Name | Protein Name | 18B10.C7(3) | 9D1.E4(10) | 1F5.D6(14) | CTD110.6 | Biological Process | Primary localization | Alternate localization |
|---|---|---|---|---|---|---|---|---|---|
| Q59GV3 | — | SWI/SNF related, matrix associated actin dependent regulator of chromatin, c2 isoform b variant | | ✓ | | | G | N | |
| Q5H9F2 | BCORL1 | BCL6 co-repressor-like 1 | | | ✓ | | G | N | |
| Q5JRC2 | WNK3 | WNK lysine deficient protein kinase 3 | | | ✓ | | S | C | |
| Q5RKT7 | RPS27A | Ribosomal protain S27a | | | ✓ | | Tl | R | |
| Q5T0K1 | TAF8 | Transcription initiation factor TFIID subunit 8 | | | ✓ | | G | N | |
| Q5T8P6 | RBM26 | RNA-binding protein 26 (Cutaneous T cell lymphoma tumor anitgen se70-2) | | | ✓ | | G | N | C |
| Q5TBM7 | HSPH1 | Heat shock 105 kDa/110 kDa protein 1 | | | ✓ | | Tl | C | |
| Q5VU77 | UBAP2L | Ubiquitan associated protein 2-like [Fragment] | | | ✓ | | U | U | |
| Q69YQ9 | CMYA5 | Cardiomyopathy-associated protein 5 | | | ✓ | | U | C | |
| Q6UVJ0 | SASS6 | Spindle assembly abnormal protein 6 homolog (DKFZp761A078) | | | ✓ | | U | C | |
| Q6ZU65 | KIAA2030 | Uncharacterized protein KIAA2030 | | | ✓ | | U | U | |
| Q7Z5Z3 | PIXIL3 | Piwi-like protein 3 | | | ✓ | | U | U | |
| Q7Z417 | NUFIP2 | Nuclear fragile X mental retardation-interacting protein 2 | | | ✓ | | G | N | C |
| Q7Z739 | YTHDF3 | YTH domain family protein 3 | | | ✓ | | U | C | |
| Q8IVW4 | CDKL3 | Cyclin-dependent kinase-like 3 | | | ✓ | | S | C | |
| Q8IWZ2 | hCG 204590: | Multiple ankyrin repeats single KH domain protein isoform 2 | | | ✓ | | U | U | |
| Q8N6V5 | NUP50 | Nucleoporin 50 kDa (Variant1) | | | ✓ | | Tp | N | |
| Q8NDX5 | PHC3 | Polyhomeotic-like protein 3 | | | ✓ | | U | N | |
| Q8TB57 | RAD54L2 | Helicase ARIP4 (RAD54-like 2) | | | ✓ | | G | U | |
| Q96QT6 | PHF12 | PHD finger protein 12 | | | ✓ | | G | U | |
| Q96RK0 | CIC | Protein capicua homolog | | | ✓ | | G | N | |
| Q96T37 | RBM15 | Putative RNA-binding protein 15 | | | ✓ | | G | N | |
| Q99496 | RNF2 | E3 ubiquitin-protein ligase RING2 | | | ✓ | | G | U | |
| Q99700 | ATXN2 | Ataxin-2 | | | ✓ | | Tl | U | |
| Q9BQG0 | MYBBP1A | Myb-binding protein 1A (P160) | | | ✓ | | G | C | |
| Q9BTC0 | DIDO1 | Death-inducer obliterator 1 (Death associated transcription factor 1) | | | | ✓ | G | No | |
| Q9C005 | OPY:30 | Protein dpy-30 hoMolog | | | | ✓ | S | N | C |
| Q9GZR7 | DDX24 | ATP-dependent RNA helicase DDX24 | | | | ✓ | G | N | No |
| Q9HB23 | — | Lysyl-tRNA synthetase | | | | ✓ | Tp | N | |
| Q9NYV4 | CRKRS | Cell division cycle 2-related protein kinase 7 | | | | ✓ | Tl | C | C |
| Q9P2N6 | KIAA1310 | Uncharacterized protein KIAA1310; Hypothetical protein FLJ10081 | | | | ✓ | s | N | |
| Q9UBL3 | ASH2L | Set1/Ash2 histone methyltransferase complex subunit ASH2 | | | | ✓ | G | N | |
| Q9UKX7 | NUP50 | Nucleoporin 50 kDa | | | | ✓ | Tp | N | |
| Q9ULM3 | YEATS2 | YEATS domain-containing protein 2 | | | | ✓ | U | U | |
| Q9UQC1 | HSP70-1 | Heat chock protein 72 | | | | | Tl | U | |
| Q9Y2N3 | POM121 | Nuclear envelope pore membrane protein POM 121 | | | | | Tp | N | ER |
| Q9Y3S1 | WNK2 | Serine/threonine-protein kinase WNK2 (Protein kinase, lysine deficient 2) | | | | | M | U | C |
| Q9Y5G6 | PCDHGA7 | Protocadherin gamma A7 precursor | | | | | s | PM | |
| A2RUN2 | AR | Androgen receptor | | | | | s | N | |
| O00193 | C11orf58 | Small acidic protein | | | | | U | U | |
| O95757 | HSPA4L | Heat shock 70 kDa protein 4L | | | | | Tl | C | No |
| P09234 | SNRPC | U1 small nuclear ribonucleoprotein C | | | | | G | C | N, No |
| P42677 | RPS27 | 40 S ribosomal protein S27 | | | | | s | No | |
| P46013 | MKi67 | Antigen KI-67 | | | | | G | N | |
| P46776 | RPL27A | 60 S ribosomal protein L27a | | | | | Tl | R | No |
| P46976 | GYG1 | Glycogenin-1 | | | | | M | U | |

TABLE 10-continued

List of enriched novel O-GlcNAc proteins.

| SwissProt Number | Gene Name | Protein Name | 18B10.C7(3) | 9D1.E4(10) | 1F5.D6(14) | CTD110.6 | Biological Process | Primary localization | Alternate localization |
|---|---|---|---|---|---|---|---|---|---|
| P61353 | RPL27A | 60 S ribosomal protein L27 | | | | ✓ | Tl | C | No |
| P62316 | SNRPD2 | Small nuclear ribonucleoprotein Sm D2 | | | | ✓ | G | N | |
| P62318 | SNRPD3 | Small nuclear ribonucleoprotein Sm D3 | | | | ✓ | G | N | No |
| P62753 | RPS6 | 40 S ribosomal protein S6 | | | | ✓ | Tl | R | No |
| P84098 | RPL19 | 60 S ribosomal protein L19 | | | | ✓ | Tl | R | |
| Q13765 | NASA | Nascent polypeptide-associated complex subunit alpha | | | | ✓ | S | N | C, R |
| Q14247 | CTTN | Src substrate cortactin | | | | ✓ | C | C | PM |
| Q15637 | SF1 | Splicing factor 1 | | | | ✓ | G | N | |
| Q5JRC6 | PHF6 | PHD finger protein 6 | | | | ✓ | G | No | N |
| Q5SW79 | CEP170 | Centrosomal protein of 170 kDa | | | | ✓ | S | N | C |
| Q5T2J2 | C20orf117 | Novel protein C20orf117 | | | | ✓ | U | U | |
| Q5THK1 | C22orf30 | Uncharacterized protein C22orf30 | | | | ✓ | U | U | |
| Q6ZQN2 | — | CDNA FLJ46846 fis, clone UTERU3004635, moderately similar to Neuroblast differentiation associated protein AHNAK. | | | | | U | U | |
| Q7Z6E9 | RBBP6 | Retinoblastoma-binding protein 6 | | | | ✓ | Tl | U | |
| Q8WUR7 | C15orf40 | UPF0235 protein C15orf40 | | | | ✓ | U | U | |
| Q96MX3 | ZNF553 | Zinc finger protein 553 | | | | ✓ | G | U | |
| Q9UNX3 | RPL26L1 | 60 S ribosomal protein L26-like 1 | | | | | U | R | No |

*Abbreviations: G, Gene expression/Transcription; M, Metabolism; S, Signal transduction: Tl, Translation; Tp, Transport U, Unknown, C, Cytoplasm; N, Nucleus; No, Nucleolus; ER, Endoplasmic reticulum; G, Golgi apparatus; Ex, Extracellular.

The extensive list of O-GlcNAc modified proteins made it possible to assign biological functions using HPRD (FIG. 22b). A large number of identified proteins are involved in transcriptional/translational regulation and signal transduction (Tables 9-11), which is consistent with recent reports that functionally implicates O-GlcNAc modification on insulin signaling and transcriptional control (Vosseller et al., 2002 Proc. Natl. Acad. Sci. U.S.A. 99, 5313-5318; Dentin et al., 2008 Science 319, 1402-1405; Housley et al., 2008 J. Biol. Chem. 283, 16283-16292). Of particular interest is that several of the glycoproteins are involved in the ubiquitin pathway. A role for O-GlcNAc has already been established for regulation of the proteasome (Zhang et al., 2003 Cell 115, 715-725) but our data indicate that O-GlcNAc may also be actively involved in earlier steps of the degradation cascade. SEC23 components and interacting proteins were also captured by multiple antibodies suggesting a possible role for O-GlcNAc modification in anterograde trafficking of intracellular vesicles. Finally, several ribosomal proteins were observed, which is in agreement with the recent finding that O-GlcNAc modification of ribosomal proteins plays a role in stress granule and processing body assembly (Ohn et al., 2008 Nat. Cell Biol. 10, 1224-1231).

Several interesting examples of newly identified O-GlcNAc proteins were identified by only one of the antibodies and included proteins participating in other types of posttranslational modifications such as WNK2 and WNK3 for phosphorylation and RanBP2 and SUMO4 for SUMOylation. Also, a range of proteins that modulate gene expression at the chromatin levels such as SMARCC1 and CARM1 were identified. This indicates that the different MAbs recognize subtly different sequential and/or structural epitopes that all include an O-GlcNAc modified residue.

In conclusion, the three-component immunogen methodology has been successfully employed to generate a panel of pan-GlcNAc specific MAbs, which offer powerful new tools for exploring the biological implications of this type of protein glycosylation. The newly identified O-GlcNAc modified proteins open new avenues to explore the importance of this type of posttranslational for a variety of biological processes. It is to be expected that the three-component immunization technology will find wide application for the generation of MAbs for other forms of protein glycosylation.

TABLE 11

Proteins enriched by more than one of the antibodies

| SwissProt Number | Gene Name | Protein Name | Mab 3 | Mab 10 | Mab 14 | CTD 110.6 | Biological Process | Primary localization | Alternate localization |
|---|---|---|---|---|---|---|---|---|---|
| Q9Y520 | BAT2D1 | BAT2-iso (BAT2 domain-containing protein 1; HBxAg transactivated protein 2) | ✓ | ✓ | ✓ | ✓ | U | C | |
| Q06587 | RING1 | E3 ubiquitin-protein ligase RING1 | ✓ | ✓ | ✓ | ✓ | G | N | No |
| P49790 | NUP153 | Nuclear pore complex protein Nup153 | ✓ | ✓ | ✓ | ✓ | Tp | N | |
| P35658 | NUP214 | Nuclear pore complex protein Nup214 | ✓ | ✓ | ✓ | ✓ | Tp | N | |
| Q9Y6Y8 | SEC23IP | SEC23-interacting protein | ✓ | ✓ | ✓ | ✓ | Tp | ER | C, N, G |
| Q5T6F2 | UBAP2 | Ubiquitin-associated protein 2 | ✓ | ✓ | ✓ | ✓ | U | U | |
| Q13151 | HNRPA0 | Heterogeneous nuclear ribonucleoprotein A0 | ✓ | ✓ | ✓ | | G | N | No |
| Q9GZZ1 | NAT13 | N-acetyltransferase 13 (Mak3) | ✓ | ✓ | ✓ | | U | C | |
| P16401 | HIST1H1B | Histone H1.5 | | ✓ | ✓ | ✓ | G | N | No |
| P78406 | RAE1 | mRNA export factor (MRNP41) | | ✓ | ✓ | ✓ | G | N | C |
| P52948 | NUP98 | Nuclear pore complex protein Nup98-Nup96 precursor [Contains: Nuclear pore complex protein Nup98 | | ✓ | ✓ | ✓ | Tp | N | C |
| Q9P2N5 | RBM27 | RNA-binding protein 27 | | ✓ | ✓ | ✓ | U | C | N |
| Q05BK6 | TFG | TFG protein (TRK-fused gene protein) | | ✓ | ✓ | ✓ | S | C | |
| Q14011 | CIRBP | Cold-inducible RNA-binding protein | ✓ | ✓ | | ✓ | S | N | |
| P26373 | RPL13 | 60 S ribosomal protein L13 | ✓ | | ✓ | ✓ | Tl | R | No |
| O75821 | EIF3S4 | Eukaryotic translation initiation factor 3 subunit 4 | ✓ | | ✓ | ✓ | Tl | C | |
| Q2KHR3 | QSER1 | Glutamine and serine-rich protein 1 (FLJ21924) | ✓ | | ✓ | ✓ | U | U | |
| P16402 | HIST1H1D | Histone H1.3 | ✓ | | ✓ | ✓ | G | N | |
| Q52LJ0 | FAM98B | Protein FAM98B | ✓ | | ✓ | ✓ | U | U | |
| Q8NC51 | SERBP1 | Plasminogen activator inhibitor 1 RNA-binding protein (SERPINE1 mRNA binding protein 1) | ✓ | | ✓ | ✓ | G | C | N |
| Q5JRG1 | NUPL1 | Nucleoporin like 1 | | ✓ | ✓ | ✓ | U | U | N |
| Q8IX12 | CCAR1 | Cell division cycle and apoptosis regulator protein 1 | | ✓ | ✓ | | S | C | |
| Q86X55 | CARM1 | Histone-arginine methyltransferase CARM1 (Coactivator associated arginine methyltransferase 1) | | ✓ | ✓ | | M | N | |
| AIL431 | PPIAL4 | Peptidyl-prolyl cis-trans isomerase A-like 4 (Cyclophilin LC | | ✓ | ✓ | | U | C | |
| P55735 | SEC13 | Protein SEC13 homolog | | | ✓ | ✓ | Tp | ER | N, C |
| Q92522 | H1FX | Histone H1x | ✓ | | ✓ | | G | N | No |
| Q8IYH5 | ZZZ3 | Zinc finger ZZ-type-containing protein 3 | ✓ | | ✓ | | G | N | |
| P32969 | RPL9 | 60 S ribosomal protein L9 | ✓ | ✓ | | | Tl | R | No |
| P07737 | PFN1 | Profilin-1 | ✓ | ✓ | | | S | C | Ex |
| Q9Y3F4 | STRAP | Serine-threonine kinase receptor-associated protein | ✓ | ✓ | | | S | C | |

Abbreviations: G, Gene Expression/Transcription; M, Metabolism; S, Signal transduction; Tl, Translation; Tp, Transport; U, Unknown; C, Cytoplasm; N, Nucleus; No, Nucleolus; ER, Endoplasmic reticulum; G, Golgi apparatus; Ex, Extracellular.

Methods

Reagents and General Procedures for Synthesis.

Fmoc-L-Amino acid derivatives and resins were purchased from NovaBioChem and Applied Biosystems, peptide synthesis grade N, N-dimethylformamide (DMF) from EM Science and N-methylpyrrolidone (NMP) from Applied Biosystems. Egg phosphatidylcholine (PC), egg phosphatidylglycerol (PG), cholesterol, monophosphoryl lipid A (MPL-A) and dodecyl phosphocholine (DPC) were obtained from Avanti Polar Lipids. All other chemical reagents were purchased from Aldrich, Acros, Alfa Aesar and Fischer and used without further purification. All solvents employed were reagent grade. Reversed phase high performance liquid chromatography (RP-HPLC) was performed on an Agilent 1100 series system equipped with an auto-injector, fraction-collector and UV-detector (detecting at 214 nm) using an Agilent ZorbaxEclipse™ C8 analytical column (5 μm, 4.6×150 mm) at a flow rate of 1 ml min$^{-1}$' Agilent Zorbax Eclipse™ C8 semi preparative column (5 μm, 10×250 mm) at a flow rate of 3 ml min$^{-1}$ or Phenomenex Jupiter™ C4 semi preparative column (5 μm, 10×250 mm) at a flow rate of 2 ml min$^{-1}$. All runs were performed using a linear gradients of 0 to 100% solvent B over 40 min. (solvent A=5% acetonitrile, 0.1% trifluoroacetic acid (TFA) in water, solvent B=5% water, 0.1% TFA in acetonitrile). Matrix assisted laser desorption ionization time of flight mass spectrometry (MALDI-ToF) mass spectra were recorded on an ABI 4700 proteomic analyzer.

General Methods for Solid-Phase Peptide Synthesis (SPPS).

Peptides were synthesized by established protocols on an ABI 433A peptide synthesizer (Applied Biosystems) equipped with UV-detector using N$^{\alpha}$-Fmoc-protected amino acids and 2-(1H-bezotriazole-1-yl)-oxy-1,1,3,3-tetraethyl hexafluorophosphate (HBTU)/1-hydroxybenzotriazole (HOBt; Knorr et al., 1989 Tetrahedron Lett. 30, 1927-1930) as the activating reagents. Single coupling steps were performed with conditional capping. The following protected amino acids were used: N$^{o}$-Fmoc-Arg(Pbf)-OH, N$^{\alpha}$-Fmoc-Asp(O$^t$Bu)-OH, N$^{\alpha}$-Fmoc-Asp-Thr($\Psi^{Me,Me}$pro)-OH, N$^{\alpha}$-Fmoc-Ile-Thr($\Psi^{Me,Me}$pro)-OH, N$^{\alpha}$-Fmoc-Lys(Boc)-OH, N$^{\alpha}$-Fmoc-Ser($^t$Bu)-OH, N$^{\alpha}$-Fmoc-Thr($^t$Bu)-OH, N$^{\alpha}$-Fmoc-Tyr($^t$Bu)-OH. The coupling of the glycosylated amino acid N$^{\alpha}$-FmocSer-(AcO3-α-D-O-GlcNAc)OH, N$^{\alpha}$-FmocSer-(AcO3-α-D-S-GlcNAc)OH, was carried out manually using O-7-azabenzotriazol-1-yl)-N,N,N',N'-tetramethyl-uronium hexafluorophosphate (HATU)/1-hydroxy-7-azabenzotriazole (HOAt) as a coupling agent. The coupling of N$^{\alpha}$-Fmoc-S-(2,3-bis(palmitoyloxy)-(2R-propyl)-(R)-cysteine (Metzger et al., 1991 Int. J. Pept. Protein Res. 38, 545-554; Roth et al., 2004 Bioconjugate Chem. 15, 541-553) which was prepared from (R)-glycidol were carried out using benzotriazole-1-yl-oxy-tris-pyrrolidino-phosphonium hexafluorophosphate (PyBOP)/HOBt as coupling agent. Progress of the manual couplings was monitored by standard Kaiser test (Kaiser et al., 1970 Anal. Biochem. 34, 595).

Synthesis of Lipopeptide 63.

The synthesis of 63 was carried out on a H-Gly-sulfamylbutyryl Novasyn TG resin as described in the general method section for peptide synthesis. After coupling of the first five amino acids, the remaining steps were performed manually. N-α-Fmoc-S-(2,3-bis(palmitoyloxy)-(2R-propyl)-(R)-cysteine (267 mg, 0.3 mmol) was dissolved in DMF (5 ml) and PyBOP (156.12 mg, 0.3 mmol), HOBt (40 mg, 0.3 mmol) and DIPEA (67 μl, 0.4 mmol) were premixed for 2 min, and was added to the resin. The coupling reaction was monitored by the Kaiser test and was complete after standing for 12 h. Upon completion of the coupling, the N-Fmoc group of was cleaved using 20% piperidine in DMF (6 ml) and palmitic acid (77 mg, 0.3 mmol) was coupled to the free amine of as described above using PyBOP (156.12 mg, 0.3 mmol), HOBt (40 mg, 0.3 mmol) and DIPEA (67 μl, 0.4 mmol) in DMF. The resin was thoroughly washed with DMF (10 ml), DCM (10 ml) and MeOH (10 ml) and then dried in vacuo. The resin was swelled in DCM (5 ml) for 1 h and treated with DIPEA (0.5 ml, 3 mmol), iodoacetonitrile (0.36 ml, 5 mmol) in NMP (6 ml). It is important to note that the iodoacetonitrile was filtered through a plug of basic alumina before addition to the resin. The resin was agitated under the exclusion of light for 24 h, filtered and washed with NMP (5 ml×4), DCM (5 ml×4) and THF (5 ml×4). The activated N-acyl sulfonamide resin was swollen in DCM (5 ml) for 1 h, drained and transferred to a 50 ml round bottom flask. To the resin-containing flask was added THF (4 ml), benzyl mercaptan (0.64 ml, 5 mmol) and sodium thiophenate (27 mg, 0.2 mmol). After agitation for 24 h, the resin was filtered and washed with hexane (5 ml×2). The combined filtrate and washings were collected and concentrated in vacuo to approximately ⅓ of its original volume. The crude product was then precipitated by the addition of tert-butyl methyl ether (0° C.; 60 ml) and recovered by centrifugation at 3000 rpm for 15 min, and after the decanting of the ether the peptide precipitate was dissolved in mixture DCM and MeOH (1.5 ml/1.5 ml). The thiol impurity present in the peptide precipitate was removed by passing it through a LH-20 size exclusion column. The fractions containing product were collected and solvents removed to give the fully protected peptide thioester. The protected peptide was treated with a reagent B (TFA 88%, phenol 5%, H$_2$O 5%, TIS 2%; 5 ml) for 4 h at room temperature. The TFA solution was then added dropwise to a screw cap centrifuge tube containing ice cold tert-butyl methyl ether (40 ml) and the resulting suspension was left overnight at 4° C., after which the precipitate was collected by centrifugation at 3000 rpm (20 min), and after the decanting of the ether the peptide precipitate was re-suspended in ice cold tert-butyl methyl ether (40 ml) and the process of washing was repeated twice. The crude peptide was purified by HPLC on a semi preparative C-4 reversed phase column using a linear gradient of 0 to 100% solvent B in A over a 40 min, and the appropriate fractions were lyophilized to afford 63 (110 mg, 65%). C$_{90}$H$_{165}$N$_{11}$O$_{13}$S$_2$, MALDI-ToF MS: observed, [M+Na] 1695.2335 Da; calculated, [M+Na] 1695.4714 Da (FIG. 25).

Synthesis of Glycopeptide 64.

SPPS was performed on Rink amide resin (0.1 mmol) as described in the general procedures. The first four amino acids, Ser-Ala-Asn-Met, were coupled on the peptide synthesizer using a standard protocol. After the completion of the synthesis, a manual coupling was carried out using Nα-FmocSer-(AcO$_3$-α-D-O-GlcNAc)OH (0.2 mmol, 131 mg), with O-(7-azabenzotriazol-1-yl)-N,N,N',N'-tetramethyl-uronium hexafluorophosphate (HATU; 0.2 mmol, 76 mg), 1-hydroxy-7-azabenzotriazole (HOAt; 0.2 mmol, 27 mg) and diisopropylethylamine (DIPEA; 0.4 mmol, 70 μl) in NMP (5 ml) for 12 h. The coupling reaction was monitored by standard Kaiser test. The resin was then washed with NMP (6 ml) and methylene chloride (DCM; 6 ml), and resubjected to the same coupling conditions to ensure completion of the coupling. The glycopeptide was then elongated on the peptide synthesizer after which the resin was thoroughly washed with NMP (6 ml), DCM (6 ml) and MeOH (6 ml) and dried in vacuo. The resin was swelled in DCM (5 ml) for 1 h and then treated with hydrazine (60%) in MeOH (10 ml) for 2 h and washed thoroughly with NMP (5 ml×2), DCM (5 ml×2) and MeOH (5 ml×2) and dried in vacuo. The resin was swelled in DCM (5 ml) for 1 h, after which it was treated with reagent K (TFA (81.5%), phenol (5%), thioanisole (5%), water (5%), EDT (2.5%), TIS (1%)) (30 ml) for 2 h at room temperature. The resin was filtered and washed with neat TFA (2 ml). The filtrate was then concentrated in vacuo to approximately ⅓ of its original volume. The peptide was precipitated using diethyl ether (0° C.) (30 ml) and recovered by centrifugation at 3000 rpm for 15 min. The crude peptide was purified by RP-HPLC on a semi preparative C-8 column using a linear gradient of 0 to 100% solvent B in solvent A over a 40 min period and the appropriate fractions were lyophilized to afford 64 (118 mg, 40%). $C_{129}H_{204}N_{32}O_{40}S_2$, MALDI-ToF MS: observed [M+], 2907.5916 Da; calculated [M+], 2905.4354 Da (FIG. 26).

Synthesis of Glycopeptide 65.

SPPS was performed on Rink amide resin (0.1 mmol) as described in the general procedures. The first four amino acids, Ser-Ala-Asn-Met, were coupled on the peptide synthesizer using a standard protocol. After the completion of the synthesis, a manual coupling was carried out using Nα-FmocSer-(AcO₃-α-D-S-GlcNAc)OH (0.2 mmol, 134 mg), with O-(7-azabenzotriazol-1-yl)-N,N,N',N'-tetramethyl-uronium hexafluorophosphate (HATU; 0.2 mmol, 76 mg), 1-hydroxy-7-azabenzotriazole (HOAt; 0.2 mmol, 27 mg) and diisopropylethylamine (DIPEA; 0.4 mmol, 70 μl) in NMP (5 ml) for 12 h. The coupling reaction was monitored by standard Kaiser test. The resin was then washed with NMP (6 ml) and methylene chloride (DCM; 6 ml), and resubjected to the same coupling conditions to ensure complete coupling. The resulting glycopeptide was then elongated on the peptide synthesizer. After the completion of the synthesis, the resin was thoroughly washed with NMP (6 ml), DCM (6 ml) and MeOH (6 ml) and dried in vacuo. The resin was swelled in DCM (5 ml) for 1 h and then treated with hydrazine (60%) in MeOH (10 ml) for 2 h and washed thoroughly with NMP (5 ml×2), DCM (5 ml×2) and MeOH (5 ml×2) and dried in vacuo. The resin was swelled in DCM (5 ml) for 1 h, after which it was treated with TFA (81.5%), phenol (5%), thioanisole (5%), water (5%), EDT (2.5%), TIS (1%) (30 ml) for 2 h at room temperature. The resin was filtered and washed with neat TFA (2 ml). The filtrate was then concentrated in vacuo to approximately ⅓ of its original volume. The peptide was precipitated using diethyl ether (30 ml, 0° C.) and recovered by centrifugation at 3000 rpm for 15 min. The crude peptide was purified by RP-HPLC on a semi preparative C-8 column using a linear gradient of 0 to 100% solvent B in solvent A over a 40 min period and the appropriate fractions were lyophilized to afford 65 (95 mg, 34%). $C_{129}H_{204}N_{32}O_{39}S_3$, MALDI-ToF MS: observed [M+], 2923.6716 Da; calculated [M+], 2923.3861 Da (FIG. 27).

Synthesis of Glycolipopeptide 52.

The lipopeptide thioester 63 (4.3 mg, 2.5 μmol), glycopeptide 64 (5.0 mg, 1.7 μmol) and dodecyl phosphocholine (6.0 mg, 17.0 μmol) were dissolved in a mixture of trifluoroethanol and CHCl₃ (2.5 ml/2.5 ml). The solvents were removed under reduced pressure to give a lipid/peptide film, which was hydrated for 4 h at 37° C. using 200 mM phosphate buffer (pH 7.5, 3 ml) in the presence of tris (carboxyethyl)phosphine (2% w/v, 40.0 μg) and EDTA (0.1% w/v, 20.0 μg). The mixture was ultrasonicated for 1 min. To the vesicle suspension was added sodium 2-mercaptoethane sulfonate (2% w/v, 40.0 μg) to initiate the ligation reaction. The reaction was carried out in an incubator at 37° C. and the progress of the reaction was periodically monitored by MALDI-ToF, which showed disappearance of glycopeptide 64 within 2 h. The reaction was then diluted with 2-mercaptoethanol (20%) in ligation buffer (2 ml) and the crude peptide was purified by semi preparative C-4 reversed phase column using a linear gradient of 0 to 100% solvent B in A over a 40 min, and lyophilization of the appropriate fractions afforded 52 (4.3 mg, 57%). $C_{212}H_{360}N_{43}O_{53}S_3$, MALDI-ToF MS: observed, 4461.9177 Da, calculated, 4455.578 Da (FIG. 23).

Synthesis of Glycolipopeptide 53.

Lipopeptide thioester 63 (2.5 mg, 1.5 μmol), glycopeptide 65 (3.0 mg, 1.0 μmol) and dodecyl phosphocholine (3.5 mg, 10 μmol) were dissolved in a mixture of trifluoroethanol and CHCl₃ (2.5 ml/2.5 ml). The solvents were removed under reduced pressure to give a lipid/peptide film, which hydrated for 4 h at 37° C. using 200 mM phosphate buffer (pH 7.5, 2 ml) in the presence of tris(carboxyethyl)phosphine (2% w/v, 40.0 μg) and EDTA (0.1% w/v, 20.0 μg). The mixture was ultrasonicated for 1 min. To the vesicle suspension was added sodium 2-mercaptoethane sulfonate (2% w/v, 40.0 μg) to initiate the ligation reaction. The reaction was carried out in an incubator at 37° C. and the progress of the reaction was periodically monitored by MALDI-ToF, which showed disappearance of glycopeptide within 2 h. The reaction was then diluted with 2-mercaptoethanol (20%) in ligation buffer (2 ml). The crude peptide was purified by semi preparative C-4 reversed phase column using a linear gradient of 0 to 100% solvent B in A over a 40 min, and lyophilization of the appropriate fractions afforded 53 (2.8 mg, 64%). $C_{212}H_{360}N_{43}O_{52}S_4$, MALDI-ToF MS: observed, 4469.9112 Da, calculated, 4471.6437 Da (FIG. 24).

Compounds 66-70 were prepared as described in the standard procedures section on Rink amide resin (0.1 mmol). Glycopeptide 66 (78 mg, 61%); $C_{48}H_{82}N_{14}O_{21}S_2$, MALDI-ToF MS: observed [M+Na], 1277.4746 Da; calculated [M+Na], 1277.5220 Da (FIG. 29). Peptide 67 (89 mg, 83%); $C_{40}H_{69}N_{13}O_{16}S_2$, MALDI-ToF MS: observed [M+Na], 1074.4789 Da; calculated [M+Na], 1074.4427 Da (FIG. 30). Glycopeptide 68 (57 mg, 48%); $C_{45}H_{77}N_{13}O_{20}S$, MALDI-ToF MS: observed [M+Na], 1174.4740 Da; calculated [M+Na], 1174.5129 Da (FIG. 31). Peptide 69 (76 mg, 78%). $C_{37}H_{64}N_{12}O_{15}S$, MALDI-ToF MS: observed [M+Na], 969.8162 Da; calculated [M+Na], 970.8657 Da (FIG. 32). Glycosylated amino acid 70 (12 mg, 33%), $C_{14}H_{25}N_3O_8$, MALDI-ToF MS: observed [M+Na], 386.2749 Da; calculated [M+Na] 386.3636 Da (FIG. 32).

General Procedure for the Conjugation to BSA-MI.

The conjugations were performed as instructed by Pierce Endogen Inc. In short, the purified (glyco)peptide 66 or 67 (2.5 equiv. excess to available MI-groups on BSA) was dissolved in the conjugation buffer (sodium phosphate, pH 7.2 containing EDTA and sodium azide; 100 μl) and added to a solution of maleimide activated BSA (2.4 mg) in the conjugation buffer (200 μl). The mixture was incubated at room temperature for 2 h and then purified by a D-Salt™ dextran de-salting column (Pierce Endogen, Inc.), equilibrated and eluted with sodium phosphate buffer, pH 7.4 containing 0.15 M sodium chloride. Fractions containing the conjugate were identified using the BCA protein assay. Carbohydrate content was determined by quantitative monosaccharide analysis by HPAEC/PAD. General Procedure for the Preparation of Liposomes.

Egg PC, egg PG, cholesterol, MPL-A and compound 52 or 53 (15 μmol, molar ratios 60:25:50:5:10) were dissolved in a mixture of trifluoroethanol and MeOH (1:1, v/v, 5 ml). The solvents were removed in vacuo to produce a thin lipid film, which was hydrated by suspending in HEPES buffer (10 mM, pH 6.5) containing NaCl (145 mM; 1 ml) under argon atmosphere at 41° C. for 3 h. The vesicle suspension was sonicated for 1 min and then extruded successively through 1.0, 0.6, 0.4, 0.2 and 0.1 μm polycarbonate membranes (Whatman, Nucleopore Track-Etch Membrane) at 50° C. to obtain SUVs. The sugar content of liposomes was determined by heating a mixture of SUVs (50 μl) and aqueous TFA (2 M, 200 μl) in a sealed tube for 4 h at 100° C. The solution was then concentrated in vacuo and analyzed by high-pH anion exchange chromatography using a pulsed amperometric detector (HPAEC-PAD; Methrome) and CarboPac columns PA-10 and PA-20 (Dionex).

Dose and Immunization Schedule.

Groups of five mice (female BALB/c, age 8-10 weeks, from Jackson Laboratories) were immunized four times at two-week intervals. Each boost included 3 μg of saccharide in the liposome formulation. Serum samples were obtained before immunization (pre-bleed) and 1 week after the final immunization. The final bleeding was done by cardiac bleed.

Hybridoma Culture and Antibody Production.

Spleens of two mice immunized with 52 were harvested and standard hybridoma culture technology gave 30 IgG producing hybridoma cell lines. Three hybridomas (18B10.C7(3), 9D1.E4(10), 1F5.D6(14)) were cultured at a one-liter scale and the resulting antibodies were purified by saturated ammonium sulfate precipitation followed by Protein G column chromatography to yield, in each case, approximately 10 mg of IgG.

Reagents for Biological Experiments.

Protease inhibitor cocktail was obtained from Roche (Indianapolis, Ind.). PUGNAc O-(2-acetamido-2-deoxy-D-glucopyranosylidene)amino N-phenyl carbamate was ordered from Toronto Research Chemicals, Inc (Ontario, Canada). Mouse IgM anti-O-GlcNAc (CTD110.6; corner et al., 2001 Anal. Biochem. 293, 169-177) and rabbit polyclonal anti-OGT (AL28) antibodies were previously generated in Dr. Gerald W. Hart's laboratory (Johns Hopkins University School of Medicine, Baltimore, Md.). Rabbit polyclonal anti-OGA antibody was a kind gift from Dr. Sidney W. Whiteheart (University of Kentucky College of Medicine). Rabbit polyclonal anti-CKII alpha antibodies (NB100-377 for immunoblotting and NB100-378 for immunoprecipitation) were purchased from Novus Biologicals (Littleton, Colo.). Mouse monoclonal antibody against α-tubulin and anti-Mouse IgM (u chain)-agarose was obtained from Sigma (St. Louis, Mo.). Normal rabbit IgG agarose, normal rabbit IgG agarose and Protein A/G PLUS agarose were ordered from Santa Cruz Biotechnology, Inc. (Santa Cruz, Calif.).

Serologic Assays.

Anti-GSTPVS(β-O-GlcNAc)SANM (68) IgG, IgG1, IgG2a, IgG2b, IgG3 and IgM antibody titers were determined by enzyme-linked immunosorbent assay (ELISA), as described previously (Buskas and Boons, 2004 Chem. Eur. J. 10, 3517-3524; Ingale et al., 2007 Nat. Chem. Biol. 3, 663-66). Briefly, Immulon II-HB flat bottom 96-well microtiter plates (Thermo Electron Corp.) were coated overnight at 4° C. with 100 μl per well of a conjugate of the glycopeptide conjugated to BSA through a maleimide linker (BSA-MI-GSTPVS(β-O-GlcNAc) SANM; BSA-MI-66) at a concentration of 2.5 μg ml-1 in coating buffer (0.2 M borate buffer, pH 8.5 containing 75 mM sodium chloride). Serial dilutions of the sera or MAb containing cell supernatants were allowed to bind to immobilized GSTPVS(β-O-GlcNAc)SANM for 2 h at room temperature. Detection was accomplished by the addition of alkaline phosphatase-conjugated anti-mouse IgG (Jackson ImmunoResearch Laboratories Inc.), IgG1 (Zymed), IgG2a (Zymed), IgG2b (Zymed), IgG3 (BD Biosciences Pharmingen) or IgM (Jacksons ImmunoResearch Laboratories) antibodies. After addition of p-nitrophenyl phosphate (Sigma), the absorbance was measured at 405 nm with wavelength correction set at 490 nm using a microplate reader (BMG Labtech). The antibody titer was defined as the highest dilution yielding an optical density of 0.1 or greater over that of background.

To explore competitive inhibition of the binding of MAbs to GSTPVS(β-O-GlcNAc)SANM (68) by the corresponding glycopeptide, peptide and sugar, MAbs were diluted in diluent buffer in such a way that, without inhibitor, expected final OD values were approximately 1. For each well 60 μl of the diluted MAbs were mixed in an uncoated microtiter plate with 60 μl diluent buffer, glycopeptide 68 (GSTPVS (β-O-GlcNAc)SANM), peptide 69 (GSTPVSSANM; SEQ ID NO: 11) or sugar 70 (β-O-GlcNAc-Ser) in diluent buffer with a final concentration of 0-500 μM. After incubation at room temperature for 30 min, 100 μl of the mixtures were transferred to a plate coated with BSA-MICGSTPVS(β-O-GlcNAc)SANM (BSA-MI-66). The microtiter plates were incubated and developed as described above using the appropriate alkaline phosphatase-conjugated detection antibody.

Plasmids Construction.

The human OGT and OGA cDNA were PCR amplified in a two-step manner to introduce an attB1 site and a HA epitope at the 5' end as well as an attB2 site at the 3' end to facilitate Gateway cloning strategy (Invitrogen, Carlsbad, Calif.). The primers include (1) Sense primer for first PCR to incorporate HA epitope into ogt after the start codon: 5'-CCCCATGTATCCATATGACGTCCCAGACTATGC-CGCGTCTTCCGTGGGCAACGT-3' (SEQ ID NO: 14); (2) Sense primer containing an attB1 site for using HA-ogt PCR product as the template: 5'-GGGGACAAGTTTGTA-CAAAAAAGCAGGCTGGATGATGTATCCATAT-GACGTCCCAG ACTATGCCGCGTCTTCCG-3' (SEQ ID NO: 15); (3) Antisense primer with 3' attB2 site for both ogt PCR: 5'-GGGGACCACTTTGTACAAGAAAGCTGGGT-TCTATGCTGACTCAGTGACTTCAACGGG CTTAAT-CATGTGG-3' (SEQ ID NO: 16); (4) Sense primer for first PCR to incorporate HA epitope into oga after the start codon: 5'-CCCCATGTATCCATATGACGTCCCAGAC-TATGCCGTGCAGAAGGA GAGTCAAGC-3' (SEQ ID NO: 17); (5) Sense primer containing an attB1 site for using HA-oga PCR product as the template: 5'-GGGGA-CAAGTTTGTACAAAAAAGCAGGCTGGATGATG-TATCCATATG ACGTCCCAGACTATGCCGTGCA-GAAGG-3' (SEQ ID NO: 18); (6) Antisense primer with 3' attB2 site for both oga PCR: 5'-GGGGACCACTTTGTA-CAAGAAAGCTGGGTTCACAGGCTCCGACCAA GTAT-3' (SEQ ID NO: 19). The purified DNA fragments were then subjected to Gateway cloning according to manufacturer's instruction yielding final expression constructs, pDEST26/HA-OGT and pDEST26/HA-OGA.

Cell Culture, Transfection and Treatment.

HEK 293T cells were obtained from ATCC (Manassas, Va.) and maintained in Dulbecco's modified Eagle's medium (4.5 g 1-1 glucose, Cellgro/Mediatech, Inc., Herndon, Va.) supplemented with 10% fetal bovine serum (GIBCO/Invitrogen, Carlsbad, Calif.) in 37° C. incubator humidified with 5% $CO_2$. Transfection was performed with 8 μg of DNA and Lipofectamine 2000 reagent (Invitrogen Carlsbad, Calif.) per 10 cm plate of cells according to manufacturer's instruction. Mock transfection was performed in the absence of DNA. Cells were harvested 48 h post-transfection. For immunoprecipitation experiments, cells were washed of the plates with ice-cold PBS and store as a pellet at −80° C. until used. For immunoblotting experiments, cells were washed twice with ice-cold PBS and scraped in lysis buffer (10 mM Tris-HCl, pH 7.5, 150 mM NaCl, 1% Igepal CA-630, 0.1% SDS, 4 mM EDTA, 1 mM DTT, 0.1 mM PUGNAc, Protease inhibitor cocktail) and the lysates were clarified in a microfuge with 16,000 g, for 25 min at 4° C. The protein concentration was quantified with Bradford protein assay with standard procedure (Bio-Rad, Hercules, Calif.) and boiled in sample buffer for 5 min. For mass spectrometry experiment, 2×15 cm plates of 293T cells were treated with 50 μM of PUGNAc for 24 h, cells were pellet and stored as above.

Immunoprecipitation and Western blotting. To prepare the nucleocytosolic fraction for CKII immunoprecipitation, HEK293T cell pellets with mock or OGT transfection were resuspended in 4 volumes of hypotonic buffer (5 mM Tris-HCl, pH 7.5, Protease inhibitor cocktail) and transferred into a 2 ml homogenizer. After incubating on ice for 10 min, the cell suspension was subjected to dounce homogenization followed by another 5 min incubation on ice. One volume of hypertonic buffer (0.1 M Tris-HCl, pH 7.5, 2 M NaCl, 5 mM EDTA, 5 mM DTT, Protease inhibitor cocktail) was then added to the lysate. The lysate was incubated on ice for 5 min followed by another round of dounce homogenization. The resulting lysates were transferred to microfuge tubes containing PUGNAc (final concentration 10 μM) and centrifuged at 18,000 g for 25 min at 4° C. Protein concentration was determined using Bradford protein assay (Bio-Rad, Hercules, Calif.). Prior to IP, the lysates were supplemented with 1% Igepal CA-630 and 0.1% SDS, and precleared with a mixture of normal rabbit or mouse IgG AC and protein A/G PLUS agarose at 4° C. for 30 min. Following clarification, the precleared supernatant was incubated at 4° C. in the presence of antibodies of interested for 4 at 4° C. After adding protein A/G PLUS agarose, the samples were incubated for another 2 h at 4° C. and extensively washed with IP wash buffer (10 mM Tris-HCl, pH 7.5, 150 mM NaCl, 1% Igepal CA-630, 0.1% SDS). Finally, SDSPAGE sample buffer was added into the IP complex and boiled for 3 min. Supernatant was resolved by a 10% or 4-15% Tris-HCl precast minigel (Bio-Rad, Hercules, Calif.), and transferred to Immobilon-P transfer membrane (Millipore, Bedford, Mass.). The membranes were blocked with either 3% BSA (O-GlcNAc blots) or 5% milk (protein blots) in TBST (TBS with 0.1% TWEEN 20), and probed with each antibody (1:1000 dilution for O-GlcNAc blots, 1:8000 dilution for CKII, OGT and OGA blots, and 1:10,000 dilution for a-tubulin blot) at 4° C. for overnight followed by incubating with secondary antibodies conjugated to HRP at room temperature for 2 h. The final detection of HRP activity was performed using SuperSignal chemiluminescent substrates (Thermo Scientific, Rockford, Ill.) as followed: MAbs 18B10.C7(3), 9D1.E4(10) and 1F5.D6(14) used Femto; CKII, OGT, OGA and tubulin used PICO. The films were exposed to CL-XPosure film (Thermo Scientific, Rockford, Ill.). After developing the image on the film, the blot was then stripped with 0.1 M glycine (pH 2.5) at room temperature for 1 h, wash with ddH2O and reprobed for loading control (CKII or a-tubulin) as described above.

Conjugation of MAbs to Agarose and Sample Preparation for LC-MS/MS Analysis.

MAbs 18B10.C7(3), 9D1.E4(10) and 1F5.D6(14) or CTD110.6 were covalently conjugated to Protein A/G PULS agarose or anti-Mouse IgM agarose via disuccinimidyl substrate (DSS, Thermo Scientific, Rockford, Ill.) according to manufacturer's instruction. PUGNAc treated HEK293T nucleocytosolic fraction was prepared as above in larger scale, incubated with antibody conjugated agarose, and washed as above. To elute proteins off the agarose, 0.1 M of glycine (pH 2.5) was added and the eluates were immediately neutralized with 1 M Tris-HCl (pH 8.0). The samples were then reduced and alkylated as previously described 8 and subjected to LysC digestion at 37° C. for overnight. After digestion, the samples were as previously described (Lim et al., 2008 J. Proteome Res. 7, 1251-1263).

Mass Spectrometry.

The samples were resuspended with 19.5 μl of 0.1% formic acid (in water) and 0.5 μl of 80% acetonitrile/0.1% formic acid (in water) and filtered with 0.2 μm filters (Nanosep, PALL). Samples were then loaded off-line onto a nanospray C18 column and separated with a 160-min linear gradient as previously described (Lim et al., 2008 J. Proteome Res. 7, 1251-1263) using Finnigan LTQ/XL mass spectrometer (ThermoFisher, San Jose, Calif.). Each sample was subjected to 3 runs with different settings: (1) ETD (electron transferred dissociation) mode, where a full MS spectrum was collected followed by 6 MS/MS spectra following ETD (enabled supplemental activation) of the most intense peaks. The dynamic exclusion was set at 1 for 30 sec of duration. (2) CID-NL (collision induced dissociation-pseudo neutral loss) mode, where a full MS spectrum was collected followed by 8 MS/MS spectra following CID of the most intense peaks. Upon encountering a pseudo neutral loss event (a loss of GlcNAc, 203.08), a MS8 spectrum will be created based of the MS/MS spectrum. The dynamic exclusion has the same setting as ETD method. (3) DDNL-ETD (Data dependent neutral loss MS8 under CID followed by ETD activation upon every neutral loss event), where MS/MS spectra from top 5 peaks of each full MS scan were collected with CID (35% normalized collision energy) and monitored for a neutral loss of 203.08 during which a MS8 spectrum will be created. A repeat scan event with neutral loss will be performed using ETD enabled with supplemental activation. The dynamic exclusion was also set the same as above.

Data Analysis and Validation.

MS spectra were searched against the human (*Homo sapiens*, 32876 entries, Aug. 13, 2007 released) forward and reverse databases extracted from the Swiss-Prot human proteome database using the TurboSequest algorithm (Bioworks 3.3, Thermo Finnigan). The DTA files were generated for spectra with a threshold of 15 ions and a TIC of 1e3. Dynamic mass increases of 15.99, 57.02 and 203.08 Da were considered for oxidized methione, alkylated cysteine and O-GlcNAc modified serine/threonine respectively. The resulting OUT files each samples obtained forward and reversed databases searched were further parsed with ProtoeIQ (Bioinquire) and filtered with 1% FDR (metric used: F-value) and starting peptide coverage for ProFDR at 5.

Statistical Analysis.

Statistical significance between groups was determined by two-tailed, unpaired Student's t test. Differences were considered significant when $P<0.05$.

Example XI

O-GlcNAc Modified Proteins in Rat Liver

Changes in cell and tissue levels of O-GlcNAc have typically been associated with a range of chronic pathophysiological conditions including aging (Fulop et al., Am J Physiol Cell Physiol 2007; 292:C1370-8; Rex-Mathes et al., Biochimie 2001; 83:583-90; Fulop et al., Biogerontology 2008; 9:139-51), cancer (Chou et al., J Biol Chem 1995; 270:18961-5; Shaw et al., Oncogene 1996; 12:921-30; Donadio et al., J Cell Biochem 2008; 103:800-11), neurodegenerative disorders (Hanover, FASEB J. 2001; 15:1865-187; Wells et al., Biochem Biophys Res Commun 2003; 302:435-41; Love and Hanover, Sci STKE 2005; 2005:re13; Dias et al., Mol Biosyst 2007; 3:766-72) as well as diabetes and diabetic complications (Buse, Am J Physiol Endocrinol Metab 2006; 290:E1-E8; Copeland et al., Am J Physiol Endocrinol Metab 2008; 295:E17-28). However, a number of studies have recently demonstrated that acute augmentation of O-GlcNAc levels is associated with increased tolerance of cells to stress and conversely, inhibition of O-GlcNAc formation decreases cell survival (Champattanachai et al., Am J Physiol Cell Physiol 2007; 292:C178-87; Champattanachai et al., Am J Physiol Cell Physiol 2008; 294: C1509-20; Zachara et al., J Biol Chem 2004; 279:30133-30142). We have also shown in a rat model of trauma-hemorrhage that increasing O-GlcNAc synthesis with glucosamine or inhibiting O-GlcNAc degradation with PUGNAc during resuscitation leads to improved organ function, decreased tissue injury, reduced inflammatory responses and lower mortality (Not et al., Faseb J 2008; 22:1227; Not et al., SHOCK 2007; 28:345-351; Yang et al., Shock 2006; 25:600-607; Zou et al., Shock 2007; 27:402-408). Surprisingly, however, it has been found that resuscitation results in marked loss of overall O-GlcNAc levels in multiple tissues, which was sustained for up to 24 hrs and that treatment with either glucosamine or PUGNAc prevented this loss (Not et al., Faseb J 2008; 22:1227; Zou et al., Shock 2007; 27:402-408). Moreover, significant correlations have been shown between the overall level of tissue 0-GlcNAc levels and indices of tissue injury (Not et al., Faseb J 2008; 22:1227; Liu et al., Am J Physiol Heart Circ Physiol 2007; 293:H1391-9); however, to date identification of specific proteins that exhibit changes in O-GlcNAc modification in response to trauma-hemorrhage and resuscitation has not been examined. In FIG. 33, we show that similar to CTD110.6, all three MAbs generated in this study demonstrated significantly lower overall hepatic O-GlcNAc levels 24 hrs following trauma-hemorrhage and resuscitation compared to sham controls.

TABLE 12

Monoclonal O-GlcNAc antibodies.

| Antibody | Type | Conc. | Primary | Secondary |
|---|---|---|---|---|
| CTD 110.6 | IgM | | 1:5000 | 1:10000 |
| #3 (18B10.C7) | IgG1 | 0.86 mg/mL | 1:1000 | 1:2500 |
| #10 (9D1.E4) | IgG1 | 0.59 mg/mL | 1:1000 | 1:2500 |
| #14 (1F5.D6) | IgG2a | 0.97 mg/mL | 1:1000 | 1:2500 |

To provide insight into proteins whose O-GlcNAc status is modified, the antibodies (Table 12) were employed for immuno-precipitation of O-GlcNAc modified proteins from livers samples of rats subjected to trauma-hemorrhage and resuscitated and sham controls (FIG. 33). Thus, agarose covalently conjugated MAbs were mixed with liver extracts and subjected to Lys-C digestion and the recovered peptides and glycopeptides were analyzed by LC-MS/MS on an LTQ-XL. Protein assignments and false-discovery rates (1% at the protein level) were calculated using TurboSequest and ProteoIQ. Proteins were excluded that appeared in control experiments (mixture of Protein A/G PLUS agarose and anti-Mouse IgM agarose) and localization was confirmed with the aid of Human Protein Reference Database (HPRD) and UniProt. In the control (sham) group, we identified 69 O-GlcNAc modified proteins, whereas in trauma-hemorrhage and resuscitated group, 30 different O-GlcNAc modified proteins were identified (FIG. 34, Table 13). These results demonstrate that the antibodies can be employed to identify O-GlcNAc modified proteins from tissue samples.

TABLE 13

O-GlcNAc modified proteins identified in rat liver.

| UniProt ID | Gene Name | Sequence Name | Sham Total Peptides | THR Total Peptides | Biological Process | Primary Localization | Alternate Localization |
|---|---|---|---|---|---|---|---|
| P07756 | Cps1 | carbamoyl-phosphate synthetase 1 | 20 | 7 | M | Mitochondrion | |
| P63039 | Hspd1 | heat shock protein 1 (chaperonin) | 7 | 0 | S | Mitochondrion | Cytoplasm; ER; Golgi; Nucleolus |
| Q9WVK7 | Hadh | L-3-hydroxyacyl-Coenzyme A dehydrogenase | 4 | 0 | M | Mitochondrion | |
| P04785 | P4hb | prolyl 4-hydroxylase, beta polypeptide | 5 | 1 | M | ER | Nucleus; Extracellular; Nucleolus |
| — | — | PREDICTED: similar to host cell factor C1 | 8 | 14 | G | Nucleus | Cytoplasm |
| P22791 | Hmgcs2 | hydroxymethylglutaryl-CoA synthase 2 | 6 | 2 | M | Mitochondrion | |
| Q66HT1 | Aldob | aldolase B, fructose-bisphosphate | 4 | 3 | M | Cytoplasm | |
| P48500 | Tpi1 | triosephosphate isomerase 1 | 0 | 4 | M | Cytoplasm | |
| Q9JIH7 | Wnk1 | WNK lysine deficient protein kinase 1 | 6 | 12 | S | Cytoplasm | |
| O09171 | Bhmt | betaine-homocysteine methyltransferase | 3 | 3 | M | Cytoplasm | |
| P13437 | Acaa2 | acetyl-Coenzyme A acyltransferase 2 | 4 | 2 | M | Mitochondrion | |
| — | — | PREDICTED: similar to heat shock protein 8 | 5 | 0 | M | Cytoplasm | Plasma Membrane |
| O08658 | Nup88 | nucleoporin 88 kDa | 0 | 3 | Tp | Nucleus | |
| Q5XFW8 | Sec13 | SEC13 homolog | 5 | 4 | Tp | ER | Nucleus; Cytoplasm |
| P05197 | Eef2 | eukaryotic translation elongation factor 2 | 3 | 1 | Tl | Cytoplasm | Nucleus; Cytosol |

TABLE 13-continued

O-GlcNAc modified proteins identified in rat liver.

| UniProt ID | Gene Name | Sequence Name | Sham Total Peptides | THR Total Peptides | Biological Process | Primary Localization | Alternate Localization |
|---|---|---|---|---|---|---|---|
| P52759 | Hrsp12 | heat-responsive protein 12 (Ribonuclease UK114; 14.5 kDa translational inhibitor protein) | 3 | 0 | Tl | Cytoplasm | Plasma membrane; Golgi, ER; Nucleus |
| Q66HA5 | Cc2d1 | coiled-coil and C2 domain containing 1A | 0 | 3 | G, S | Cytoplasm | Nucleus |
| O35077 | Gpd1 | glycerol-3-phosphate dehydrogenase 1 (soluble) | 3 | 0 | M | Cytoplasm | |
| P10860 | Glud1 | glutamate dehydrogenase 1 | 4 | 0 | M | Mitochondrion | |
| — | — | PREDICTED: similar to Alpha-enolase (2-phospho-D-glycerate hydro-lyase) (Non-neural enolase) (NNE) (Enolase 1) | 3 | 1 | M | Cytoplasm | Plasma membrane; Nucleus; Extracellular |
| — | — | PREDICTED: similar to HBxAg transactivated protein 2 | 2 | 4 | U | Cytoplasm | |
| — | — | PREDICTED: similar to aldehyde dehydrogenase 4 family, member A1 | 3 | 0 | M | Mitochondrion | |
| P16638 | Acly | ATP citrate lyase isoform 2 | 2 | 0 | M | Cytoplasm | |
| Q3T114 | Prrc1 | proline-rich coiled-coil 1 | 0 | 3 | U | Golgi | Cytoplasm |
| P15999 | Atp5a1 | ATP synthase, H+ transporting, mitochondrial F1 complex, alpha subunit 1, cardiac muscle | 3 | 0 | M, Tp | Mitochondrion | |
| — | — | ubiquitin-associated protein 2 | 0 | 2 | U | Cytoplasm | |
| B6DYP7 | Gsta2 | glutathione S-transferase alpha 2 | 3 | 0 | M | Cytoplasm | |
| P06761 | Hspa5 | heat shock protein 5 (BIP; Heat shock 70 kDa protein 5; 78 kDa glucose-regulated protein) | 3 | 2 | M | ER | Plasma membrane; Cytoplasm; Nucleolus |
| B5DFC3 | Sec23a | SEC23 homolog A | 4 | 2 | Tp | Cytoplasm | ER; Cytoplasmic vesicle |
| Q6AYR1 | Tfg | Trk-fused | 0 | 2 | S | Cytoplasm | |
| P02692 | Fabp1 | fatty acid binding protein 1 | 3 | 0 | Tp | Cytoplasm | Nucleus |
| P67779 | Phb | PREDICTED: prohibitin | 2 | 0 | S | Mitochondrion | Plasma membrane; Nucleus; Nucleolus; Cytoplasm; Extracellular |
| Q02974 | Khk | ketohexokinase | 2 | 0 | M | Cytoplasm? | |
| P56558 | Ogt | O-linked N-acetylglucosamine transferase | 0 | 2 | M, S, G | Nucleus | Cytoplasm; Mitochondrion |
| — | — | PREDICTED: similar to nucleoporin 214 kDa | 3 | 7 | Tp | Nucleus | |
| P06757 | Adh1 | alcohol dehydrogenase 1 | 2 | 1 | M | Cytoplasm | |
| Q6P6R2 | Dld | dihydrolipoamide dehydrogenase | 2 | 0 | M | Mitochondrion | |
| Q9JM53 | Aifm1 | apoptosis-inducing factor, mitochondrion-associated 1 | 2 | 0 | S | Mitochondrion | Nucleus; Cytoplasm |
| — | — | PREDICTED: similar to Actin, cytoplasmic 2 (Gamma-actin) | 2 | 0 | Str | Cytoplasm | |
| — | — | granulin isoform a | 0 | 1 | S | Extracellular | Cytoplasm |
| Q9WVK3 | Pecr | peroxisomal trans-2-enoyl-CoA reductase | 2 | 0 | M | Peroxisome | |
| P11884 | Aldh2 | mitochondrial aldehyde dehydrogenase 2 | 3 | 2 | M | Mitochondrion | Cytoplasm |
| B2RYJ5 | Tmprss13 | transmembrane protease, serine 13 | 0 | 1 | M | Transmembrane | |
| O88764 | Dapk3 | Death-associated protein kinase 3 | 0 | 1 | S | Nucleus | Cytoplasm |

TABLE 13-continued

O-GlcNAc modified proteins identified in rat liver.

| UniProt ID | Gene Name | Sequence Name | Sham Total Peptides | THR Total Peptides | Biological Process | Primary Localization | Alternate Localization |
|---|---|---|---|---|---|---|---|
| P70581 | Nup11 | nucleoporin like 1 (Nucleoporin p58/p45) | 3 | 3 | U | Nucleus | |
| P25093 | Fah | fumarylacetoacetate hydrolase | 2 | 0 | M | Cytoplasm | Extracellular |
| B0BMW2 | Hsd17b10 | hydroxysteroid (17-beta) dehydrogenase 10 | 1 | 0 | M | Mitochondrion | ER; Plasma membrane |
| P07824 | Arg1 | arginase 1 | 2 | 0 | M | Cytoplasm; Plasma Membrane | Extracellular |
| P11232 | Txn | thioredoxin | 2 | 0 | M | Cytoplasm | Nucleus; Extracellular |
| B5DF65 | Blvrb | biliverdin reductase B (flavin reductase (NADPH)) | 1 | 1 | M | Cytoplasm | |
| — | — | filamin, beta | 1 | 0 | | | |
| B0BN46 | Grhpr | glyoxylate reductase/hydroxypyruvate reductase | 1 | 0 | M | Cytoplasm | |
| Q9Z2Q1 | Sec31a | SEC31 homolog A | 2 | 0 | Tp | ER | Cytoplasm; Golgi |
| P63245 | Gnb2l1 | guanine nucleotide binding protein, beta polypeptide 2-like 1 (RACK1) | 1 | 0 | S | Cytoplasm | Nucleus; Plasma membrane |
| — | — | PREDICTED: similar to L-lactate dehydrogenase A chain (LDH-A) (LDH muscle subunit) (LDH-M) | 2 | 0 | M | Cytoplasm | Nucleolus; Cytosol |
| Q66HF1 | Ndufs1 | NADH dehydrogenase (ubiquinone) Fe-S protein 1, 75 kDa | 1 | 0 | M | Mitochondrion | |
| — | — | PREDICTED: similar to aldehyde dehydrogenase family 7, member A1 | 1 | 0 | M | U | |
| P38918 | Akr7a3 | aldo-keto reductase family 7, member A3 (aflatoxin aldehyde reductase) | 1 | 0 | M | Cytoplasm | |
| P14173 | Ddc | dopa decarboxylase (aromatic L-amino acid decarboxylase) | 1 | 0 | M | Cytoplasm | |
| P14141 | Ca3 | carbonic anhydrase III | 2 | 0 | M | Cytoplasm | Extracellular |
| — | — | PREDICTED: similar to SEC24 related gene family, member C isoform 5 | 2 | 3 | Tp | ER | Cytoplasm |
| P45953 | Acadvl | acyl-Coenzyme A dehydrogenase, very long chain | 1 | 0 | M | Mitochondrion | |
| — | — | PREDICTED: similar to solute carrier family 25, member 5 | 1 | 0 | M | Mitochondrion | |
| — | — | PREDICTED: similar to Glycine cleavage system H protein, mitochondrial precursor | 1 | 0 | M | Mitochondrion | |
| P13697 | Me1 | malic enzyme 1 (NADP-dependent malic enzyme) | 1 | 0 | M | Cytoplasm | |
| P29147 | Bdh1 | 3-hydroxybutyrate dehydrogenase, type 1 | 1 | 0 | M | Mitochondrial membrane | |
| — | — | PREDICTED: similar to hydroxyacyl-Coenzyme A dehydrogenase/3-ketoacyl-Coenzyme A thiolase/enoyl-Coenzyme A hydratase (trifunctional protein), alpha subunit | 1 | 0 | M | Mitochondrion | |
| Q4V8I9 | Ugp2 | UDP-glucose pyrophosphorylase 2 | 1 | 0 | M | Cytoplasm | |
| Q9JKB7 | Gda | guanine deaminase | 1 | 0 | M | Cytoplasm | Plasma membrane |
| Q5U2T3 | Spats2l | hypothetical protein LOC316426 (SPATS2-like protein) | 2 | 0 | U | U | |

TABLE 13-continued

O-GlcNAc modified proteins identified in rat liver.

| UniProt ID | Gene Name | Sequence Name | Sham Total Peptides | THR Total Peptides | Biological Process | Primary Localization | Alternate Localization |
|---|---|---|---|---|---|---|---|
| P00786 | Ctsh | cathepsin H | 1 | 0 | M | Lysosome | Microsome, Nucleus, Mitochondrion |
| Q02253 | Aldh6a1 | aldehyde dehydrogenase family 6, subfamily A1 | 1 | 0 | M | Mitochondrion | |
| P19112 | Fbp1 | fructose-1,6-biphosphatase 1 | 1 | 0 | M | Cytoplasm | |
| P07632 | Sod1 | superoxide dismutase 1, soluble | 1 | 0 | M | Cytoplasm | Peroxisome; Nucleus; Extracellular |
| Q68FZ8 | Pccb | propionyl Coenzyme A carboxylase, beta polypeptide | 1 | 0 | M | Mitochondrion | |
| B6ID08 | Mt2A | metallothionein 2A | 1 | 0 | U | U | |
| — | — | PREDICTED: similar to Calcium-binding mitochondrial carrier protein Aralar2 (Mitochondrial aspartate glutamate carrier 2) (Solute carrier family 25 member 13) (Citrin) | 1 | 0 | Tp | Mitochondrion | |
| P13803 | Etfa | electron-transfer-flavoprotein, alpha polypeptide | 1 | 0 | M, Tp | Mitochondrion | |
| — | — | PREDICTED: similar to Cytochrome P450 2C7 (CYPIIC7) (P450F) (PTF1) | 1 | 0 | M | Mitochondrion | |
| — | — | PREDICTED: similar to Nice-4 protein homolog isoform 1 | 1 | 5 | U | Nucleus | |
| Q5SGE0 | Lrpprc | leucine-rich PPR-motif containing protein | 1 | 0 | G | Nucleus | Cytoplasm; Plasma membrane |

* Abbreviations: G, gene expression/transcription; M, metabolism; S, signal transduction; Tl, translation; Tp, transport; U, unknown.

The complete disclosure of all patents, patent applications, and publications, and electronically available material (including, for example, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. The foregoing description and examples have been given for clarity of understanding only. No unnecessary limitations are to be understood therefrom. The invention is not limited to the exact details shown and described, for variations obvious to one skilled in the art will be included within the invention defined by the claims.

---

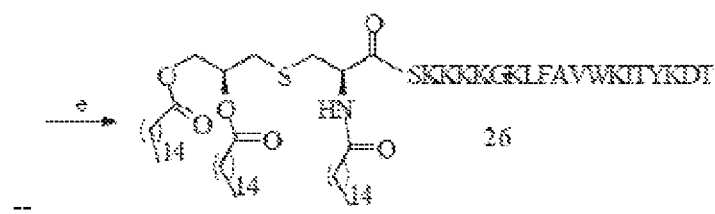

What is claimed is:

1. A glycolipopeptide comprising:
   at least one carbohydrate component comprising a MUC-1 glycopeptide comprising at least one B-epitope;
   at least one peptide component comprising a microbial peptide comprising at least one T-epitope; and
   at least one lipid component comprising $Pam_3CysSK_n$, wherein n=0, 1, 2, 3, 4, or 5.

2. The glycolipopeptide of claim 1 wherein the T-epitope comprises a helper T epitope.

3. The glycolipopeptide of claim 1 wherein the T-epitope comprises amino acid sequence KLFAVWKITYKDT (SEQ ID NO:3).

4. The glycolipopeptide of claim 1 wherein the glycopeptide comprises at least one O-GalNAc moiety.

5. The glycolipopeptide of claim 1 wherein the MUC-1 glycopeptide comprises the amino acid sequence TSAPDT(α-D-GalNAc)RPAP.

6. The glycolipopeptide of claim 1 wherein the lipid component comprises $Pam_3CysSK_4$.

7. A pharmaceutical composition comprising:
   the glycolipopeptide of claim 1 and
   a pharmaceutically acceptable carrier.

8. The pharmaceutical composition of claim 7 comprising a liposome comprising the glycolipopeptide.

9. The glycolipopeptide of claim 1, wherein the glycolipopeptide comprises an N-terminus comprising the lipid component.

10. The glycolipopeptide of claim 1, wherein the lipid component comprises $Pam_3CysSK_4$, the peptide component comprises KLFAVWKITYKDT (SEQ ID NO:3), and the carbohydrate component comprises TSAPDT-(αGalNAc)-RPAP.

* * * * *

UNITED STATES PATENT AND TRADEMARK OFFICE
CERTIFICATE OF CORRECTION

PATENT NO. : 9,446,144 B2
APPLICATION NO. : 14/145745
DATED : September 20, 2016
INVENTOR(S) : Boons et al.

It is certified that error appears in the above-identified patent and that said Letters Patent is hereby corrected as shown below:

On the Title Page

In [71], Remove "Alex Haley, Athens, GA (US)" from list of Applicants

In the Specification

Column 59, Line 23, change "$Pam_7CysSK_4$" to --$Pam_2CysSK_4$--

Column 59, delete Table 2. Insert therefore:

Table 2. ELISA anti-MUC-1 antibody titers* after 4 immunizations with the glycolipopeptide/liposome formulations.

| Entry | Group | IgG1 |
|---|---|---|
| 1. | 1. $Pam_2CysSK_4$-MUC-1 (2) | 24,039 |
| 2. | 2. $Pam_2CysSK_4$-MUC-1 (2) + QS-21 | 36,906 |
| 3. | 3. $Pam_2CysSK_4$-MUC-1 (3) | 183,085 |
| 4. | 4. $Pam_2CysSK_4$-MUC-1 (3) + QS-21 | 450,494 |

* ELISA plates were coated with a BSA-BrAc-MUC-1 conjugate. Anti-MUC1 antibody titers are presented as means of groups of five mice. Titers are defined as the highest dilution yielding an optical density of 0.1 or greater over background of blank mouse sera.

Signed and Sealed this
Eighth Day of August, 2017

Joseph Matal
*Performing the Functions and Duties of the
Under Secretary of Commerce for Intellectual Property and
Director of the United States Patent and Trademark Office*

Column 59, delete Table 3. Insert therefore:

Table 3. ELISA anti-MUC-1 antibody titers* after 4 immunizations with the glycolipopeptide/liposome formulations.

| Entry | Group | IgG1 | IgG2a | IgG2b | IgG3 |
|---|---|---|---|---|---|
| 1. | 1. Pam2CysSK4-MUC-1 (2) | 74,104 | 3,599 | 5,515 | 17,437 |
| 2. | 2. Pam2CysSK4-MUC-1 (2) + QS-21 | 126,754 | 22,709 | 5,817 | 20,017 |
| 3. | 3. Pam3CysSK4-MUC-1 (3) | 448,023 | 57,139 | 61,094 | 115,131 |
| 4. | 4. Pam3CysSK4-MUC-1 (3) + QS-21 | 653,615 | 450,756 | 70,574 | 305,661 |

* ELISA plates were coated with a BSA-BrAc-MUC-1 conjugate. Anti-MUC1 antibody titers are presented as means of groups of five mice. Titers are defined as the highest dilution yielding an optical density of 0.1 or greater over background of blank mouse sera.

Column 83/84, Scheme 18, delete Compound 26. Insert therefore: